US008258265B2

(12) United States Patent
Koide

(10) Patent No.: US 8,258,265 B2
(45) Date of Patent: *Sep. 4, 2012

(54) RECONSTITUTED POLYPEPTIDES

(75) Inventor: Shohei Koide, Chicago, IL (US)

(73) Assignee: Research Corporation Technologies, Inc., Tucson, AZ (US)

(*) Notice: Subject to any disclaimer, the term of this patent is extended or adjusted under 35 U.S.C. 154(b) by 220 days.

This patent is subject to a terminal disclaimer.

(21) Appl. No.: 11/848,135

(22) Filed: Aug. 30, 2007

(65) Prior Publication Data

US 2009/0253899 A1    Oct. 8, 2009

Related U.S. Application Data

(63) Continuation of application No. 10/457,070, filed on Jun. 6, 2003.

(60) Provisional application No. 60/386,991, filed on Jun. 6, 2002.

(51) Int. Cl.
*C07K 16/00* (2006.01)

(52) U.S. Cl. .................. 530/387.1; 424/133.1

(58) Field of Classification Search ............... 530/387.1; 424/133.1
See application file for complete search history.

(56) References Cited

U.S. PATENT DOCUMENTS

| | | | |
|---|---|---|---|
| 4,963,355 | A | 10/1990 | Kim et al. |
| 6,348,584 | B1 | 2/2002 | Hodgson et al. |
| 6,391,855 | B1 | 5/2002 | Blaschuk et al. |
| 6,462,189 | B1 | 10/2002 | Koide |
| 6,673,901 | B2 | 1/2004 | Koide |
| 6,703,199 | B1 | 3/2004 | Koide |
| 6,818,418 | B1 | 11/2004 | Lipovsek et al. |
| 7,078,490 | B2 | 7/2006 | Koide |
| 7,115,396 | B2 | 10/2006 | Lipovsek et al. |
| 7,119,171 | B2 | 10/2006 | Koide |
| 7,153,661 | B2 | 12/2006 | Koide |
| 2003/0027319 | A1 | 2/2003 | Koide |
| 2003/0186385 | A1 | 10/2003 | Koide |
| 2004/0259155 | A1 | 12/2004 | Chan et al. |
| 2005/0038229 | A1 | 2/2005 | Lipovsek et al. |
| 2006/0240018 | A1 | 10/2006 | Koide |
| 2006/0257953 | A1 | 11/2006 | Koide |

FOREIGN PATENT DOCUMENTS

| | | |
|---|---|---|
| JP | 8-511417 | 3/1996 |
| WO | WO 94/18221 | 8/1994 |
| WO | WO 94/24278 | 10/1994 |
| WO | WO 95/27045 | 10/1995 |
| WO | WO 98/56915 | 12/1998 |
| WO | WO 00/34784 | 6/2000 |
| WO | WO 01/64942 | 9/2001 |
| WO | WO 02/04523 | 1/2002 |
| WO | WO 03/104418 | 12/2003 |
| WO | WO 2004/019878 | 3/2004 |
| WO | WO 2005/056764 | 6/2005 |

OTHER PUBLICATIONS

U.S. Appl. No. 10/457,070 (US not published).*
Alzari et al., "Three-dimensional structure of antibodies," *Annu. Rev. Immunol.*, 1998, 555-580.
Archer et al., "An alternative 3D NMR technique for correlating backbone 15N with side chain Hb resonances in large proteins," *J. Magn. Reson.*, 1991, 95:636-641.
Aukhil et al., "Cell-and heparin-binding domains of the hexabrachion arm identified by tenascin expression protein," *J. Biol. Chem.* 1993, 268:2542-2553.
Barbas et al., "Assembly of combinatorial antibody libraries on phage surfaces: the gene III site," *Proc. Natl. Acad. Sci USA*, 1991, 88:7978-7982.
Barbas et al., "Semisynthetic combinatorial antibody libraries: A chemical solution to the diversity problem," *Proc. Natl. Acad. Sci. USA*, 1992, 89:4457-4461.
Baron et al., "$^1$H NMR Assignment and Secondary Structure of the Cell Adhesion Type III Module of Fibronectin," *Biochemistry*, 1992, 31:2068-2073.
Baron et al., "Protein modules," *Trends Biochem. Sci.*, 1991, 16:13-17.
Bass et al., "Hormone Phage: An Enrichment Method for Variant Proteins With Altered Binding Properties," *Proteins: Struct. Funct. Genet.*, 1990, 8:309-314.
Batori et al., *Protein Engineering*, 2002, 15(12):1015-1020.
Barth et al., *Protein Science*, 2000, 9, 942-955.
Bax and Grzesiek, "Methodological Advances in Protein NMR," *Acc. Chem. Res.*, 1993, 26(4):131-138.
Bazan, "Structural design and molecular evolution of a cytokine receptor superfamily," *Proc. Natl. Acac. Sci. USA*, 1990, 87:6934-6938.
Becktel and Schellman, "Protein Stability Curves," *Biopolymers*, 1987, 26:1859-1877.
Berggård et al., "Fragment Complementation Studies of Protein Stabilization by Hydrophobic Core Residues," *Biochemistry*, 40:1257-1264.
Bhat et al., "Bound water molecules and conformational stabilization help mediate an antigen-antibody association," *Proc. Natl. Acad. Sci. USA*, 1994, 91:1089-1093.
Bianchi et al., "High Level Expression and Rational Mutagenesis of a Designed Protein, the Minibody. From the insoluble to a Soluble Molecule," *J. Mol. Biol.*, 1994, 236:649-659.
Billeter et al., "Precise vicinal coupling constants $^3J_{HN}\alpha$ in proteins from nonlinear fits of J-modulated [$^{15}$N, $^1$H]-COSY experiments," *J. Biomol. NMR*, 1992, 2:257-274.
Bodenhausen et al., "Natural abundance nitrogen-15 NMR by enhanced heteronuclear spectroscopy," *Chem. Phys. Lett.*, 1980, 69(1):185-189.
Boder et al., "Yeast Surface Display for Directed Evolution of Protein Expression, Affinity, and Stability," *Methods Enzymol.*, 2000, 328:430-444.
Boder et al., "Yeast surface display for screening combinatorial polypeptide libraries," *Nat. Biotechnol.*, 1997, 15:553-557.

(Continued)

*Primary Examiner* — Lynn Bristol
(74) *Attorney, Agent, or Firm* — Viksnins Harris & Padys PLLP

(57) ABSTRACT

The present invention provides modified fibronectin type III (Fn3) molecules, and nucleic acid molecules encoding the modified Fn3 molecules. Also provided are methods of preparing these molecules, and kits to perform the methods.

13 Claims, 48 Drawing Sheets

OTHER PUBLICATIONS

Bork et al., "Proposed acquisition of an animal protein domain by bacteria," *Proc. Natl. Acad. Sci. USA*, 1992, 89:8990-8994.

Bork et al., "The immunoglobulin Fold. Structural Classification, Sequence Patterns and Common Core," *J. Mol. Biol.*, 1994, 242:309-320.

Briknarová et al., *J. Mol. Biol*, 2003, 332:205-215.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.*, 1990, 111:2129-2138.

Burke et al., "Measurement of Peptide Binding Affinities Using Fluorescence Polarization," *Phage Display of Peptides and Proteins*, 1996, Chapter 18, pp. 305-326, Academic Press, San Diego.

Campbell et al., "Building proteins with fibronectin type III modules," *Structure*, 1994, 2:333-337.

Chen et al., "Characterization of the WW Domain of Human Yes-associated Protien and Its Polyproline-containing Ligands," *J. Biol. Chem.*, 1997, 272(27):17070-17077.

Chen et al., "Mapping of the Binding Interfaces of the Proteins of the Bacterial Phosphotransferase System, HPr and IIA$^{glc}$," *Biochemistry*, 1993, 32:32-37.

Clackson et al., "In vitro selection from protein and peptide libraries," *Trends Biotechnol.*, 1994, 12:173-184.

Clarke et al., "Folding and Stability of a Fibronectin Type III Domain of Human Tenascin," *J. Mol. Biol.*, 1997, 270:771-778.

Clore et al., "Structures of Larger Proteins in Solution: Three- and Four-Dimensional Heteronuclear NMR Spectroscopy," *Science*, 1991, 252:1390-1399.

Connolly, "Solvent-Accessible Surfaces of Proteins and Nucleic Acids," *Science*, 1983, 221(4612):709-713.

Conrath et al., "Camel Single-domain Antibodies as Modular Building Units in Bispecific and Bivalent Antibody Constructs," J. Biol. Chem., 2001, 276:7346-7350.

Cordingley et al., "Substrate Requirements of Human Rhinovirus 3C Protease for Peptide Cleavage in vitro," *J. Biol. Chem.*, 1990, 265(16):9062-9065.

Corey et al., "Trypsin display on the surface of bacteriophage," *Gene*, 1993, 128:129-134.

Cota and Clarke, "Folding of beta-sandwich proteins: Three-state transition of a fibronecrtin type III module," *Protein Sci.*, 2000, 9:112-120.

Cota et al., "Two Proteins with the Same Structure Respond very Differently to Mutation: The Role of Plasticity in Protein Stability," *J. Mol. Biol.*, 2000, 302:713-725.

Creighton, "Fragmentation of a Protein into Peptides," *Proteins: structures and molecular properties*, 1993, Freeman, New York, pp. 38-40.

Dao-pin et al., "Contributions of Engineered Surface Salt Bridges to the Stability of T4 Lysozyme Determined by Directed Mutagenesis," *Biochemistry*, 1991, 30:7142-7153.

Davies et al., "Antibody VH Domains as Small Recognition Units," *Bio/Technol.*, 1995, 13:475-479.

Davies et al., "Single antibody domains as small recognition units: design and in vitro antigen selection of camelized, human VH domains with improved protein stability," *Protein Eng.*, 1996, 9(6):531-537.

de Prat Gay et al., "Generation of a Family of Protein Fragments for Structure-Folding Studies. 1. Folding Complementation of Two Fragments of Chymotrypsin Inhibitor-2 Formed by Cleavage at Its Unique Methionine Residue," *Biochemistry*, 1994, 3:7957-7963.

de Vos et al., "Human growth and extracellular domain of its receptor: crystal structure of the complex," *Science*, 1992, 255:306-312.

Delaglio et al., "NMRPipe: a multidimensional spectral processing system based on UNIX pipes," *J. Biomol. NMR*, 1995, 6:277-293.

Deng et al., "Site-Directed Mutagenesis of Virtually Any Plasmid by Eliminating a Unique Site," *Anal. Biochem.*, 1992, 200:81-88.

Desiderio et al., "A Semi-synthetic Repertoire of Intrinsically Stable Antibody Fragments Derived from a Single-framework Scaffold," *J. Mol. Biol.*, 2001, 310:603-615.

Dickinson et al., "Active Site Modification of Factor VIIa Affects Interactions of the Protease Domain with Tissue Factor," *J. Biol. Chem.*, 1997, 272:19875-19879.

Dickinson et al., "Crystal structure of the tenth type III cell adhesion module of human fibronectin," *J. Mol. Biol.*, 1994, 236:1079-1092.

Dictionary definition of "stability constant" (from ChemiCool website).

Dill, "Dominant Forces in Protein Folding," *Biochemistry*, 1990, 29:7133-7155.

Djavadi-Ohaniance et al., "Measuring antibody affinity in solution," *Antibody Engineering. A Practical Approach*, (McCafferty et al., eds.), pp. 77-97, Oxford Univ. Press, Oxford.

Doolittle, "The Multiplicity of Domains in Proteins," *Annu. Rev. Biochem.*, 1995, 64:287-314.

Dougall et al., "Antibody-structure-based design of pharmacological agents," *Trends Biotechnol.*, 1994, 12:372-379.

Dutta et al., *Protein Science*, 2005, 14:2838-2848.

Duttweiler, "A highly sensitive and non-lethal β-galactosidase plate assay for yeast," *Trends in Genetics*, 1996, 12:340-341.

Dwyer et al., "High Affinity RNase S-Peptide Variants Obtained by Phage Display Have a Novel "Hot-Spot" of Binding Energy," *Biochemistry*, 2001, 40:13491-13500.

Ely et al., "Common molecular scaffold for two unrelated RGD molecules," *Protein Engineering*, 1995, 8(8)823-827.

Farrow et al., "Backbone Dynamics of a Free and Phosphopeptide-Complexed Src Homology 2 Domain Studied by $^{15}$N NMR Relaxation," *Biochemistry*, 1994 , 33:5984-6003.

Fields et al., "A novel genetic system to detect protein-protein interactions," *Nature*, 1989, 340:245-246.

Finley et al., "Interaction mating reveals binary and ternary connections between *Drosophila* cell cycle regulators," *Proc. Natl. Acad. Sci. USA*, 1994, 91:12980-12984.

Fujiwara et al., A Single-Chain Antibody/Epitope System for Functional Analysis of Protein-Protein Interactions, *Biochemistry*, 2002, 41:12729-12738.

Garrett et al., "A Common Sense Approach to Peak Picking in Two-, Three-, and Four-Dimensional Spectra Using Automatic Computer Analysis of Contour Diagrams," *J. Magn. Reson.*, 1991, 95:214-220.

Geyer et al., "Selection of Genetic Agents from Random Peptide Aptamer Expression Libraries," *Methods Enzymol.*, 2000, 328:171-208.

Ghosh et al., "Structure of NF-κB p50 homodimer bound to a κB site," *Nature*, 1995, 373:303-310.

Golemis et al., "Two-hybrid System/Interaction Trap," *Cells: A laboratory manual*, 1997, 69:1-40, CSH Laboratory Press, Cold Spring Harbor, NY.

Green et al., "Contributions of the Polar, Uncharged Amino Acids to the Stability of Staphylococcal Nuclease: Evidence for Mutational Effects on the Free Energy of the Denatured State," *Biochemisty*, 1992, 31: 5717-5728.

Gribskov et al., "The codon preference plot: graphic analysis of protein coding sequences and prediction of gene expression," *Nuc. Acids. Res.*, 1984, 12:539-549.

Grimsley et al., "Increasing protein stability by altering long-range coulombic interactions," *Protein Sci.*, 1999, 8:1843-1849.

Gronenborn et al., "Identification of the Contact Surface of a Streptococcal Protein G Domain Complexed with a Human Fc Fragment," *J. Mol. Biol.*, 1993, 233:331-335.

Gronenborn et al., "A Novel, Highly Stable Fold of the Immunoglobulin Binding Domain of Streptococcal Protein G," *Science*, 1991, 253:657-661.

Grumet et al., "Structure of a New Nervous System Glycoprotein, Nr-CAM, and Its Reltaionship to Subgroups of Neural Cell Adhesion Molecules," *J. Cell Biol.*, 1991, 113(6):1399-1412.

Grzesiek and Bax, "Correlating Backbone Amide and Side Chain Resonances in Larger Proteins by Multiple Relayed Triple Resonance NMR," *J. Am. Chem. Soc.*, 1992, 114:6291-6293.

Grzesiek and Bax, "Amino acid type determination in the sequential assignment procedures uniformly $^{13}$C/$^{15}$N-enriched proteins," *J. Biomol. NMR*, 1993, 3:185-204.

Grzesiek et al., "Correlation of Backbone Amide and Aliphatic Side-Chain Resonances in $^{13}$C/$^{15}$N-Enriched Proteins by Isotropic Mixing of $^{13}$C Magnetization," *J. Magn. Reson. B*, 1993, 101:114-119.

Gyuris et al., "Cdi1, a Human G1 and S Phase Protein Phosphatase That Associates with Cdk2," *Cell*, 1993, 75:791-803.

Harpaz and Chothia, "Many of the Immunoglobulin Superfamily Domains in Cell Adhesion Molecules and Surface Receptors Belong to a New Structural Set Which is Close to That Containing Variable Domains," *J. Mol. Biol.*, 1994, 238:528-539.

Hawkins et al., "Selection of Phage Antibodies by Binding Affinity. Mimicking Affinity Maturation," *J. Mol. Biol.*, 1992, 226:889-896.

Hawkins et al., "The Contribution of Contact and Non-contact Residues of Antibody in the Affinity of Binding to Antigen. The Interaction of Mutant D1.3 Antibodies with Lysozyme," *J. Mol. Biol.*, 1993, 234:958-964.

Helms and Wetzel, "Destabilizing loop swaps in the CDRs of an immunoglobulin $V_L$ domain," *Protein Science*, 1995, 4:2073-2081.

Helms and Wetzel, "Proteolytic excision and in situ cyclization of a bioactive loop from an REI-$V_L$ presentation scaffold," *Protein Science*, 1994, 3:1108-1113.

Hendsch and Tidor, "Do salt bridges stabilize proteins? A continuum electrostatis analysis," *Protein Sci.*, 1994, 3:211-226.

Hendsch et al., "Protein Stabilization by Removal Unsatisfied Polar Groups: Computational Approaches and Experimental Tests," *Biochemistry*, 1996, 35:7621-7625.

Hennecke et al., "Random Circular Permutation of DsbA Reveals Segments that are Essential for Protein Folding and Stability," *J. Mol. Biol.*, 1999, 286:1197-1215.

Hoess, "Protein Design and Phage Display," *Chem. Rev.*, 2001, 101:3205-3218.

Holliger et al., "'Diabodies': Small bivalent and bispecific antibody fragments," *Proc. Natl. Acad. Sci. USA*, 1993, 90:6444-6448.

Holm and Sander, "FSSP: select structural neighbours of 1fnf," *Science*, 1996, 273(5275):595-560.

Holm and Sander, "Mapping the Protein Universe," *Science*, 1996, 273:595-602.

Honda et al., "Fragment Reconstituted of a Small Protein: Folding Energetics of the Reconstituted Immunoglobulin Binding Domain B1 of Streptococcal Protein G," *Biochemistry*, 1999, 38:1203-1213.

Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Res.* 1996, 56:3055-3061.

Ikura and Bax, "Isotope-Filtered 2D NMR of Protein-Peptide Complex: Study of a Skeletal Muscle Myosin Light Chain Kinase Fragment Bound to Calmodulin," *J. Am. Chem. Soc.*, 1992, 114:2433-2440.

Ikura et al., "Improved three-dimensional $^1H$-$^{13}C$-$^1H$ correlation spectroscopy of a $^{13}C$-labeled protein using constant-time evolution," *J. Biomol. NMR*, 1991, 1:299-304.

Jacobs and Schultz, "Catalytic antibodies," *J. Am. Chem. Soc.*, 1987, 109:2174-2176.

Janda et al., "Chemical Selection for Catalysis in Combinatorial Antibody Libraries," *Science*, 1997, 275:945-948.

Johnson and Blevins, "NMR View: A computer program for the visualization and analyis of NMR data," *J. Biomol. NMR*, 1994, 4:603-614.

Johnsson and Varshavsky, "Split ubiquitin as a sensor protein interactions in vivo," *Proc. Natl. Acad. Sci. USA*, 1994, 91:10340-10344.

Jones et al., "Replacing the complementarity-determining regions in a human antibody with those from a mouse," *Nature*, 1986, 321:522-525.

Jones, "The immunoglobulin superfamily," *Curr. Opinion Struct. Biol.*, 1993, 3:846-852.

Jourdan and Searle, "Cooperative Assembly of a Nativelike Ubiquitin Structure through Peptide Fragment Complexation: Energetics of Peptide Association and Folding," *Biochemsitry*, 2000, 39:12355-12364.

Kabsch and Sander, "Dictionary of Protein Secondary Structure: Pattern Recognition of Hydrogen-Bonded and Geometrical Features," *Biopolymers*, 1983, 22:2577-2637.

Kamtekar et al., "Protein Design by Binary Patterning of Polar and Nonpolar Amino Acids," *Science*, 1993, 262(5140):1680-1685.

Kapust et al., "Tobacco etch virus protease: mechanism of autolysis and rational design of stable mutants with wild-type catalytic proficiency," *Protein Eng.*, 2001, 14:993-1000.

Karatan et al., *Chem. & Biol.*, 2004, 11:835-844.

Kauzmann, "Some Factors in the Interpretation of Protein Denaturation," *Adv. Prot. Chem.*, 1959, 14:1-63.

Kay et al., "A Gradient-Enhanced HCCH-TOCSY Experiment for Recording Side-Chain $^1H$ and $^{13}C$ Correlations in $H_2O$ Samples of Proteins," *J. Magn. Reson. B*, 1993, 101:333-337.

Kay et al., "Backbone Dynamics of Proteins As Studies by $^{15}N$ Inverse Detected Heteronuclear NMR Spectroscopy: Application to Staphylococcal Nuclease," *Biochemistry*, 1989, 28:8972-8979.

Kay et al., "Pure Absorption Gradient Enhanced Heteronuclear Single Quantum Correlation Spectroscopy with Improved Sensitivity," *J. Am. Chem. Soc.*, 1992, 114:10663-10665.

Kay, "Field gradient techniques in NMR spectroscopy," *Curr. Opinion Struct. Biol.*, 1995, 5:674-681.

Kay, "Pulsed-Field Gradient-Enhanced Three-Dimensional NMR Experiment for Correlating $^{13}C\alpha/\beta$, $^{13}C'$, and $^1H\alpha$ Chemical Shifts in Uniformly $^{13}C$-Labeled Proteins Dissolved in $H_2O$," *J. Am. Chem. Soc.*, 1993,115:2055-2057.

Kippen et al., "Folding of Barnase in Parts," *Biochemistry*, 1994, 33:3778-3786.

Kohno et al., "A new general method for the biosynthesis of stable isotope-enriched peptides using a decahistidine-tagged ubiquitin fusion system: An application to the production of mastoparan-X uniformly enriched with $^{15}N$ and $^{15}N/^{13}C$," *J. Biomol. NMR*, 1998, 12:109-121.

Koide et al., "Characterization of a Folding Intermediate of Apoplastocyanin Trapped by Proline Isomerization," *Biochemistry*, 1993, 32:12299-12310.

Koide et al., "Directed Evolution of Fibronectin Type III Domain to Novel Ligand Binding Proteins," *FASEB Journal*, 1997, 11(9):A1155.

Koide et al., *PNAS*, 2007, 104:6632-6637.

Koide et al., "Probing proteins conformational changes in living cells by using designer binding proteins: Application to the estrogen receptor," *Proc. Natl. Acad. Sci. USA*, 2002, 99:1253-1258.

Koide et al., "Stabilization of a Fibronectin Type III Domain by the Removal of Unfavorable Electrostatic Interactions on the Protein Surfaace," *Biochemistry*, 2001, 40:10326-10333.

Koide et al., "The Fibronectin Type III Domain as a Scaffold for Novel Binding Proteins," *J. Mol. Biol.*, 1998, 294:1141-1151.

Koide et al., "Multistep Denaturation of *Borrelia burgdorferi* OspA, a Protein Containing a Single-Layer β-Sheet," *Biochemistry*, 1999, 38:4757-4767.

Kornblihtt et al., "Primary structure of human fibronectin: differential splicing may generate at least 10 polypeptides from a single gene," *EMBO J.*, 1985, 4:1755-1759.

Kraulis, "MOLSCRIPT: a program to produce both detailed and schematic plots of protein structures" *J. Appl. Cryst.*, 1991, 24:946-950.

Kuhlman et al., "$pK_a$ Values and the pH Dependent Stability of the N-Terminal Domain of L9 as Probes of Electrostatic Interactions in the Denatured State. Differation between Local and Nonlocal Interactions," *Biochemistry*, 1999, 38:4896-4903.

Kunkel, "Rapid and efficient site-specific mutagenesis without phenotypic selection." *Proc. Natl. Acad. Sci. USA*, 1985, 82:488-492.

Ladurner et al., "Complementation of Peptide Fragments of the Single Domain Protein Chymotrypsin Inhibitor 2," *J. Mol. Biol.*, 1997, 273:317-329.

Lazar, "Transforming Growth Factor α: Mutation of Aspartic Acid 47 and Leucine 48 Results in Different Biological Activities," *Molecular and Cellular Biology*, 1988, 8(3):1247-1252.

Leahy et al., "Structure of a fibronectin type III domain from tenascin phased by MAD analysis of the selenomethionyl protein," *Science*, 1992, 258:987-991.

Leahy et al., "2.0 Å Crystal Structure of a Four-Domain Segment of Human Fibronectin Encompassing the RGD Loop and Synergy Region," *Cell*, 1996, 84:155-164.

Lee et al., "A pulsed field gradient isotope-filtered 3D $^{13}C$ HMQC-NOESY experiment for extracting intermolecular NOE contacts in molecular complexes," *FEBS Lett.*, 1994, 350:87-90.

Lee et al., "Strong Inhibition of Fibrinogen Binding to Platelet Receptor $\alpha_{IIb}\beta_3$ by RGD Sequences Installed Into a Presentation Scaffold," *Protein Engineering*, 1993, 6(7):745-754.

Lee et al., "Three-Dimensional Solution Structure of a Single Zinc Finger DNA-Binding Domain," *Science*, 1989, 245:635-637.

Lerner and Barbas III, "Using the Process of Reactive Immunization to Induce Catalytic Antibodies with Complex Mechanisms: Aldolases," *Acta Chemica Scandinavica*, 1996, 50:672-678.

Li et al., "Minimization of a Polypeptide Hormone," *Science*, 1995, 270:1657-1660.

Li et al., "The Metal Ion Binding Properties of Calreticulin Modulate Its Conformational Flexibility and Thermal Stability," *Biochemistry*, 2001, 40:11193-11201.

Lihui Xu et al., "Directed Evolution of High-affinity Antibody Mimics Using mRNA Display," Chemistry & Biology 2002, 9:933-942.

Lin et al., "Structure Function Relationships in Glucagon: Properties of Highly Purified Des-His$^1$-, Monoiodo-, and [Des-Asn$^{28}$-, Thr$^{29}$](homoserine lactone$^{27}$)-glucagon," *Biochemistry*, 1975, 14(8):1559-1563.

Litvinovich et al., "Reversible unfolding of an isolated heparin and DNA binding fragment, the first type III module from fibronectin," *Biochim. Biphys. Acta*, 1992, 1119:57-62.

Logan et al., "Side chain and backbone assignments in isotopically labeled proteins from two heteronuclear triple resonance experiments," *FEBS Lett.*, 1992, 314:413-418.

Loladze et al., "Engineering a Thermostable Protein via Optimization of Charge-Charge Interactions on the Protein Surface," *Biochemistry*, 1999, 38:16419-16423.

Lowman et al., "Selecting High-Affinity Binding Proteins by Monovalent Phage Display," *Biochemistry*, 1991, 30:10832-10838.

Main et al., "The Three-Dimensional Structure of the Tenth Type III Module of Fibronectin: An Insight into RGD-Mediated Interactions," *Cell*, 1992, 71:671-678.

Malakauskas and Mayo, "Design, structure and stability of a hyperthermophilic protein variant," *Nat. Struct. Biol.*, 1998, 5:470-475.

Martin et al., "The affinity-selection of a minibody polypeptide inhibitor of human interleukin-6," *EMBO J.*, 1994, 13:5303-5309.

Martin, "Commercially valuable catalyic antibodies: the life to come," *Drug Discov. Today*, 1996, 1:239-247.

Martí-Renom et al., "Comparative protein structure modeling of genes and genomes," *Annu. Rev. Biophys. Biomol. Struct.*, 2000, 29:291-325.

Masat et al., "A simpler sort of antibody," *Proc. Natl. Acad. Sci. USA*, 1994, 91:893-896.

Matthews, "Structural and genetic analysis of protein stability," *Annu. Rev. Biochem.*, 1993, 62:139-160.

McCafferty et al., "Phage antibodies: filamentous phage displaying antibody variable domains," *Nature*, 1990, 348:552-554.

McClain et al., "Design and Characterization of a Heterodimeric Coiled Coil that Forms Exclusively with an Antiparallel Relative Helix Orientation," *J. Am. Chem. Soc.*, 2001, 123:3151-3152.

McConnell and Hoess, "Tendamistat as a Scaffold for Conformationally Constrained Phage Peptide Libraries," *J. Mol. Biol.*, 1995, 250:460-470.

McIntosh et al., "The p$K_a$ of the General Acid/Base Carboxyl Group of a Glycosidase Cycles during Catalysis: A $^{13}$C-NMR Study of *Bacillus circulans* Xylanase," *Biochemistry*, 1996, 35:9958-9966.

Merkel and Regan, "Modulating Protein Folding Rates in Vivo and in Vitro by Side-Chain Interactions between the Parallel β Strands of Green Fluorescent Protein," *J. Biol. Chem.*, 2000, 275:29200-29206.

Metzler et al., "The Three-Dimensional Solution Structure SH2 Domain from p55*blk* Kinase," *Biochemistry*, 1996, 35:6201-6211.

Michnick et al., "Detection of Protein-Protein Interactions by Protein Fragment Complementation Strategies," *Methods Enzymol.*, 2000, 328:208-230.

Minor and Kim, "Measurement of the β-sheet-forming propensities of amino acids," *Nature*, 1994, 367:660-663.

Muhandiram et al., "An enhanced-sensitivity pure absorption gradient 4D $^{15}$N, $^{13}$C-edited NOESY experiment," *J. Biomol. NMR*, 1993, 3:463-470.

Müller et al., "Structure of the NF-κB p50 homodimer bound to DNA," *Nature*, 1995, 373:311-117.

Myers et al., "Denaturant *m* values and heat capacity changes: Relation to changes in accessible surface areas of protein unfolding," *Protein Sci.*, 1995, 4:2138-2148.

Nicholls et al., "Protein Folding and Association: Insights From the Interfacial and Thermodynamic Properties of Hydrocarbons," *Proteins*, 1991, 11:281-296.

Nilges et al., "Determination of three-dimensional structures of proteins from interproton distance data by hybrid distance geometry-dynamical simulated annealing calculations," *FEBS Lett.*, 1988, 229:317-324.

Nilges et al., "Sampling Properties of Simulated Annealing and Distance Geometry," *Computational Aspects of the Study of Biological Macromolecules by Nuclear Magnetic Resonance Spectroscopy*, 1991, (Hoch, J.C., Poulsen, F.M. and Redfield, C., eds.), pp. 451-455, Plenum Press, New York.

Oakley and Kim, "A Buried Polar Interaction Can Direct the Relative Orientation of Helices in a Coiled Coil," *Biochemstry*, 1998, 37:12603-12610.

Ojennus et al., "Reconstitution of a native-like SH2 domain from disordered peptide fragments examined by multidimensional heteronuclear NMR," *Protein Science*, 2001, 10:2162-2175.

O'Neil and Hoess, "Phage display: protein engineering by directed evolution," *Curr. Opinion Struct. Biol.*, 1995, 5:443-449.

O'Neil et al., "Phage Display of Random Peptides on a Protein Scaffold," *Techniques in Protein Chemistry V*, 1994, (Crabb, L., ed.) pp. 517-524, Academic Press, San Diego.

Pabo et al., "Design and Selection of Novel Cys$_2$His$_2$ Zinc Finger Proteins," *Annu. Rev. Biochem.*, 2001, 70:313-340.

Pace and Scholtz, "Measuring the conformational stability of a protein," *Protein structure. A practical approach*, 1997, (Creighton, T. E. Ed.) pp. 299-321, IRL Press, Oxford.

Pace et al., "Forces contributing to the conformational stability of proteins," *Faseb J.*, 1996, 10:75-83.

Pace et al., "Urea Denaturation of Barnase: pH Dependence and Characterization of the Unfolded State," *Biochemistry*, 1992, 31:2728-2734.

Parmley and Smith, "Antibody-selectable filamentous fd phage vectors: affinity purification of target genes," *Gene*, 1988, 73:305-318.

Pascal et al., "Nuclear Magnetic Resonance Structure of an SH2 Domains of Phospholipase C-γl Complexed with a High Affinity Binding Peptide," *Cell*, 1994, 77:461-472.

Pascal et al., "Simultaneous Acquisition of $^{15}$N- and $^{13}$C-Edited NOE Spectra of Proteins Dissolved in H$_2$O," *J. Magn. Reson. B*, 1994, 103:197-201.

Patten et al., "Applications of DNA shuffling of pharmaceuticals and vaccines," *Curr. Opin. Biotechnol.*, 1997, 8:724-733.

Pelletier et al., "Oligomerization domain-directed reassmbly of active dihydrofolate reductase from rationally designed fragments," *Proc. Natl. Acad. Sci. USA*, 1998, 95:12141-12146.

pYD1 Yeast Display Vector Kit Catalog No. V835-01, Invitrogen.

Perl et al., "Two exposed amino acid residues confer thermostability on a cold shock protein," *Nat. Struct. Biol.*, 2000, 7:380-383.

Perutz et al., "The p$K_a$ Values of Two Histidine Residues in Human Haemoglobulin, the Bohr Effect, and the Dipole Moments of α-Helies," *J. Mol. Biol.*, 1985, 183:491-498.

Pessi et al., "A designed metal-binding protein with a novel fold," *Nature*, 1993, 362:367-369.

Pierschbacher and Ruoslahti, "Cell attachment activity of fibronectin can be duplicated by small synthetic fragments of the molecule," *Nature*, 1984, 309:30-33.

Plaxco et al., "A Comparison of the Folding Kinetics and Thermodynamics of Two Homologous Fibronectin Type III Modules," *J. Mol. Biol.*, 1997, 270:763-770.

Plaxco et al., "Rapid refolding of a proline-rich all-β-sheet fibronectin type III module," *Proc. Natl. Acad. Sci. USA*, 1996, 93:10703-10706.

Rader and Barbas, "Phage display of combinatorial antibody libraries," *Curr. Opin. Biotech.*, 1997, 8:503-508.

Raquet et al., "Detection of Altered Protein Conformations in Living Cells," *J. Mol. Biol.*, 2001, 305:927-938.

Rees et al., "Antibody design: beyond the natural limits," *Trends Biotechnol.*, 1994, 12:199-206.

Roberts et al., "Affinity maturation of proteins displayed on surface of M13 bacteriophage as major coat protein fusions," *Methods Enzymol.*, 1996, 267:68-82.

Roberts et al., "Directed evolution of protein: Selection of potent neutrophil elastase inhibitors displayed on M13 fusion phage," *Proc. Natl. Acad. Sci. USA*, 1992, 89:2429-2433.

Rosenblum and Barbas, "Synthetic Antibodies," *Antibody Engineering*, 1995, pp. 89-116, Oxford University Press, Oxford.

Sali et al., "Surface Electrostatic Interactions Contribute Little to Stability of Barnase," *J. Mol. Biol.*, 1991, 220:779-788.

Sancho and Fersht, "Dissection of an Enzyme by Protein Engineering. The N and C-Terminal Fragments of Barnase Form a Native-like Complex with Restored Enzymic Activity," *J. Mol. Biol.*, 1992, 224:741-747.

Sandhu et al., "Dual Asymmetric PCR: One-Step Construction of Synthetic Genes," *BioTech.*, 1992, 12:14-16.

Santoro and Bolen, "Unfolding Free Energy Changes Determined by the Linear Extrapolation Method. 1. Unfolding of Phenylmethanesulfonl α-Chymotrypsin Using Different Nenaturants," *Biochemistry*, 1988, 27:8063-8068.

Savchenko et al., "*Pyrococcus furiosus* α-Amylase Is Stabilized by Calcium and Zinc," *Biochemistry*, 2002, 41:6193-6201.

Sblattero and Bradbury, "Exploiting recombination in single bacteria to make large phage anibody libraries," *Nat. Biotechnol.*, 2000, 18:75-80.

Sblattero et al., "In vivo recombination as a tool to generate molecular diversity in phage antibody libraries," *Rev. Mol. Biotechnol.*, 2001, 74:303-315.

Schiweck and Skerra, "The Rational Construction of an Antibody Against Cystatin: Lesson from the Crystal Structure of an Artificial $F_{ab}$ Fragment," *J. Mol. Biol.*, 1997, 268:934-951.

Schwartz et al., "A superactive insulin: [B10-Aspartic acid]insulin(human)," *Proc. Nat'l. Acad. Sci. USA*, 1987, 84:6408-6411.

Sheridan, *Nature Biotechnology*, 2007, 25(4):365-366.

Shortle et al., "Contributions of the Large Hydrophobic Amino Acids to the Stability of Staphylococcal Nuclease," *Biochemistry*, 1990, 29(35):8033-8041.

Shusta et al., "Directed evolution of a stable scaffold for T-cell receptor engineering," *Nature Biotechnology*, 2000, 18(7):754-759.

Skerra, "Engineered protein scaffolds for molecular recognition," *J. Mol. Recognit.*, 2000, 13:167-187.

Smith and Regan, "Guidelines for Protein Design: The Energetics of β Sheet Side Chain Interactions," *Science*, 1995, 270:980-982.

Smith and Scott, "Libraries of Peptides and Proteins Displayed on Filamentous Phage," *Methods Enzymol.*, 1993, 217:228-257.

Smith et al., "A Thermodynamic Scale for the β-Sheet Forming Tendencies of the Amino Acids," *Biochemistry*, 1994, 33:5510-5517.

Smith et al., "Studying α-Helix and β-Sheet Formation in Small Proteins," *Techniques Prot. Chem. VI*, 1995, 6:323-332.

Smith, "Filamentous Fusion Phage: Novel Expression Vectors That Display Cloned Antigens on the Virion Surface," *Science*, 1985, 228:1315-1317.

Smyth and von Itzstein, "Design and Synthesis of Biologically Active Antibody Mimic Based on an Antibody-Antigen Crystal Structure," *J. Am. Chem. Soc.*, 1994, 11:2725-2733.

Spector et al., "Rational Modification of Protein Stability by the Mutation of Charged Surface Residues," *Biochemistry*, 2000, 39:872-879.

Stratagene Catalogue, 1988, p. 39.

Studier et al., "Use of T7 RNA Polymerase to Direct Expression of Cloned Genes," *Methods Enzymol.*, 1990, 185:60-89.

Suzuki, "Recent Advances in Abzyme Studies," *J. Biochem.*, 1994, 115:623-628.

Taira et al., "Evaluation of the importance of hydrophobic interactions in drug binding to dihydrofolate reductase," *J. Med. Chem.*, 1988, 31(1):129-137.

Tasayco and Chao, "NMR Study of the Reconstitution of the β-Sheet of Thioredoxin by Fragment Complementation," *Proteins*, 1995, 22:41-44.

Tasayco et al., "Interaction between Two Discontiguos Chain Segments from the β-Sheet of *Escherichia coli* Thioredoxin Suggests an Initiation Site for Folding," *Biochemistry*, 2000, 39:10613-10618.

Tello et al., "Immunoglobulin Superfamily Interactions," *Biochem. Soc. Trans.*, 1993, 21:943-946.

Thomas, "Hapten Design for the Generation of Catalytic Antibodies," *Appl. Biochem. Biotech.*, 1994, 47:347-372.

Timasheff, "Solvent effects on protein stability," *Curr. Op. Struct. Biol.*, 1992, 2:35-39.

van den Beucken et al., "Building Novel Binding Ligands B7.1 and B7.2 Based on Human Antibody Single Variable Light Chain Domains," *J. Mol. Biol.*, 2001, 310(3):591-601.

Velick et al., "Excitation and energy transfer and the quantative sstudy of the antibody hapten reaction", *PNAS*, 1960, 46(11):1470-1482.

Venturini et al., "Phage Display of the Minibody: A β-Scaffold for the Selection of Conformationally-Constrained Peptides," *Protein Peptide Letters*, 1994, 1:70-75.

Verhoeyen et al., "Reshaping Human Antibodies: Grafting an Antilysozyme Activity," *Science*, 1988, 239:1534-1536.

Vuister and Bax, "Resolution Enhancement and Spectral Editing of Uniformly $^{13}$C-Enriched Proteins by Homonuclear Broadband $^{13}$C Decoupling," *J. Magn. Reson.*, 1992, 98:428-435.

Vuister et al., "Increased Resolution and Improved Spectral Quality in Four-Dimensional $^{13}$C/$^{13}$C-Separated HMQC-NOESY-HMQC Spectra Using Pulsed Field Gradients," *J. Magn. Reson. B*, 1993, 101:210-213.

Ward et al., "Binding activities of a repertoire of single immunoglobulin variable domains secreted from *Escherichia coli*," *Nature*, 1989, 341:544-546.

Webster et al., "Antibody-antigen interactions," *Curr. Opinion Struct. Biol.*, 1994, 4:123-129.

Williams and Barclay, "The Immunoglobulin Superfamily—Domains for Cell Surface Recognition," *Ann. Rev. Immunol.*, 1988, 6:381-405.

Wilson and Stanfield, "Antibody-antigen interactions," *Curr. Opinion Struct. Biol.*, 1993, 3:113-118.

Wilson and Stanfield, "Antibody-antigen interactions: new structures and new conformational changes," *Curr. Opinion Struct Biol.*, 1994, 4:857-867.

Winter et al., "Making antibodies by phage display technology," *Annu. Rev. Immunol.*, 1994, 12:433-455.

Wiseman et al., "Rapid Measurement of Binding Constants and Heats of Binding Using a New Titration Calorimeter," *Anal. Biochem.*, 1989, 179:131-137.

Wittekind and Mueller, HNCACB, a High-Sensitivity 3D NMR Experiment to Correlate Amide-Proton and Nitrogen Resonance with Alpha- and Beta-Carbon Resonances in Proteins, *J. Magn. Reson. B*, 1993, 101:201-205.

Wittke et al., "Probing the Molecular Environment of Membrane Proteins In Vivo," *Mol. Biol. Cell*, 1999, 10:2519-2530.

Wu et al., "Length Distribution of CDRH3 in Antibodies," *Proteins: Struct. Funct. Genet.*, 1993, 16:1-7.

Yamazaki et al., "Segmental Isotope Labeling for Protein NMR Using Peptide Splicing," *J. Am. Chem. Soc.*, 1998, 120(22):5591-5592.

Yamazaki et al., "Two-Dimensional NMR Experiments for Correlating $^{13}$Cβ and $^1$Hδ/ε Chemical Shifts of Aromatic Residues in $^{13}$C-Labeled Proteins via Scalar Couplings," *J. Am. Chem. Soc.*, 1993, 115:11054-11055.

Yang and Honig, "Electrostatic effects on protein stability," *Curr. Opin. Struct. Biol.*, 1992, 2:40-45.

Zhang et al., "Backbone $^1$H and $^{15}$N resonance assignments of the N-terminal SH3 domain of drk in folded and unfolded states using enhanced-sensitivity pulsed field gradient NMR techniques," *J. Biomol. NMR*, 1994, 4:845-858.

Zhang et al., "Circular Permutation of T4 Lysozyme," *Biochemistry*, 1993, 32:12311-12318.

\* cited by examiner

```
NdeI                              PstI                            EcoRI
   1         11        21        31        41
mq VSDVPRDLEV VAATPTSLLI SWDAPAVTVR YYRITYGETG GNSPVQEFTV
            A        B                  C              D

SalI              SacI              XhoI
  51         61        71        81        91
   PGSKSTATIS GLKPGVDYTI TVYAVTGRGD SPASSKPISI NYRT
        E            F                     G
```

FIG. 2

```
NdeI
CATATGCAGGTTTCTGATGTTCCGCGTGACCTGGAAGTTGTTGCTGCGACCCCGACTAGC
    MetGlnValSerAspValProArgAspLeuGluValValAlaAlaThrProThrSer
    -2 -1  1                     10                         A

BclI PvuII           PstI  BC loop                BsiWI
CTGCTGATCAGCTGGGATGCTCCTGCAGTTACCGTGCGTTATTACCGTATCACGTACGGT
LeuLeuIleSerTrpAspAlaProAlaValThrValArgTyrTyrArgIleThrTyrGly
    20      B                  30                           C EcoRI
GAAACCGGTGGTAACTCCCCGGTTCAGGAATTCACTGTACCTGGTTCCAAGTCTACTGCT
GluThrGlyGlyAsnSerProValGlnGluPheThrValProGlySerLysSerThrAla
    40                 D    50                              E SalI                    Bst1107I
ACCATCAGCGGCCTGAAACCGGGTGTCGACTATACCATCACTGTATACGCTGTTACTGGC
ThrIleSerGlyLeuLysProGlyValAspTyrThrIleThrValTyrAlaValThrGly
    60                      70          F FG loop       SacI                                  XhoI
CGTGGTGACAGCCCAGCGAGCTCCAAGCCAATCTCGATTAACTACCGTACCTAGTAACTC
ArgGlyAspSerProAlaSerSerLysProIleSerIleAsnTyrArgThr
    80                  90      G
```

FIG. 5

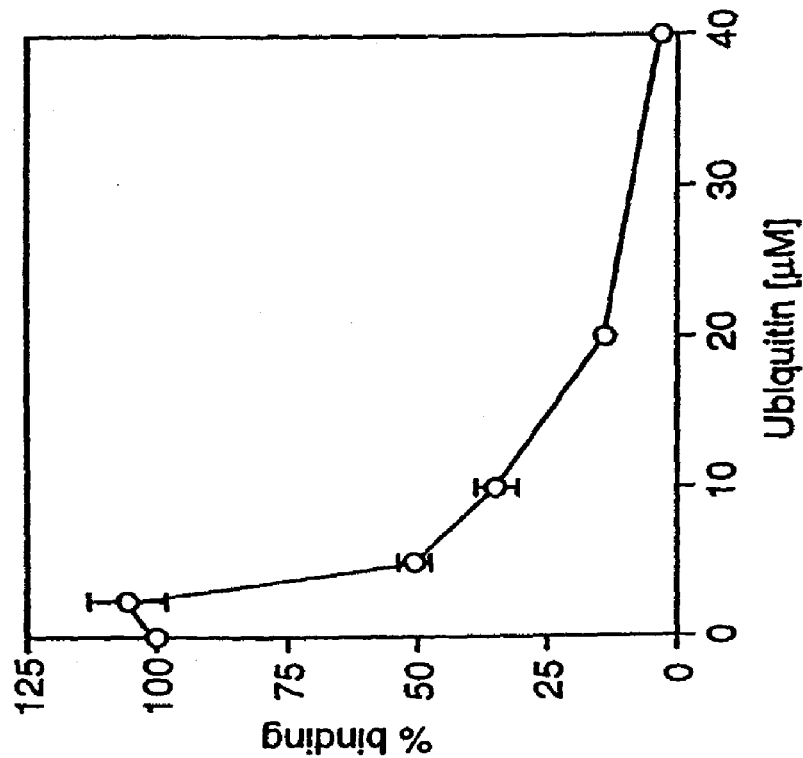
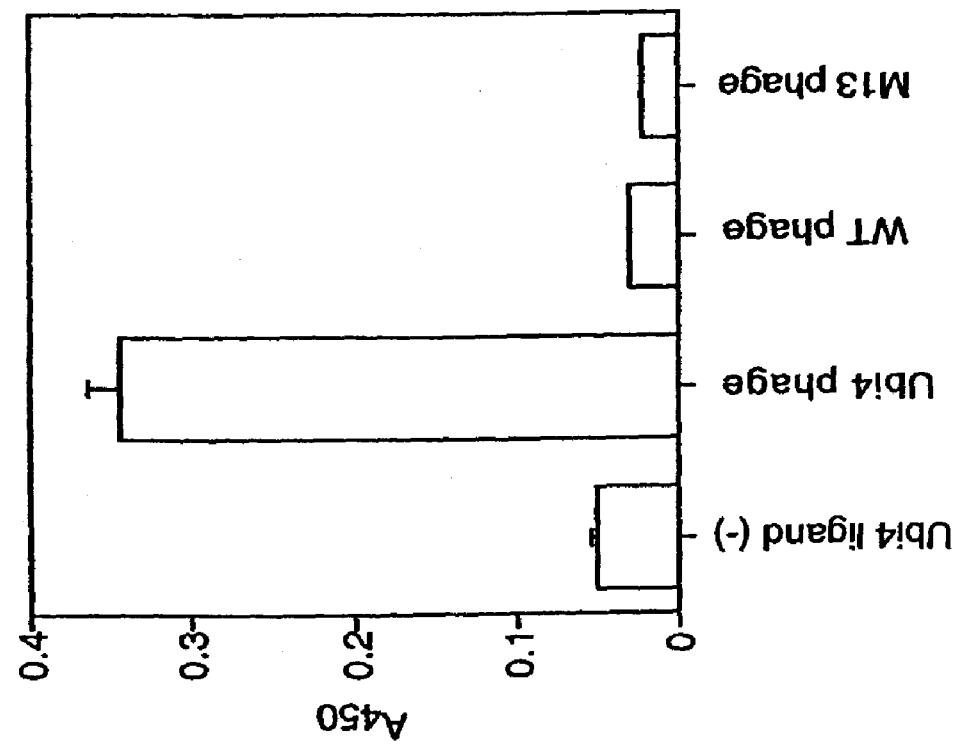
FIG. 15B
FIG. 15A

FNABC 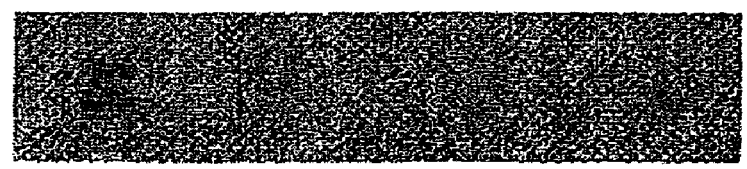
pTarget 
FNDEFG    FNDEFG0319    FNDEFG4699    pBait
FIG. 44

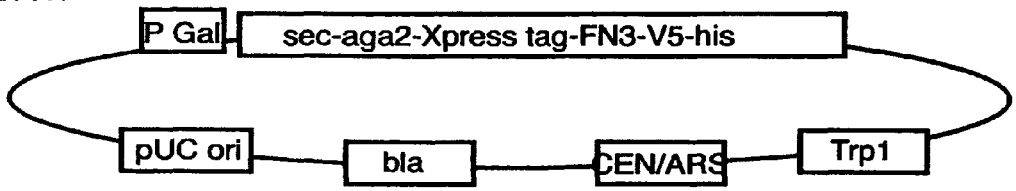
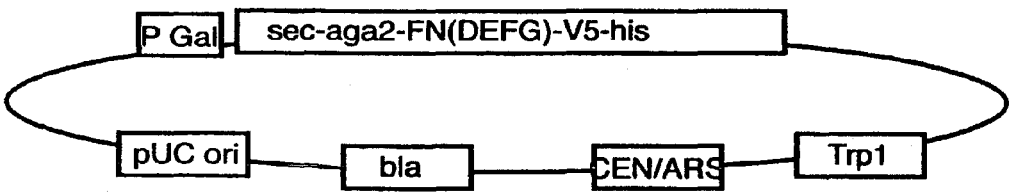
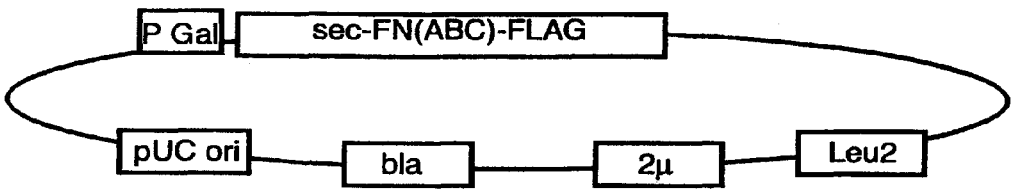
FIG. 46

RECONSTITUTED POLYPEPTIDES

CLAIM OF PRIORITY

This application is a continuing application of U.S. application Ser. No. 10/457,070, which was filed on Jun. 6, 2003, which application claims priority to U.S. Provisional Application Ser. No. 60/386,991, which was filed on Jun. 6, 2002, which applications are incorporated herein by reference.

GOVERNMENTAL RIGHTS

Portions of the present invention were made with support of the United States Government via a grant from the National Institutes of Health under grant numbers R29-GM 55042 and R01-DK63090, and via a grant from the Department of Defense under grant number DAMD17-01-1-0385. The U.S. Government therefore may have certain rights in the invention.

BACKGROUND OF THE INVENTION

U.S. patent application Ser. Nos. 09/096,749, which corresponds to Publication No. US 2002 0019517, and Ser. No. 09/903,412 are hereby incorporated by reference in their entirety.

Antibody Structure

A standard antibody (Ab) is a tetrameric structure consisting of two identical immunoglobulin (Ig) heavy chains and two identical light chains. The heavy and light chains of an Ab consist of different domains. Each light chain has one variable domain (VL) and one constant domain (CL), while each heavy chain has one variable domain (VH) and three or four constant domains (CH) (Alzari et al., 1988). Each domain, consisting of ~110 amino acid residues, is folded into a characteristic β-sandwich structure formed from two β-sheets packed against each other, the immunoglobulin fold. The VH and VL domains each have three complementarity determining regions (CDR1-3) that are loops, or turns, connecting β-strands at one end of the domains (FIG. 1: A, C). The variable regions of both the light and heavy chains generally contribute to antigen specificity, although the contribution of the individual chains to specificity is not always equal. Antibody molecules have evolved to bind to a large number of molecules by using six randomized loops (CDRs). However, the size of the antibodies and the complexity of six loops represents a major design hurdle if the end result is to be a relatively small peptide ligand.

Antibody Substructures

Functional substructures of Abs can be prepared by proteolysis and by recombinant methods. They include the Fab fragment, which contains the VH-CH1 domains of the heavy chain and the VL-CL1 domains of the light chain joined by a single interchain disulfide bond, and the Fv fragment, which contains only the VH and VL domains. In some cases, a single VH domain retains significant affinity (Ward et al., 1989). It has also been shown that a certain monomeric κ light chain will specifically bind to its cognate antigen. (L. Masat et al., 1994). Separated light or heavy chains have sometimes been found to retain some antigen-binding activity (Ward et al., 1989). These antibody fragments are not suitable for structural analysis using NMR spectroscopy due to their size, low solubility or low conformational stability.

Another functional substructure is a single chain Fv (scFv), made of the variable regions of the immunoglobulin heavy and light chain, covalently connected by a peptide linker (S-z Hu et al., 1996). These small ($M_r$ 25,000) proteins generally retain specificity and affinity for antigen in a single polypeptide and can provide a convenient building block for larger, antigen-specific molecules. Several groups have reported biodistribution studies in xenografted athymic mice using scFv reactive against a variety of tumor antigens, in which specific tumor localization has been observed. However, the short persistence of scFvs in the circulation limits the exposure of tumor cells to the scFvs, placing limits on the level of uptake. As a result, tumor uptake by scFvs in animal studies has generally been only 1-5% ID/g as opposed to intact antibodies that can localize in tumors ad 30-40% ID/g and have reached levels as high as 60-70% ID/g.

A small protein scaffold called a "minibody" was designed using a part of the Ig VH domain as the template (Pessi et al., 1993). Minibodies with high affinity (dissociation\constant ($K_d$)~$10^{-7}$ M) to interleukin-6 were identified by randomizing loops corresponding to CDR1 and CDR2 of VH and then selecting mutants using the phage display method (Martin et al., 1994). These experiments demonstrated that the essence of the Ab function could be transferred to a smaller system. However, the minibody had inherited the limited solubility of the VH domain (Bianchi et al., 1994).

It has been reported that camels (*Camelus dromedarius*) often lack variable light chain domains when IgG-like material from their serum is analyzed, suggesting that sufficient antibody specificity and affinity can be derived form VH domains (three CDR loops) alone. Davies and Riechmann recently demonstrated that "camelized" VH domains with high affinity ($K_d$~$10^{-7}$ M) and high specificity can be generated by randomizing only the CDR3. To improve the solubility and suppress nonspecific binding, three mutations were introduced to the framework region (Davies & Riechmann, 1995). It has not been definitively shown, however, that camelization can be used, in general, to improve the solubility and stability of VHs.

An alternative to the "minibody" is the "diabody." Diabodies are small bivalent and bispecific antibody fragments, i.e., they have two antigen-binding sites. The fragments contain a heavy-chain variable domain ($V_H$) connected to a light-chain variable domain ($V_L$) on the same polypeptide chain ($V_H$-$V_L$). Diabodies are similar in size to an Fab fragment. By using a linker that is too short to allow pairing between the two domains on the same chain, the domains are forced to pair with the complementary domains of another chain and create two antigen-binding sites. These dimeric antibody fragments, or "diabodies," are bivalent and bispecific (P. Holliger et al., 1993).

Since the development of the monoclonal antibody technology, a large number of 3D structures of Ab fragments in the complexed and/or free states have been solved by X-ray crystallography (Webster et al., 1994; Wilson & Stanfield, 1994). Analysis of Ab structures has revealed that five out of the six CDRs have limited numbers of peptide backbone conformations, thereby permitting one to predict the backbone conformation of CDRs using the so-called canonical structures (Lesk & Tramontano, 1992; Rees et al., 1994). The analysis also has revealed that the CDR3 of the VH domain (VH-CDR3) usually has the largest contact surface and that its conformation is too diverse for canonical structures to be defined; VH-CDR3 is also known to have a large variation in length (Wu et al., 1993). Therefore, the structures of crucial regions of the Ab-antigen interface still need to be experimentally determined.

Comparison of crystal structures between the free and complexed states has revealed several types of conformational rearrangements. They include side-chain rearrangements, segmental movements, large rearrangements of VH- CDR3 and changes in the relative position of the VH and VL domains (Wilson & Stanfield, 1993). In the free state, CDRs, in particular those which undergo large conformational changes upon binding, are expected to be flexible. Since X-ray crystallography is not suited for characterizing flexible parts of molecules, structural studies in the solution state have not been possible to provide dynamic pictures of the conformation of antigen-binding sites.

Mimicking the Antibody-binding Site

CDR peptides and organic CDR mimetics have been made (Dougall et al., 1994). CDR peptides are short, typically cyclic, peptides which correspond to the amino acid sequences of CDR loops of antibodies. CDR loops are responsible for antibody-antigen interactions. Organic CDR mimetics are peptides corresponding to CDR loops which are attached to a scaffold, e.g., a small organic compound.

CDR peptides and organic CDR mimetics have been shown to retain some binding affinity (Smyth & von Itzstein, 1994). However, as expected, they are too small and too flexible to maintain full affinity and specificity. Mouse CDRs have been grafted onto the human Ig framework without the loss of affinity (Jones et al., 1986; Riechmann et al., 1988), though this "humanization" does not solve the above-mentioned problems specific to solution studies.

Mimicking Natural Selection Processes of Abs

In the immune system, specific Abs are selected and amplified from a large library (affinity maturation). The processes can be reproduced in vitro using combinatorial library technologies. The successful display of Ab fragments on the surface of bacteriophage has made it possible to generate and screen a vast number of CDR mutations (McCafferty et al., 1990; Barbas et al., 1991; Winter et al., 1994). An increasing number of Fabs and Fvs (and their derivatives) is produced by this technique, providing a rich source for structural studies. The combinatorial technique can be combined with Ab mimics.

A number of protein domains that could potentially serve as protein scaffolds have been expressed as fusions with phage capsid proteins. Review in Clackson & Wells, Trends Biotechnol. 12:173-184 (1994). Indeed, several of these protein domains have already been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of *Streptococcus* (O'Neil et al., Techniques in Protein Chemistry V (Crabb, L., ed.) pp. 517-524, Academic Press, San Diego (1994)). These scaffolds have displayed a single randomized loop or region.

Researchers have used the small 74 amino acid α-amylase inhibitor Tendamistat as a presentation scaffold on the filamentous phage M13 (McConnell and Hoess, 1995). Tendamistat is a β-sheet protein from *Streptomyces tendae*. It has a number of features that make it an attractive scaffold for peptides, including its small size, stability, and the availability of high resolution NMR and X-ray structural data. Tendamistat's overall topology is similar to that of an immunoglobulin domain, with two β-sheets connected by a series of loops. In contrast to immunoglobulin domains, the β-sheets of Tendamistat are held together with two rather than one disulfide bond, accounting for the considerable stability of the protein. By analogy with the CDR loops found in immunoglobulins, the loops the Tendamistat may serve a similar function and can be easily randomized by in vitro mutagenesis.

Tendamistat, however, is derived from *Streptomyces tendae*. Thus, while Tendamistat may be antigenic in humans, its small size may reduce or inhibit its antigenicity. Also, Tendamistat's stability is uncertain. Further, the stability that is reported for Tendamistat is attributed to the presence of two disulfide bonds. Disulfide bonds, however, are a significant disadvantage to such molecules in that they can be broken under reducing conditions and must be properly formed in order to have a useful protein structure. Further, the size of the loops in Tendamistat are relatively small, thus limiting the size of the inserts that can be accommodated in the scaffold. Moreover, it is well known that forming correct disulfide bonds in newly synthesized peptides is not straightforward. When a protein is expressed in the cytoplasmic space of *E. coli*, the most common host bacterium for protein overexpression, disulfide bonds are usually not formed, potentially making it difficult to prepare large quantities of engineered molecules.

Thus, there is an on-going need for small polypeptides that bind with a target molecule, such as an artificial antibody. These polypeptides can be used for a variety of therapeutic, diagnostic, research and catalytic applications. There is also an on-going need for polypeptides that bind to more than one target molecule, and for protein fragments (or binding pairs) that associate or reconstitute to form a protein.

The following abbreviations have been used in describing amino acids, peptides, or proteins: Ala or A, Alanine; Arg or R, Arginine; Asn or N asparagine; Asp or D, aspartic acid; Cys or C, cysteine; Gln or Q, glutamine; Glu or E, glutamic acid; Gly or G, glycine; H is or H, histidine; Ile or I, isoleucine; Leu or L, leucine; Lys or K, lysine; Met or M, methionine; Phe or F, phenylalanine; Pro or P, proline; Ser or S, serine; Thr or T, threonine; Trp or W, tryptophan; Tyr or Y, tyrosine; Val or V, valine.

The following abbreviations have been used in describing nucleic acids, DNA, or RNA: A, adenosine; T, thymidine; G, guanosine; C, cytosine.

SUMMARY OF THE INVENTION

As used herein the indefinite article "a" or "an" carries the meaning of "one or more."

Reconstitution of a protein is where two polypeptide fragments from a single original protein are bound together, though not necessarily by covalent bonding. "Association" is where two polypeptides fragments from the same or different starting proteins are bound together. Again, the binding is not necessarily by covalent bonding. For a general discussion of protein reconstitution/reassociation, see Ojennus et al. (2001). Fragments of Fn3 will reconstitute and/or reassociate at a pH range of between pH 1 and pH 10 at 30° C. At neutral pH, they will still reassociate at 50° C.

A "coiled coil" is a widespread structural motif that is found in fibrous proteins such as myosin and keratin. A coiled coil constitutes two or more interacting α-helices, supercoiled around one another, that are associated in a parallel or an anti-parallel orientation. The α-helices of naturally occurring coiled coils are generally parallel. Sequence features within a natural coiled coil can lead to preference for an antiparallel helix orientation rather than the more commonly observed parallel alignment. See, Oakley and Kim, *Biochemistry* 37:12603-12610 (1998) for a detailed discussion of coiled coils. Another binding pair that could be used to encourage reassociation of two fragments is the intein system, described by Yamazaki et al. (1998).

The present invention provides an Fn3 monobody binding pair. The binding pair is made up of two parts, a first Fn3 monobody polypeptide having two to six β-strand domains (which optionally has a polypeptide tail region attached to one or both of the terminal β-strand domains) with a loop region linked between each β-strand domain, and a second Fn3 monobody polypeptide having two to six β-strand domains (which optionally has a polypeptide tail region attached to one or both of the terminal β-strand domains) with a loop region linked between each β-strand domain. A "polypeptide tail region" is a polypeptide that is one to 25 amino acids in length that is not part of the β-strand domain. A "terminal β-strand" is one of the two β-strands in the monobody that is bound to a loop region at only one of its ends. For example, in a monobody that has three β-strands and two loop regions, one would have a first terminal β-strand, a loop region, an internal β-strand, a loop region, and then a second terminal β-strand. Thus, the terminal β-strands are linked to only one loop region, whereas the internal β-strand is linked at both ends of the β-strand.

The first Fn3 fragment associates with the second Fn3 fragment with a dissociation constant of less than $10^{-6}$ moles/liter. For example, if a monobody polypeptide has two β-strand domains, it contains a single loop region in the polypeptide; if the monobody polypeptide has three β-strand domains, it contains two loop regions in the polypeptide (configured such that the β-strands alternate with the loop regions); if a monobody polypeptide has four β-strand domains, it would have three loop regions in the polypeptide; etc. At least one loop region of the binding pair is capable of binding to a specific binding partner (SBP) to form a polypeptide:SBP complex having a dissociation constant, as measured in the binding reaction of the corresponding uncut, full-length FN3 monobody molecule, of less than $10^{-6}$ moles/liter. The present invention also provides nucleic acid molecules that encode the polypeptides that form the binding pair.

The present invention further provides methods and kits for making the polypeptides of the binding pair. These polypeptides may contain a unique peptide sequence that can be cleaved with a specific chemical agent such that two predetermined peptides are generated. It is well known that unique peptide sequences can be cleaved with specific chemical reagents (e.g., cyanogen bromide) or with a proteases (e.g., thrombin, enterokinase, factor X, tobacco etch virus (TEV) protease, human rhinovirus 3C protease). See, Creighton 1993, Kapust 2001, Cordingley 1990.

The first Fn3 polypeptide of the binding pair of the present invention may further contain a first auxiliary domain, and the second Fn3 polypeptide may further contain a second auxiliary domain, wherein the first auxiliary domain has a binding affinity for the second auxiliary domain with a dissociation constant of less than $10^{-5}$ moles/liter. In one embodiment, an auxiliary region is a cysteine residue. For example, the first auxiliary region is a first cysteine and the second auxiliary region is a second cysteine, such that the first cysteine and the second cysteine form a disulfide bond. Disulfide bonds would generally not be present in a final monobody. However, crosslinking via a disulfide bond is a good approach to enhance the assembly of complementary fragments so that they will stay as a heterodimer. Such heterodimers are used to produce a combinatorial library of very large size. One would perform screening of such a library using phage display or other methods. Once one found desired monobody heterodimers (i.e., specific pairs of fragments), they would be reformatted into uncut, full-length proteins. Thus, disulfide-linked monobodies are instead very useful vehicles for library construction, even though disulfide linkages are not present in a final product. Cysteine residues may also be present in the loop regions and/or the β-strand regions.

In other embodiments, the auxiliary domains are a natural protein/peptide pair, a peptide-binding protein and its target peptide, or two fragments of a protein that have been artificially generated. Examples include coiled coils, or a C-intein and N-intein pair.

The present invention further provides a fibronectin type III (Fn3) monobody binding pair having two parts: a first fibronectin type III (Fn3) monobody polypeptide containing two to six β-strand domains with a loop region linked between each β-strand domain, wherein a polypeptide tail region is attached to one or both terminal β-strands, and a second Fn3 monobody polypeptide containing two to six β-strand domains with a loop region linked between each β-strand domain, wherein a polypeptide tail region is attached to one or both terminal β-strands, wherein the first Fn3 fragment associates with the second Fn3 fragment with a dissociation constant of less than $10^{-6}$ moles/liter.

The present invention provides variegated nucleic acid libraries encoding Fn3 monobody polypeptides, where one or more of the loop regions of the monobody polypeptides can be modified by insertions, deletions or substitutions. The present invention also provides polypeptide libraries made from these nucleic acid libraries.

The present invention provides a fibronectin type III (Fn3) monobody polypeptide made of two to six β-strand domains with a loop region linked between each β-strand domain. The monobody polypeptide is capable of binding to a target molecule with a dissociation constant of less than $10^{-6}$ moles/liter.

BRIEF DESCRIPTION OF THE DRAWINGS

FIG. 2. Amino acid sequence (SEQ ID NO:110) and restriction sites of the synthetic Fn3 gene. The residue numbering is according to Main et al. (1992). Restriction enzyme sites designed are shown above the amino acid sequence. β-Strands are denoted by underlines. The N-terminal "mq" sequence has been added for a subsequent cloning into an expression vector (disclosed as SEQ ID NO:137). The His•tag (Novagen) fusion protein has an additional sequence, MGSSHHHHHHSSGLVPRGSH (SEQ ID NO:114), preceding the Fn3 sequence shown above.

FIG. 5. Designed Fn3 gene showing DNA (SEQ ID NO:111) and amino acid (SEQ ID NO:112) sequences. The amino acid numbering is according to Main et al. (1992). The two loops that were randomized in combinatorial libraries are enclosed in boxes.

(b) Competition phage ELISA of Ubi4-Fn3. Ubi4-Fn3-phages were preincubated with soluble ubiquitin at an indicated concentration, followed by the phage ELISA detection in ubiquitin-coated wells.

(c) Competition phage ELISA testing the specificity of the Ubi4 clone. The Ubi4 phages were preincubated with 250 µg/ml of soluble proteins, followed by phage ELISA as in (b).

(d) ELISA using free proteins.

Figure 16:
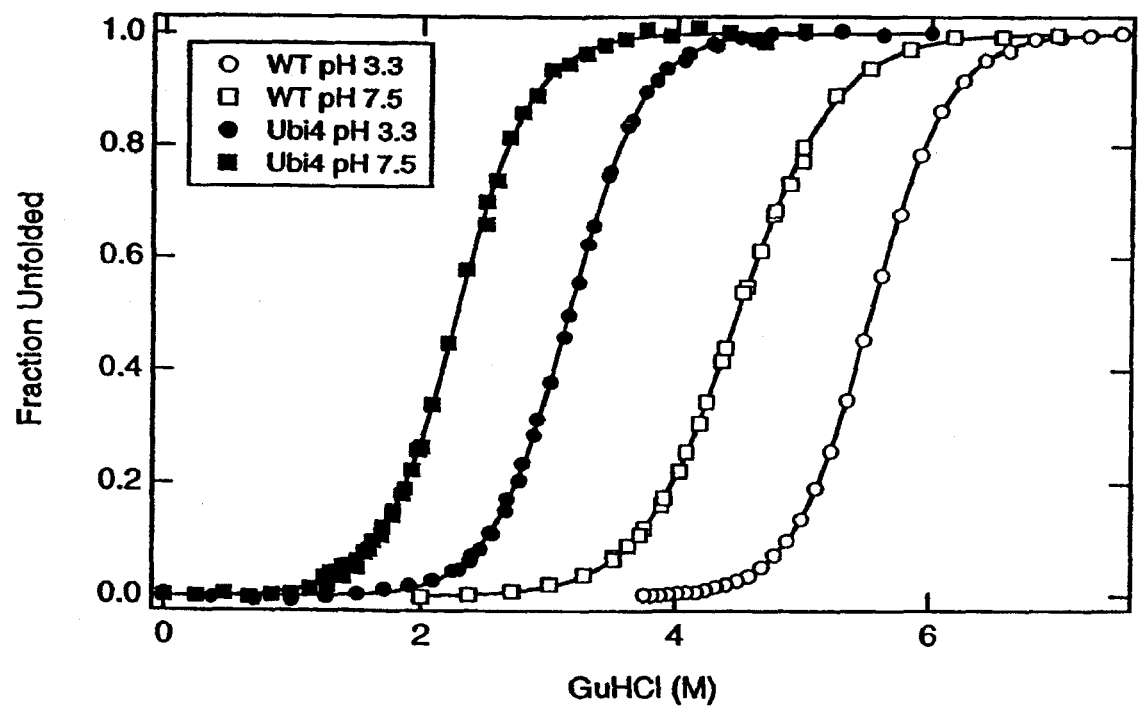

FIG. 16. Equilibrium unfolding curves for Ubi4-Fn3 (closed symbols) and wild-type Fn3 (open symbols). Squares indicate data measured in TBS (Tris HCl buffer (50 mM, pH 7.5) containing NaCl (150 mM)). Circles indicate data measured in Gly HCl buffer (20 mM, pH 3.3) containing NaCl (300 mM). The curves show the best fit of the transition curve based on the two-state model. Parameters characterizing the transitions are listed in Table 8.

Figure 17A:
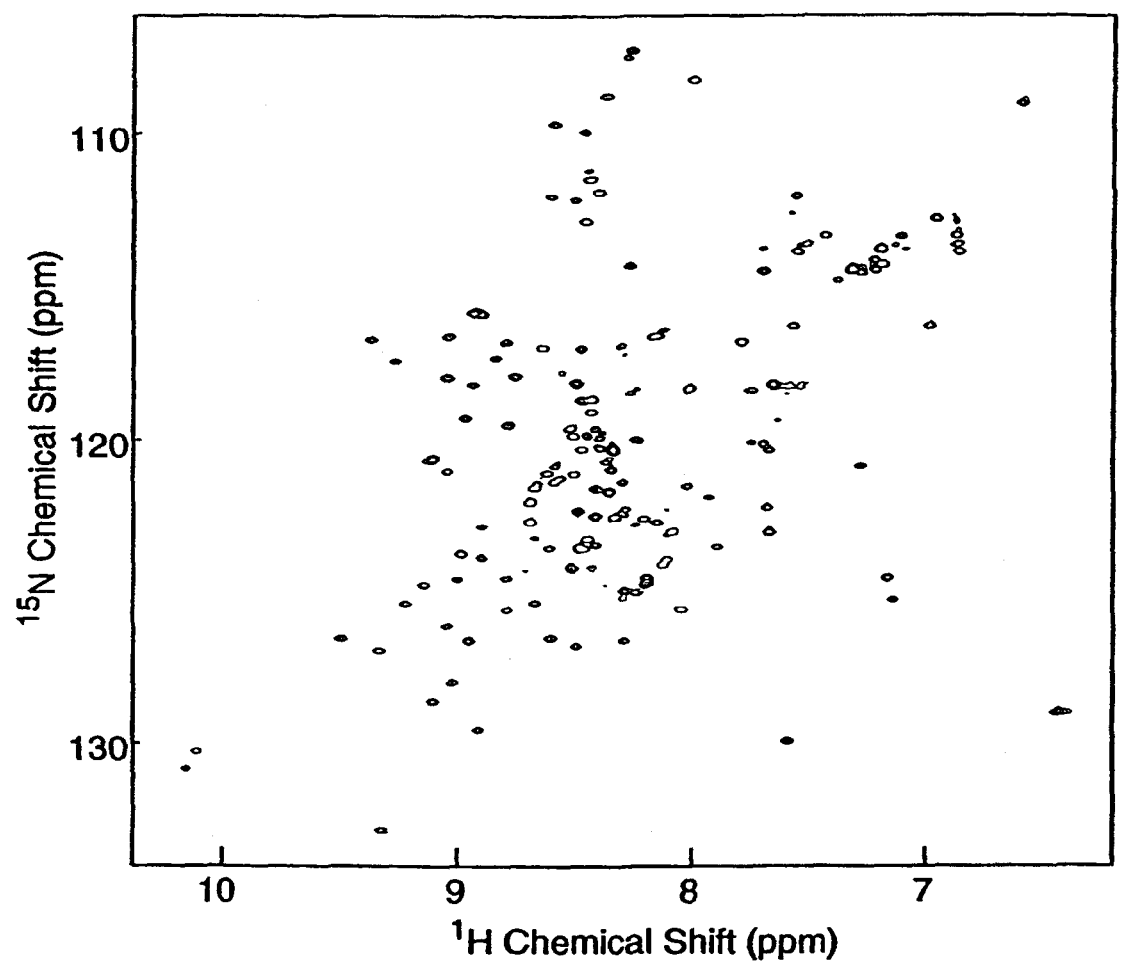
Figure 17B:
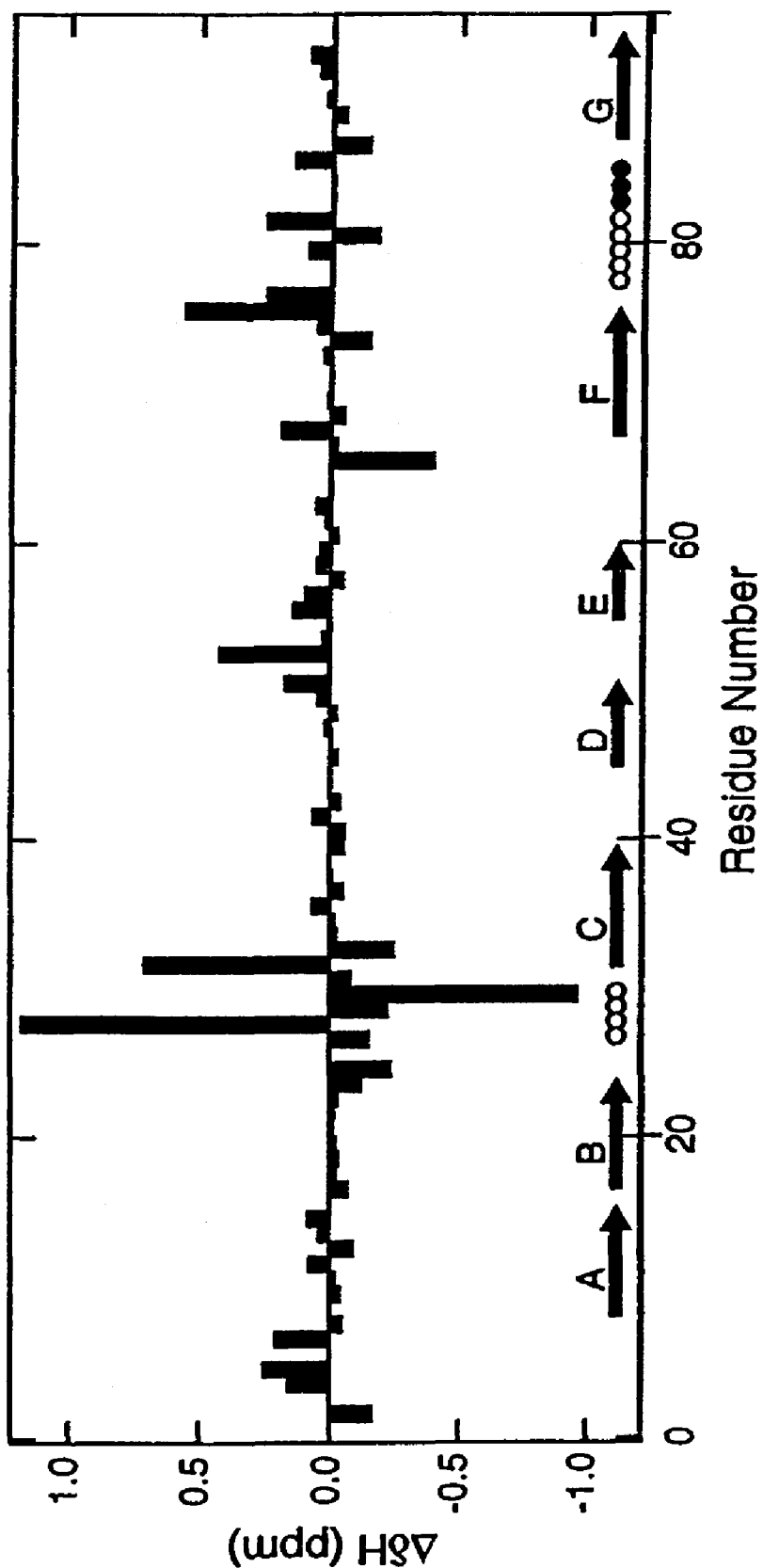
Figure 17C:
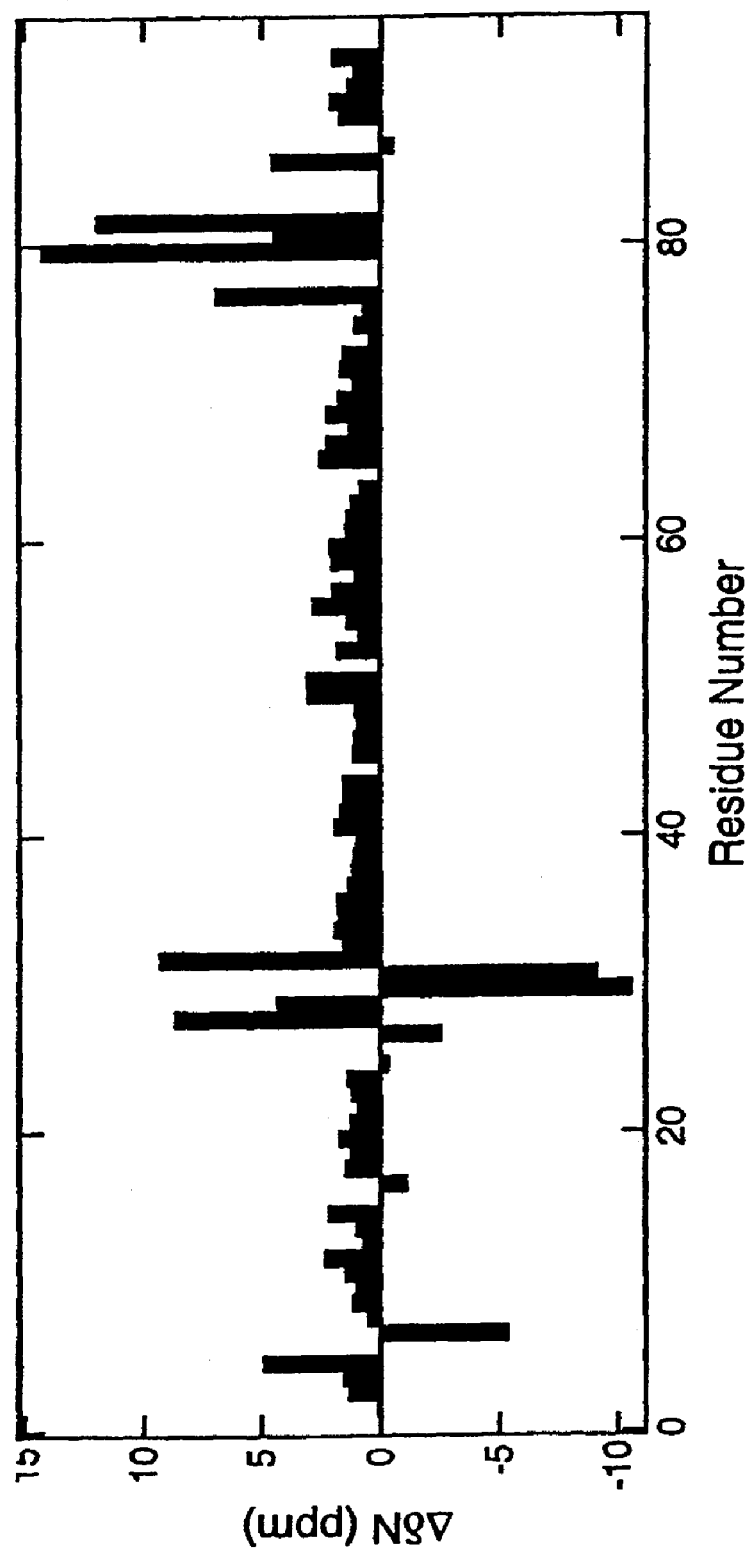

FIG. 17. (a) $^1$H, $^{15}$N-HSQC spectrum of [$^{15}$N]-Ubi4-K Fn3. (b). Difference ($\delta_{wild-type} - \delta_{Ubi4}$) of $^1$H (b) and $^{15}$N (c) chemical shifts plotted versus residue number. Values for residues 82-84 (shown as filled circles) where Ubi4-K deletions are set to zero. Open circles indicate residues that are mutated in the Ubi4-K protein. The locations of β-strands are indicated with arrows.

Figure 18A:
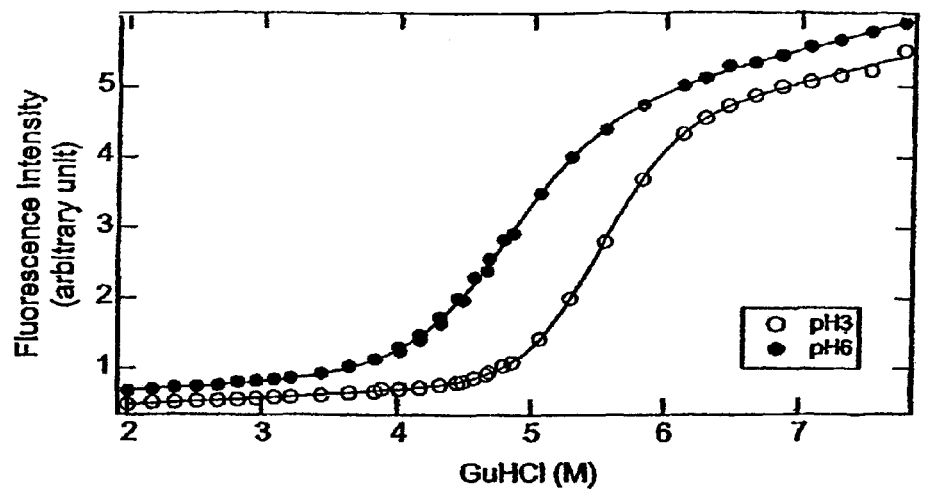
Figure 18B:
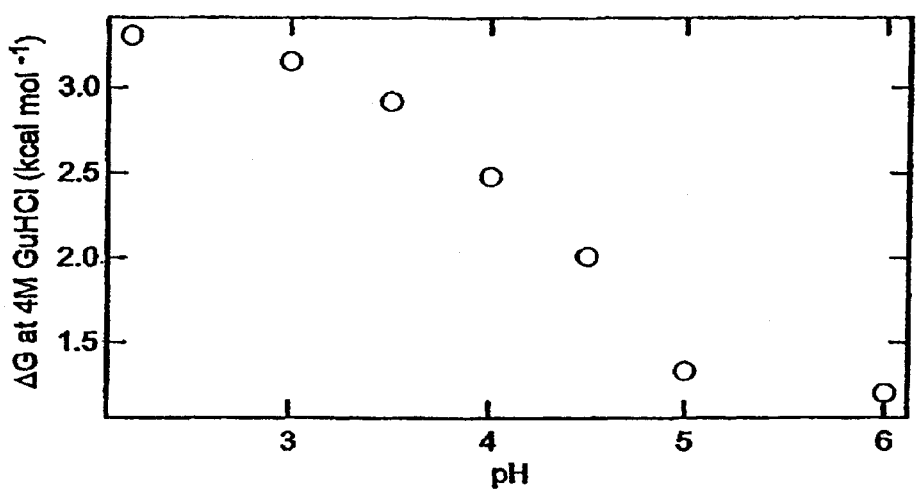
Figure 18C:
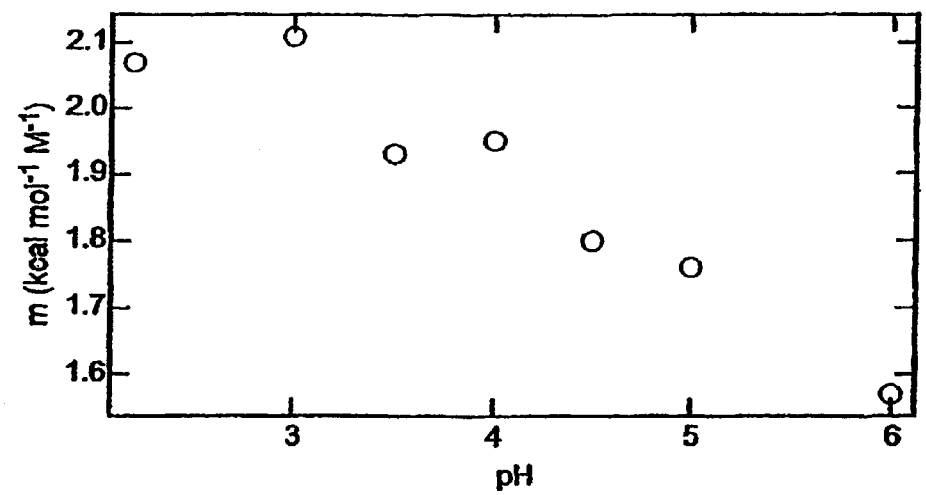

FIG. 18. (A) Guanidine hydrochloride (GuHCl)-induced denaturation of FNfn10 monitored by Trp fluorescence. The fluorescence emission intensity at 355 nm is shown as a function of GuHCl concentration. The lines show the best fits of the data to the two-state transition model. (B) Stability of FN3 at 4 M GuHCl plotted as a function of pH. (C) pH dependence of the m value.

Figure 19:
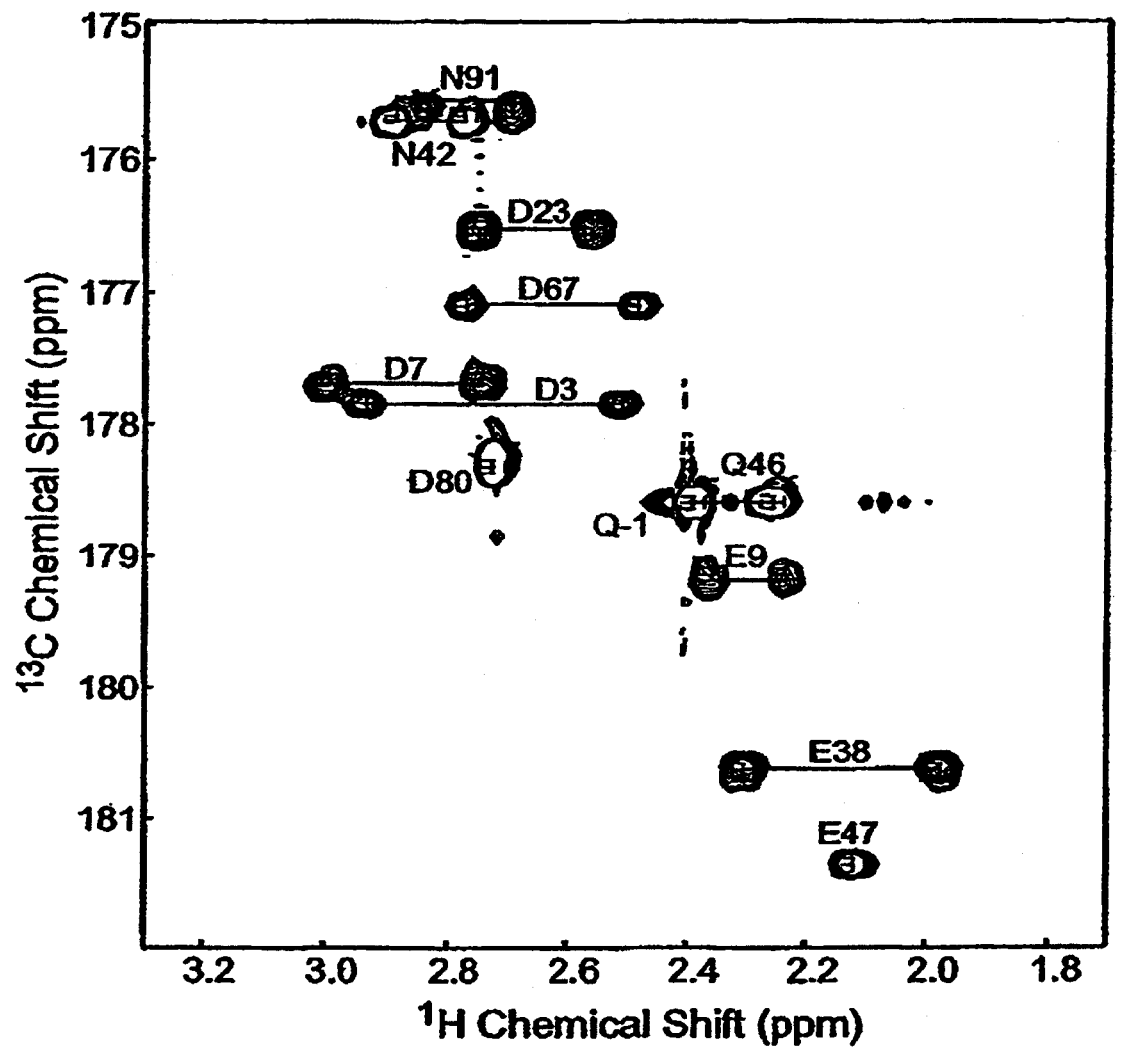

FIG. 19. A two-dimensional H(C)CO spectrum of FNfn10 showing the $^{13}$C chemical shift of the carboxyl carbon (vertical axis) and the $^1$H shift of $^1$H$^\beta$ of Asp or $^1$H$^\gamma$ of Glu, respectively (horizontal axis). Cross peaks are labeled with their respective residue numbers.

Figure 20A:
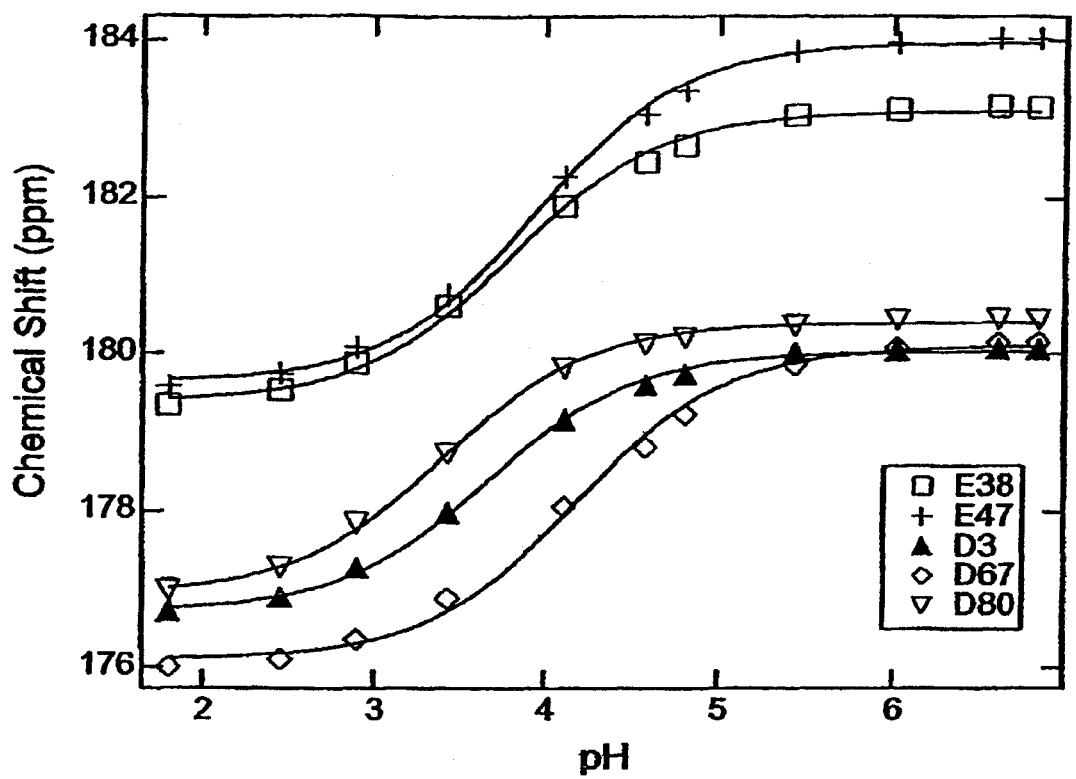
Figure 20B:
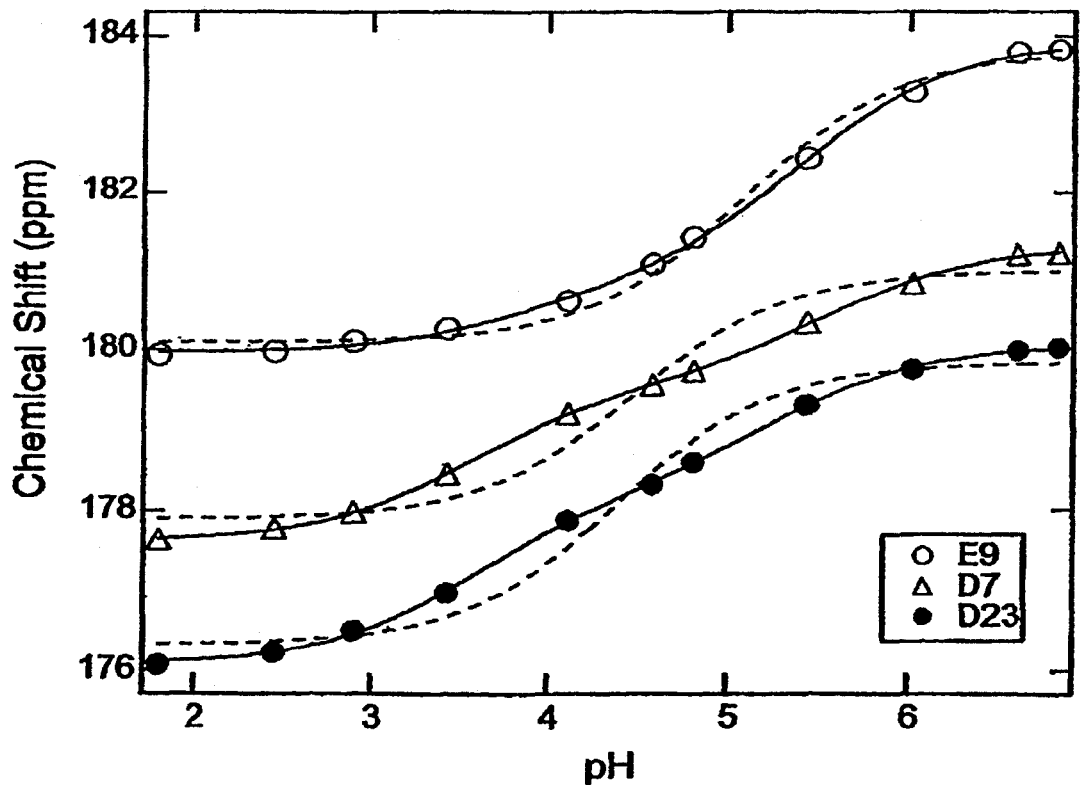

FIG. 20. pH-Dependent shifts of the $^{13}$C chemical shifts of the carboxyl carbons of Asp and Glu residues in FNfn10. Panel A shows data for Asp 3, 67 and 80, and Glu 38 and 47. The lines are the best fits of the data to the Henderson-Hasselbalch equation with one ionizable group (McIntosh, L. P., Hand, G., Johnson, P. E., Joshi M. D., Koerner, M., Plesniak, L. A., Ziser, L., Wakarchuk, W. W. & Withers, S. G. (1996) *Biochemistry* 35, 9958-9966). Panel B shows data for Asp 7 and 23 and Glu 9. The continuous lines show the best fits to the Henderson-Hasselbalch equation with two ionizable groups, while the dashed lines show the best fits to the equation with a single ionizable group.

Figure 21B:
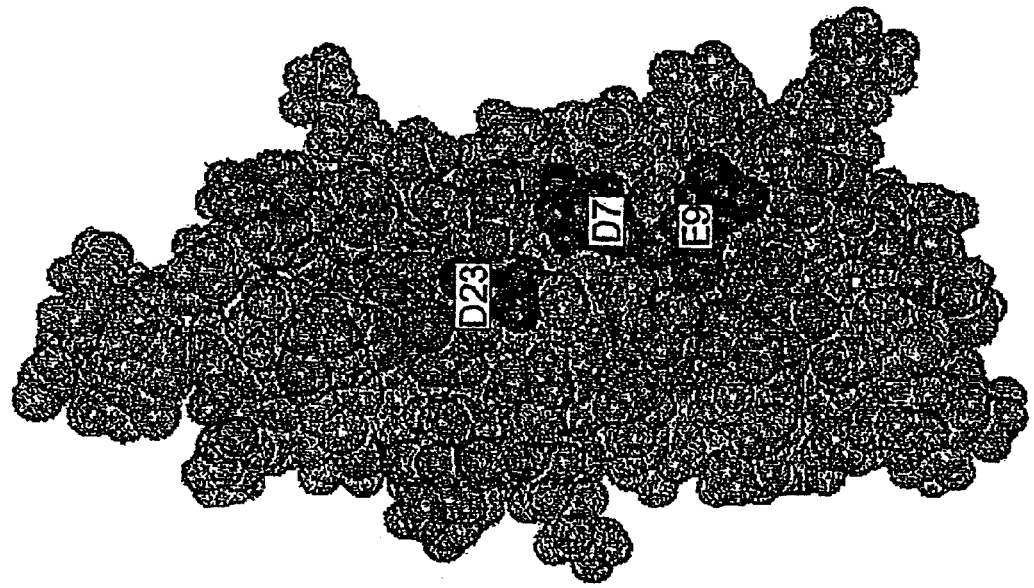
Figure 21A:
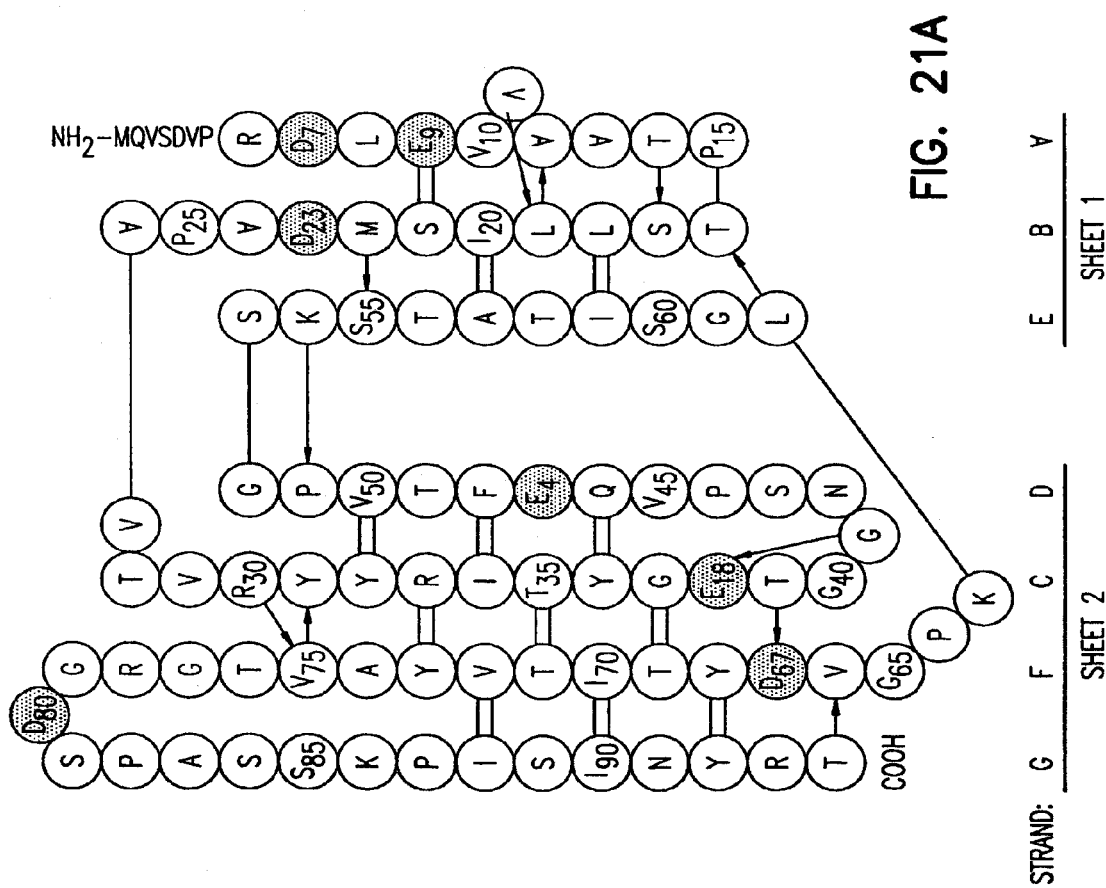

FIG. 21. (A) The amino acid sequence of FNfn10 (SEQ ID NO:121) shown according to its topology (Main, A. L., Harvey, T. S., Baron, M., Boyd, J., & Campbell, I. D. (1992) *Cell* 71, 671-678). Asp and Glu residues are highlighted with gray circles. The thin lines and arrows connecting circles indicate backbone hydrogen bonds. (B) A CPK model of FN3 showing the locations of Asp 7 and 23 and Glu 9.

Figure 22:
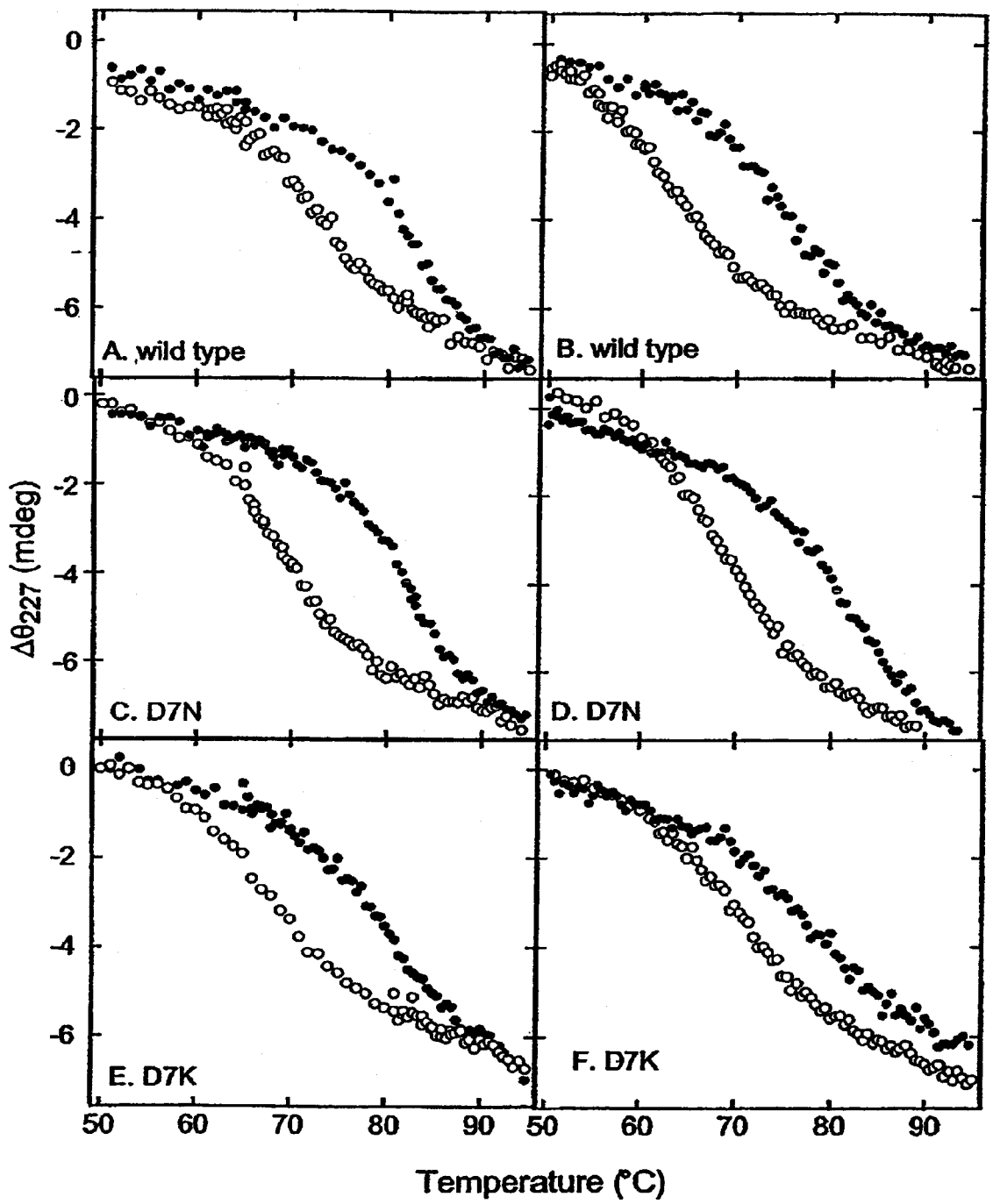

FIG. 22. Thermal denaturation of the wild-type and mutant FNfn10 proteins at pH 7.0 and 2.4 in the presence of 6.3 M urea and 0.1 or 1.0 M NaCl. Change in circular dichroism signal at 227 nm is plotted as a function of temperature. The filled circles show the data in the presence of 1 M NaCl and the open circles are data in the presence of 0.1 M NaCl. The left column shows data taken at pH 2.4 and the right column at pH 7.0. The identity of proteins is indicated in the panels.

Figure 23:
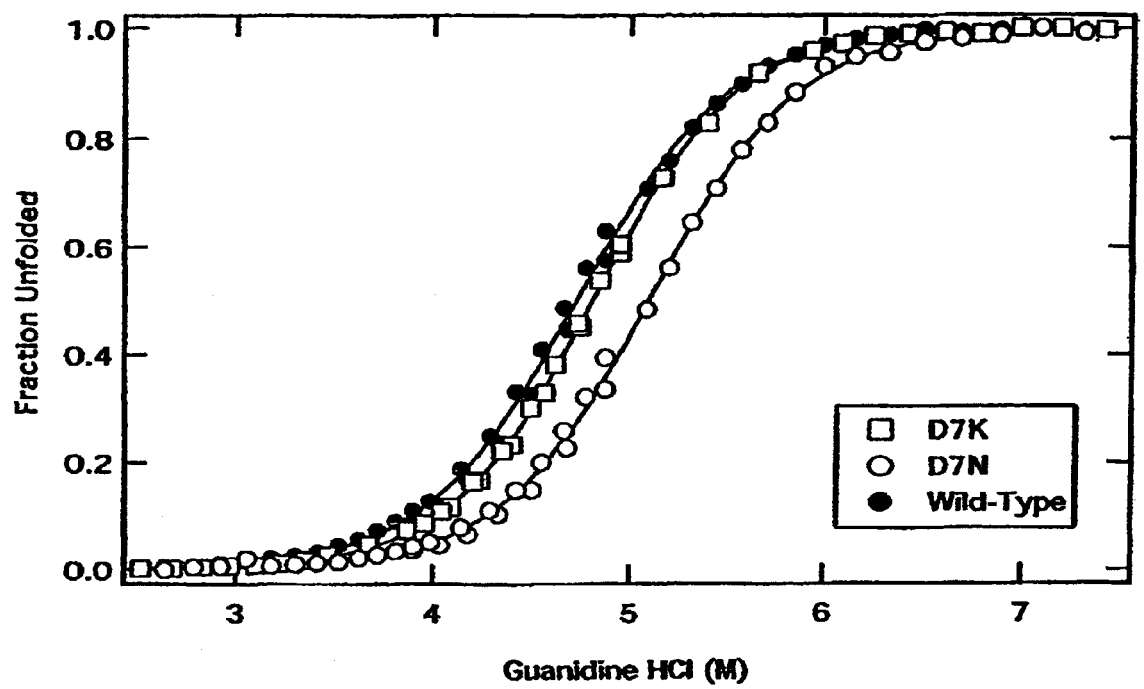

FIG. 23. GuHCl-induce denaturation of FNfn10 mutants monitored with fluorescence. Fluorescence data was converted to the fraction of unfolded protein according to the two-state transition model (Loladze, V. V., Ibarra-Molero, B., Sanchez-Ruiz, J. M. & Makhatadze, G. I. (1999) *Biochemistry* 38, 16419-16423), and plotted as a function of GuHCl.

Figure 24:
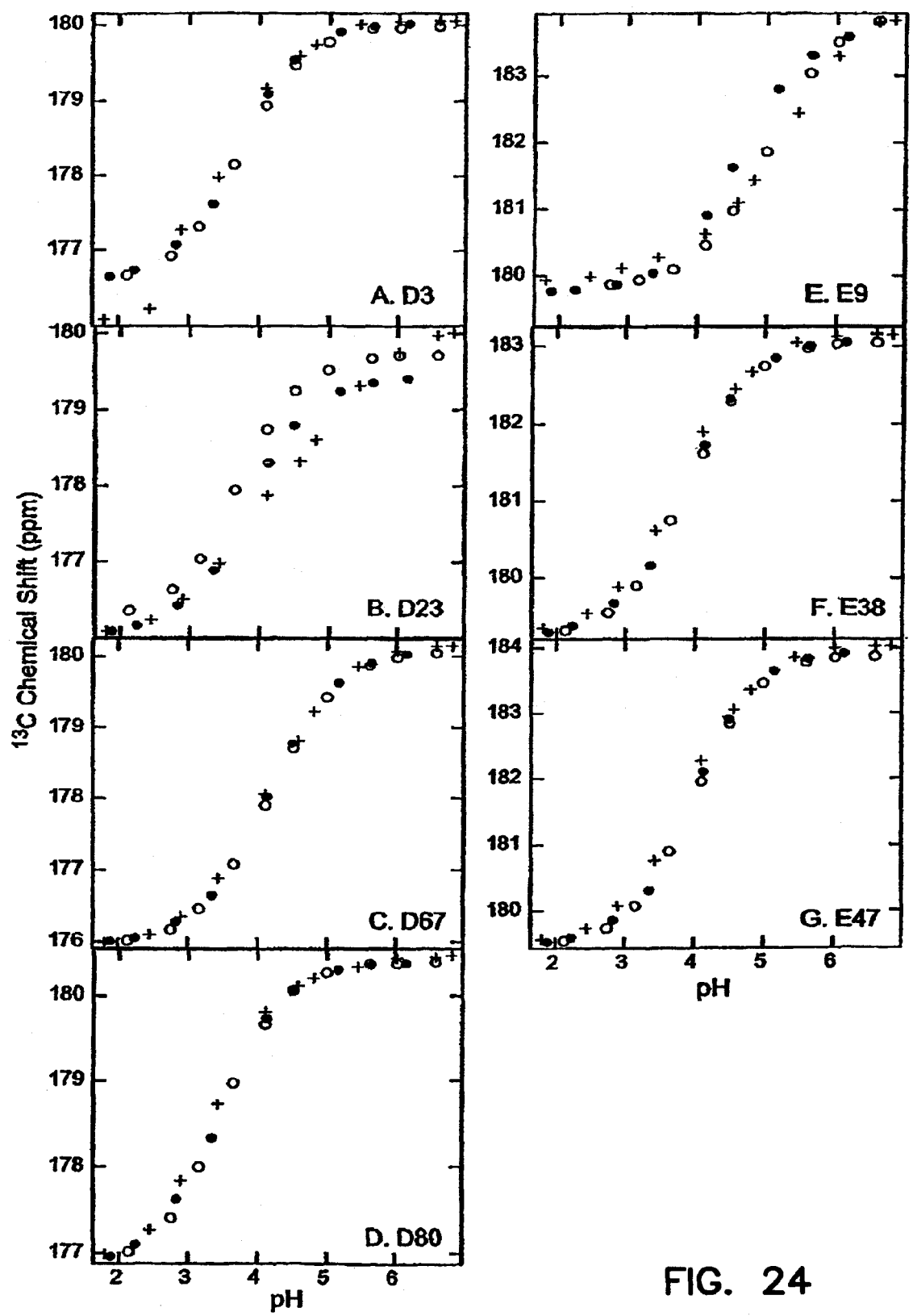

FIG. 24. pH Titration of the carboxyl $^{13}$C resonance of Asp and Glu residues in D7N (open circles) and D7K (closed circles) FNfn10. Data for the wild-type (crosses) are also shown for comparison. Residue names are denoted in the individual panels.

Figure 25:
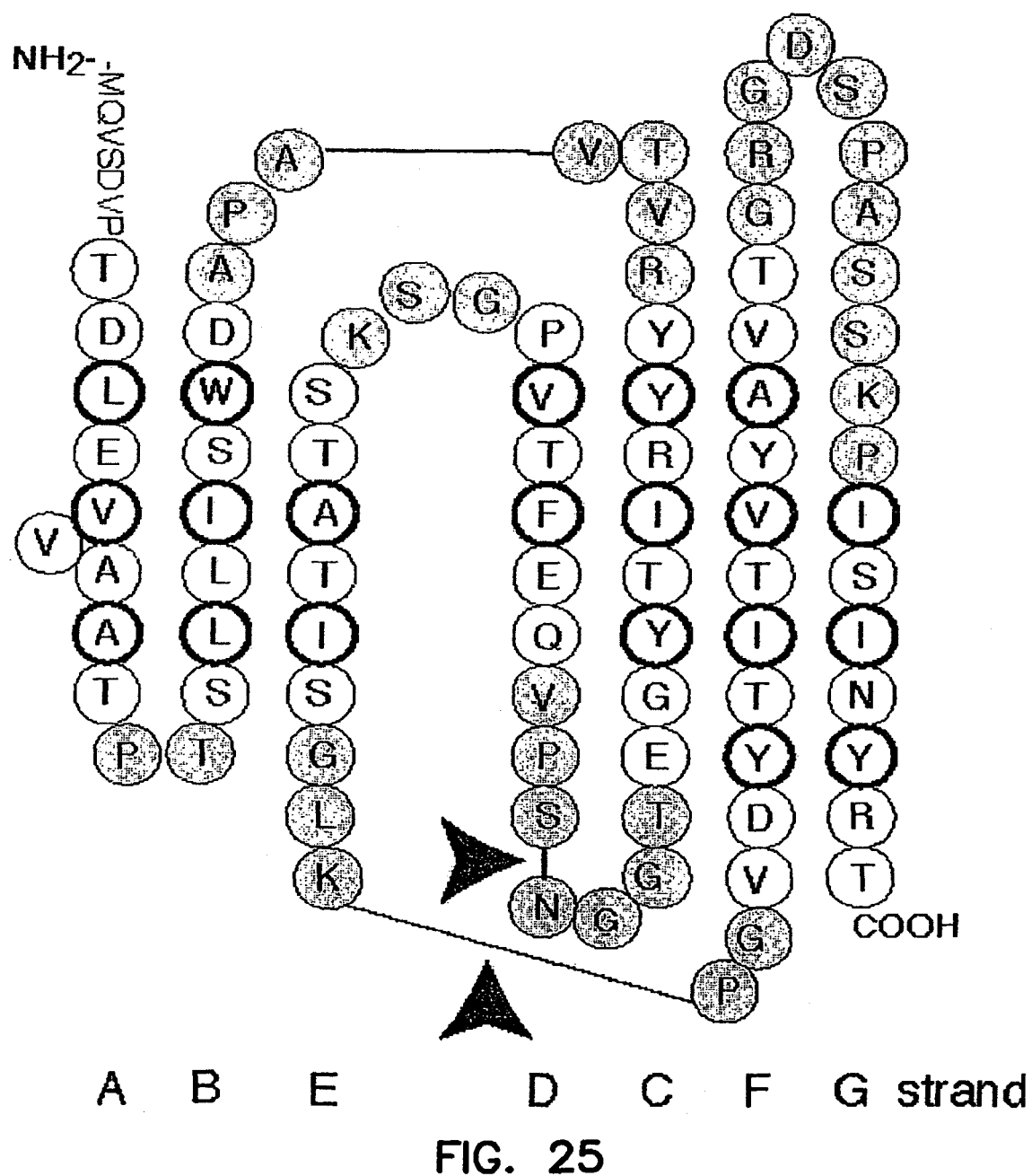

FIG. 25. Topographic illustration of the sites for the introduction of the cleavage site insertion (GGMGG; SEQ ID NO:122) in CD and EF loop respectively (SEQ ID NO:123).

Figures 26A, 26B:
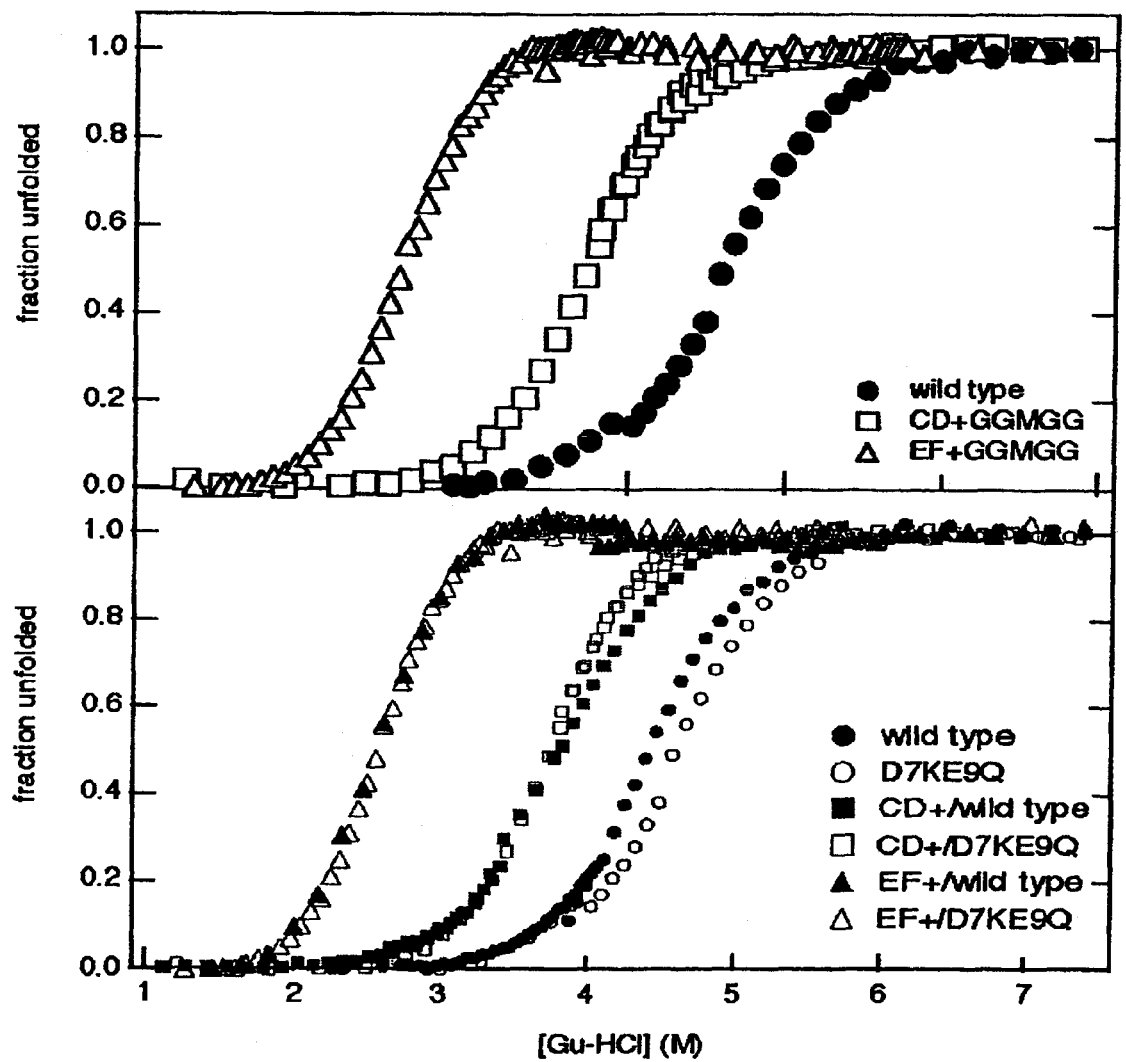

FIGS. 26A-B. Guanidine hydrochloride induced unfolding of mutant proteins with an engineered cleavage site. Circles represent protein without insertion, squares an insertion in the CD loop and triangles an insertion in the EF loop (GGMGG disclosed as SEQ ID NO:122). 26A: Comparison of insertion sites. 26B: Comparison of the effect on wild type protein to the D7KE9Q mutant proteins. Fitting parameters for the curves are listed in table IV-1.

Figure 27:
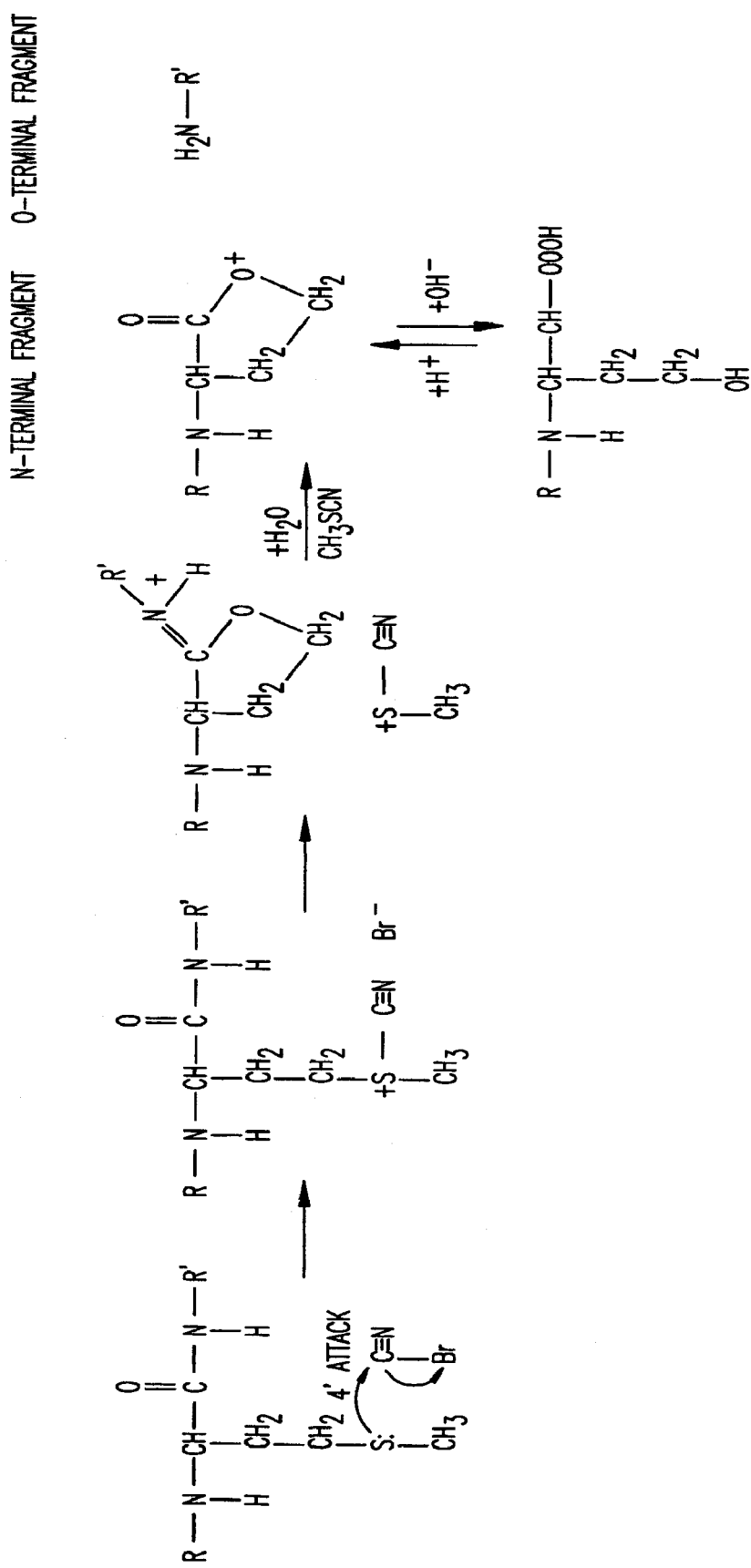

FIG. 27. Cleavage of a peptide bond after methionine by cyanogen bromide.

Figure 28:
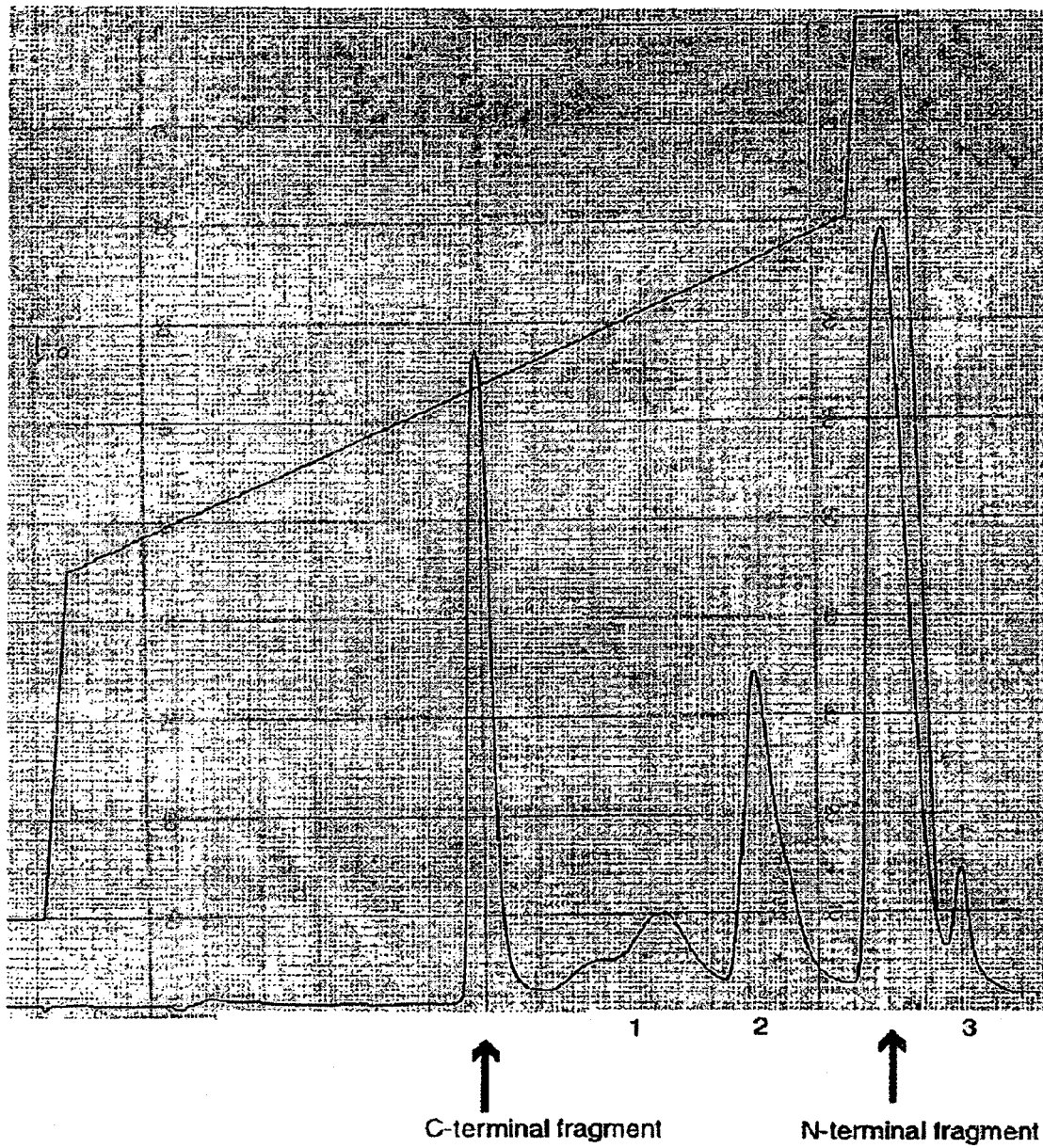

FIG. 28. Chromatogram of the reverse phase separation of CD-loop cleaved fragments of CD92. The actual fragments are marked, additional fractions: 1 partially uncleaved protein, 2 N-terminal fragment with HisTag leader sequence, 3 acidic degradation product of the N-terminal fragment.

FIGS. 29A-C. 29A shows gel filtration chromatograms of a mixture of N- and C-terminal at 3 μM concentration, 29B shows elution of C-terminal alone, and 29C shows elution of N-terminal alone.

Figure 30:
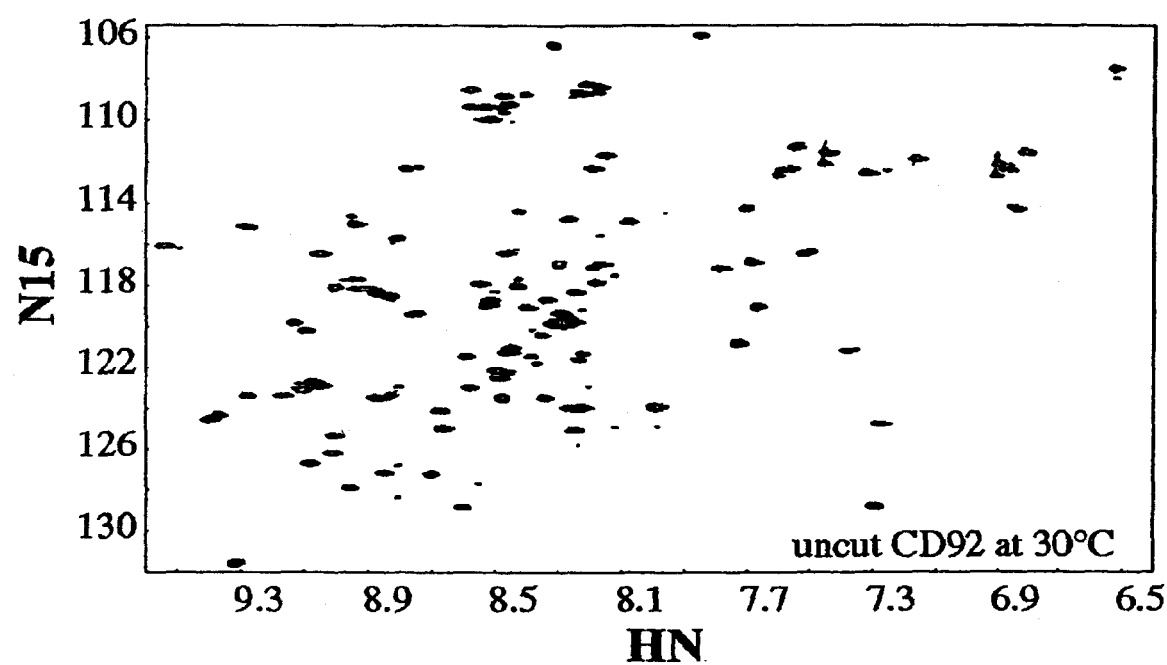

FIG. 30. $^1$H-$^{15}$N-HSQC spectrum of uncleaved CD92 protein

Figure 31A:
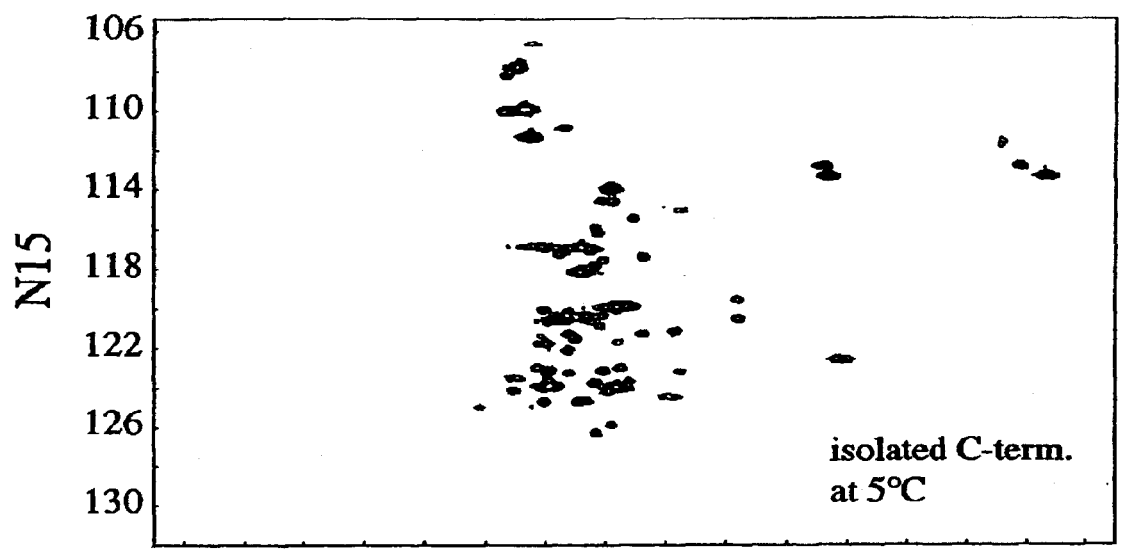
Figure 31B:
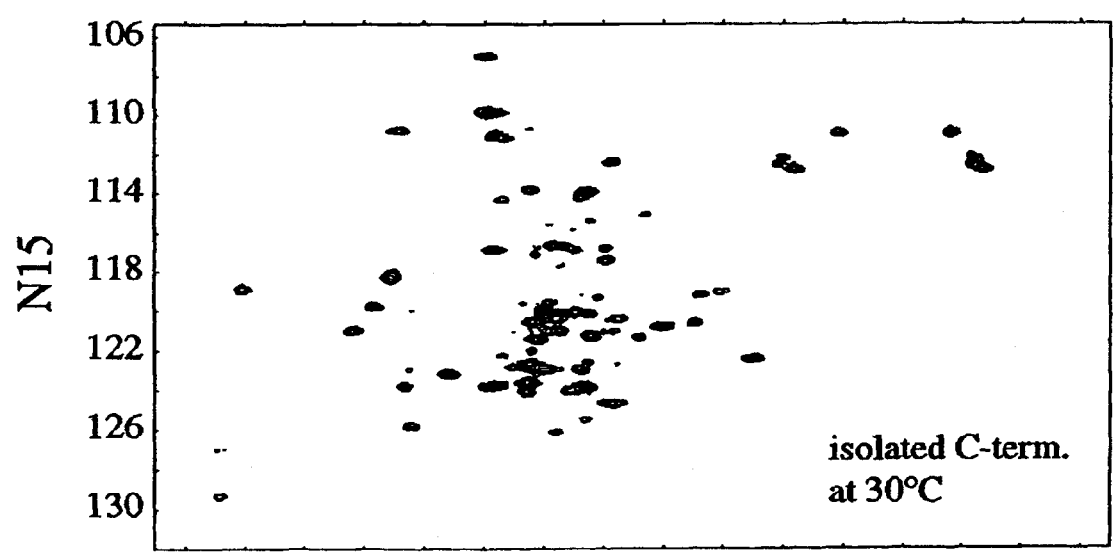

FIGS. 31A-B. $^1$H-$^{15}$N-HSQC spectra of the isolated C-terminal fragment at 5° C. (31A) and at 30° C. (31B). At lower temperature, the fragment appears mostly unfolded, while at higher temperatures oligomerization revealed additional, more dispersed peaks.

Figure 32:
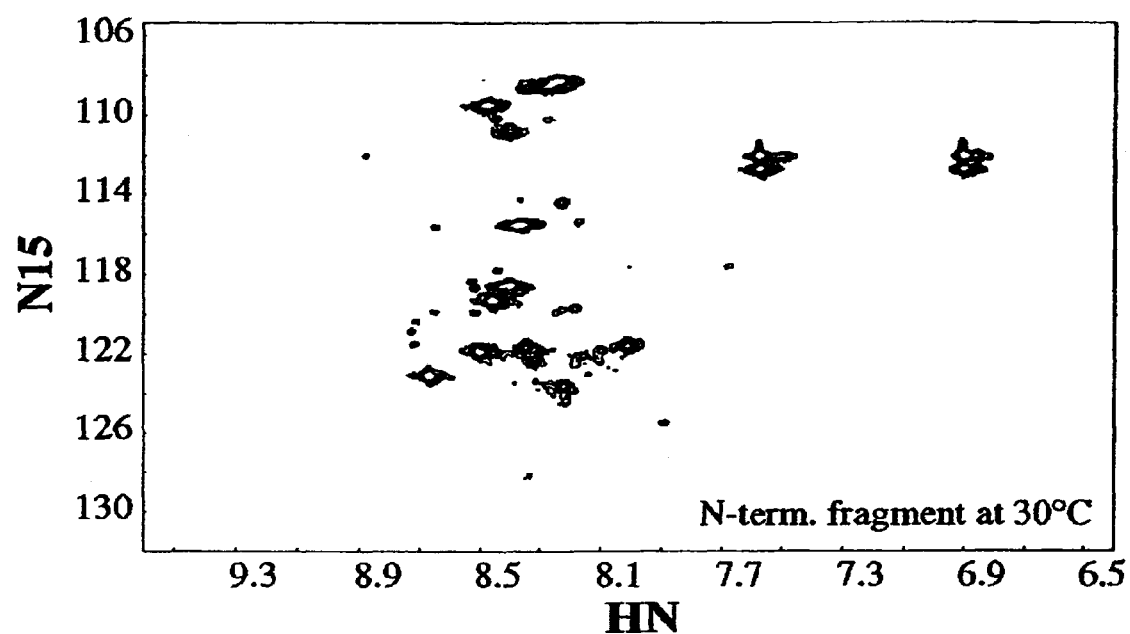

FIG. 32. $^1$H-$^{15}$N-HSQC spectra of the isolated N-terminal fragment at 30° C. The sample is likely in a oligomeric conformation indicated by the apparent line broadening.

Figures 33A, 33B:
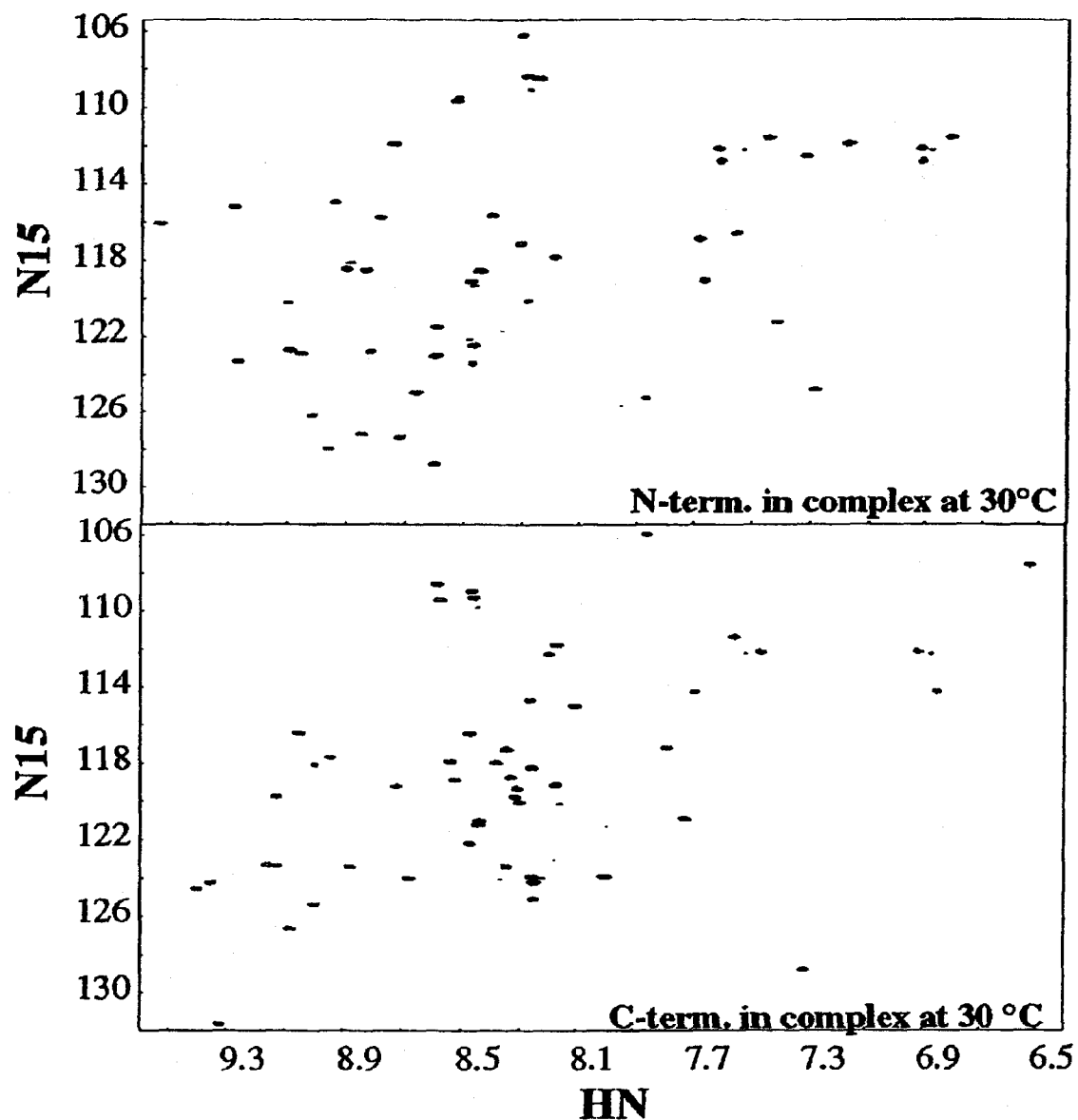

FIGS. 33A-B. $^1$H-$^{15}$N-HSQC spectra of the N-terminal (33A) and the C-terminal fragment (33B) in partially labeled complex at 30° C.

Figures 34A, 34B:
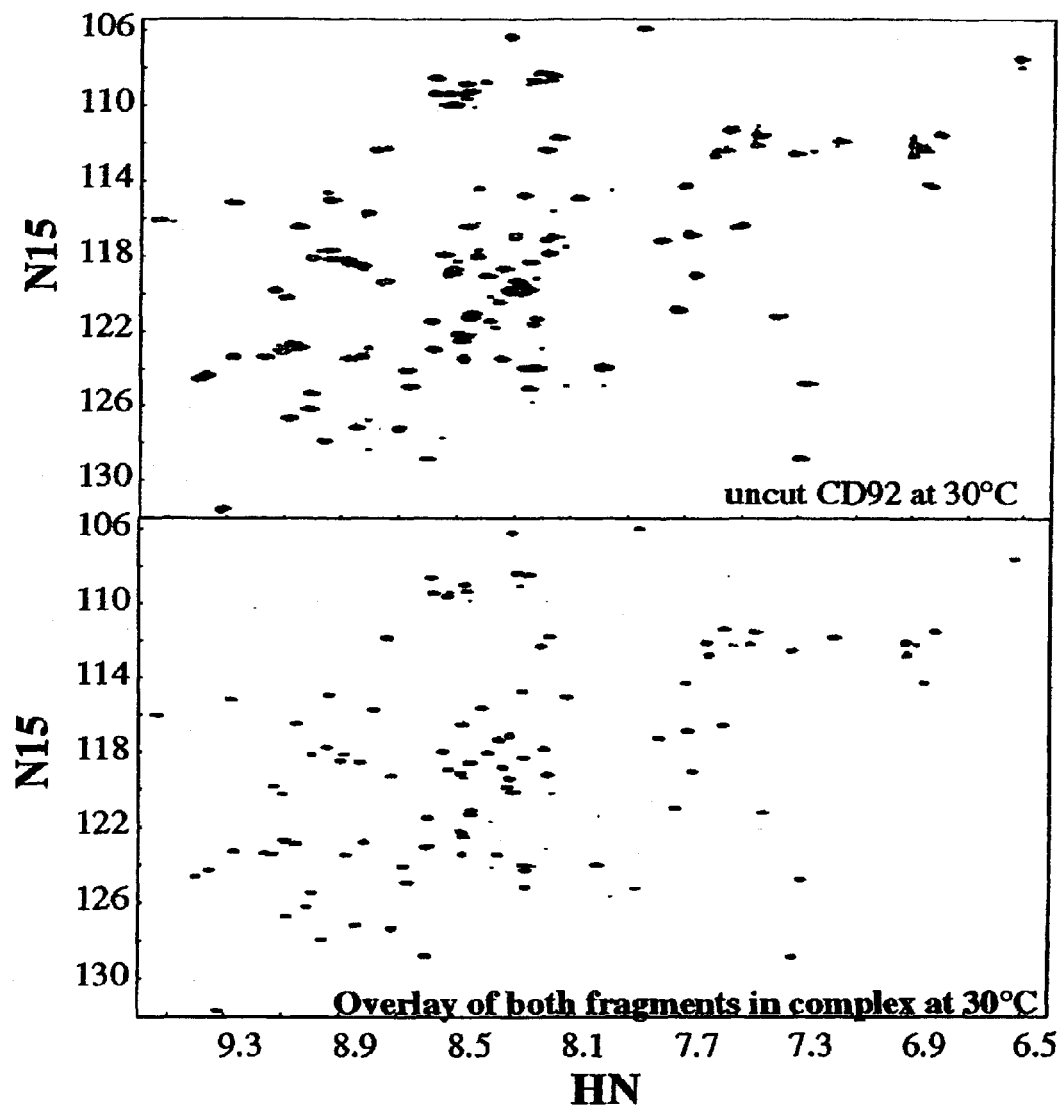

FIGS. 34A-B. Direct comparison of the parental protein and the complex formed by the fragments. 34A shows uncut CD92 at 30° C., and 34B shows an overlay of both fragments in complex at 30° C.

Figure 35:
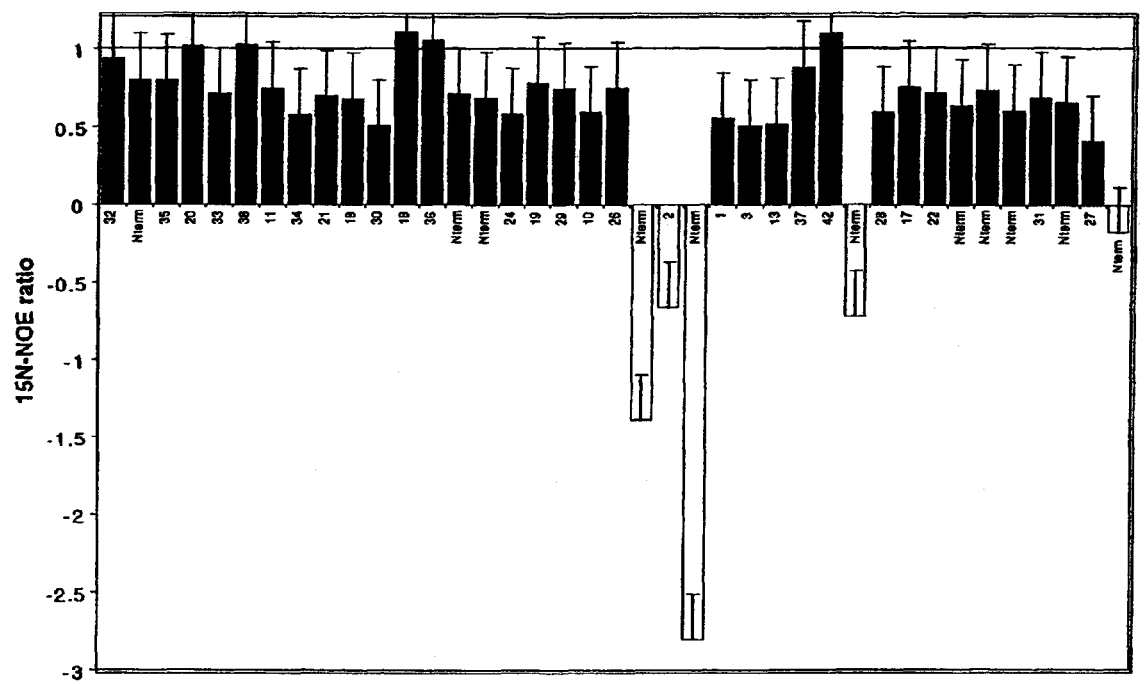

FIG. 35. The ratio of 15N-NOE signal for the N-terminally labeled complex over that of the reference spectrum revealed that the formed complex is as stable as a fully folded protein. Only 5 residues show an increased motion on the investigated timescale, most likely on either terminus of the fragment. The very N-terminus of FNfn10 is known to be disordered, and the six C-terminal residues of this fragment include 4 glycines (sequence GGNGGhS; SEQ ID NO:124), where (hS) stands for the homoserine lactone that resulted in the cleavage. Error was estimated from the noise in the spectra to be ±0.29.

Figure 36:
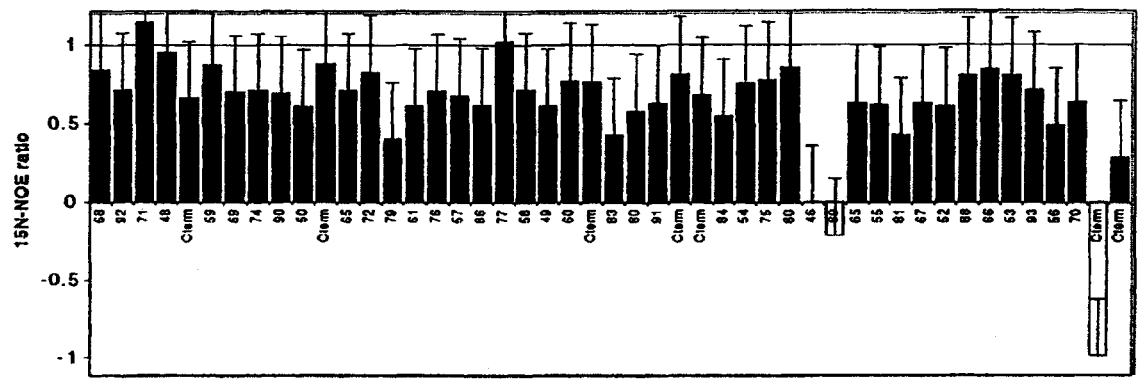

FIG. 36. The ratio of 15N-NOE signal for the C-terminally labeled complex over that of the reference spectrum revealed that the formed complex is as stable as a fully folded protein. Error was estimated from the noise in the spectra to be ±0.36.

Figure 37:
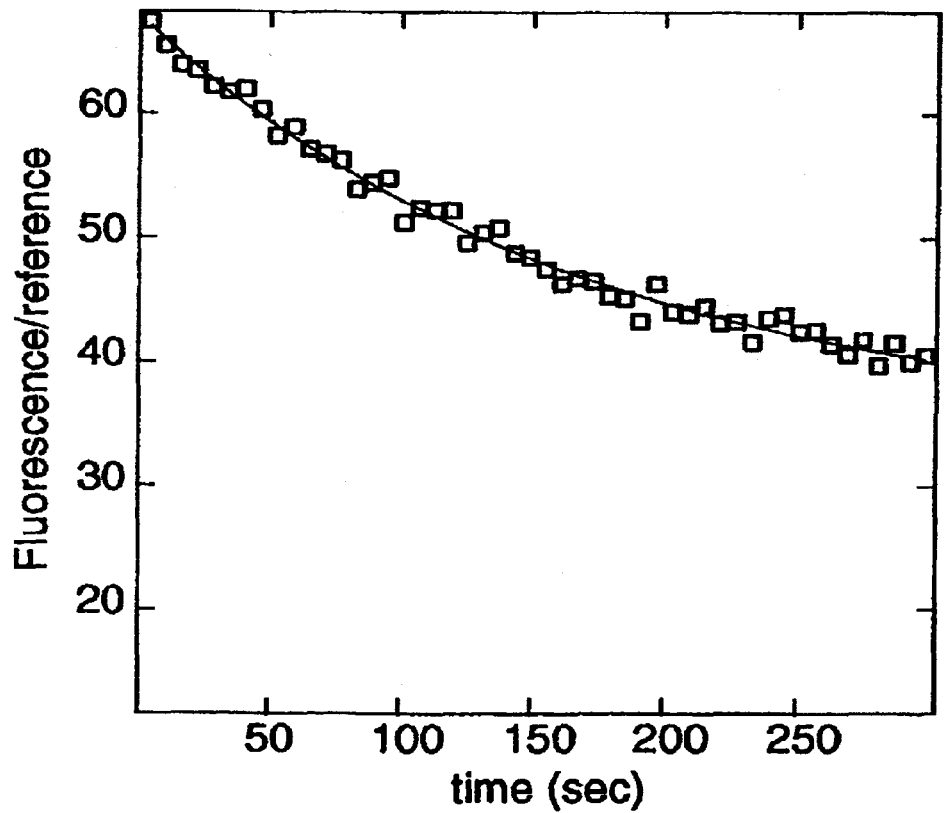
Figure 38:
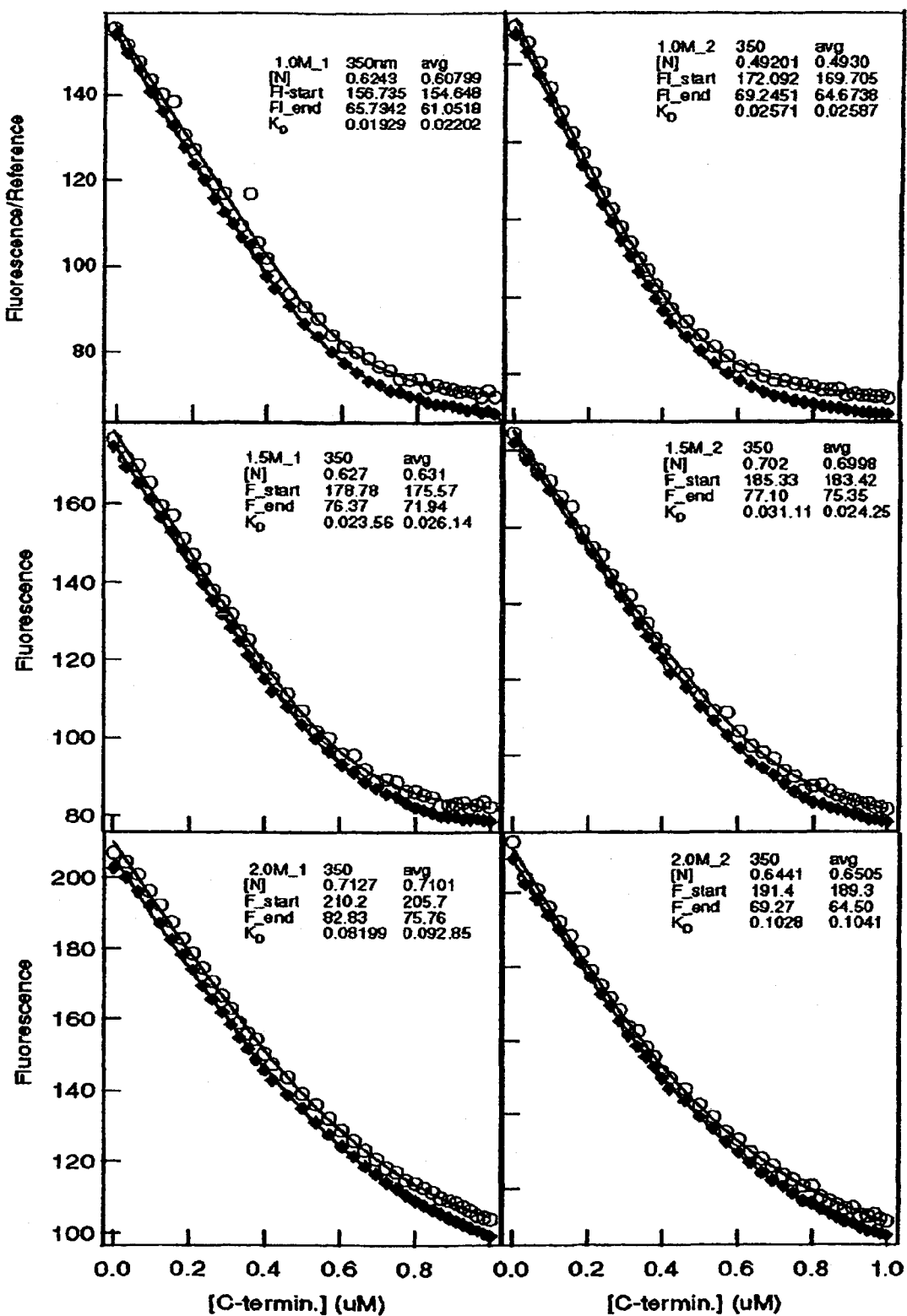

FIG. 37. Time course of the fluorescence intensity due to nonspecific adherence to the cuvette.

FIGS. 38A-F. Representative series of the reconstitution of CD92 fragments monitored by fluorescence at 1M (38A, 38B), 1.5M (38C, 38D) and 2M (38E, 38F) urea. For each urea concentration, two separate experiments are shown, each displaying fluorescence at the maximum of the fluorescence at 350 nm (hollow circles) and that averaged over the data of 350 nm to 360 nm (filled diamonds), along with their respective fitted analytical curves (lines). For the calculation, values from the fitting of the averaged curves were used.

Figure 39:
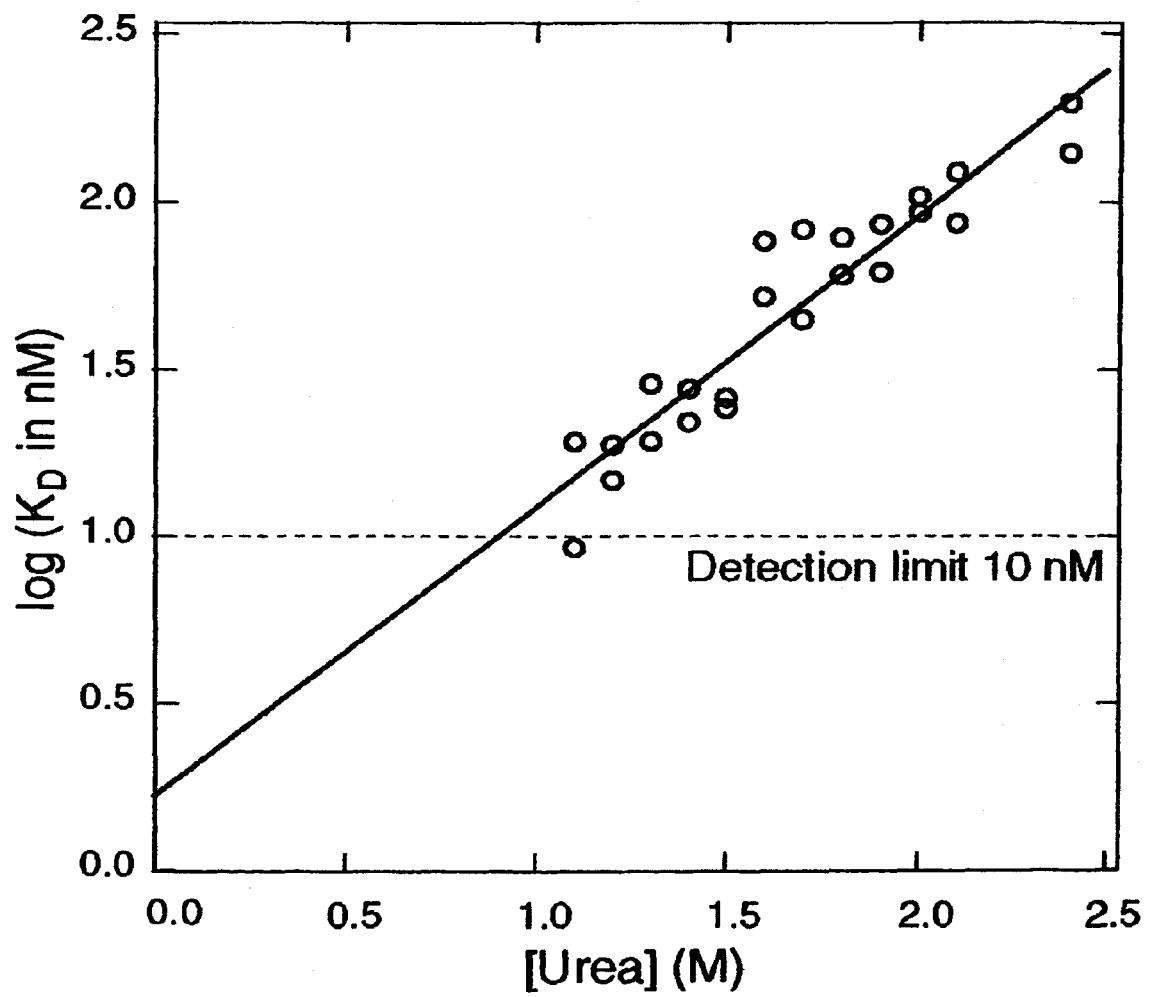

FIG. 39. Dependence of the measured dissociation constant on urea concentration.

Figure 40:
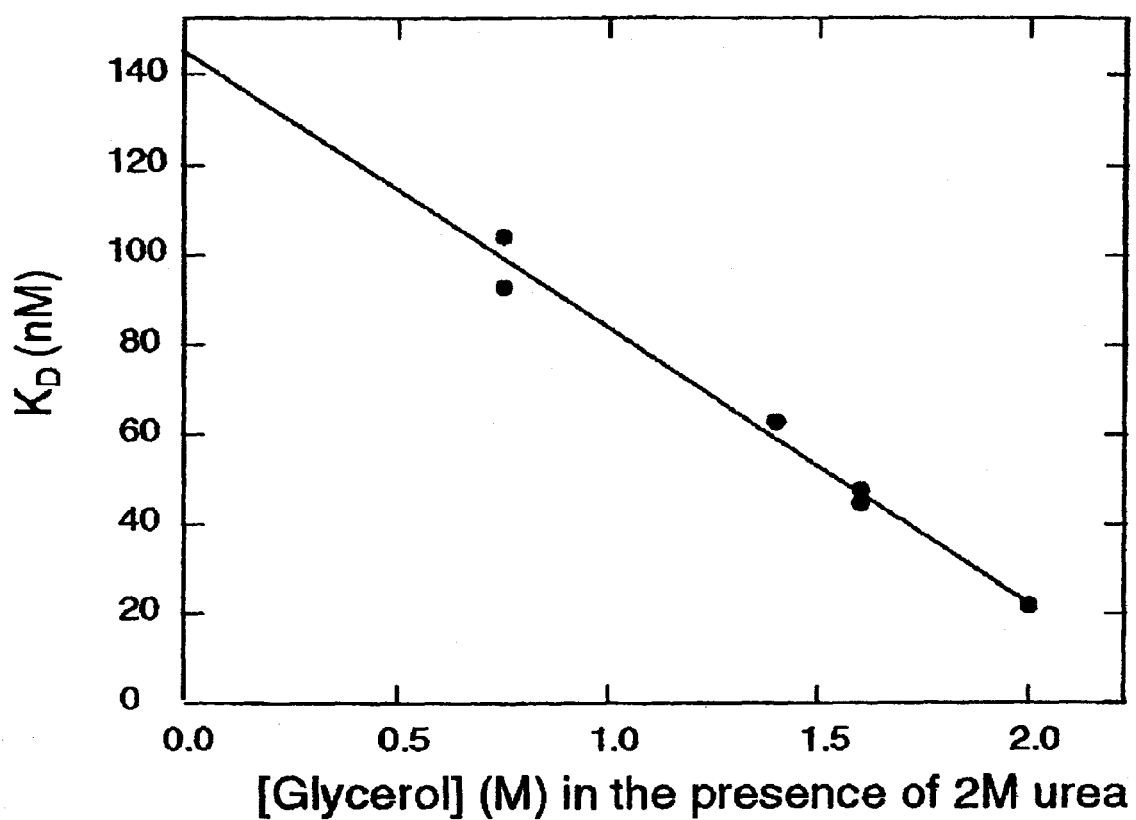

FIG. 40. Dependence of the measured dissociation constant on glycerol.

Figure 41:
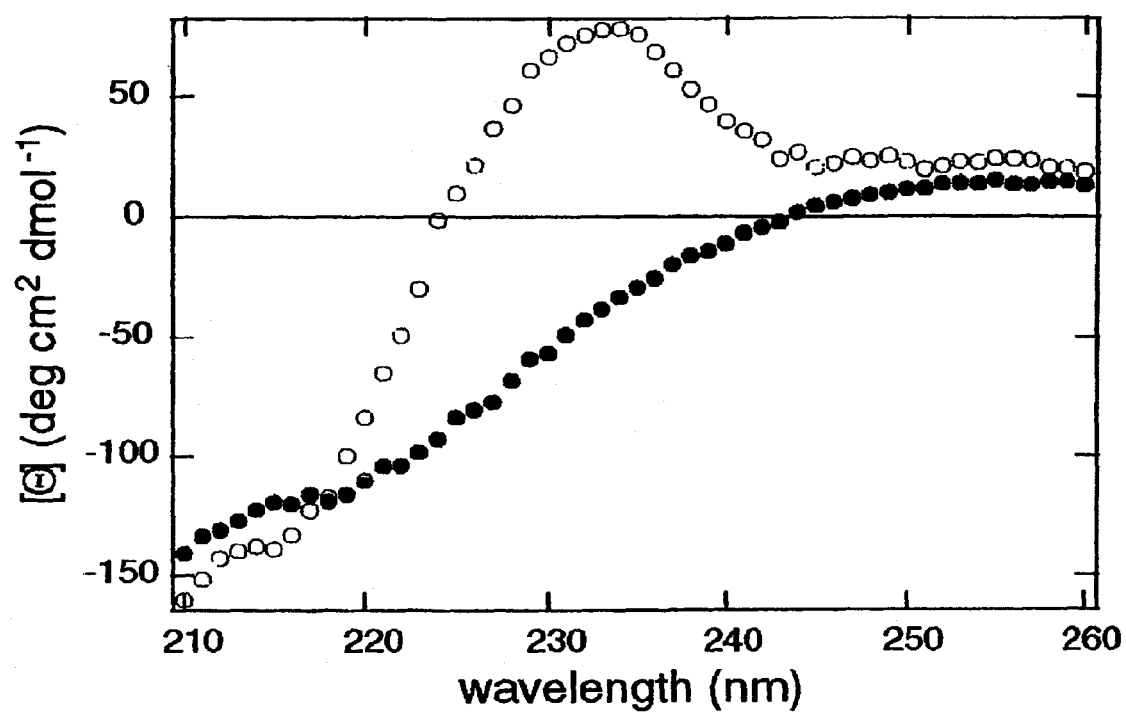

FIG. 41. Far UV CD spectra for the two fragments. Filled circles represent the N-terminal, hollow ones the C-terminal.

Figure 42:
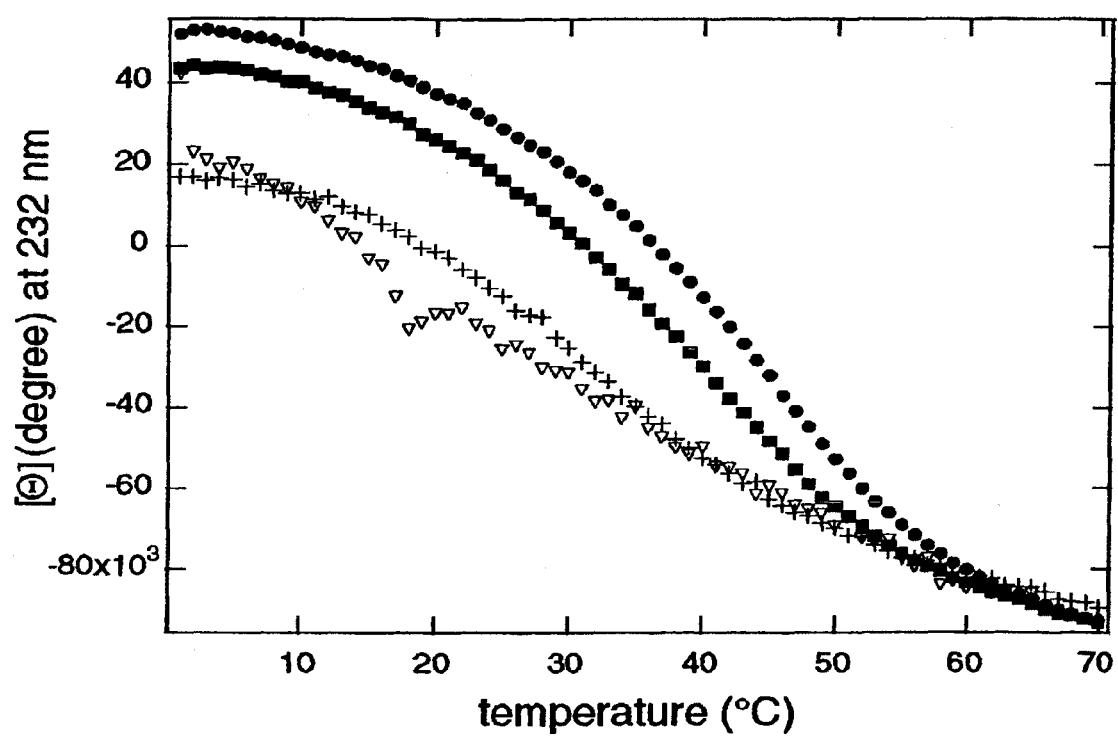

FIG. 42: Dependence of the β-turn inflection seen in the CD spectrum of the C-terminal fragment. C-terminal fragment concentration are 100 μM (circles), 50 μM (squares), 10 μM (crosses) and 1.5 μM (triangles), where the lowest concentration curve was measured in buffer equal to the fluorescence experiments above. All others were measured in 20 mM sodium phosphate buffer at pH 6. Temperature and Cooperativity of unfolding change with concentration.

Figure 43:
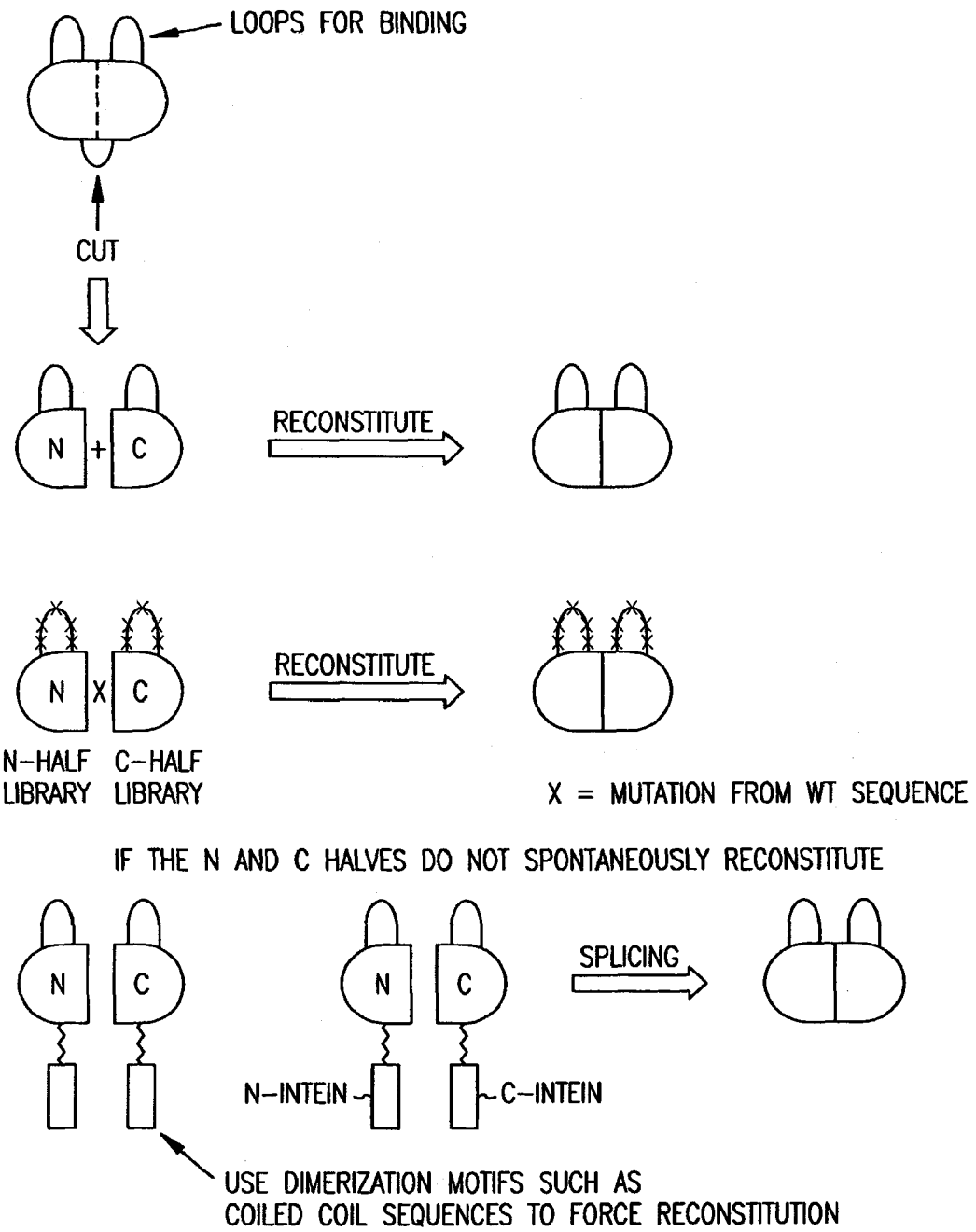

FIG. 43. Scheme for library construction using fragment reconstitution.

FIG. 44. In vivo reconstitution of monobodies. Yeast strain EGY48 with a plasmid that encodes for the N-terminal half of the FNfn10 fused to the B42 DNA binding domain, (FNABC)-NLS-B42 fusion protein, was mated with strain RFY206 with a plasmid that encodes for a LexA-C terminal half of FNfn10 fusion featuring either wild-type (FNDEFG) or a monobody FG loop. FNEDFG0319 has the FG loop of monobody pYT0319, and FNEDFG4699 that of monobody pYT4699, which have been selected for two different target proteins. As a control, EGY48 with pTarget plasmid (Origene) and RFY206 with pBait plasmid (Origene) were used. After the mated cells were replicated on YC Gal Raf-his -ura -trp media supplemented with 1 μM E2 and incubated over night, the b-galactosidase assay was performed using agarose overlay method.

Figure 45:
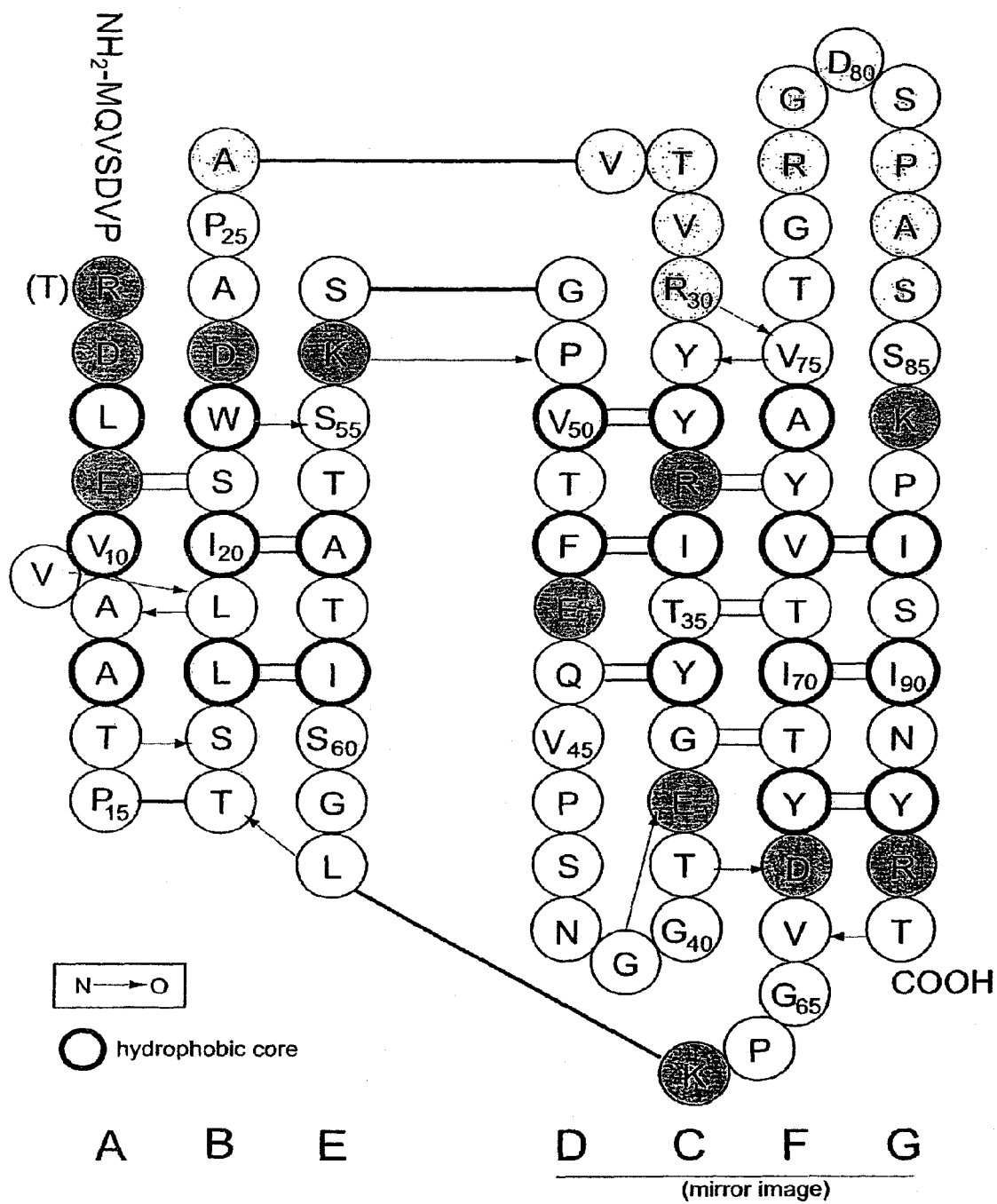

FIG. 45. Topographic illustration of the Fn3 molecule (SEQ ID NO:139).

FIG. 46. Schematic drawings of vectors for yeast surface display of FN3 and FN3 fragments. pYDFN1 is for surface display of full-length FN3. It also contains the X-press epitope tag, V5 epitope tag and His6 tag (SEQ ID NO:136) for detection of displayed FN3. pGalAgaFN(C)V5 is for surface display of an FN3 fragment (residues 43-94) that is fused to V5 and His6 tags (SEQ ID NO:136). pGalsecFn(N)FLAG is for secretion of an FN3 fragment (residues 1-42) that is fused to the FLAG tag.

Figure 47:
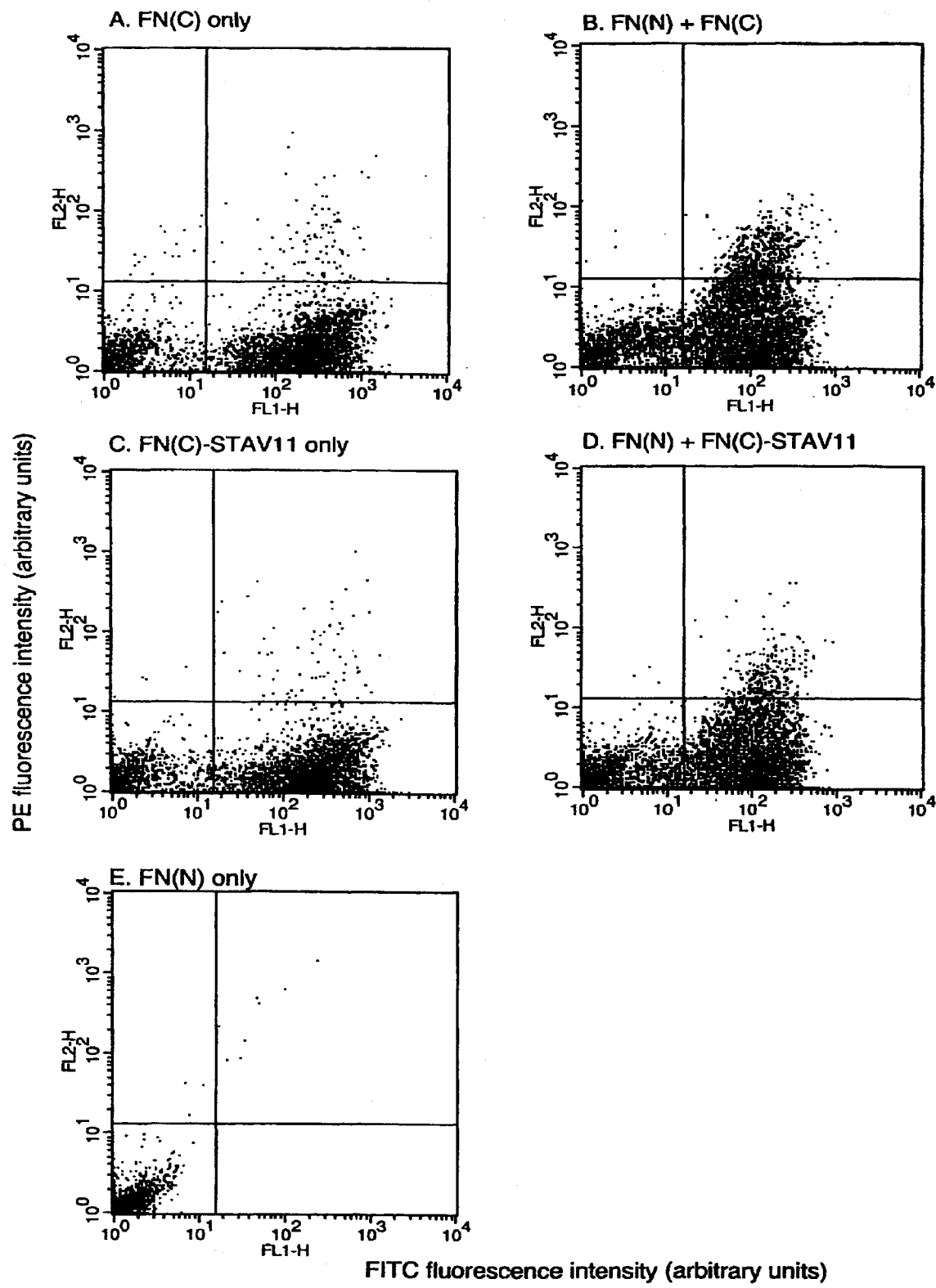

FIG. 47. FACS analysis of surface expression of FN3 fragments. The horizontal axis is the fluorescence intensity of FITC, which indicates the amount of the FN3 C-terminal fragment that is fused to the Aga2 protein and anchored on the cell surface. The vertical axis indicates the fluorescence intensity of PE, which indicates the amount of the FN3 N-terminal fragment that is secreted as a soluble protein. Each dot represents one yeast cell.

(A) Yeast cells expressing the wild-type C-terminal fragment only. (B) Yeast cells expressing both the wild-type N- and C-terminal fragments. (C) Yeast cells expressing only the C-terminal fragment of the streptavidin binding monobody, STAV1. (D) Yeast cells expressing the wild-type N-terminal fragment and the C-terminal fragment of STAV1. (E) Yeast cells expressing only the wild-type N-terminal fragment.

DETAILED DESCRIPTION OF THE INVENTION

For the past decade the immune system has been exploited as a rich source of de novo catalysts. Catalytic antibodies have been shown to have chemoselectivity, enantioselectivity, large rate accelerations, and even an ability to reroute chemical reactions. In most cases the antibodies have been elicited to transition state analog (TSA) haptens. These TSA haptens are stable, low-molecular weight compounds designed to mimic the structures of the energetically unstable transition state species that briefly (approximate half-life $10^{-13}$ s)

appear along reaction pathways between reactants and products. Anti-TSA antibodies, like natural enzymes, are thought to selectively bind and stabilize transition state, thereby easing the passage of reactants to products. Thus, upon binding, the antibody lowers the energy of the actual transition state and increases the rate of the reaction. These catalysts can be programmed to bind to geometrical and electrostatic features of the transition state so that the reaction route can be controlled by neutralizing unfavorable charges, overcoming entropic barriers, and dictating stereoelectronic features of the reaction. By this means even reactions that are otherwise highly disfavored have been catalyzed (Janda et al. 1997). Further, in many instances catalysts have been made for reactions for which there are no known natural or man-made enzymes.

The success of any combinatorial chemical system in obtaining a particular function depends on the size of the library and the ability to access its members. Most often the antibodies that are made in an animal against a hapten that mimics the transition state of a reaction are first screened for binding to the hapten and then screened again for catalytic activity. An improved method allows for the direct selection for catalysis from antibody libraries in phage, thereby linking chemistry and replication.

A library of antibody fragments can be created on the surface of filamentous phage viruses by adding randomized antibody genes to the gene that encodes the phage's coat protein. Each phage then expresses and displays multiple copies of a single antibody fragment on its surface. Because each phage possesses both the surface-displayed antibody fragment and the DNA that encodes that fragment, and antibody fragment that binds to a target can be identified by amplifying the associated DNA.

Immunochemists use as antigens materials that have as little chemical reactivity as possible. It is almost always the case that one wishes the ultimate antibody to interact with native structures. In reactive immunization the concept is just the opposite. One immunizes with compounds that are highly reactive so that upon binding to the antibody molecule during the induction process, a chemical reaction ensues. Later this same chemical reaction becomes part of the mechanism of the catalytic event. In a certain sense one is immunizing with a chemical reaction rather than a substance per se. Reactive immunogens can be considered as analogous to the mechanism-based inhibitors that enzymologists use except that they are used in the inverse way in that, instead of inhibiting a mechanism, they induce a mechanism.

Man-made catalytic antibodies have considerable commercial potential in many different applications. Catalytic antibody-based products have been used successfully in prototype experiments in therapeutic applications, such as prodrug activation and cocaine inactivation, and in nontherapeutic applications, such as biosensors and organic synthesis.

Catalytic antibodies are theoretically more attractive than noncatalytic antibodies as therapeutic agents because, being catalytic, they may be used in lower doses, and also because their effects are unusually irreversible (for example, peptide bond cleavage rather than binding). In therapy, purified catalytic antibodies could be directly administered to a patient, or alternatively the patient's own catalytic antibody response could be elicited by immunization with an appropriate hapten. Catalytic antibodies also could be used as clinical diagnostic tools or as regioselective or stereoselective catalysts in the synthesis of fine chemicals.

I. Mutation of Fn3 Loops and Grafting of Ab Loops onto Fn3

An ideal scaffold for CDR grafting is highly soluble and stable. It is small enough for structural analysis, yet large enough to accommodate multiple CDRs so as to achieve tight binding and/or high specificity.

A novel strategy to generate an artificial Ab system on the framework of an existing non-Ab protein was developed. An advantage of this approach over the minimization of an Ab scaffold is that one can avoid inheriting the undesired properties of Abs. Fibronectin type III domain (Fn3) was used as the scaffold. Fibronectin is a large protein which plays essential roles in the formation of extracellular matrix and cell-cell interactions; it consists of many repeats of three types (I, II and III) of small domains (Baron et al., 1991). Fn3 itself is the paradigm of a large subfamily (Fn3 family or s-type Ig family) of the immunoglobulin superfamily (IgSF). The Fn3 family includes cell adhesion molecules, cell surface hormone and cytokine receptors, chaperoning, and carbohydrate-binding domains (for reviews, see Bork & Doolittle, 1992; Jones, 1993; Bork et al., 1994; Campbell & Spitzfaden, 1994; Harpez & Chothia, 1994).

Recently, crystallographic studies revealed that the structure of the DNA binding domains of the transcription factor NF-kB is also closely related to the Fn3 fold (Ghosh et al., 1995; Müller et al., 1995). These proteins are all involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., 1992) and by X-ray crystallography (Leahy et al., 1992; Dickinson et al., 1994). The structure is best described as a P-sandwich similar to that of Ab VH domain except that Fn3 has seven β-strands instead of nine (FIG. 1). There are three loops on each end of Fn3; the positions of the BC, DE and FG loops approximately correspond to those of CDR1, 2 and 3 of the VH domain, respectively (FIG. 1 C, D).

Fn3 is small (~95 residues), monomeric, soluble and stable. It is one of few members of IgSF that do not have disulfide bonds; VH has an interstrand disulfide bond (FIG. 1 A) and has marginal stability under reducing conditions. Fn3 has been expressed in *E. coli* (Aukhil et al., 1993). In addition, 17 Fn3 domains are present just in human fibronectin, providing important information on conserved residues which are often important for the stability and folding (for sequence alignment, see Main et al., 1992 and Dickinson et al., 1994). From sequence analysis, large variations are seen in the BC and FG loops, suggesting that the loops are not crucial to stability. NMR studies have revealed that the FG loop is highly flexible; the flexibility has been implicated for the specific binding of the 10th Fn3 to $\alpha_5\beta_1$ integrin through the Arg-Gly-Asp (RGD) motif. In the crystal structure of human growth hormone-receptor complex (de Vos et al., 1992), the second Fn3 domain of the receptor interacts with hormone via the FG and BC loops, suggesting it is feasible to build a binding site using the two loops.

The tenth type III module of fibronectin has a fold similar to that of immunoglobulin domains, with seven β strands forming two antiparallel β sheets, which pack against each other (Main et al., 1992). The structure of the type II module consists of seven β strands, which form a sandwich of two antiparallel β sheets, one containing three strands (ABE) and the other four strands (C'CFG) (Williams et al., 1988). The triple-stranded P sheet consists of residues Glu-9-Thr-14 (A), Ser-17-Asp-23 (B), and Thr-56-Ser-60 (E). The majority of the conserved residues contribute to the hydrophobic core, with the invariant hydrophobic residues Trp-22 and Try-68 lying toward the N-terminal and C-terminal ends of the core, respectively. The β strands are much less flexible and appear to provide a rigid framework upon which functional flexible loops are built. The topology is similar to that of immunoglobulin C domains.
Gene Construction and Mutagenesis A synthetic gene for tenth Fn3 of human fibronectin (FIG. 2) was designed which includes convenient restriction sites for ease of mutagenesis and uses specific codons for high-level protein expression (Gribskov et al., 1984).

Figure 7:
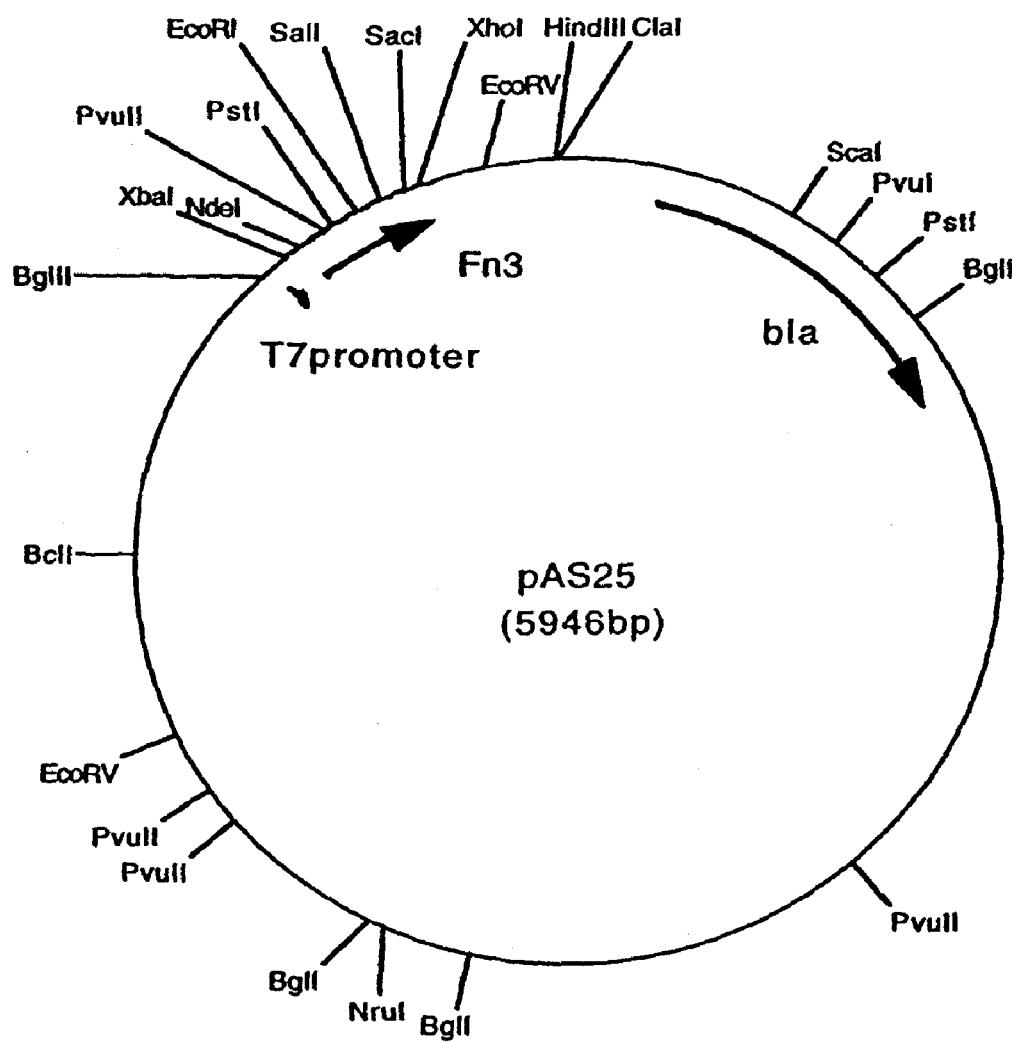
FIG. 7. Map of plasmid pAS25. Plasmid pAS25 is the expression vector of Fn3.

The gene was assembled as follows: (1) the gene sequence was divided into five parts with boundaries at designed restriction sites (FIG. 2); (2) for each part, a pair of oligonucleotides that code opposite strands and have complementary overlaps of ~15 bases was synthesized; (3) the two oligonucleotides were annealed and single strand regions were filled in using the Klenow fragment of DNA polymerase; (4) the double-stranded oligonucleotide was cloned into the pET3a vector (Novagen) using restriction enzyme sites at the termini of the fragment and its sequence was confirmed by an Applied Biosystems DNA sequencer using the dideoxy termination protocol provided by the manufacturer; (5) steps 2-4 were repeated to obtain the whole gene (plasmid pAS25) (FIG. 7).

Although the present method takes more time to assemble a gene than the one-step polymerase chain reaction (PCR) method (Sandhu et al., 1992), no mutations occurred in the gene. Mutations would likely have been introduced by the low fidelity replication by Taq polymerase and would have required time-consuming gene editing. The gene was also cloned into the pET15b (Novagen) vector (pEW1). Both vectors expressed the Fn3 gene under the control of bacteriophage T7 promoter (Studler et al 1990); pAS25 expressed the 96-residue Fn3 protein only, while pEW1 expressed Fn3 as a fusion protein with poly-histidine peptide (His•tag). Recombinant DNA manipulations were performed according to Molecular Cloning (Sambrook et al., 1989), unless otherwise stated.

Mutations were introduced to the Fn3 gene using either cassette mutagenesis or oligonucleotide site-directed mutagenesis techniques (Deng & Nickoloff, 1992). Cassette mutagenesis was performed using the same protocol for gene construction described above; double-stranded DNA fragment coding a new sequence was cloned into an expression vector (pAS25 and/or pEW1). Many mutations can be made by combining a newly synthesized strand (coding mutations) and an oligonucleotide used for the gene synthesis. The resulting genes were sequenced to confirm that the designed mutations and no other mutations were introduced by mutagenesis reactions.
Design and Synthesis of Fn3 Mutants with Antibody CDRs Two candidate loops (FG and BC) were identified for grafting. Antibodies with known crystal structures were examined in order to identify candidates for the sources of loops to be grafted onto Fn3. Anti-hen egg lysozyme (HEL) antibody D1.3 (Bhat et al., 1994) was chosen as the source of a CDR loop. The reasons for this choice were: (1) high resolution crystal structures of the free and complexed states are available (FIG. 4 A; Bhat et al., 1994), (2) thermodynamics data for the binding reaction are available (Tello et al., 1993), (3) D1.3 has been used as a paradigm for Ab structural analysis and Ab engineering (Verhoeyen et al., 1988; McCafferty et al., 1990) (4) site-directed mutagenesis experiments have shown that CDR3 of the heavy chain (VH-CDR3) makes a larger contribution to the affinity than the other CDRs (Hawkins et al., 1993), and (5) a binding assay can be easily performed. The objective for this trial was to graft VH-CDR3 of D1.3 onto the Fn3 scaffold without significant loss of stability.

An analysis of the D1.3 structure (FIG. 4) revealed that only residues 99-102 ("RDYR") (SEQ ID NO:120) make direct contact with hen egg-white lysozyme (HEL) (FIG. 4 B), although VH-CDR3 is defined as longer (Bhat et al., 1994). It should be noted that the C-terminal half of VH-CDR3 (residues 101-104) made significant contact with the VL domain (FIG. 4 B). It has also become clear that D1.3 VH-CDR3 (FIG. 4 C) has a shorter turn between the strands F and G than the FG loop of Fn3 (FIG. 4 D). Therefore, mutant sequences were designed by using the RDYR (99-102) (SEQ ID NO:120) of D1.3 as the core and made different boundaries and loop lengths (Table 1). Shorter loops may mimic the D1.3 CDR3 conformation better, thereby yielding higher affinity, but they may also significantly reduce stability by removing wild-type interactions of Fn3.

TABLE 1

Amino acid sequences of D1.3 VH CDR3, VH8 CDR3 and Fn3 FG loop and list of planned mutants.

|  | 96  100  105 |  |
|---|---|---|
| D1.3 | ARERDYR<u>LDYWGQG</u> | (SEQ ID NO: 1) |
| VH8 | ARGAVVSYYA<u>MDYWGQG</u> | (SEQ ID NO: 2) |
|  | 75 80    85 |  |
| Fn3 | <u>YAV</u>TGRGDSPASSKPI | (SEQ ID NO: 3) |
| Mutant | Sequence |  |
| D1.3-1 | YAERDYRLDY----PI | (SEQ ID NO: 4) |
| D1.3-2 | YAVRDYRLDY----PI | (SEQ ID NO: 5) |
| D1.3-3 | YAVRDYRLDYASSKPI | (SEQ ID NO: 6) |
| D1.3-4 | YAVRDYRLDY---KPI | (SEQ ID NO: 7) |
| D1.3-5 | YAVRDYR-----SKPI | (SEQ ID NO: 8) |
| D 1.3-6 | YAVTRDYRL--SSKPI | (SEQ ID NO: 9) |
| D1.3-7 | YAVTERDYRL-SSKPI | (SEQ ID NO: 10) |
| VH8-1 | YAVAVVSYYAMDY-PI | (SEQ ID NO: 11) |
| VH8-2 | YAVTAVVSYYASSKPI | (SEQ ID NO: 12) |

Underlines indicate residues in β-strands. Bold characters indicate replaced residues.

In addition, an anti-HEL single VH domain termed VH8 (Ward et al., 1989) was chosen as a template. VH8 was selected by library screening and, in spite of the lack of the VL domain, VH8 has an affinity for HEL of 27 nM, probably due to its longer VH-CDR3 (Table 1). Therefore, its VH-CDR3 was grafted onto Fn3. Longer loops may be advantageous on the Fn3 framework because they may provide higher affinity and also are close to the loop length of wild-type Fn3. The 3D structure of VH8 was not known and thus the VH8 CDR3 sequence was aligned with that of D1.3 VH-CDR3; two loops were designed (Table 1).
Mutant Construction and Production Site-directed mutagenesis experiments were performed to obtain designed sequences. Two mutant Fn3s, D1.3-1 and D1.3-4 (Table 1) were obtained and both were expressed as soluble His•tag fusion proteins. D1.3-4 was purified and the His•tag portion was removed by thrombin cleavage. D1.3-4 is soluble up to at least 1 mM at pH 7.2. No aggregation of the protein has been observed during sample preparation and NMR data acquisition.

Protein Expression and Purification

E. coli BL21 (DE3) (Novagen) were transformed with an expression vector (pAS25, pEW1 and their derivatives) containing a gene for the wild-type or a mutant. Cells were grown in M9 minimal medium and M9 medium supplemented with Bactotrypton (Difco) containing ampicillin (200 µg/ml). For isotopic labeling, $^{15}N$ NH$_4$Cl and/or $^{13}C$ glucose replaced unlabeled components. 500 ml medium in a 2 liter baffle flask were inoculated with 10 ml of overnight culture and agitated at 37° C. Isopropylthio-β-galactoside (IPTG) was added at a final concentration of 1 mM to initiate protein expression when OD (600 nm) reaches one. The cells were harvested by centrifugation 3 hours after the addition of IPTG and kept frozen at −70° C. until used.

Fn3 without His·tag was purified as follows. Cells were suspended in 5 ml/(g cell) of Tris (50 mM, pH 7.6) containing ethylenediaminetetraacetic acid (EDTA; 1 mM) and phenylmethylsulfonyl fluoride (1 mM). HEL was added to a final concentration of 0.5 mg/ml. After incubating the solution for 30 minutes at 37° C., it was sonicated three times for 30 seconds on ice. Cell debris was removed by centrifugation. Ammonium sulfate was added to the solution and precipitate recovered by centrifugation. The pellet was dissolved in 5-10 ml sodium acetate (50 mM, pH 4.6) and insoluble material was removed by centrifugation. The solution was applied to a Sephacryl™ S100HR column (Pharmacia) equilibrated in the sodium acetate buffer. Fractions containing Fn3 then was applied to a ResourceS® column (Pharmacia) equilibrated in sodium acetate (50 mM, pH 4.6) and eluted with a linear gradient of sodium chloride (0-0.5 M). The protocol can be adjusted to purify mutant proteins with different surface charge properties.

Fn3 with His·tag was purified as follows. The soluble fraction was prepared as described above, except that sodium phosphate buffer (50 mM, pH 7.6) containing sodium chloride (100 mM) replaced the Tris buffer. The solution was applied to a Hi-Trap™ chelating column (Pharmacia) preloaded with nickel and equilibrated in the phosphate buffer. After washing the column with the buffer, His·tag-Fn3 was eluted in the phosphate buffer containing 50 mM EDTA. Fractions containing His·tag-Fn3 were pooled and applied to a Sephacryl™ S100-HR column, yielding highly pure protein. The His·tag portion was cleaved off by treating the fusion protein with thrombin using the protocol supplied by Novagen. Fn3 was separated from the His·tag peptide and thrombin by a ResourceS column using the protocol above.

The wild-type and two mutant proteins so far examined are expressed as soluble proteins. In the case that a mutant is expressed as inclusion bodies (insoluble aggregate), it is first examined if it can be expressed as a soluble protein at lower temperature (e.g., 25-30° C.). If this is not possible, the inclusion bodies are collected by low-speed centrifugation following cell lysis as described above. The pellet is washed with buffer, sonicated and centrifuged. The inclusion bodies are solubilized in phosphate buffer (50 mM, pH 7.6) containing guanidinium chloride (GdnCl, 6 M) and will be loaded on a Hi-Trap chelating column. The protein is eluted with the buffer containing GdnCl and 50 mM EDTA.

Conformation of Mutant Fn3, D1.3-4

The $^1H$ NMR spectra of His·tag D1.3-4 fusion protein closely resembled that of the wild-type, suggesting the mutant is folded in a similar conformation to that of the wild-type. The spectrum of D1.3-4 after the removal of the His·tag peptide showed a large spectral dispersion. A large dispersion of amide protons (7-9.5 ppm) and a large number of downfield (5.0-6.5 ppm) C$^α$ protons are characteristic of a β-sheet protein (Wüthrich, 1986).

Figure 12:
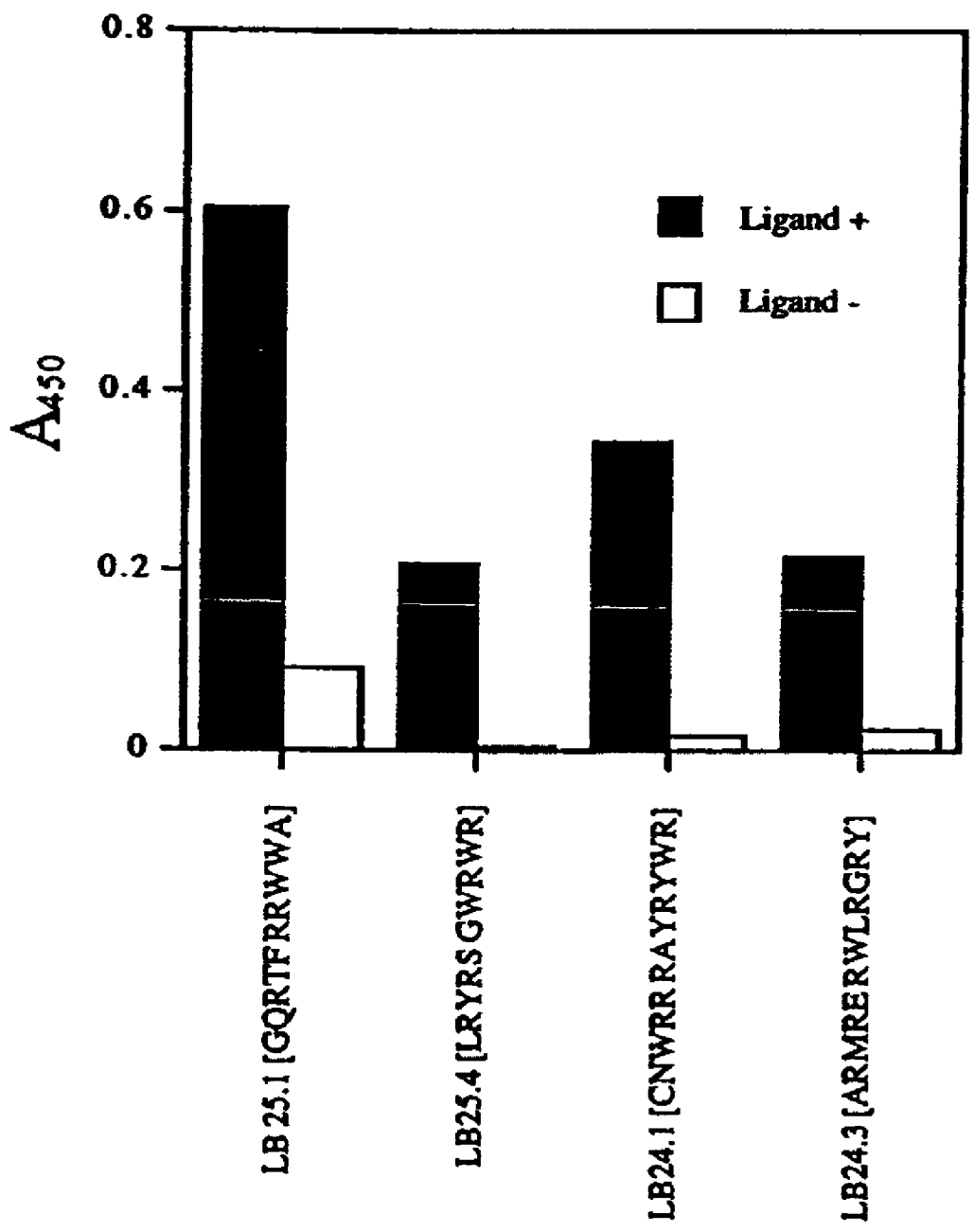
FIG. 12. (Fluorescein-1) Phage ELISA of four clones, Plb25.1 (containing SEQ ID NO:115), Plb25.4 (containing SEQ ID NO:116), pLB24.1 (containing SEQ ID NO:117) and pLB24.3 (containing SEQ ID NO:118). Experimental conditions are the same as ubiquitin-1 above.

The 2D NOESY spectrum of D1.3-4 provided further evidence for a preserved conformation. The region in the spectrum showed interactions between upfield methyl protons (<0.5 ppm) and methyl-methylene protons. The Val72 γ methyl resonances were well separated in the wild-type spectrum (−0.07 and 0.37 ppm; (Baron et al., 1992)). Resonances corresponding to the two methyl protons are present in the D1.3-4 spectrum (−0.07 and 0.44 ppm). The cross peak between these two resonances and other conserved cross peaks indicate that the two resonances in the D1.3-4 spectrum are highly likely those of Val72 and that other methyl protons are in nearly identical environment to that of wild-type Fn3. Minor differences between the two spectra are presumably due to small structural perturbation due to the mutations. Val72 is on the F strand, where it forms a part of the central hydrophobic core of Fn3 (Main et al., 1992). It is only four residues away from the mutated residues of the FG loop (Table 1). The results are remarkable because, despite there being 7 mutations and 3 deletions in the loop (more than 10% of total residues; FIG. 12, Table 2), D1.3-4 retains a 3D structure virtually identical to that of the wild-type (except for the mutated loop). Therefore, the results provide strong support that the FG loop is not significantly contributing to the folding and stability of the Fn3 molecule and thus that the FG loop can be mutated extensively.

TABLE 2

Sequences of oligonucleotides

| Name | Sequence |
|---|---|
| FN1F | CGGGATCCCATATGCAGGTTTCTGATGTTCCGCGTGAC CTGGAAGTTGTTGCTGCGACC (SEQ ID NO: 13) |
| FN1R | TAACTGCAGGAGCATCCCAGCTGATCAGCAGGCTAGTC GGGGTCGCAGCAACAAC (SEQ ID NO: 14) |
| FN2F | CTCCTGCAGTTACCGTGCGTTATTACCGTATCACGTAC GGTGAAACCGGTG (SEQ ID NO: 15) |
| FN2R | GTGAATTCCTGAACCGGGGAGTTACCACCGGTTTCACC G (SEQ ID NO: 16) |
| FN3F | AGGAATTCACTGTACCTGGTTCCAAGTCTACTGCTACC ATCAGCGG (SEQ ID NO: 17) |
| FN3R | GTATAGTCGACACCCGGTTTCAGGCCGCTGATGGTAGC (SEQ ID NO: 18) |
| FN4F | CGGGTGTCGACTATACCATCACTGTATACGCT (SEQ ID NO: 19) |
| FN4R | CGGGATCCGAGCTCGCTGGGCTGTCACCACGGCCAGTA ACAGCGTATACAGTGAT (SEQ ID NO: 20) |
| FN5F | CAGCGAGCTCCAAGCCAATCTCGATTAACTACGGT (SEQ ID NO: 21) |
| FN5R | CGGGATCCTCGAGTTACTAGGTACGGTAGTTAATCGA (SEQ ID NO: 22) |
| FN5R' | CGGGATCCACGCGTGCCACCGGTACGGTAGTTAATCGA (SEQ ID NO: 23) |
| gene3F | CGGGATCCACGCGTCCATTCGTTTGTGAATATCAAGGC CAATCG (SEQ ID NO: 24) |

TABLE 2-continued

Sequences of oligonucleotides

| Name | Sequence |
|------|----------|
| gene3R | CCGG<u>AAGCTTT</u>AAGACTCCTTATTACGCAGTATGTTAGC<br>(SEQ ID NO: 25) |
| 38TAABgIII | CTGTTACTGGCCGTGAGATCTAACCAGCGAGCTCCA<br>(SEQ ID NO: 26) |
| BC3 | GATCAGCTGGGATGCTCCTNNKNNKNNKNNKNNKTAT<br>TACCGTATCACGTA<br>(SEQ ID NO: 27) |
| FG2 | TGTATACGCTGTTACTGGCNNKNNKNNKNNKNNKNNK<br>NNKTCCAAGCCAATCTCGAT<br>(SEQ ID NO: 28) |
| FG3 | CTGTATACGCTGTTACTGGCNNKNNKNNKNNKCCAGC<br>GAGCTCCAAG<br>(SEQ ID NO: 29) |
| FG4 | CATCACTGTATACGCTGTTACTNNKNNKNNKNNKNNKT<br>CCAAGCCAATCTC<br>(SEQ ID NO: 30) |

Restriction enzyme sites are underlined. N and K denote an equimolar mixture of A, T. G and C and that of G and T, respectively.

Structure and Stability Measurements

Structures of Abs were analyzed using quantitative methods (e.g., DSSP (Kabsch & Sander, 1983) and PDBfit (D. McRee, The Scripps Research Institute)) as well as computer graphics (e.g., Quanta (Molecular Simulations) and What if (G. Vriend, European Molecular Biology Laboratory)) to superimpose the strand-loop-strand structures of Abs and Fn3.

The stability of monobodies was determined by measuring temperature- and chemical denaturant-induced unfolding reactions (Pace et al., 1989). The temperature-induced unfolding reaction was measured using a circular dichroism (CD) polarimeter. Ellipticity at 222 and 215 nm was recorded as the sample temperature was slowly raised. Sample concentrations between 10 and 50 μM were used. After the unfolding baseline was established, the temperature was lowered to examine the reversibility of the unfolding reaction. Free energy of unfolding was determined by fitting data to the equation for the two-state transition (Becktel & Schellman, 1987; Pace et al., 1989). Nonlinear least-squares fitting was performed using the program Igor (WaveMetrics) on a Macintosh computer.

The structure and stability of two selected mutant Fn3s were studied; the first mutant was D1.3-4 (Table 2) and the second was a mutant called AS40 which contains four mutations in the BC loop ($A^{26}V^{27}T^{28}V^{29}$)⇒ TQRQ) (SEQ ID NO:140 ⇒141). AS40 was randomly chosen from the BC loop library described above. Both mutants were expressed as soluble proteins in E. coli and were concentrated at least to 1 mM, permitting NMR studies.

The mid-point of the thermal denaturation for both mutants was approximately 69° C., as compared to approximately 79° C. for the wild-type protein. The results indicated that the extensive mutations at the two surface loops did not drastically decrease the stability of Fn3, and thus demonstrated the feasibility of introducing a large number of mutations in both loops.

Stability was also determined by guanidinium chloride (GdnCl)- and urea-induced unfolding reactions. Preliminary unfolding curves were recorded using a fluorometer equipped with a motor-driven syringe; GdnCl or urea were added continuously to the protein solution in the cuvette. Based on the preliminary unfolding curves, separate samples containing varying concentration of a denaturant were prepared and fluorescence (excitation at 290 nm, emission at 300-400 nm) or CD (ellipticity at 222 and 215 nm) were measured after the samples were equilibrated at the measurement temperature for at least one hour. The curve was fitted by the least-squares method to the equation for the two-state model (Santoro & Bolen, 1988; Koide et al., 1993). The change in protein concentration was compensated if required.

Once the reversibility of the thermal unfolding reaction is established, the unfolding reaction is measured by a Microcal MC-2 differential scanning calorimeter (DSC). The cell (~1.3 ml) will be filled with FnAb solution (0.1-1 mM) and ΔCp (=ΔH/ΔT) will be recorded as the temperature is slowly raised. $T_m$ (the midpoint of unfolding), ΔH of unfolding and ΔG of unfolding is determined by fitting the transition curve (Privalov & Potekhin, 1986) with the Origin software provided by Microcal.

Thermal Unfolding

Figure 1A:
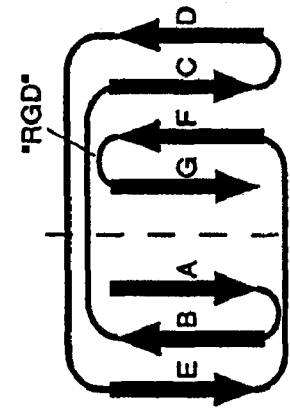
FIG. 1. β-Strand and loop topology (A, B) and MOL-SCRIPT representation (C, D; Kraulis, 1991) of the VH domain of anti-lysozyme immunoglobulin D1.3 (A, C; Bhat et al., 1994) and 10th type III domain of human fibronectin (B, D; Main et al., 1992). The locations of complementarity determining regions (CDRs, hypervariable regions) and the integrin-binding Arg-Gly-Asp (RGD) sequence are indicated.
Figure 1B:
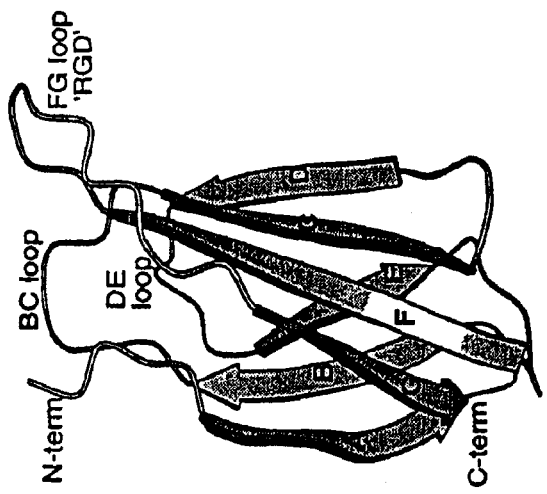
Figure 1C:
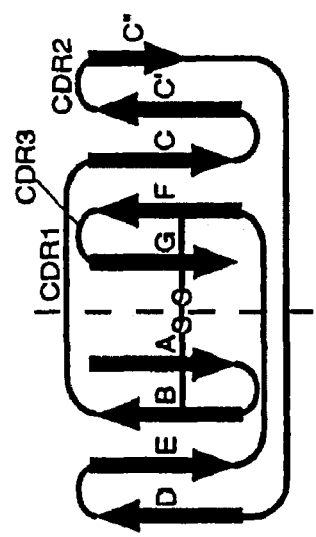
Figure 1D:
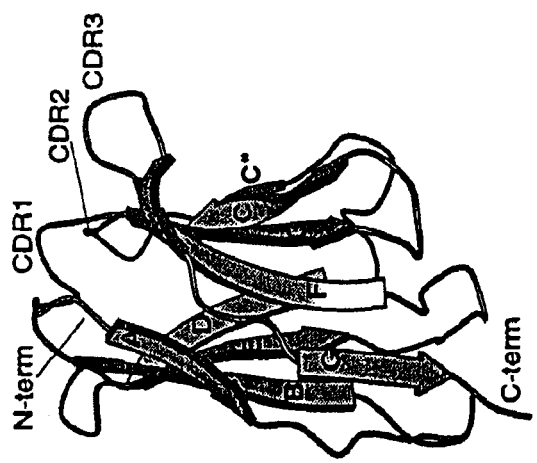
Figure 3A:
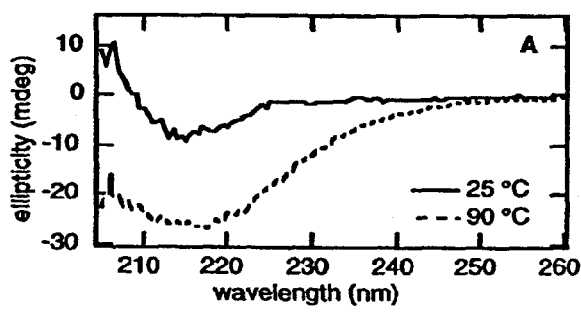
FIG. 3. A, Far UV CD spectra of wild-type Fn3 at 25° C. and 90° C. Fn3 (50 μM) was dissolved in sodium acetate (50 mM, pH 4.6). B, thermal denaturation of Fn3 monitored at 215 nm. Temperature was increased at a rate of 1° C./min.
Figure 3B:
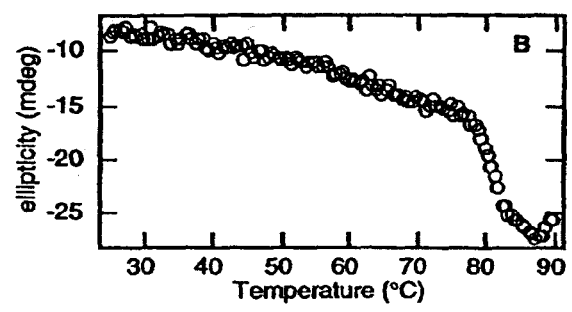
Figure 4A:
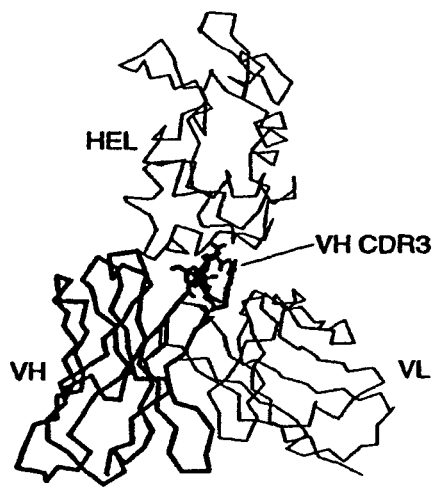
FIG. 4. A, Cα trace of the crystal structure of the complex of lysozyme (HEL) and the Fv fragment of the anti-hen egg-white lysozyme (anti-HEL) antibody D1.3 (Bhat et al., 1994). Side chains of the residues 99-102 of VH CDR3, which make contact with HEL, are also shown. B, Contact surface area for each residue of the D1.3 VH-HEL and VH-VL interactions plotted vs. residue number of D1.3 VH, Surface area and secondary structure were determined using the program DSSP (Kabsh and Sander, 1983). C and D, schematic drawings of the β-sheet structure of the F strand-loop-G strand moieties of D1.3 VH (C) and Fn3 (D). The boxes denote residues in β-strands and ovals those not in strands. The shaded boxes indicate residues of which side chains are significantly buried. The broken lines indicate hydrogen bonds.
Figure 4B:
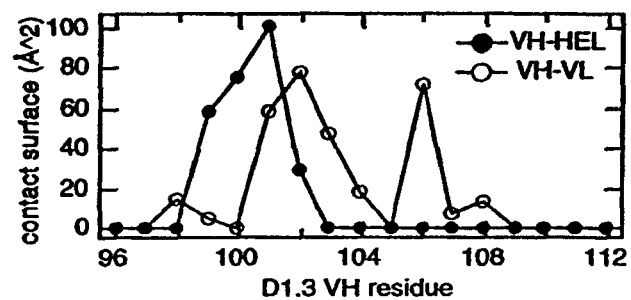
Figure 4C:
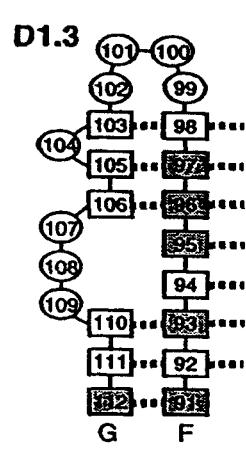
Figure 4D:
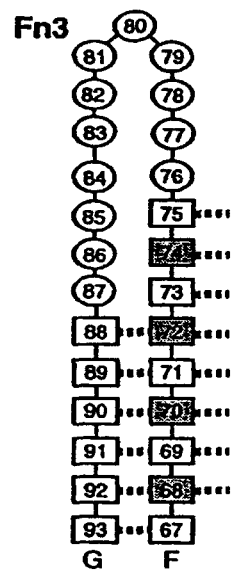

A temperature-induced unfolding experiment on Fn3 was performed using circular dichroism (CD) spectroscopy to monitor changes in secondary structure. The CD spectrum of the native Fn3 shows a weak signal near 222 nm (FIG. 3A), consistent with the predominantly β-structure of Fn3 (Perczel et al., 1992). A cooperative unfolding transition is observed at 80-90° C., clearly indicating high stability of Fn3 (FIG. 3B). The free energy of unfolding could not be determined due to the lack of a post-transition baseline. The result is consistent with the high stability of the first Fn3 domain of human fibronectin (Litvinovich et al., 1992), thus indicating that Fn3 domains are in general highly stable.

Binding Assays

The binding reactions of monobodies were characterized quantitatively using an isothermal titration calorimeter (ITC) and fluorescence spectroscopy.

The enthalpy change (ΔH) of binding were measured using a Microcal Omega ITC (Wiseman et al., 1989). The sample cell (~1.3 ml) was filled with Monobody solution (≦100 μM, changed according to $K_d$), and the reference cell filled with distilled water; the system was equilibrated at a given temperature until a stable baseline is obtained; 5-20 μl of ligand solution (≦2 mM) was injected by a motor-driven syringe within a short duration (20 sec) followed by an equilibration delay (4 minutes); the injection was repeated and heat generation/absorption for each injection was measured. From the change in the observed heat change as a function of ligand concentration, ΔH and $K_d$ was determined (Wiseman et al., 1989). ΔG and ΔS of the binding reaction was deduced from the two directly measured parameters. Deviation from the theoretical curve was examined to assess nonspecific (multiple-site) binding. Experiments were also be performed by placing a ligand in the cell and titrating with an FnAb. It should be emphasized that only ITC gives direct measurement of ΔH, thereby making it possible to evaluate enthalpic and entropic contributions to the binding energy. ITC was successfully used to monitor the binding reaction of the D1.3 Ab (Tello et al., 1993; Bhat et al., 1994).

Intrinsic fluorescence is monitored to measure binding reactions with $K_d$ in the sub-μM range where the determination of $K_d$ by ITC is difficult. Trp fluorescence (excitation at ~290 nm, emission at 300-350 nm) and Tyr fluorescence (excitation at ~260 nm, emission at ~303 nm) is monitored as the Fn3-mutant solution (≦10 μM) is titrated with ligand solution (≦100 μM). $K_d$ of the reaction is determined by the nonlinear least-squares fitting of the bimolecular binding equation. Presence of secondary binding sites is examined using Scatchard analysis. In all binding assays, control experiments are performed busing wild-type Fn3 (or unrelated monobodies) in place of monobodies of interest.

II. Production of Fn3 Mutants with High Affinity and Specificity Monobodies

Library screening was carried out in order to select monobodies that bind to specific ligands. This is complementary to the modeling approach described above. The advantage of combinatorial screening is that one can easily produce and screen a large number of variants ($\geqq 10^8$), which is not feasible with specific mutagenesis ("rational design") approaches. The phage display technique (Smith, 1985; O'Neil & Hoess, 1995) was used to effect the screening processes. Fn3 was fused to a phage coat protein (pIII) and displayed on the surface of filamentous phages. These phages harbor a single-stranded DNA genome that contains the gene coding the Fn3 fusion protein. The amino acid sequence of defined regions of Fn3 were randomized using a degenerate nucleotide sequence, thereby constructing a library. Phages displaying Fn3 mutants with desired binding capabilities were selected in vitro, recovered and amplified. The amino acid sequence of a selected clone can be identified readily by sequencing the Fn3 gene of the selected phage. The protocols of Smith (Smith & Scott, 1993) were followed with minor modifications.

The objective was to produce Monobodies which have high affinity to small protein ligands. HEL and the B1 domain of staphylococcal protein G (hereafter referred to as protein G) were used as ligands. Protein G is small (56 amino acids) and highly stable (Minor & Kim, 1994; Smith et al., 1994). Its structure was determined by NMR spectroscopy (Gronenborn et al., 1991) to be a helix packed against a four-strand β-sheet. The resulting FnAb-protein G complexes (~150 residues) is one of the smallest protein-protein complexes produced to date, well within the range of direct NMR methods. The small size, the high stability and solubility of both components and the ability to label each with stable isotopes ($^{13}$C and $^{15}$N; see below for protein G) make the complexes an ideal model system for NMR studies on protein-protein interactions.

The successful loop replacement of Fn3 (the mutant D1.3-4) demonstrate that at least ten residues can be mutated without the loss of the global fold. Based on this, a library was first constructed in which only residues in the FG loop are randomized. After results of loop replacement experiments on the BC loop were obtained, mutation sites were extended that include the BC loop and other sites.

Construction of Fn3 Phage Display System

An M13 phage-based expression vector pASM1 has been constructed as follows: an oligonucleotide coding the signal peptide of OmpT was cloned at the 5' end of the Fn3 gene; a gene fragment coding the C-terminal domain of M13 pIII was prepared from the wild-type gene III gene of M13 mp18 using PCR (Corey et al., 1993) and the fragment was inserted at the 3' end of the OmpT-Fn3 gene; a spacer sequence has been inserted between Fn3 and pIII. The resultant fragment (OmpT-Fn3-pIII) was cloned in the multiple cloning site of M13 mp18, where the fusion gene is under the control of the lac promoter. This system will produce the Fn3-pIII fusion protein as well as the wild-type pIII protein. The co-expression of wild-type pIII is expected to reduce the number of fusion pIII protein, thereby increasing the phage infectivity (Corey et al., 1993) (five copies of pIII are present on a phage particle). In addition, a smaller number of fusion pIII protein may be advantageous in selecting tight binding proteins, because the chelating effect due to multiple binding sites should be smaller than that with all five copies of fusion pIII (Bass et al., 1990). This system has successfully displayed the serine protease trypsin (Corey et al., 1993). Phages were produced and purified using *E. coli* K91kan (Smith & Scott, 1993) according to a standard method (Sambrook et al., 1989) except that phage particles were purified by a second polyethylene glycol precipitation and acid precipitation.

Successful display of Fn3 on fusion phages has been confirmed by ELISA using an Ab against fibronectin (Sigma), clearly indicating that it is feasible to construct libraries using this system.

An alternative system using the fUSE5 (Parmley & Smith, 1988) may also be used. The Fn3 gene is inserted to fUSE5 using the SfiI restriction sites introduced at the 5'- and 3'-ends of the Fn3 gene PCR This system displays only the fusion pIII protein (up to five copies) on the surface of a phage. Phages are produced and purified as described (Smith & Scott, 1993). This system has been used to display many proteins and is robust. The advantage of fUSE5 is its low toxicity. This is due to the low copy number of the replication form (RF) in the host, which in turn makes it difficult to prepare a sufficient amount of RF for library construction (Smith & Scott, 1993).

Construction of Libraries

The first library was constructed of the Fn3 domain displayed on the surface of M13 phage in which seven residues (77-83) in the FG loop (FIG. 4D) were randomized. Randomization will be achieved by the use of an oligonucleotide containing degenerated nucleotide sequence. A double-stranded nucleotide was prepared by the same protocol as for gene synthesis (see above) except that one strand had an $(NNK)_6(NNG)$ sequence at the mutation sites, where N corresponds to an equimolar mixture of A, T, G and C and K corresponds to an equimolar mixture of G and T. The (NNG) codon at residue 83 was required to conserve the SacI restriction site (FIG. 2). The (NNK) codon codes all of the 20 amino acids, while the NNG codon codes 14. Therefore, this library contained ~$10^9$ independent sequences. The library was constructed by ligating the double-stranded nucleotide into the wild-type phage vector, pASM1, and the transfecting *E. coli* XL1 blue (Stratagene) using electroporation. XL1 blue has the lacI$^q$ phenotype and thus suppresses the expression of the Fn3-pIII fusion protein in the absence of lac inducers. The initial library was propagated in this way, to avoid selection against toxic Fn3-pIII clones. Phages displaying the randomized Fn3-pIII fusion protein were prepared by propagating phages with 91kan as the host. K91kan does not suppress the production of the fusion protein, because it does not have lacI$^q$. Another library was also generated in which the BC loop (residues 26-20) was randomized.

Selection of Displayed Monobodies

Screening of Fn3 phage libraries was performed using the biopanning protocol (Smith & Scott, 1993); a ligand is biotinylated and the strong biotin-streptavidin interaction was used to immobilize the ligand on a streptavidin-coated dish. Experiments were performed at room temperature (~22° C.). For the initial recovery of phages from a library, 10 μg of a biotinylated ligand were immobilized on a streptavidin-coated polystyrene dish (35 mm, Falcon 1008) and then a phage solution (containing ~$10^{11}$ pfu (plaque-forming unit)) was added. After washing the dish with an appropriate buffer (typically TBST, Tris-HCl (50 mM, pH 7.5), NaCl (150 mM) and Tween 20 (0.5%)), bound phages were eluted by one or combinations of the following conditions: low pH, an addition of a free ligand, urea (up to 6 M) and, in the case of anti-protein G Monobodies, cleaving the protein G-biotin linker by thrombin. Recovered phages were amplified using the standard protocol using K91kan as the host (Sambrook et al., 1989). The selection processes were repeated 3-5 times to concentrate positive clones. From the second round on, the amount of the ligand were gradually decreased (to ~1 μg) and the biotinylated ligand were mixed with a phage solution before transferring a dish (G. P. Smith, personal communication). After the final round, 10-20 clones were picked, and their DNA sequence will be determined. The ligand affinity of the clones were measured first by the phage-ELISA method (see below).

To suppress potential binding of the Fn3 framework (background binding) to a ligand, wild-type Fn3 may be added as a competitor in the buffers. In addition, unrelated proteins (e.g., bovine serum albumin, cytochrome c and RNase A) may be used as competitors to select highly specific Monobodies.

Binding Assay

The binding affinity of Monobodies on phage surface is characterized semi-quantitatively using the phage ELISA technique (Li et al., 1995). Wells of microtiter plates (Nunc) are coated with a ligand protein (or with streptavidin followed by the binding of a biotinylated ligand) and blocked with the Blotto solution (Pierce). Purified phages (~$10_{10}$ pfu) originating from single plaques (M13)/colonies (fUSE5) are added to each well and incubated overnight at 4° C. After washing wells with an appropriate buffer (see above), bound phages are detected by the standard ELISA protocol using anti-M13 Ab (rabbit, Sigma) and anti-rabbit Ig-peroxidase conjugate (Pierce) or using anti-M13 Ab-peroxidase conjugate (Pharmacia). Colormetric assays are performed using TMB (3,3', 5,5'-tetramethylbenzidine, Pierce). The high affinity of protein G to immunoglobulins presents a special problem; Abs cannot be used in detection. Therefore, to detect anti-protein G Monobodies, fusion phages are immobilized in wells and the binding is then measured using biotinylated protein G followed by the detection using streptavidin-peroxidase conjugate.

Production of Soluble Monobodies

After preliminary characterization of mutant Fn3s using phage ELISA, mutant genes are subcloned into the expression vector pEW1. Mutant proteins are produced as His•tag fusion proteins and purified, and their conformation, stability and ligand affinity are characterized.

III. Increased Stability of Fn3 Scaffolds

The definition of "higher stability" of a protein is the ability of a protein to retain its three-dimensional structure required for function at a higher temperature (in the case of thermal denaturation), and in the presence of a higher concentration of a denaturing chemical reagent such as guanidine hydrochloride. This type of "stability" is generally called "conformational stability." It has been shown that conformational stability is correlated with resistance against proteolytic degradation, i.e., breakdown of protein in the body (Kamtekar et al. 1993).

Improving the conformational stability is a major goal in protein engineering. Here, mutations have been developed by the inventor that enhance the stability of the fibronectin type III domain (Fn3). The inventor has developed a technology in which Fn3 is used as a scaffold to engineer artificial binding proteins (Koide et al., 1998). It has been shown that many residues in the surface loop regions of Fn3 can be mutated without disrupting the overall structure of the Fn3 molecule, and that variants of Fn3 with a novel binding function can be engineered using combinatorial library screening (Koide et al., 1998). The inventor found that, although Fn3 is an excellent scaffold, Fn3 variants that contain large number of mutations are destabilized against chemical denaturation, compared to the wild-type Fn3 protein (Koide et al., 1998). Thus, as the number of mutated positions are mutated in order to engineer a new binding function, the stability of such Fn3 variants further decreases, ultimately leading to marginally stable proteins. Because artificial binding proteins must maintain their three-dimensional structure to be functional, stability limits the number of mutations that can be introduced in the scaffold. Thus, modifications of the Fn3 scaffold that increase its stability are useful in that they allow one to introduce more mutations for better function, and that they make it possible to use Fn3-based engineered proteins in a wider range of applications.

The inventor found that wild-type Fn3 is more stable at acidic pH than at neutral pH (Koide et al., 1998). The pH dependence of Fn3 stability is characterized in FIG. 18. The pH dependence curve has an apparent transition midpoint near pH 4 (FIG. 18). These results suggest that by identifying and removing destabilizing interactions in Fn3 one is able to improve the stability of Fn3 at neutral pH. It should be noted that most applications of engineered Fn3, such as diagnostics, therapeutics and catalysts, are expected to be used near neutral pH, and thus it is important to improve the stability at neutral pH. Studies by other investigators have demonstrated that the optimization of surface electrostatic properties can lead to a substantial increase in protein stability (Perl et al. 2000, Spector et al. 1999, Loladze et al. 1999, Grimsley et al. 1999).

The pH dependence of Fn3 stability suggests that amino acids with $pK_a$ near 4 are involved in the observed transition. The carboxyl groups of aspartic acid (Asp) and glutamic acid (Glu) have $pK_a$ in this range (Creighton, T. E. 1993). It is well known that if a carboxyl group has unfavorable (i.e. destabilizing) interactions in a protein, its $pK_a$ is shifted to a higher value from its standard, unperturbed value (Yang and Honig 1992). Thus, the $pK_a$ values of all carboxyl groups in Fn3 were determined using nuclear magnetic resonance (NMR) spectroscopy, to identify carboxyl groups with unusual $pK_a$'s, as shown below.

First, the $^{13}C$ resonance for the carboxyl carbon of each Asp and Glu residue were assigned (FIG. 19). Next pH titration of $^{13}C$ resonances was performed for these groups (FIG. 20). The $pK_a$ values for these residues are listed in Table 3.

TABLE 3

$pK_a$ values for Asp and Glu residues in Fn3.

| Residue | $pK_a$ |
| --- | --- |
| E9 | 5.09 |
| E38 | 3.79 |
| E47 | 3.94 |
| D3 | 3.66 |
| D7 | 3.54, 5.54* |
| D23 | 3.54, 5.25* |
| D67 | 4.18 |
| D80 | 3.40 |

The standard deviation in the $pK_a$ values are less than 0.05 pH units.
*Data for D7 and D23 were fitted with a transition curve with two $pK_a$ values.

These results show that Asp 7 and 23, and Glu 9 have up-shifted $pK_a$'s with respect to their unperturbed $pK_a$'s (approximately 4.0), indicating that these residues are involved in unfavorable interactions. In contrast, the other Asp and Glu residues have $pK_a$'s close to the respective unperturbed values, indicating that the carboxyl groups of these residues do not significantly contribute to the stability of Fn3.

In the three-dimensional structure of Fn3 (Main et al. 1992), Asp 7 and 23, and Glu 9 form a patch on the surface (FIG. 21), with Asp 7 centrally located in the patch. This spatial proximity of these negatively charged residues explains why these residues have unfavorable interactions in Fn3. At low pH where these residues are protonated and neutral, the unfavorable interactions are expected to be mostly relieved. At the same time, the structure suggests that the stability of Fn3 at neutral pH could be improved if the electrostatic repulsion between these three residues is removed. Because Asp 7 is centrally located among the three residues, it was decided to mutate Asp 7. Two mutants were prepared, D7N and D7K (i.e., the aspartic acid at amino acid residue number 7 was substituted with an asparagine residue or a lysine residue, respectively). The former replaces the negative charge with a neutral residue of virtually the same size. The latter places a positive charge at residue 7.

The degrees of stability of the mutant proteins were characterized in thermal and chemical denaturation measurements. In thermal denaturation measurements, denaturation of the Fn3 proteins was monitored using circular dichroism spectroscopy at the wavelength of 227 nm. All the proteins underwent a cooperative transition (FIG. 22). From the transition curves, the midpoints of the transition ($T_m$) for the wild-type, D7N and D7K were determined to be 62, 69 and 70° C. in 0.02 M sodium phosphate buffer (pH 7.0) containing 0.1 M sodium chloride and 6.2 M urea. Thus, the mutations increased the $T_m$ of wild-type Fn3 by 7-8° C.

Chemical denaturation of Fn3 proteins was monitored using fluorescence emission from the single Trp residue of Fn3 (FIG. 23). The free energies of unfolding in the absence of guanidine HCl ($\Delta G^0$) were determined to be 7.4, 8.1 and 8.0 kcal/mol for the wild-type, D7N and D7K, respectively (a larger $\Delta G^0$ indicates a higher stability). The two mutants were again found to be more stable than the wild-type protein.

These results show that a point mutation on the surface can significantly enhance the stability of Fn3. Because these mutations are on the surface, they minimally alter the structure of Fn3, and they can be easily introduced to other, engineered Fn3 proteins. In addition, mutations at Glu 9 and/or Asp 23 also enhance the stability of Fn3. Furthermore, mutations at one or more of these three residues can be combined.

Thus, Fn3 is the fourth example of a monomeric immunoglobulin-like scaffold that can be used for engineering binding proteins. Successful selection of novel binding proteins have also been based on minibody, tendamistat and "camelized" immunoglobulin VH domain scaffolds (Martin et al., 1994; Davies & Riechmann, 1995; McConnell & Hoess, 1995). The Fn3 scaffold has advantages over these systems. Bianchi et al. reported that the stability of a minibody was 2.5 kcal/mol, significantly lower than that of Ubi4-K. No detailed structural characterization of minibodies has been reported to date. Tendamistat and the VH domain contain disulfide bonds, and thus preparation of correctly folded proteins may be difficult. Davies and Riechmann reported that the yields of their camelized VH domains were less than 1 mg per liter culture (Davies & Riechmann, 1996).

Thus, the Fn3 framework can be used as a scaffold for molecular recognition. Its small size, stability and well-characterized structure make Fn3 an attractive system. In light of the ubiquitous presence of Fn3 in a wide variety of natural proteins involved in ligand binding, one can engineer Fn3-based binding proteins to different classes of targets.

IV. Reassociation of the Fibronectin Type III Domain by Fragment Complementation Specific binding molecules are useful for many purposes. One example of specific binding molecules is antibodies generated by the immune system. When an individual is exposed to a "foreign" target molecule, the individual's immune system usually produces antibodies specific for the target molecule. Antibodies, or other specific binding molecules, can be useful in laboratory and commercial settings as well. At times, particular antibodies can be isolated from animals that have been exposed to certain target molecules. It can also be useful to generate artificially assembled libraries of specific binding molecules, which are then screened for their abilities to bind to different target molecules.

Phage display selection (Rader and Barbas 1997; Hoess 2001) and yeast two-hybrid assays (Fields and Song 1989; Geyer and Brent 2000) are among the most widely used experiments for the selection of proteins from a library. Protein selection mirrors the process in the immune response that selects circulating antibodies having an affinity for a particular antigen. The transformation efficiency of the host organism used to make the library, however, limits the available size of the library. In order to expand the binding capabilities and/or efficiencies, mutations can be introduced into a protein sequence after an initial selection (Hawkins et al. 1992; Roberts et al. 1996; Patten et al. 1996). This method mirrors somatic mutations in the immune response in affinity maturation experiments.

One source of diversity in the immune response lies in the combination of the light and heavy chains to form an antibody. Proper assembly of a light and heavy chain pair is required for the protein to be functional. Successful assembly of the heavy and light chains produced from a single vector has been demonstrated (Barbas et al. 1991), and phage display methods have been developed that make it possible to "mix and match" the heavy and light chains to produce a diverse set of antibodies (Sblattero and Bradbury 2000; Sblattero et al. 2001). In contrast to immunoglobulins, most engineered binding proteins, including monobodies, are based on a monomeric proteins (Skerra 2000). This monomeric nature of these engineered binding proteins makes it difficult to explore heterodimerization reactions to increase the diversity of a library. However, if an engineered binding protein could be manipulated so that its two separate pieces self-assemble into a functional form, a more diverse library could be achieved By using such a two-part scheme, two fragments could be separately diversified to generate their respective libraries, and then the two libraries could be combined to produce a very large library of the reconstituted protein.

Protein Fragment Reconstitution

When a protein is cleaved in two fragments, individual fragments are usually unfolded, and they often fail to reconstitute the original fold when mixed. However, fragments of a number of proteins have been shown to reconstitute into a native-like complex (de Prat Gay and Fersht 1994; Kippen et al. 1994; Tasayco and Chao 1995; Ladurner et al. 1997; Pelletier et al. 1998; Tasayco et al. 2000; Berggard et al. 2001). In order to achieve fragment complementation with a low dissociation constant (i.e., high affinity), it is imperative that a protein is cleaved at a location that does not disrupt interactions important for the stability of the protein. Most cleavage reactions in successful reconstitution experiments have been placed in a flexible region of target proteins.

Use of Fragment Reconstitution in Protein Interaction Assays

Several screening strategies exploit fragment reconstitution of proteins. For example, the split ubiquitin assay (Johnsson and Varshavsky 1994; Raquet et al. 2001) allows in vivo detection of protein-protein interactions (Wittke et al. 1999). A bacterial fragment complementation assay (Pelletier et al. 1998; Michnick et al. 2000) similarly uses fragment reconstitution of dihydrofolate reductase to examine protein-protein interactions in *E. coli*. In these assays, two proteins of interest are respectively fused to complementary fragments of a reporter protein (ubiquitin or dihydrofolate reductase) and successful reconstitution of the reporter protein would indicate interaction between the two proteins.

Protein Reconstitution to Efficiently Generate Combinatorial Libraries

Many molecular display technologies, where genetic information and functional information are physically linked, such as phage display (Kay et al. 1996) and yeast display (Boder and Wittrup 1997) depend on transformation of microbes. Such transformation step tends to limit the number of independent clones in a library that can be generated in a single transformation reaction to ~109 in *Escherichia coli* and ~107 in yeast. If one wishes to generate a biological combinatorial library where two discrete segments of a protein are diversified, one would typically need to generate a single DNA vector in which two segments are diversified and transform bacteria (or yeast). In this case the library size is still limited by the efficiency of the transformation reaction. One could use in vivo recombination reactions to increase the library diversity as demonstrated for antibody fragments (Sblattero and Bradbury 2000; Sblattero et al. 2001). However, when applied to a monomeric protein, such approaches introduce artificial amino acid segment in the protein, whose effects on the stability and structure are unpredictable.

The production of diverse combinatorial libraries would be greatly simplified, and expanded, if one could reconstitute a binding protein from two physically separate libraries, as in the combination of light and heavy chains described above. A library of a protein reconstituted from two libraries of complementary fragments has an effective size of the product of the sizes of the two primary libraries. Thus, if one can efficiently combine (and reconstitute) two (or more) fragment libraries, the resulting library would have much greater diversity than the sum of the diversity of the fragment libraries. In this scheme, the fragments must reconstitute with high affinity. Mutations introduced into either fragment potentially decrease the affinity of reconstitution. If a high affinity reconstitution library could be engineered using a particular scaffold, intriguing new opportunities to dramatically increase the library diversity would open up. Because fragments of a protein do not often reconstitute with high affinity and specificity, experimental studies are needed to explore this possibility for specific protein systems of interest.

As discussed above, the tenth fibronectin type III domain of human fibronectin (FNfn10) is a small, monomeric β-sandwich protein, similar to immunoglobulins. Small antibody mimics have been made using FNfn10 as a scaffold. As discussed herein, mutations are introduced into various loop regions of the fold. Fragments of FNfn10 that were produced by cleavage of a peptide bond in the CD loop and EF loop were tested to determine whether reconstitution occurs.

As described above, monobodies are engineered binding proteins using the scaffold of the fibronectin type III domain (FN3). Surface loops connecting beta-strands were modified to confer novel binding function. The present inventor has further developed the monobody technology and showed that monobodies that bind to a given target can be engineered by screening combinatorial libraries in which amino acid residues in one or more surface loops are diversified. Monobodies are compatible with virtually any molecular display techniques including, but not limited to, phage display, yeast surface display, mRNA display and also yeast two-hybrid techniques.

As described above, the efficiency of introducing a nucleic acid library (transformation) in a host usually limits the achievable size of a biological library. For example, one can only construct a phage display library (host: *E. coli*) of ~$10^9$ independent clones and a yeast two-hybrid library (host: yeast) of ~$10^7$ independent clones from a single transformation reaction. Theoretically libraries containing $10^9$ and ~$10^7$ clones include all possible sequences for only 6 and 4 randomized positions, respectively. Because the present inventor typically diversified more than six positions, typical monobody libraries contained only a small fraction of possible sequences. This may lead to a failure to identify a monobody that binds to a target, or a failure to isolate the optimal monobody. Thus, it is of considerable interest to increase the size of a biological library.

In the present invention, a method has been developed to significantly increase the size of a monobody library. This method exploits the reconstitution of a monobody from two fragments, where each contains one or more functional loops for target binding (see FIG. 43). A combinatorial library is made for each fragment, and then a final, larger library is constructed by combining libraries for the fragments. This is conceptually analogous to the formation of immunoglobulins from two separate chains, the heavy and light chains. This strategy is particularly suited for the yeast surface display and yeast two-hybrid method, because yeast cells of opposite mating types can mate efficiently. For example, if one has a library for the N-terminal half of the monobody with a size of $10^5$ and a library for the C-terminal half with a size of $10^5$, combining these two will theoretically yield a library of $10^{10}$. This is at least 10,000 fold greater than the typical size of a single library constructed in yeast. One can apply the in vivo recombination techniques (Sblattero and Bradbury 2000; Sblattero et al. 2001) to a plasmid vector containing two separate genes, where each gene encodes a fragment of a monobody. This is possible because one can insert arbitrary DNA sequences between the two genes for the fragments without causing deleterious effects on the protein.

In order to achieve this reconstitution method, it first needed to be demonstrated that two fragments of FN3 can actually reconstitute. Since fragment reconstitution with high affinity does not always occur, experimental verification was necessary. First, one needs to decide where to cut the FN3 scaffold. The CD loop was chosen as the initial cut site. The CD loop is at the opposite end of the protein from the BC and FG loops that have been extensively used for binding. Using a yeast two-hybrid system the inventor confirmed that the wild-type N-terminal fragment ("FNABC") interacted with the wild-type and mutated C-terminal fragments ("FNDEFG" and its derivatives) (FIG. 1). In addition, data suggested that the dissociation constant (Kd) between FNABC and FN DEFG was in the single nanomolar range, indicating very tight and specific interaction (see EXAMPLE XXI). The present results demonstrated that when cut in the CD loop, the two fragments of FN3 can reconstitute with high affinity. Thus monobody libraries can be constructed using the fragment reconstitution strategy.

In certain situations, particular mutations in the monobody (e.g. in the BC, DE or FG loops) may have detrimental effects on reconstitution. In such a situation, it is possible to attach a heterodimerization motif (such as coiled coil; see e.g. McClain et al., 2001) at the C-terminus of FNABC and at the N-terminus of FNDEFG to augment the reconstitution affinity of the two fragments. Alternatively, an N-intein can be attached to the end of one of the fragment pair, and a C-intein attached to the end of the other half of the fragment pair to reconstitute the binding protein into one contiguous polypeptide (see e.g., Yamazaki et al. 1998). Furthermore, a cystein residue can be introduced in each fragment in such a way that a disulfide bond is formed between the two complementary fragments.

There are many other different classes of binding pairs that could potentially be used to augment the reconstitution affinity of monobody fragments. Examples include the following:
1. natural proteins/peptides that are known to associate
    coiled coils (Oakley & Kim)
    nuclease-nuclease inhibitor (e.g., Barnase and Barster, see the World-Wide-Web at
    ncbi.nlm.nih.gov:80/entrez/
        query.fcgi?cmd=Retrieve&db=PubMed&list_uids=7789535&dopt=Abstract)
2. a peptide-binding protein and its target peptides
    src homology 3 (SH3) domain and proline-rich peptides (Yu et al., see the World-Wide-Web at
    ncbi.nlm.nih.gov:80/entrez/
        query.fcgi?cmd=Retrieve&db=PubMed&list_uids=7510218&dopt=Abstract)
    WW domain and proline-rich peptides (Chen et al.)
    src homology 2 (SH2) domain and phosphotyrosine containing peptides (see the World-Wide-Web at
    ncbi.nlm.nih.gov:80/entrez/
        query.fcgi?cmd=Retrieve&db=PubMed&list_uids=9383403&dopt=Abstract)
3. fragments of a protein that have been artificially generated (similar to the Fn3 fragments discussed extensively in the present specification)
    chymotrypsin inhibitor 2 (Ladurner et al. 1997)
    barnase (Sancho, J. & Fersht, A. R. see the World-Wide-Web at
    ncbi.nlm.nih.gov:80/entrez/
        query.fcgi?cmd=Retrieve&db=PubMed&list_uids=1569553&dopt=Abstract)
    ribonuclease S(S-protein/S-peptide) (Dwyer et al. 2001)
    green fluorescence protein (Merkel and Regan 2000)
4. inteins (Yamazaki et al. 1998)

Fragments of Fn3 as a Heterodimerization Unit

Complementary fragments of FN3 ("split FN3") can also be exploited as heterodimerization motifs that bring two proteins of interest in close proximity. Two proteins of interest, X and Y, are each fused to a fragment of FN3. Upon association of the FN3 fragments, X and Y are held in close proximity. For this purpose, FN3 fragments are derived from the wild-type sequence of FN3, as demonstrated in Example XXII, or from variants of FN3 with increased stability. In addition, mutations are introduced such that the new mutant fragments associate, but they do not associate with fragments derived from the wild-type sequence (see Example XXIII). Multiple sets of such unique binding pairs are designed using this strategy. Such pairs can be generated by first introducing a highly destabilizing mutations in one fragment and then screen a library of the other fragment in which appropriate positions are diversified. One can use this system to examine effects of bringing two proteins together in cell biology (Fujiwara et al. 2002). One can use this system to assemble nanostructures, such as on a silicon surface. In the nanotechnology field, there are not many tools to attach pieces with high selectivity. Having many different building blocks is clearly useful when assembling complex structures that require different attachment tools.

The following examples are intended to illustrate but not limit the invention.

EXAMPLE I

Construction of the Fn3 Gene

A synthetic gene for tenth Fn3 of fibronectin (FIG. 1) was designed on the basis of amino acid residue 1416-1509 of human fibronectin (Kornblihtt, et al., 1985) and its three dimensional structure (Main, et al., 1992). The gene was engineered to include convenient restriction sites for mutagenesis and the so-called "preferred codons" for high level protein expression (Gribskov, et al., 1984) were used. In addition, a glutamine residue was inserted after the N-terminal methionine in order to avoid partial processing of the N-terminal methionine which often degrades NMR spectra (Smith, et al., 1994). Chemical reagents were of the analytical grade or better and purchased from Sigma Chemical Company and J. T. Baker, unless otherwise noted. Recombinant DNA procedures were performed as described in "Molecular Cloning" (Sambrook, et al., 1989), unless otherwise stated. Custom oligonucleotides were purchased from Operon Technologies. Restriction and modification enzymes were from New England Biolabs.

The gene was assembled in the following manner. First, the gene sequence (FIG. 5) was divided into five parts with boundaries at designed restriction sites: fragment 1, NdeI-PstI (oligonucleotides FN1F and FN1R (Table 2); fragment 2, PstI-EcoRI (FN2F and FN2R); fragment 3, EcoRI-SalI (FN3F and FN3R); fragment 4, SalI-SacI (FN4F and FN4R); fragment 5, SacI-BamHI (FN5F and FN5R). Second, for each part, a pair of oligonucleotides which code opposite strands and have complementary overlaps of approximately 15 bases was synthesized. These oligonucleotides were designated FN1F-FN5R and are shown in Table 2. Third, each pair (e.g., FN1F and FN1R) was annealed and single-strand regions were filled in using the Klenow fragment of DNA polymerase. Fourth, the double stranded oligonucleotide was digested with the relevant restriction enzymes at the termini of the fragment and cloned into the pBlueScript® SK plasmid (Stratagene®) which had been digested with the same enzymes as those used for the fragments. The DNA sequence of the inserted fragment was confirmed by DNA sequencing using an Applied Biosystems DNA sequencer and the dideoxy termination protocol provided by the manufacturer. Last, steps 2-4 were repeated to obtain the entire gene.

Figure 6:
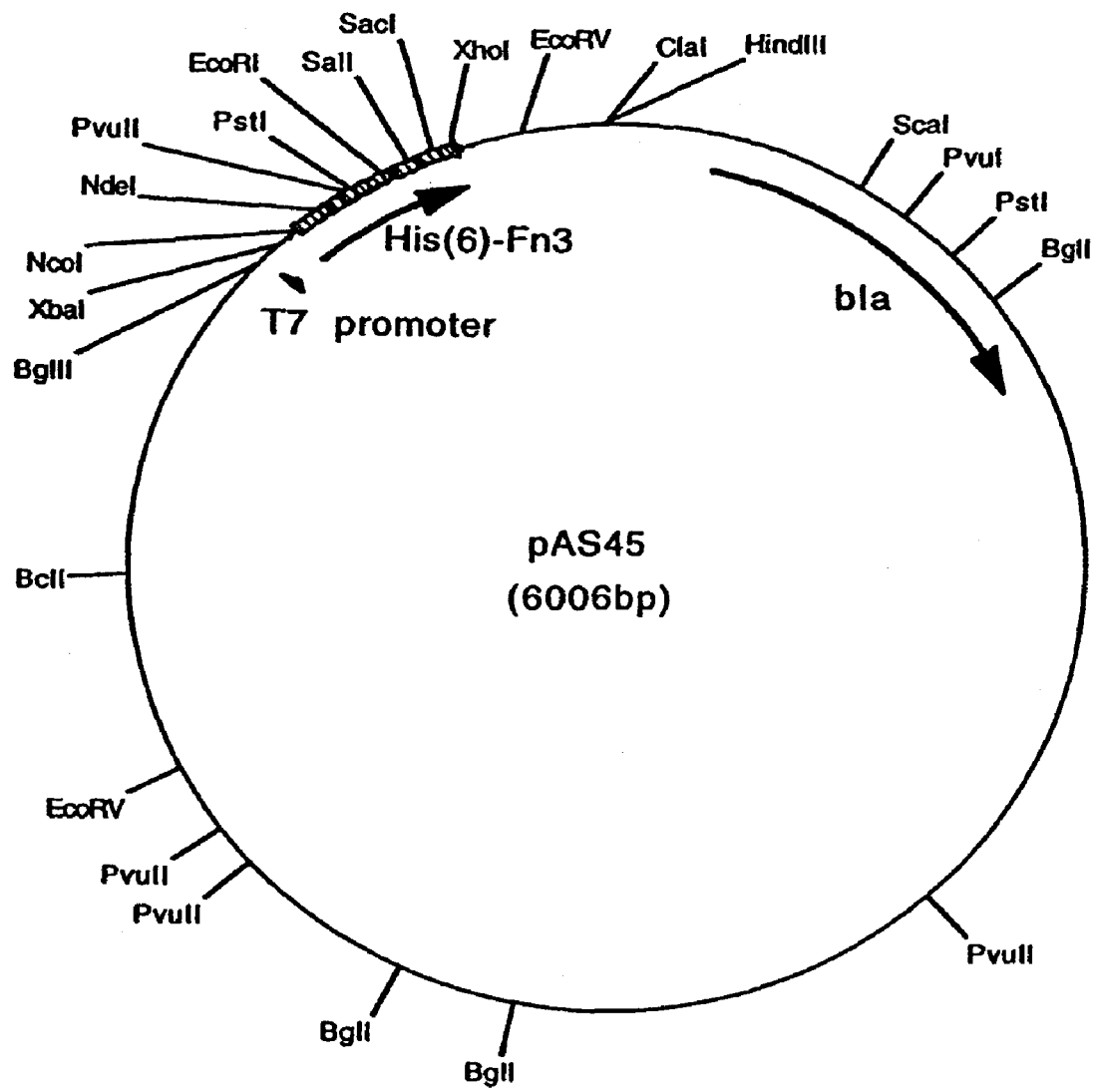
FIG. 6. Map of plasmid pAS45. Plasmid pAS45 is the expression vector of His•tag-Fn3 (6×His tag disclosed as SEQ ID NO:136).

The gene was also cloned into the pET3a and pET15b (Novagen) vectors (pAS45 and pAS25, respectively). The maps of the plasmids are shown in FIGS. 6 and 7. *E. coli* BL21 (DE3) (Novagen) containing these vectors expressed the Fn3 gene under the control of bacteriophage T7 promotor (Studier, et al., 1990); pAS24 expresses the 96-residue Fn3 protein only, while pAS45 expresses Fn3 as a fusion protein with poly-histidine peptide (His•tag). High level expression of the Fn3 protein and its derivatives in *E. coli* was detected as an intense band on SDS-PAGE stained with CBB.

The binding reaction of the monobodies is characterized quantitatively by means of fluorescence spectroscopy using purified soluble monobodies.

Intrinsic fluorescence is monitored to measure binding reactions. Trp fluorescence (excitation at ~290 nm, emission at 300 350 nm) and Tyr fluorescence (excitation at ~260 nm, emission at 303 nm) is monitored as the Fn3-mutant solution ($\leq 100 \mu M$) is titrated with a ligand solution. When a ligand is fluorescent (e.g. fluorescein), fluorescence from the ligand may be used. $K_d$ of the reaction will be determined by the nonlinear least-squares fitting of the bimolecular binding equation.

If intrinsic fluorescence cannot be used to monitor the binding reaction, monobodies are labeled with fluorescein-NHS (Pierce) and fluorescence polarization is used to monitor the binding reaction (Burke et al., 1996).

EXAMPLE II

Modifications to Include Restriction Sites in the Fn3 Gene

The restriction sites were incorporated in the synthetic Fn3 gene without changing the amino acid sequence Fn3. The positions of the restriction sites were chosen so that the gene construction could be completed without synthesizing long (>60 bases) oligonucleotides and so that two loop regions could be mutated (including by randomization) by the cassette mutagenesis method (i.e., swapping a fragment with another synthetic fragment containing mutations). In addition, the restriction sites were chosen so that most sites were unique in the vector for phage display. Unique restriction sites allow one to recombine monobody clones which have been already selected in order to supply a larger sequence space.

EXAMPLE III

Construction of M13 Phage Display Libraries

Figure 8:
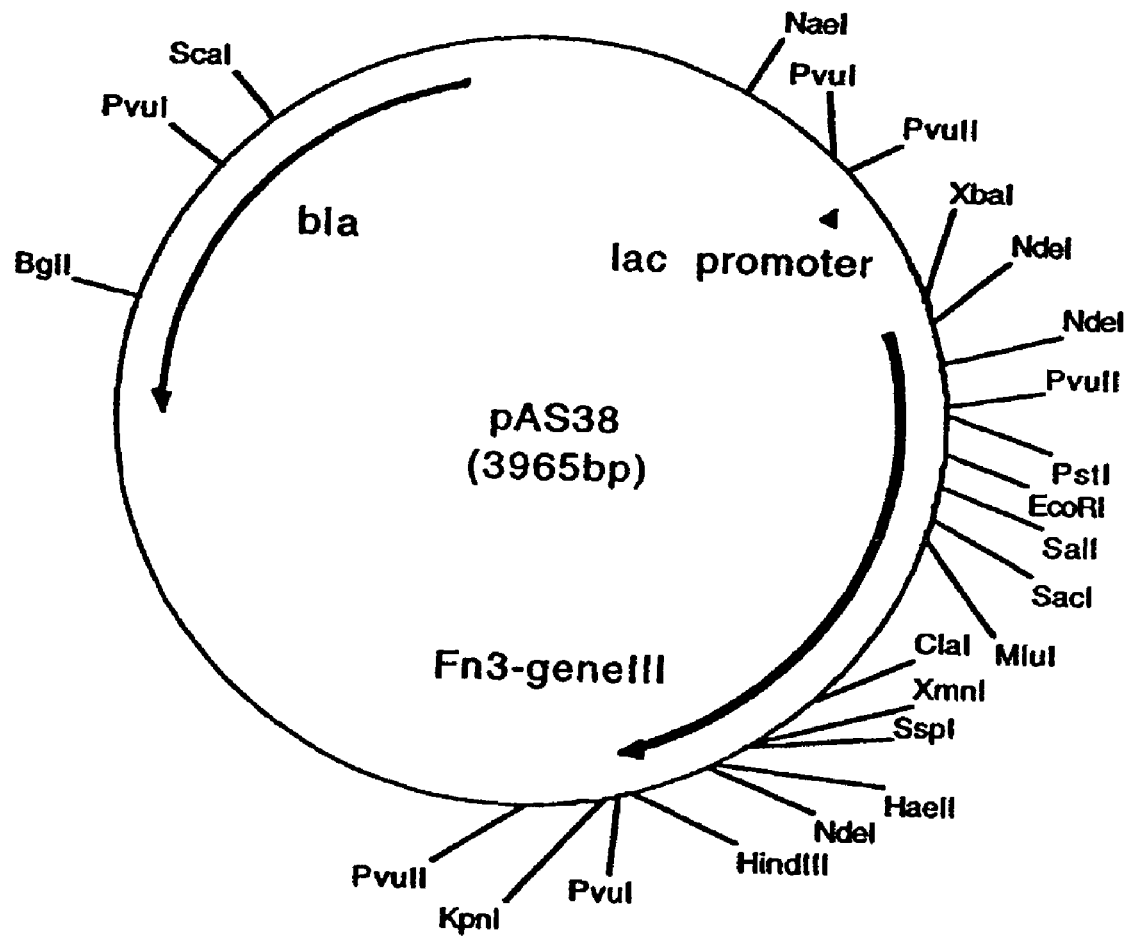
FIG. 8. Map of plasmid pAS38. pAS38 is a phagemid vector for the surface display of Fn3.

A vector for phage display, pAS38 (for its map, see FIG. 8) was constructed as follows. The XbaI-BamHI fragment of pET12a encoding the signal peptide of OmpT was cloned at the 5' end of the Fn3 gene. The C-terminal region (from the FN5F and FN5R oligonucleotides, see Table 2) of the Fn3 gene was replaced with a new fragment consisting of the FN5F and FN5R' oligonucleotides (Table 2) which introduced a MluI site and a linker sequence for making a fusion protein with the pIII protein of bacteriophage M13. A gene fragment coding the C-terminal domain of M13 pIII was prepared from the wild-type gene III of M13 mp18 using PCR (Corey, et al., 1993) and the fragment was inserted at the 3' end of the OmpT-Fn3 fusion gene using the MluI and HindIII sites.

Phages were produced and purified using a helper phage, M13K07, according to a standard method (Sambrook, et al., 1989) except that phage particles were purified by a second polyethylene glycol precipitation. Successful display of Fn3 on fusion phages was confirmed by ELISA (Harlow & Lane, 1988) using an antibody against fibronectin (Sigma) and a custom anti-FN3 antibody (Cocalico Biologicals, PA, USA).

EXAMPLE IV

Libraries Containing Loop Variegations in the AB Loop

A nucleic acid phage display library having variegation in the AB loop is prepared by the following methods. Randomization is achieved by the use of oligonucleotides containing degenerated nucleotide sequence. Residues to be variegated are identified by examining the X-ray and NMR structures of Fn3 (Protein Data Bank accession numbers, 1FNA and 1TTF, respectively). Oligonucleotides containing NNK (N and K here denote an equimolar mixture of A, T, G, and C and an equimolar mixture of G and T, respectively) for the variegated residues are synthesized (see oligonucleotides BC3, FG2, FG3, and FG4 in Table 2 for example). The NNK mixture codes for all twenty amino acids and one termination codon (TAG). TAG, however, is suppressed in the *E. coli* XL-1 blue. Single-stranded DNAs of pAS38 (and its derivatives) are prepared using a standard protocol (Sambrook, et al., 1989). Site-directed mutagenesis is performed following published methods (see for example, Kunkel 1985) using a Muta-Gene® kit (BioRad). The libraries are constructed by electroporation of *E. coli* XL-1 Blue electroporation competent cells (200 µl; Stratagene) with 1 µg of the plasmid DNA using a BTX electrocell manipulator ECM 395 1 mm gap cuvette. A portion of the transformed cells is plated on an LB-agar plate containing ampicillin (100 µg/ml) to determine the transformation efficiency. Typically, $3 \times 10^8$ transformants are obtained with 1 µg of DNA, and thus a library contains $10^8$ to $10^9$ independent clones. Phagemid particles were prepared as described above.

EXAMPLE V

Loop Variegations in the BC, CD, DE, EF or FG Loop

A nucleic acid phage display library having five variegated residues (residues number 26-30) in the BC loop, and one having seven variegated residues (residue numbers 78-84) in the FG loop, was prepared using the methods described in Example IV above. Other nucleic acid phage display libraries having variegation in the CD, DE or EF loop can be prepared by similar methods.

EXAMPLE VI

Loop variegations in the FG and BC Loop

A nucleic acid phage display library having seven variegated residues (residues number 78-84) in the FG loop and five variegated residues (residue number 26-30) in the BC loop was prepared. Variegations in the BC loop were prepared by site-directed mutagenesis (Kunkel, et al.) using the BC3 oligonucleotide described in Table 1. Variegations in the FG loop were introduced using site-directed mutagenesis using the BC loop library as the starting material, thereby resulting in libraries containing variegations in both BC and FG loops. The oligonucleotide FG2 has variegating residues 78-84 and oligonucleotide FG4 has variegating residues 77-81 and a deletion of residues 82-84.

A nucleic acid phage display library having five variegated residues (residues 78-84) in the FG loop and a three residue deletion (residues 82-84) in the FG loop, and five variegated residues (residues 26-30) in the BC loop, was prepared. The shorter FG loop was made in an attempt to reduce the flexibility of the FG loop; the loop was shown to be highly flexible in Fn3 by the NMR studies of Main, et al. (1992). A highly flexible loop may be disadvantageous to forming a binding site with a high affinity (a large entropy loss is expected upon the ligand binding, because the flexible loop should become more rigid). In addition, other Fn3 domains (besides human) have shorter FG loops (for sequence alignment, see FIG. 12 in Dickinson, et al. (1994)).

Randomization was achieved by the use of oligonucleotides containing degenerate nucleotide sequence (oligonucleotide BC3 for variegating the BC loop and oligonucleotides FG2 and FG4 for variegating the FG loops).

Site-directed mutagenesis was performed following published methods (see for example, Kunkel, 1985). The libraries were constructed by electrotransforming *E. coli* XL-1 Blue (Stratagene). Typically a library contains $10^8$ to $10^9$ independent clones. Library 2 contains five variegated residues in the BC loop and seven variegated residues in the FG loop. Library 4 contains five variegated residues in each of the BC and FG loops, and the length of the FG loop was shortened by three residues.

EXAMPLE VII fd Phage Display Libraries Constructed With Loop Variegations

Phage display libraries are constructed using the fd phage as the genetic vector. The Fn3 gene is inserted in fUSE5 (Parmley & Smith, 1988) using SfiI restriction sites which are introduced at the 5' and 3' ends of the Fn3 gene using PCR. The expression of this phage results in the display of the fusion pIII protein on the surface of the fd phage. Variegations in the Fn3 loops are introduced using site-directed mutagenesis as described hereinabove, or by subcloning the Fn3 libraries constructed in M13 phage into the fUSE5 vector.

EXAMPLE VIII

Other Phage Display Libraries

T7 phage libraries (Novagen, Madison, Wis.) and bacterial pili expression systems (Invitrogen) are also useful to express the Fn3 gene.

EXAMPLE IX

Isolation of Polypeptides which Bind to Macromolecular Structures

The selection of phage-displayed monobodies was performed following the protocols of Barbas and coworkers (Rosenblum & Barbas, 1995). Briefly, approximately 1 µg of a target molecule ("antigen") in sodium carbonate buffer (100 mM, pH 8.5) was immobilized in the wells of a microtiter plate (Maxisorp, Nunc) by incubating overnight at 4° C. in an air tight container. After the removal of this solution, the wells were then blocked with a 3% solution of BSA (Sigma, Fraction V) in TBS by incubating the plate at 37° C. for 1 hour. A phagemid library solution (50 µl) containing approximately $10^{12}$ colony forming units (cfu) of phagemid was absorbed in each well at 37° C. for 1 hour. The wells were then washed with an appropriate buffer (typically TBST, 50 mM Tris-HCl (pH 7.5), 150 mM NaCl, and 0.5% Tween20) three times (once for the first round). Bound phage were eluted by an acidic solution (typically, 0.1 M glycine-HCl, pH 2.2; 50 µl) and recovered phage were immediately neutralized with 3 µl of Tris solution. Alternatively, bound phage were eluted by incubating the wells with 50 µl of TBS containing the antigen (1-10 µM). Recovered phage were amplified using the standard protocol employing the XL1Blue cells as the host (Sambrook, et al.). The selection process was repeated 5-6 times to concentrate positive clones. After the final round, individual clones were picked and their binding affinities and DNA sequences were determined.

The binding affinities of monobodies on the phage surface were characterized using the phage ELISA technique (Li, et al., 1995). Wells of microtiter plates (Nunc) were coated with an antigen and blocked with BSA. Purified phages ($10^8$-$10^{11}$ cfu) originating from a single colony were added to each well and incubated 2 hours at 37° C. After washing wells with an appropriate buffer (see above), bound phage were detected by the standard ELISA protocol using anti-M13 antibody (rabbit, Sigma) and anti-rabbit Ig-peroxidase conjugate (Pierce). Colorimetric assays were performed using Turbo-TMB (3,3', 5,5'-tetramethylbenzidine, Pierce) as a substrate.

The binding affinities of monobodies on the phage surface were further characterized using the competition ELISA method (Djavadi-Ohaniance, et al., 1996). In this experiment, phage ELISA is performed in the same manner as described above, except that the phage solution contains a ligand at varied concentrations. The phage solution was incubated a 4° C. for one hour prior to the binding of an immobilized ligand in a microtiter plate well. The affinities of phage displayed monobodies are estimated by the decrease in ELISA signal as the free ligand concentration is increased.

After preliminary characterization of monobodies displayed on the surface of phage using phage ELISA, genes for positive clones were subcloned into the expression vector pAS45. *E. coli* BL21(DE3) (Novagen) was transformed with an expression vector (pAS45 and its derivatives). Cells were grown in M9 minimal medium and M9 medium supplemented with Bactotryptone (Difco) containing ampicillin (200 µg/ml). For isotopic labeling, $^{15}N$ $NH_4Cl$ and/or $^{13}C$ glucose replaced unlabeled components. Stable isotopes were purchased from Isotec and Cambridge Isotope Labs. 500 ml medium in a 2 l baffle flask was inoculated with 10 ml of overnight culture and agitated at approximately 140 rpm at 37° C. IPTG was added at a final concentration of 1 mM to induce protein expression when OD (600 nm) reached approximately 1.0. The cells were harvested by centrifugation 3 hours after the addition of IPTG and kept frozen at -70° C. until used.

Fn3 and monobodies with His•tag were purified as follows. Cells were suspended in 5 ml/(g cell) of 50 mM Tris (pH 7.6) containing 1 mM phenylmethylsulfonyl fluoride. HEL (Sigma, 3× crystallized) was added to a final concentration of 0.5 mg/ml. After incubating the solution for 30 min at 37° C., it was sonicated so as to cause cell breakage three times for 30 seconds on ice. Cell debris was removed by centrifugation at 15,000 rpm in an Sorval RC-2B centrifuge using an SS-34 rotor. Concentrated sodium chloride is added to the solution to a final concentration of 0.5 M. The solution was then applied to a 1 ml HisTrap™ chelating column (Pharmacia) preloaded with nickel chloride (0.1 M, 1 ml) and equilibrated in the Tris buffer (50 mM, pH 8.0) containing 0.5 M sodium chloride. After washing the column with the buffer, the bound protein was eluted with a Tris buffer (50 mM, pH 8.0) containing 0.5 M imidazole. The His•tag portion was cleaved off, when required, by treating the fusion protein with thrombin using the protocol supplied by Novagen (Madison, Wis.). Fn3 was separated from the His•tag peptide and thrombin by a Resources® column (Pharmacia) using a linear gradient of sodium chloride (0-0.5 M) in sodium acetate buffer (20 mM, pH 5.0).

Small amounts of soluble monobodies were prepared as follows. XL-1 Blue cells containing pAS38 derivatives (plasmids coding Fn3-pIII fusion proteins) were grown in LB media at 37° C. with vigorous shaking until OD (600 nm) reached approximately 1.0; IPTG was added to the culture to a final concentration of 1 mM, and the cells were further grown overnight at 37° C. Cells were removed from the medium by centrifugation, and the supernatant was applied to a microtiter well coated with a ligand. Although XL-1 Blue cells containing pAS38 and its derivatives express FN3-pIII fusion proteins, soluble proteins are also produced due to the cleavage of the linker between the Fn3 and pIII regions by proteolytic activities of *E. coli* (Rosenblum & Barbas, 1995). Binding of a monobody to the ligand was examined by the standard ELISA protocol using a custom antibody against Fn3 (purchased from Cocalico Biologicals, Reamstown, Pa.). Soluble monobodies obtained from the periplasmic fraction of *E. coli* cells using a standard osmotic shock method were also used.

EXAMPLE X

Ubiquitin Binding Monobody

Ubiquitin is a small (76 residue) protein involved in the degradation pathway in eurkaryotes. It is a single domain globular protein. Yeast ubiquitin was purchased from Sigma Chemical Company and was used without further purification.

Libraries 2 and 4, described in Example VI above, were used to select ubiquitin-binding monobodies. Ubiquitin (1 µg in 50 µl sodium bicarbonate buffer (100 mM, pH 8.5)) was immobilized in the wells of a microtiter plate, followed by blocking with BSA (3% in TBS). Panning was performed as described above. In the first two rounds, 1 µg of ubiquitin was immobilized per well, and bound phage were elute with an acidic solution. From the third to the sixth rounds, 0.1 µg of ubiquitin was immobilized per well and the phage were eluted either with an acidic solution or with TBS containing 10 µM ubiquitin.

Figure 9:
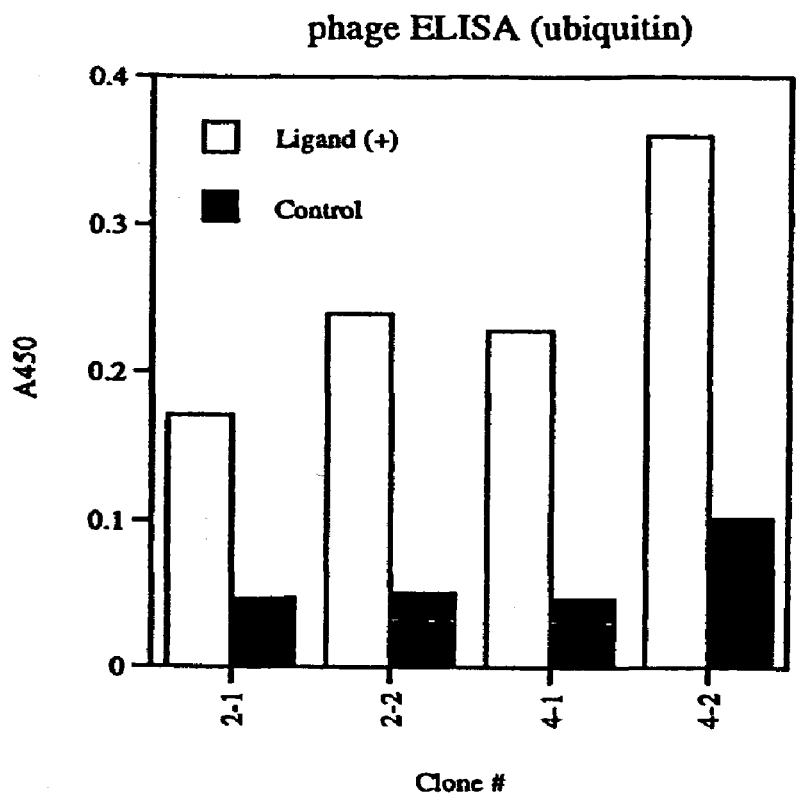
FIG. 9. (Ubiquitin-1) Characterization of ligand-specific binding of enriched clones using phage enzyme-linked immunosolvent assay (ELISA). Microtiter plate wells were coated with ubiquitin (1 µg/well; "Ligand (+)") and then blocked with BSA. Phage solution in TBS containing approximately $10^{10}$ colony forming units (cfu) was added to a well and washed with TBS. Bound phages were detected with anti-phage antibody-POD conjugate (Pharmacia) with Turbo-TMB (Pierce) as a substrate. Absorbance was measured using a Molecular Devices SPECTRAmax 250 microplate spectrophotometer. For a control, wells without immobilized ligand were used. 2-1 and 2-2 denote enriched clones from Library 2 eluted with free ligand and acid, respectively. 4-1 and 4-2 denote enriched clones from Library 4 eluted with free ligand and acid, respectively.
Figure 10:
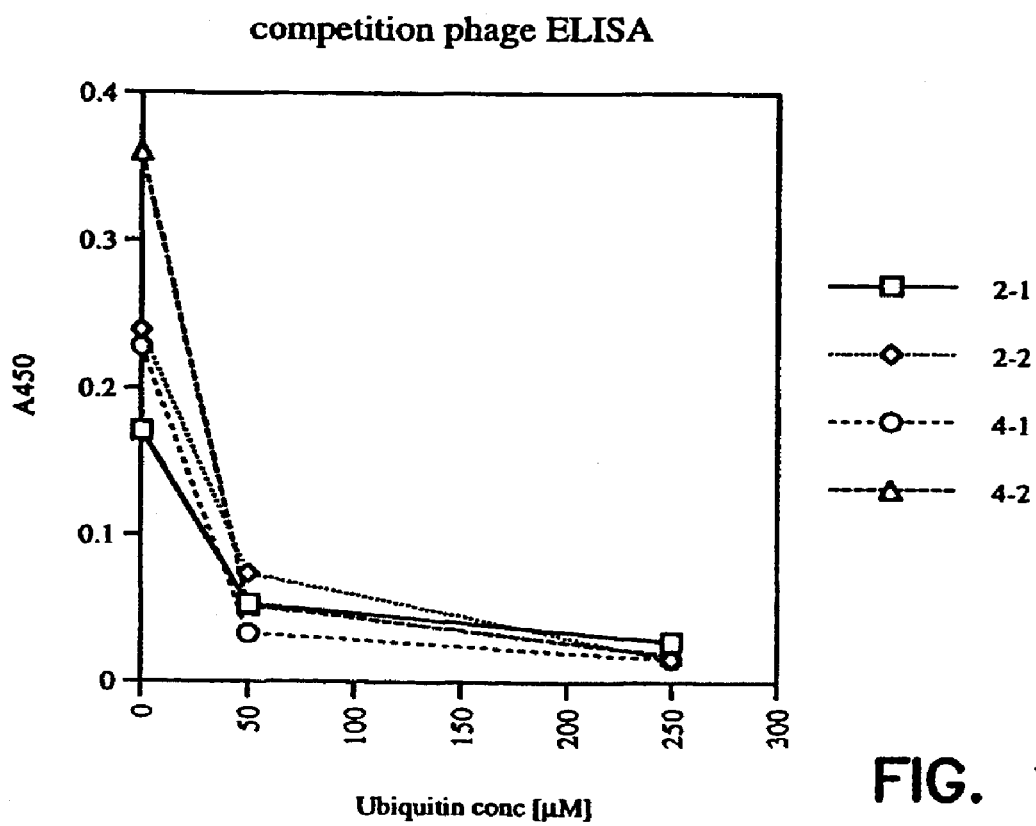
FIG. 10. (Ubiquitin-2) Competition phage ELISA of enriched clones. Phage solutions containing approximately $10^{10}$ cfu were first incubated with free ubiquitin at 4° C. for 1 hour prior to the binding to a ligand-coated well. The wells were washed and phages detected as described above.

Binding of selected clones was tested first in the polyclonal mode, i.e., before isolating individual clones. Selected clones from all libraries showed significant binding to ubiquitin. These results are shown in FIG. 9. The binding to the immobilized ubiquitin of the clones was inhibited almost completely by less than 30 µM soluble ubiquitin in the competition ELISA experiments (see FIG. 10). The sequences of the BC and FG loops of ubiquitin-binding monobodies is shown in Table 4.

TABLE 4

Sequences of ubiquitin-binding monobodies

| Name | BC loop | FG loop | Occurrence (if more than one) |
|------|---------|---------|-------------------------------|
| 211 | CARRA (SEQ ID NO: 31) | RWIPLAK (SEQ ID NO: 32) | 2 |
| 212 | CWRRA (SEQ ID NO: 33) | RWVGLAW (SEQ ID NO: 34) | |
| 213 | CKHRR (SEQ ID NO: 35) | FADLWWR (SEQ ID NO: 36) | |
| 214 | CRRGR (SEQ ID NO: 37) | RGFMWLS (SEQ ID NO: 38) | |
| 215 | CNWRR (SEQ ID NO: 39) | RAYRYRW (SEQ ID NO: 40) | |
| 411 | SRLRR (SEQ ID NO: 41) | PPWRV (SEQ ID NO: 42) | 9 |
| 422 | ARWTL (SEQ ID NO: 43) | RRWWW (SEQ ID NO: 44) | |

TABLE 4-continued

Sequences of ubiquitin-binding monobodies

| Name | BC loop | FG loop | Occurrence (if more than one) |
|------|---------|---------|-------------------------------|
| 424 | GQRTF (SEQ ID NO: 45) | RRWWA (SEQ ID NO: 46) | |

Figure 11:
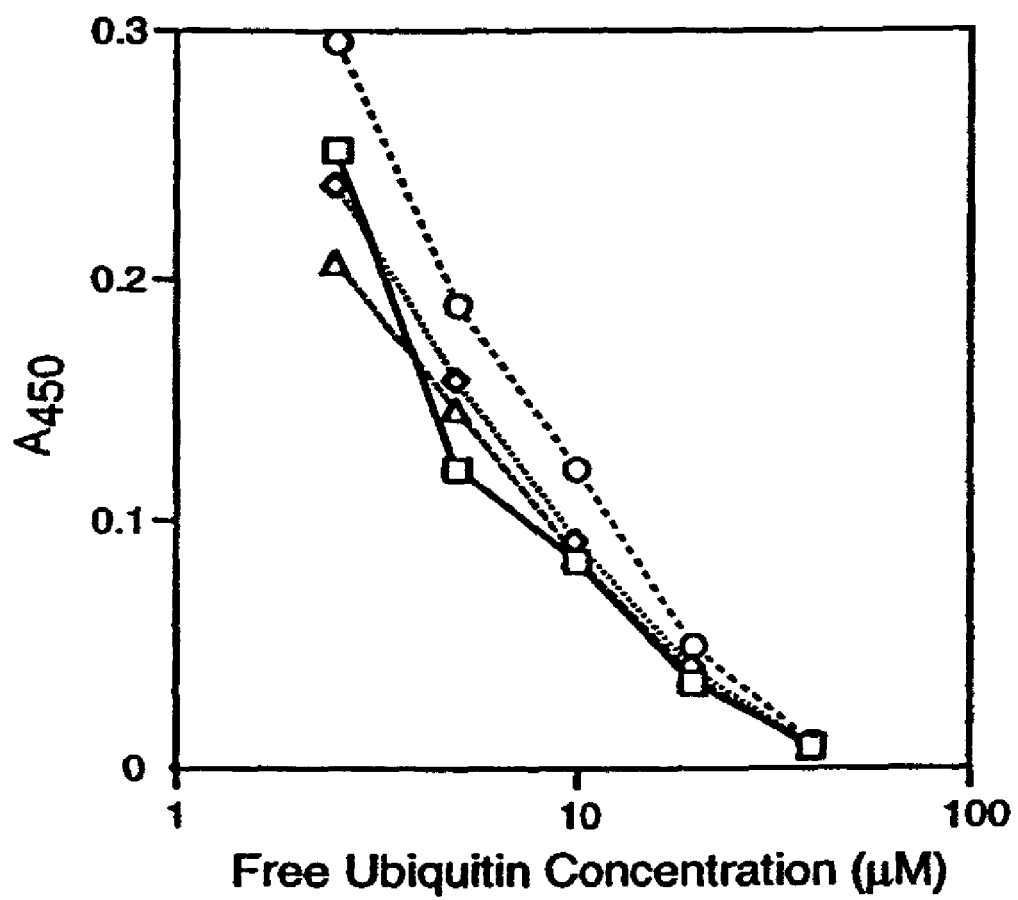
FIG. 11. Competition phage ELISA of ubiquitin-binding monobody 411. Experimental conditions are the same as described above for ubiquitin. The ELISA was performed in the presence of free ubiquitin in the binding solution. The experiments were performed with four different preparations of the same clone.

The 411 clone, which was the most enriched clone, was characterized using phage ELISA. The 411 clone showed selective binding and inhibition of binding in the presence of about 10 µM ubiquitin in solution (FIG. 11).

EXAMPLE XI

Methods for the Immobilization of Small Molecules

Target molecules were immobilized in wells of a microtiter plate (Maxisorp, Nunc) as described hereinbelow, and the wells were blocked with BSA. In addition to the use of carrier protein as described below, a conjugate of a target molecule in biotin can be made. The biotinylated ligand can then be immobilized to a microtiter plate well which has been coated with streptavidin.

In addition to the use of a carrier protein as described below, one could make a conjugate of a target molecule and biotin (Pierce) and immobilize a biotinylated ligand to a microtiter plate well which has been coated with streptavidin (Smith and Scott, 1993).

Small molecules may be conjugated with a carrier protein such as bovine serum albumin (BSA, Sigma), and passively adsorbed to the microtiter plate well. Alternatively, methods of chemical conjugation can also be used. In addition, solid supports other than microtiter plates can readily be employed.

EXAMPLE XII

Fluorescein Binding Monobody

Fluorescein has been used as a target for the selection of antibodies from combinatorial libraries (Barbas, et al. 1992). NHS-fluorescein was obtained from Pierce and used according to the manufacturer's instructions in preparing conjugates with BSA (Sigma). Two types of fluorescein-BSA conjugates were prepared with approximate molar ratios of 17 (fluorescein) to one (BSA).

The selection process was repeated 5-6 times to concentrate positive clones. In this experiment, the phage library was incubated with a protein mixture (BSA, cytochrome C (Sigma, Horse) and RNaseA (Sigma, Bovine), 1 mg/ml each) at room temperature for 30 minutes, prior to the addition to ligand coated wells. Bound phage were eluted in TBS containing 10 µM soluble fluorescein, instead of acid elution. After the final round, individual clones were picked and their binding affinities (see below) and DNA sequences were determined.

TABLE 5

| | BC | | FG | |
|---|----|----|----|----|
| | Clones from Library #2 | | | |
| WT | AVTVR | (SEQ ID NO: 47) | RGDSPAS | (SEQ ID NO: 48) |
| pLB24.1 | CNWRR | (SEQ ID NO: 49) | RAYRYRW | (SEQ ID NO: 50) |
| pLB24.2 | CMWRA | (SEQ ID NO: 51) | RWGMLRR | (SEQ ID NO: 52) |
| pLB24.3 | ARMRE | (SEQ ID NO: 53) | RWLRGRY | (SEQ ID NO: 54) |
| pLB24.4 | CARRR | (SEQ ID NO: 55) | RRAGWGW | (SEQ ID NO: 56) |
| pLB24.5 | CNWRR | (SEQ ID NO: 57) | RAYRYRW | (SEQ ID NO: 58) |
| pLB24.6 | RWRER | (SEQ ID NO: 59) | RHPWTER | (SEQ ID NO: 60) |

TABLE 5-continued

|  |  | BC |  | FG |  |
|---|---|---|---|---|---|
| pLB24.7 | CNWRR | (SEQ ID NO: 61) | RAYRYRW | (SEQ ID NO: 62) |
| pLB24.8 | ERRVP | (SEQ ID NO: 63) | RLLLWQR | (SEQ ID NO: 64) |
| pLB24.9 | GRGAG | (SEQ ID NO: 65) | FGSFERR | (SEQ ID NO: 66) |
| pLB24.11 | CRWTR | (SEQ ID NO: 67) | RRWFDGA | (SEQ ID NO: 68) |
| pLB24.12 | CNWRR | (SEQ ID NO: 69) | RAYRYRW | (SEQ ID NO: 70) |
| | | Clones from Library #4 | | |
| WT | AVTVR | (SEQ ID NO: 71) | GRGDS | (SEQ ID NO: 72) |
| pLB25.1 | GQRTF | (SEQ ID NO: 73) | RRWWA | (SEQ ID NO: 74) |
| pLB25.2 | GQRTF | (SEQ ID NO: 75) | RRWWA | (SEQ ID NO: 76) |
| pLB25.3 | GQRTF | (SEQ ID NO: 77) | RRWWA | (SEQ ID NO: 78) |
| pLB25.4 | LRYRS | (SEQ ID NO: 79) | GWRWR | (SEQ ID NO: 80) |
| pLB25.5 | GQRTF | (SEQ ID NO: 81) | RRWWA | (SEQ ID NO: 82) |
| pLB25.6 | GQRTF | (SEQ ID NO: 83) | RRWWA | (SEQ ID NO: 84) |
| pLB25.7 | LRYRS | (SEQ ID NO: 85) | GWRWR | (SEQ ID NO: 86) |
| pLB25.9 | LRYRS | (SEQ ID NO: 87) | GWRWR | (SEQ ID NO: 88) |
| pLB25.11 | GQRTF | (SEQ ID NO: 89) | RRWWA | (SEQ ID NO: 90) |
| pLB25.12 | LRYRS | (SEQ ID NO: 91) | GWRWR | (SEQ ID NO: 92) |

Figure 13:
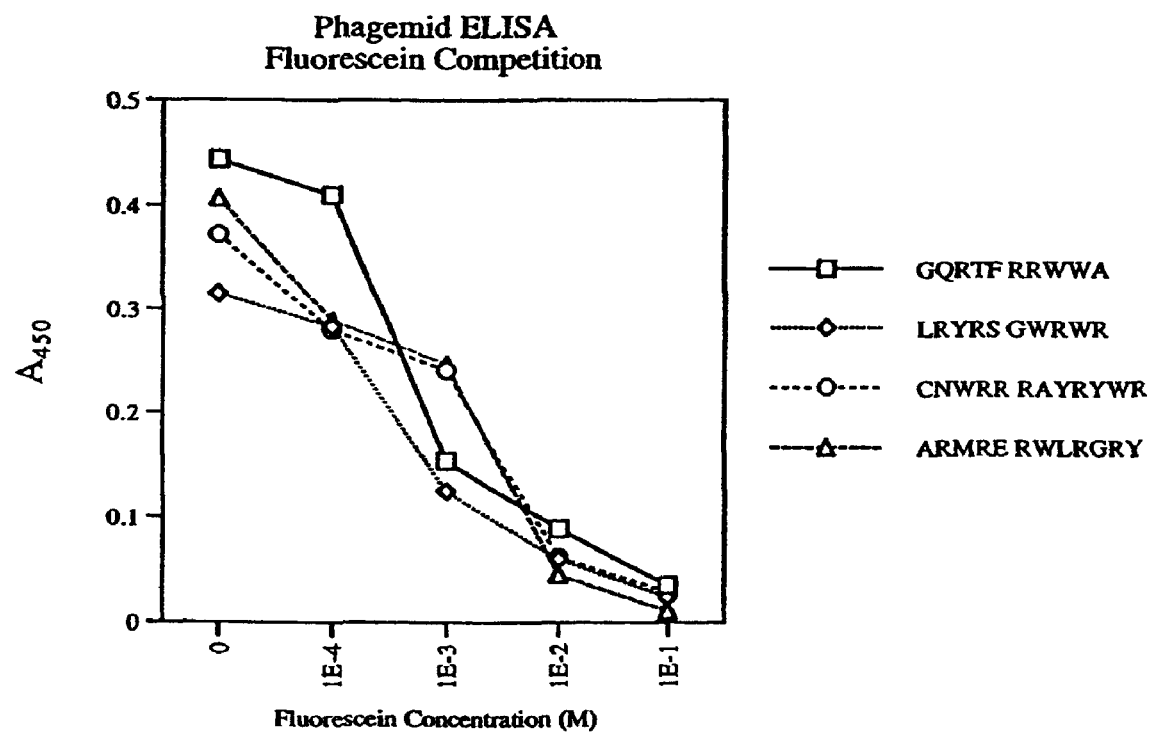
FIG. 13. (Fluorescein-2) Competition ELISA of the four clones (SEQ ID Nos:115-118). Experimental conditions are the same as ubiquitin-2 above.

Preliminary characterization of the binding affinities of selected clones were performed using phage ELISA and competition phage ELISA (see FIG. 12 (Fluorescein-1) and FIG. 13 (Fluorescein-2)). The four clones tested showed specific binding to the ligand-coated wells, and the binding reactions are inhibited by soluble fluorescein (see FIG. 13).

EXAMPLE XIII

Digoxigenin Binding Monobody

Digoxigenin-3-O-methyl-carbonyl-e-aminocaproic acid-NHS (Boehringer Mannheim) is used to prepare a digoxigenin-BSA conjugate. The coupling reaction is performed following the manufacturers' instructions. The digoxigenin-BSA conjugate is immobilized in the wells of a microtiter plate and used for panning. Panning is repeated 5 to 6 times to enrich binding clones. Because digoxigenin is sparingly soluble in aqueous solution, bound phages are eluted from the well using acidic solution. See Example XIV.

EXAMPLE XIV

TSAC (Transition State Analog Compound) Binding Monobodies

Carbonate hydrolyzing monobodies are selected as follows. A transition state analog for carbonate hydrolysis, 4-nitrophenyl phosphonate is synthesized by an Arbuzov reaction as described previously (Jacobs and Schultz, 1987). The phosphonate is then coupled to the carrier protein, BSA, using carbodiimide, followed by exhaustive dialysis (Jacobs and Schultz, 1987). The hapten-BSA conjugate is immobilized in the wells of a microtiter plate and monobody selection is performed as described above. Catalytic activities of selected monobodies are tested using 4-nitrophenyl carbonate as the substrate.

Other haptens useful to produce catalytic monobodies are summarized in H. Suzuki (1994) and in N. R. Thomas (1994).

EXAMPLE XV

NMR Characterization of Fn3 and Comparison of the Fn3 Secreted by Yeast with that Secreted by *E. Coli*

Nuclear magnetic resonance (NMR) experiments are performed to identify the contact surface between FnAb and a target molecule, e.g., monobodies to fluorescein, ubiquitin, RNaseA and soluble derivatives of digoxigenin. The information is then be used to improve the affinity and specificity of the monobody. Purified monobody samples are dissolved in an appropriate buffer for NMR spectroscopy using Amicon® ultrafiltration cell with a YM-3 membrane. Buffers are made with 90% $H_2O$/10% $D_2O$ (distilled grade, Isotec) or with 100% $D_2O$. Deuterated compounds (e.g. acetate) are used to eliminate strong signals from them.

NMR experiments are performed on a Varian Unity INOVA 600 spectrometer equipped with four RF channels and a triple resonance probe with pulsed field gradient capability. NMR spectra are analyzed using processing programs such as Felix (Molecular Simulations), nmrPipe, PIPP, and CAPP (Garrett, et al., 1991; Delaglio, et al., 1995) on UNIX workstations. Sequence specific resonance assignments are made using well-established strategy using a set of triple resonance experiments (CBCA(CO)NH and HNCACB) (Grzesiek & Bax, 1992; Wittenkind & Mueller, 1993).

Nuclear Overhauser effect (NOE) is observed between $^1H$ nuclei closer than approximately 5 Å, which allows one to obtain information on interproton distances. A series of double- and triple-resonance experiments (Table 6; for recent reviews on these techniques, see Bax & Grzesiek, 1993 and Kay, 1995) are performed to collect distance (i.e. NOE) and dihedral angle (J-coupling) constraints. Isotope-filtered experiments are performed to determine resonance assignments of the bound ligand and to obtain distance constraints within the ligand and those between FnAb and the ligand. Details of sequence specific resonance assignments and NOE peak assignments have been described in detail elsewhere (Clore & Gronenborn, 1991; Pascal, et al., 1994b; Metzler, et al., 1996).

TABLE 6

NMR experiments for structure characterization

| Experiment Name | Reference |
|---|---|
| 1. reference spectra | |
| 2D-$^1H$, $^{15}N$-HSQC | (Bodenhausen & Ruben, 1980; Kay, et al., 1992) |
| 2D-$^1H$, $^{13}C$-HSQC | (Bodenhausen & Ruben, 1980; Vuister & Bax, 1992) |

TABLE 6-continued

NMR experiments for structure characterization

| Experiment Name | Reference |
|---|---|
| 2. backbone and side chain resonance assignments of $^{13}C/^{15}N$-labeled protein | |
| 3D-CBCA(CO)NH | (Grzesiek & Bax, 1992) |
| 3D-HNCACB | (Wittenkind & Mueller, 1993) |
| 3D-C(CO)NH | (Logan et al., 1992; Grzesiek et al., 1993) |
| 3D-H(CCO)NH | |
| 3D-HBHA(CBCACO)NH | (Grzesiek & Bax, 1993) |
| 3D-HCCH-TOCSY | (Kay et al., 1993) |
| 3D-HCCH-COSY | (Ikura et al., 1991) |
| 3D-$^1$H, $^{15}$N-TOCSY-HSQC | (Zhang et al., 1994) |
| 2D-HB(CBCDCE)HE | (Yamazaki et al., 1993) |
| 3. resonance assignments of unlabeled ligand | |
| 2D-isotope-filtered $^1$H-TOCSY | |
| 2D-isotope-filtered $^1$H-COSY | |
| 2D-isotope-filtered $^1$H-NOESY | (Ikura & Bax, 1992) |
| 4. structural constraints within labeled protein | |
| 3D-$^1$H, $^{15}$N-NOESY-HSQC | (Zhang et al., 1994) |
| 4D-$^1$H, $^{13}$C-HMQC-NOESY-HMQC | (Vuister et al., 1993) |
| 4D-$^1$H, $^{13}$C, $^{15}$N-HSQC-NOESY-HSQC | (Muhandiram et al., 1993; Pascal et al., 1994a) |
| within unlabeled ligand | |
| 2D-isotope-filtered $^1$H-NOESY | (Ikura & Bax, 1992) |
| interactions between protein and ligand | |
| 3D-isotope-filtered $^1$H, $^{15}$N-NOESY-HSQC | |
| 3D-isotope-filtered $^1$H, $^{13}$C-NOESY-HSQC | (Lee et al., 1994) |
| 5. dihedral angle constraints | |
| J-molulated $^1$H, $^{15}$N-HSQC | (Billeter et al., 1992) |
| 3D-HNHB | (Archer et al., 1991) |

Backbone $^1$H, $^{15}$N and $^{13}$C resonance assignments for a monobody are compared to those for wild-type Fn3 to assess structural changes in the mutant. Once these data establish that the mutant retains the global structure, structural refinement is performed using experimental NOE data. Because the structural difference of a monobody is expected to be minor, the wild-type structure can be used as the initial model after modifying the amino acid sequence. The mutations are introduced to the wild-type structure by interactive molecular modeling, and then the structure is energy-minimized using a molecular modeling program such as Quanta (Molecular Simulations). Solution structure is refined using cycles of dynamical simulated annealing (Nilges et al., 1988) in the program X-PLOR (Brünger, 1992). Typically, an ensemble of fifty structures is calculated. The validity of the refined structures is confirmed by calculating a fewer number of structures from randomly generated initial structures in X-PLOR using the YASAP protocol (Nilges, et al., 1991). Structure of a monobody-ligand complex is calculated by first refining both components individually using intramolecular NOEs, and then docking the two using intermolecular NOEs.

Figure 14:
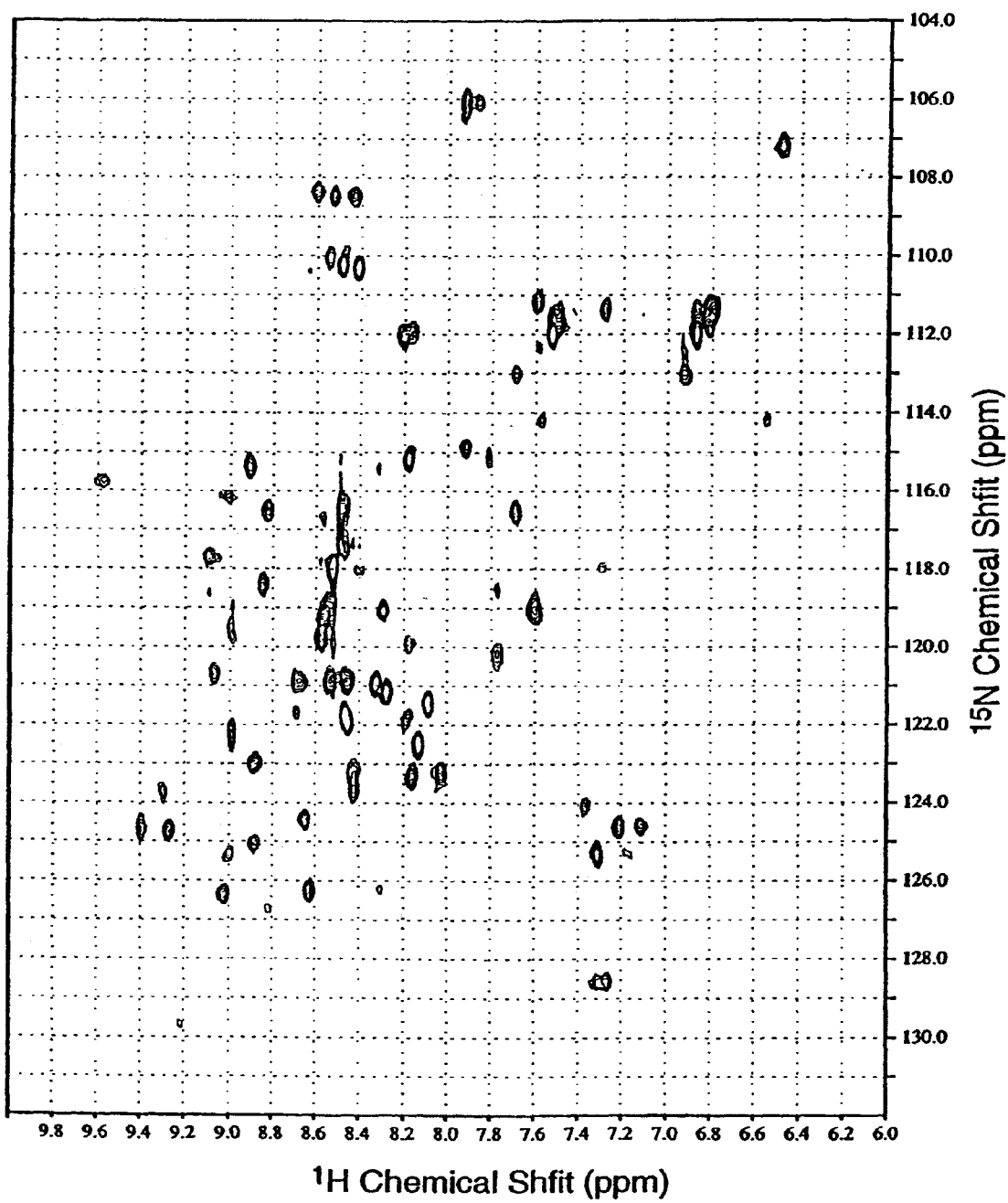
FIG. 14. $^1$H, $^{15}$N-HSQC spectrum of a fluorescence-binding monobody LB25.5. Approximately 20 µM protein was dissolved in 10 mM sodium acetate buffer (pH 5.0) containing 100 mM sodium chloride. The spectrum was collected at 30° C. on a Varian Unity INOVA 600 NMR spectrometer.

For example, the $^1$H, $^{15}$N-HSQC spectrum for the fluorescein-binding monobody LB25.5 is shown in FIG. 14. The spectrum shows a good dispersion (peaks are spread out) indicating that LB25.5 is folded into a globular conformation. Further, the spectrum resembles that for the wild-type Fn3, showing that the overall structure of LB25.5 is similar to that of Fn3. These results demonstrate that ligand-binding monobodies can be obtained without changing the global fold of the Fn3 scaffold.

Chemical shift perturbation experiments are performed by forming the complex between an isotope-labeled FnAb and an unlabeled ligand. The formation of a stoichiometric complex is followed by recording the HSQC spectrum. Because chemical shift is extremely sensitive to nuclear environment, formation of a complex usually results in substantial chemical shift changes for resonances of amino acid residues in the interface. Isotope-edited NMR experiments (2D HSQC and 3D CBCA(CO)NH) are used to identify the resonances that are perturbed in the labeled component of the complex; i.e. the monobody. Although the possibility of artifacts due to long-range conformational changes must always be considered, substantial differences for residues clustered on continuous surfaces are most likely to arise from direct contacts (Chen et al., 1993; Gronenborn & Clore, 1993).

An alternative method for mapping the interaction surface utilizes amide hydrogen exchange (HX) measurements. HX rates for each amide proton are measured for $^{15}$N labeled monobody both free and complexed with a ligand. Ligand binding is expected to result in decreased amide HX rates for monobody residues in the interface between the two proteins, thus identifying the binding surface. HX rates for monobodies in the complex are measured by allowing HX to occur for a variable time following transfer of the complex to $D_2O$; the complex is dissociated by lowering pH and the HSQC spectrum is recorded at low pH where amide HX is slow. Fn3 is stable and soluble at low pH, satisfying the prerequisite for the experiments.

EXAMPLE XVI

Construction and Analysis of Fn3-Display System Specific for Ubiquitin

An Fn3-display system was designed and synthesized, ubiquitin-binding clones were isolated and a major Fn3 mutant in these clones was biophysically characterized.

Gene construction and phage display of Fn3 was performed as in Examples I and II above. The Fn3-phage pIII fusion protein was expressed from a phagemid-display vector, while the other components of the M13 phage, including the wild-type pIII, were produced using a helper phage (Bass et al., 1990). Thus, a phage produced by this system should contain less than one copy of Fn3 displayed on the surface. The surface display of Fn3 on the phage was detected by ELISA using an anti-Fn3 antibody. Only phages containing the Fn3-pIII fusion vector reacted with the antibody.

After confirming the phage surface to display Fn3, a phage display library of Fn3 was constructed as in Example III. Random sequences were introduced in the BC and FG loops. In the first library, five residues (77-81) were randomized and three residues (82-84) were deleted from the FG loop. The deletion was intended to reduce the flexibility and improve the binding affinity of the FG loop. Five residues (26-30) were also randomized in the BC loop in order to provide a larger contact surface with the target molecule. Thus, the resulting library contains five randomized residues in each of the BC and FG loops (Table 7). This library contained approximately $10^8$ independent clones.

Library Screening

Library screening was performed using ubiquitin as the target molecule. In each round of panning, Fn3-phages were absorbed to a ubiquitin-coated surface, and bound phages were eluted competitively with soluble ubiquitin. The recovery ratio improved from $4.3 \times 10^{-7}$ in the second round to $4.5 \times 10^6$ in the fifth round, suggesting an enrichment of binding clones. After five founds of panning, the amino acid sequences of individual clones were determined (Table 7).

TABLE 7

Sequences in the variegated loops of enriched clones

| Name | BC loop | FG loop | Frequency |
|---|---|---|---|
| Wild Type | GCAGTTACCGTGCGT (SEQ ID NO: 93) AlaValThrValArg (SEQ ID NO: 94) | GGCCGTGGTGACAGC CCAGCGAGC (SEQ ID NO: 95) GlyArgGlyAspSer ProAlaSer (SEQ ID NO: 96) | — |
| Library[a] | NNKNNKNNKNNKNNK X X X X X | NNKNNKNNKNNKNNK- --------X X X X X (deletion) | — |
| clone1 (Ubi4) | TCGAGGTTGCGGCGG (SEQ ID NO: 97) SerArgLeuArgArg (SEQ ID NO: 98) | CCGCCGTGGAGGGTG (SEQ ID NO: 99) ProProTrpArgVal (SEQ ID NO: 100) | 9 |
| clone2 | GGTCAGCGAACTTTT (SEQ ID NO: 101) GlyGlnArgThrPhe (SEQ ID NO: 102) | AGGCGGTGGTGGGCT (SEQ ID NO: 103) ArgArgTrpTrpAla (SEQ ID NO: 104) | 1 |
| clone3 | GCGAGGTGGACGCTT (SEQ ID NO: 105) AlaArgTrpThrLeu (SEQ ID NO: 106) | AGGCGGTGGTGGTGG (SEQ ID NO: 107) ArgArgTrpTrpTrp (SEQ ID NO: 108) | 1 |

[a]N denotes an equimolar mixture of A, T, G and C; K denotes an equimolar mixture of G and T.

A clone, dubbed Ubi4, dominated the enriched pool of Fn3 variants. Therefore, further investigation was focused on this Ubi4 clone. Ubi4 contains four mutations in the BC loop (Arg 30 in the BC loop was conserved) and five mutations and three deletions in the FG loop. Thus 13% (12 out of 94) of the residues were altered in Ubi4 from the wild-type sequence.

Figures 15C, 15D:
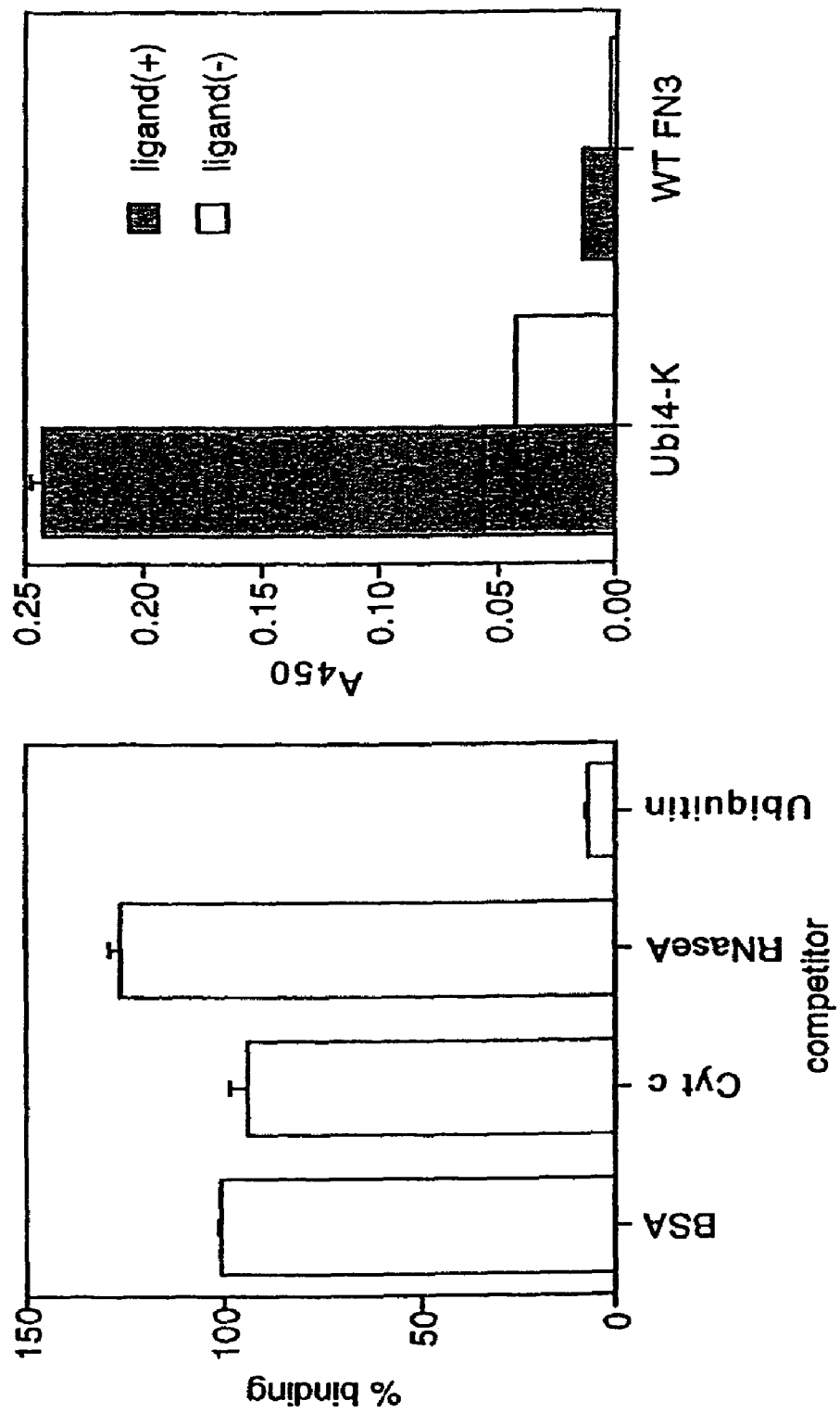
FIG. 15. Characterization of the binding reaction of Ubi4-Fn3 to the target, ubiquitin. (a) Phage ELISA analysis of binding of Ubi4-Fn3 to ubiquitin. The binding of Ubi4-phages to ubiquitin-coated wells was measured. The control experiment was performed with wells containing no ubiquitin.

FIG. 15 shows a phage ELISA analysis of Ubi4. The Ubi4 phage binds to the target molecule, ubiquitin, with a significant unity, while a phage displaying the wild-type Fn3 domain or a phase with no displayed molecules show little detectable binding to ubiquitin (FIG. 15a). In addition, the Ubi4 phage showed a somewhat elevated level of background binding to the control surface lacking the ubiquitin coating. A competition ELISA experiments shows the $IC_{50}$ (concentration of the free ligand which causes 50% inhibition of binding) of the binding reaction is approximately 5 μM (FIG. 15b). BSA, bovine ribonuclease A and cytochrome C show little inhibition of the Ubi4-ubiquitin binding reaction (FIG. 15c), indicating that the binding reaction of Ubi4 to ubiquitin does result from specific binding.

Characterization of a Mutant Fn3 Protein

The expression system yielded 50-100 mg Fn3 protein per liter culture. A similar level of protein expression was observed for the Ubi4 clone and other mutant Fn3 proteins.

Ubi4-Fn3 was expressed as an independent protein. Though a majority of Ubi4 was expressed in *E. coli* as a soluble protein, its solubility was found to be significantly reduced as compared to that of wild-type Fn3. Ubi4 was soluble up to ~20 μM at low pH, with much lower solubility at neutral pH. This solubility was not high enough for detailed structural characterization using NMR spectroscopy or X-ray crystallography.

The solubility of the Ubi4 protein was improved by adding a solubility tail, GKKGK (SEQ ID NO:109), as a C-terminal extension. The gene for Ubi4-Fn3 was subcloned into the expression vector pAS45 using PCR. The C-terminal solubilization tag, GKKGK (SEQ ID NO:109), was incorporated in this step. *E. coli* BL21 (DE3) (Novagen) was transformed with the expression vector (pAS45 and its derivatives). Cells were grown in M9 minimal media and M9 media supplemented with Bactotryptone (Difco) containing ampicillin (200 μg/ml). For isotopic labeling, $^{15}N$ $NH_4Cl$ replaced unlabeled $NH_4Cl$ in the media. 500 ml medium in a 2 liter baffle flask was inoculated with 10 ml of overnight culture and agitated at 37° C. IPTG was added at a final concentration of 1 mM to initiate protein expression when OD (600 nm) reaches one. The cells were harvested by centrifugation 3 hours after the addition of IPTG and kept frozen at −70° C. until used.

Proteins were purified as follows. Cells were suspended in 5 ml/(g cell) of Tris (50 mM, pH 7.6) containing phenylmethylsulfonyl fluoride (1 mM). Hen egg lysozyme (Sigma) was added to a final concentration of 0.5 mg/ml. After incubating the solution for 30 minutes at 37° C., it was sonicated three times for 30 seconds on ice. Cell debris was removed by centrifugation. Concentrated sodium chloride was added to the solution to a final concentration of 0.5 M. The solution was applied to a Hi-Trap™ chelating column (Pharmacia) preloaded with nickel and equilibrated in the Tris buffer containing sodium chloride (0.5 M). After washing the column with the buffer, histag-Fn3 was eluted with the buffer containing 500 mM imidazole. The protein was further purified using a ResourceS column (Pharmacia) with a NaCl gradient in a sodium acetate buffer (20 mM, pH 4.6).

With the GKKGK (SEQ ID NO:109) tail, the solubility of the Ubi4 protein was increased to over 1 mM at low pH and up to ~50 μM at neutral pH. Therefore, further analyses were performed on Ubi4 with this C-terminal extension (hereafter referred to as Ubi4-K). It has been reported that the solubility of a minibody could be significantly improved by addition of three Lys residues at the − or C-termini (Bianchi et al., 1994). In the case of protein Rop, a non-structured C-terminal tail is critical in maintaining its solubility (Smith et al., 1995).

Oligomerization states of the Ubi4 protein were determined using a size exclusion column. The wild-type Fn3 protein was monomeric at low and neutral pH's. However, the peak of the Ubi4-K protein was significantly broader than that of wild-type Fn3, and eluted after the wild-type protein. This suggests interactions between Ubi4-K and the column material, precluding the use of size exclusion chromatography to determine the oligomerization state of Ubi4. NMR studies suggest that the protein is monomeric at low pH.

The Ubi4-K protein retained a binding affinity to ubiquitin as judged by ELISA (FIG. 15d). However, an attempt to determine the dissociation constant using a biosensor (Affinity Sensors, Cambridge, U.K.) failed because of high background binding of Ubi4-K-Fn3 to the sensor matrix. This matrix mainly consists of dextran, consistent with the observation that interactions between Ubi4K interacts with the cross-linked dextran of the size exclusion column.

EXAMPLE XVII

Stability Measurements of Monobodies

Guanidine hydrochloride (GuHCl)-induced unfolding and refolding reactions were followed by measuring tryptophan fluorescence. Experiments were performed on a Spectronic AB-2 spectrofluorometer equipped with a motor-driven syringe (Hamilton Co.). The cuvette temperature was kept at 30° C. The spectrofluorometer and the syringe were controlled by a single computer using a home-built interface.

This system automatically records a series of spectra following GuHCl titration. An experiment started with a 1.5 ml buffer solution containing 5 µM protein. An emission spectrum (300-400 nm; excitation at 290 nm) was recorded following a delay (3-5 minutes) after each injection (50 or 100 µl) of a buffer solution containing GuHCl. These steps were repeated until the solution volume reached the full capacity of a cuvette (3.0 ml). Fluorescence intensities were normalized as ratios to the intensity at an isofluorescent point which was determined in separate experiments. Unfolding curves were fitted with a two-state model using a nonlinear least-squares routine (Santoro & Bolen, 1988). No significant differences were observed between experiments with delay times (between an injection and the start of spectrum acquisition) of 2 minutes and 10 minutes, indicating that the unfolding/refolding reactions reached close to an equilibrium at each concentration point within the delay times used.

Conformational stability of Ubi4-K was measured using above-described GuHCl-induced unfolding method. The measurements were performed under two sets of conditions; first at pH 3.3 in the presence of 300 mM sodium chloride, where Ubi4-K is highly soluble, and second in TBS, which was used for library screening. Under both conditions, the unfolding reaction was reversible, and we detected no signs of aggregation or irreversible unfolding. FIG. 16 shows unfolding transitions of Ubi4-K and wild-type Fn3 with the N-terminal (his)$_6$ tag and the C-terminal solubility tag. The stability of wild-type Fn3 was not significantly affected by the addition of these tags. Parameters characterizing the unfolding transitions are listed in Table 8.

TABLE 8

Stability parameters for Ubi4 and wild-type Fn3 as determined by GuHCl-induced unfolding

| Protein | $\Delta G_0$ (kcal mol$^{-1}$) | $m_G$ (kcal mol$^{-1}$ M$^{-1}$) |
|---|---|---|
| Ubi4 (pH 7.5) | 4.8 ± 0.1 | 2.12 ± 0.04 |
| Ubi4 (pH 3.3) | 6.5 ± 0.1 | 2.07 ± 0.02 |
| Wild-type (pH 7.5) | 7.2 ± 0.2 | 1.60 ± 0.04 |
| Wild-type (pH 3.3) | 11.2 ± 0.1 | 2.03 ± 0.02 |

$\Delta G_0$ is the free energy of unfolding in the absence of denaturant;
$m_G$ is the dependence of the free energy of unfolding on GuHCl concentration. For solution conditions, see FIG. 4 caption.

Though the introduced mutations in the two loops certainly decreased the stability of Ubi4K relative to wild-type Fn3, the stability of Ubi4 remains comparable to that of a "typical" globular protein. It should also be noted that the stabilities of the wild-type and Ubi4-K proteins were higher at pH 3.3 than at pH 7.5.

The Ubi4 protein had a significantly reduced solubility as compared to that of wild-type Fn3, but the solubility was improved by the addition of a solubility tail. Since the two mutated loops include the only differences between the wild-type and Ubi4 proteins, these loops must be the origin of the reduced solubility. At this point, it is not clear whether the aggregation of Ubi4-K is caused by interactions between the loops, or by interactions between the loops and the invariable regions of the Fn3 scaffold.

The Ubi4-K protein retained the global fold of Fn3, showing that this scaffold can accommodate a large number of mutations in the two loops tested. Though the stability of the Ubi4-K protein is significantly lower than that of the wild-type Fn3 protein, the Ubi4 protein still has a conformational stability comparable to those for small globular proteins. The use of a highly stable domain as a scaffold is clearly advantageous for introducing mutations without affecting the global fold of the scaffold. In addition, the GuHCl-induced unfolding of the Ubi4 protein is almost completely reversible. This allows the preparation of a correctly folded protein even when a Fn3 mutant is expressed in a misfolded form, as in inclusion bodies. The modest stability of Ubi4 in the conditions used for library screening indicates that Fn3 variants are folded on the phage surface. This suggests that a Fn3 clone is selected by its binding affinity in the folded form, not in a denatured form. Dickinson et al. proposed that Val 29 and Arg 30 in the BC loop stabilize Fn3. Val 29 makes contact with the hydrophobic core, and Arg 30 forms hydrogen bonds with Gly 52 and Val 75. In Ubi4-Fn3, Val 29 is replaced with Arg, while Arg 30 is conserved. The FG loop was also mutated in the library. This loop is flexible in the wild-type structure, and shows a large variation in length among human Fn3 domains (Main et al., 1992). These observations suggest that mutations in the FG loop may have less impact on stability. In addition, the N-terminal tail of Fn3 is adjacent to the molecular surface formed by the BC and FG loops (FIGS. 1 and 17) and does not form a well-defined structure. Mutations in the N-terminal tail would not be expected to have strong detrimental effects on stability. Thus, residues in the N-terminal tail may be good sites for introducing additional mutations.

EXAMPLE XVIII

NMR Spectroscopy of Ubi4-Fn3

Ubi4-Fn3 was dissolved in [$^2$H]-Gly HCl buffer (20 mM, pH 3.3) containing NaCl (300 mM) using an Amicon ultrafiltration unit. The final protein concentration was 1 mM. NMR experiments were performed on a Varian Unity INOVA 600 spectrometer equipped with a triple-resonance probe with pulsed field gradient. The probe temperature was set at 30° C. HSQC, TOCSY-HSQC and NOESY-HSQC spectra were recorded using published procedures (Kay et al., 1992; Zhang et al., 1994). NMR spectra were processed and analyzed using the NMRPipe and NMRView software (Johnson & Blevins, 1994; Delaglio et al., 1995) on UNIX workstations. Sequence-specific resonance assignments were made using standard procedures (Wüthrich, 1986; Clore & Gronenborn, 1991). The assignments for wild-type Fn3 (Baron et al., 1992) were confirmed using a $^{15}$N-labeled protein dissolved in sodium acetate buffer (50 mM, pH 4.6) at 30° C.

The three-dimensional structure of Ubi4-K was characterized using this heteronuclear NMR spectroscopy method. A high quality spectrum could be collected on a 1 mM solution of $^{15}$N-labeled Ubi4 (FIG. 17a) at low pH. The linewidth of amide peaks of Ubi4-K was similar to that of wild-type Fn3, suggesting that Ubi4-K is monomeric under the conditions used. Complete assignments for backbone $^1$H and $^{15}$N nuclei were achieved using standard $^1$H, $^{15}$N double resonance techniques, except for a row of His residues in the N-terminal (His)$_6$ tag. There were a few weak peaks in the HSQC spectrum which appeared to originate from a minor species containing the N-terminal Met residue. Mass spectroscopy analysis showed that a majority of Ubi4-K does not contain the N-terminal Met residue. FIG. 17 shows differences in $^1$HN and $^{15}$N chemical shifts between Ubi4-K and wild-type Fn3. Only small differences are observed in the chemical shifts, except for those in and near the mutated BC and FG loops. These results clearly indicate that Ubi4-K retains the global fold of Fn3, despite the extensive mutations in the two loops. A few residues in the N-terminal region, which is close to the two mutated loops, also exhibit significant chemical differences between the two proteins. An HSQC spectrum was also recorded on a 50 µM sample of Ubi4-K in TBS. The spectrum was similar to that collected at low pH, indicating that the global conformation of Ubi4 is maintained between pH 7.5 and 3.3.

EXAMPLE XIX

Stabilization of Fn3 Domain by Removing Unfavorable Electrostatic Interactions on the Protein Surface Introduction Increasing the conformational stability of a protein by mutation is a major interest in protein design and biotechnology. The three-dimensional structures of proteins are stabilized by combination of different types of forces. The hydrophobic effect, van der Waals interactions and hydrogen bonds are known to contribute to stabilize the folded state of proteins (Kauzmann, W. (1959) Adv. Prot. Chem. 14, 1-63; Dill, K. A. (1990) Biochemistry 29, 7133-7155; Pace, C. N., Shirley, B. A., McNutt, M. & Gajiwala, K. (1996) Faseb J 10, 75-83). These stabilizing forces primarily originate from residues that are well packed in a protein, such as those that constitute the hydrophobic core. Because a change in the protein core would induce a rearrangement of adjacent moieties, it is difficult to improve protein stability by increasing these forces without massive computation (Malakauskas, S. M. & Mayo, S. L. (1998) Nat Struct Biol 5, 470-475). Ion pairs between charged groups are commonly found on the protein surface (Creighton, T. E. (1993) Proteins: structures and molecular properties, Freeman, New York), and an ion pair could be introduced to a protein with small structural perturbations. However, a number of studies have demonstrated that the introduction of an attractive electrostatic interaction, such as an ion pair, on protein surface has small effects on stability (Dao-pin, S., Sauer, U., Nicholson, H. & Matthews, B. W. (1991) Biochemistry 30, 7142-7153; Sali, D., Bycroft, M. & Fersht, A. R. (1991) J. Mol. Biol. 220, 779-788). A large desolvation penalty and the loss of conformational entropy of amino acid side chains oppose the favorable electrostatic contribution (Yang, A.-S. & Honig, B. (1992) Curr. Opin. Struct. Biol. 2, 40-45; Hendsch, Z. S. & Tidor, B. (1994) Protein Sci. 3, 211-226). Recent studies demonstrated that repulsive electrostatic interactions on the protein surface, in contrast, may significantly destabilize a protein, and that it is possible to improve protein stability by opting surface electrostatic interactions (Loladze, V. V., Ibarra-Molero, B., Sanchez-Ruiz, J. M. & Makhatadze, G. I. (1999) Biochemistry 38, 16419-16423; Perl D., Mueller, U., Heinemann, U. & Schmid, F. X. (2000) Nat Struct Biol 7, 380-383; Spector, S., Wang, M., Carp, S. A., Robblee, J., Hendsch, Z. S., Fairman, R., Tidor, B. & Raleigh, D. P. (2000) Biochemistry 39, 872-879; Grimsley, G. R., Shaw, K. L., Fee, L. R., Alston, R. W., Huyghues-Despointes, B. M., Thurlkill, R. L., Scholtz, J. M. & Pace, C. N. (1999) Protein Sci 8, 1843-1849). In the present experiments, the inventor improved protein stability by modifying surface electrostatic interactions.

During the characterization of monobodies it was found that these proteins, as well as wild-type FNfn10, are significantly more stable at low pH than at neutral pH (Koide, A., Bailey, C. W., Huang, X. & Koide, S. (1998) J. Mol. Biol. 284, 1141-1151). These observations indicate that changes in the ionization state of some moieties in FNfn10 modulate the conformational stability of the protein, and suggest that it might be possible to enhance the conformational stability of FNfn10 at neutral pH by adjusting electrostatic properties of the protein. Improving the conformational stability of FNfn10 will also have practical importance in the use of FNfn10 as a scaffold in biotechnology applications.

Described below are experiments that detailed characterization of the pH dependence of FNfn10 stability, identified unfavorable interactions between side chain carboxyl groups, and improved the conformational stability of FNfn10 by point mutations on the surface. The results demonstrate that the surface electrostatic interactions contribute significantly to protein stability, and that it is possible to enhance protein stability by rationally modulating these interactions.

Experimental Procedures

Protein Expression and Purification

The wild-type protein used for the NMR studies contained residues 1-94 of FNfn10 (residue numbering is according to FIG. 2(a) of Koide et al. (Koide, A., Bailey, C. W., Huang, X. & Koide, S. (1998) J. Mol. Biol. 284, 1141-1151)), and additional two residues (Met-Gln) at the N-terminus (these two residues are numbered −2 and −1, respectively). The gene coding for the protein was inserted in pET3a (Novagen, WI). Eschericha coli BL21 (DE3) transformed with the expression vector was grown in the M9 minimal media supplemented with $^{13}$C-glucose and $^{15}$N-ammonium chloride (Cambridge Isotopes) as the sole carbon and nitrogen sources, respectively. Protein expression was induced as described previously (Koide, A., Bailey, C. W., Huang, X. & Koide, S. (1998) J. Mol. Biol. 284, 1141-1151). After harvesting the cells by centrifuge, the cells were lysed as described (Koide, A., Bailey, C. W., Huang, X. & Koide, S. (1998) J. Mol. Biol. 284, 1141-1151). After centrifugation, supernatant was dialyzed against 10 mM sodium acetate buffer (pH 5.0), and the protein solution was applied to a SP-Sepharose® FastFlow column (Amersham Pharmacia Biotech), and FN3 was eluted with a gradient of sodium chloride. The protein was concentrated using an Amicon® concentrator using YM-3 membrane (Millipore).

The wild-type protein used for the stability measurements contained an N-terminal histag (MGSSHHHHHHSS-GLVPRGSH) (SEQ ID NO:114) and residues−2-94 of FNfn10. The gene for FN3 described above was inserted in pET15b (Novagen). The protein was expressed and purified as described (Koide, A., Bailey, C. W., Huang, X. & Koide, S. (1998) J. Mol. Biol. 284, 1141-1151). The wild-type protein used for measurements of the pH dependence shown in FIG. 22 contained Arg 6 to Thr mutation, which had originally been introduced to remove a secondary thrombin cleavage site (Koide, A., Bailey, C. W., Huang, X. & Koide, S. (1998) J. Mol. Biol. 284, 1141-1151). Because Asp 7, which is adjacent to Arg 6, was found to be critical in the pH dependence of FN3 stability as detailed under Results, subsequent studies were performed using the wild-type, Arg 6, background. The genes for the D7N and D7K mutants were constructed using standard polymerase chain reactions, and inserted in pET15b. These proteins were prepared in the same manner as for the wild-type protein. $^{13}$C, $^{15}$N-labeled proteins for $pK_a$ measurements were prepared as described above, and the histag moiety was not removed from these proteins.

Chemical Denaturation Measurements

Proteins were dissolved to a final concentration of 5 µM in 10 mM sodium citrate buffer at various pH containing 100 mM sodium chloride. Guanidine HCl (GuHCl)-induce unfolding experiments were performed as described previously (Koide, A., Bailey, C. W., Huang, X. & Koide, S. (1998) J. Mol. Biol. 284, 1141-1151; Koide, S., Bu, Z., Risal, D., Pham, T.-N., Nakagawa, T., Tamura, A. & Engelman, D. M. (1999) Biochemistry 38, 4757-4767). GuHCl concentration was determined using an Abbe refractometer (Spectronic Instruments) as described (Pace, C. N. & Sholtz, J. M. (1997)

in *Protein structure. A practical approach* (Creighton, T. E., Ed.) Vol. pp 299-321, IRL Press, Oxford). Data were analyzed according to the two-state model as described (Koide, A, Bailey, C. W., Huang, X. & Koide, S. (1998) *J. Mol. Biol.* 284, 1141-1151; Santoro, M. M. & Bolen, D. W. (1988) *Biochemistry* 27, 8063-8068.).

Thermal Denaturation Measurements

Proteins were dissolved to a final concentration of 5 μM in 20 mM sodium phosphate buffer (pH 7.0) containing 0.1 or 1 M sodium chloride or in 20 mM glycine HCl buffer (pH 2.4) containing 0.1 or 1 M sodium chloride. Additionally 6.3 M urea was included in all solutions to ensure reversibility of the thermal denaturation reaction. In the absence of urea it was found that denatured FNfn10 adheres to quartz surface, and that the thermal denaturation reaction was irreversible. Circular dichroism measurements were performed using a Model 202 spectrometer equipped with a Peltier temperature controller (Aviv Instruments). A cuvette with a 0.5-cm pathlength was used. The ellipticity at 227 nm was recorded as the sample temperature was raised at a rate of approximately 1° C. per minute. Because of decomposition of urea at high temperature, the pH of protein solutions tended to shift upward during an experiment. The pH of protein solution was measured before and after each thermal denaturation measurement to ensure that a shift no more than 0.2 pH unit occurred in each measurement. At pH 2.4, two sections of a thermal denaturation curve (30-65° C. and 60-95° C.) were acquired from separate samples, in order to avoid a large pH shift. The thermal denaturation data were fit with the standard two-state model (Pace, C. N. & Sholtz, J. M. (1997) in *Protein structure. A practical approach* (Creighton, T. E., Ed.) Vol. pp 299-321, IRL Press, Oxford):

$$\Delta G(T) = \Delta H_m(1-T/T_m) - \Delta C_P[(T_m-T)+T\ln(T/T_m)]$$

where $\Delta G(T)$ is the Gibbs free energy of unfolding at temperature T, $\Delta H_m$ is the enthalpy change upon unfolding at the midpoint of the transition, $T_m$, and $\Delta C_P$ is the heat capacity change upon unfolding. The value for $\Delta C_P$ was fixed at 1.74 kcal mol$^{-1}$ K$^{-1}$, according to the approximation of Myers et al. (Myers, J. K., Pace, C. N. & Scholtz, J. M. (1995) *Protein Sci.* 4, 2138-2148). Most of the datasets taken in the presence of 1 M NaCl did not have a sufficient baseline for the unfolded state, and thus it was assumed the slope of the unfolded baseline in the presence of 1 M NaCl to be identical to that determined in the presence of 0.1 M NaCl.

NMR Spectroscopy

NMR experiments were performed at 30° C. on an INOVA 600 spectrometer (Varian Instruments). The C(CO)NH experiment (Grzesiek, S., Anglister, J. & Bax, A. (1993) *J. Magn. Reson. B* 101, 114-119) and the CBCACOHA experiment (Kay, L. E. (1993) *J. Am. Chem. Soc.* 115, 2055-2057) were collected on a [$^{13}$C, $^{15}$N]-wild-type FNfn10 sample (1 mM) dissolved in 50 mM sodium acetate buffer (pH 4.6) containing 5% (v/v) deuterium oxide, using a Varian 5 mm triple resonance probe with pulsed field gradient. The carboxyl $^{13}$C resonances were assigned based on the backbone $^{1}$H, $^{13}$C and $^{15}$N resonance assignments of FNfn10 (Baron, M., Main, A. L., Driscoll, P. C., Mardon, H. J., Boyd, J. & Campbell, I. D. (1992) *Biochemistry* 31, 2068-2073). pH titration of carboxyl resonances were performed on a 0.3 mM FNfn10 sample dissolved in 10 mM sodium citrate containing 100 mM sodium chloride and 5% (v/v) deuterium oxide. An 8 mm triple-resonance, pulse-field gradient probe (Nanolac Corporation) was used for pH titration. Two-dimensional H(C)CO spectra were collected using the CBCACOHA pulse sequence as described previously (McIntosh, L. P., Hand, G., Johnson, P. E., Joshi, M. D., Koerner, M., Plesniak, L. A., Ziser, L., Wakarchuk, W. W. & Withers, S. G. (1996) *Biochemistry* 35, 9958-9966). Sample pH was changed by adding small aliquots of hydrochloric acid, and pH was measured before and after taking NMR data. $^{1}$H, $^{15}$N-HSQC spectra were taken as described previously (Kay, L. E., Keifer, P. & Saarinen, T. (1992) *J. Am. Chem. Soc.* 114, 10663-10665). NMR data were processed using the NMRPipe package (Delaglio, F., Grzesiek, S., Vuister, G. W., Zhu, G., Pfeifer, J. & Bax, A. (1995) *J. Biomol. NMR* 6, 277-293), and analyzed using the NMRView software (Johnson, B. A. & Blevins, R. A. (1994) *J. Biomol. NMR* 4, 603-614).

NMR titration curves of the carboxyl $^{13}$C resonances were fit to the Henderson-Hasselbalch equation to determine $pK_a$'s:

$$\delta(pH) = (\delta_{acid} + \delta_{base} 10^{(pH-pKa)})/(1+10^{(pH-pKa)})$$

where δ is the measured chemical shift, $\delta_{acid}$ is the chemical shift associated with the protonated state, $\delta_{base}$ is the chemical shift associated with the deprotonated state, and $pK_a$ is the $pK_a$ value for the residue. Data were also fit to an equation with two ionizable groups:

$$\delta(pH) = (\delta_{AH2} + \delta_{AH} 10^{(pH-pKa1)} + \delta_A 10^{(2pH-pKa1-pKa2)})/(1+10^{(pH-pKa1)}+10^{(2pH-pKa1-pKa2)})$$

where $\delta_{AH2}$, $\delta_{AH}$ and $\delta_A$ are the chemical shifts associated with the fully protonated, singularly protonated and deprotonated states, respectively, and $pK_{a1}$ and $pK_{a2}$ are $pK_a$'s associated with the two ionization steps. Data fitting was performed using the nonlinear least-square regression method in the program Igor Pro (WaveMetrix, OR) on a Macintosh computer.

Results pH Dependence of FNfn10 Stability

Previously, it was found that FNfn10 is more stable at acidic pH than at neutral pH (Koide, A., Bailey, C. W., Huang, X. & Koide, S. (1998) *J. Mol. Biol.* 284, 1141-1151). In the present experiments, the pH dependence of its stability was further characterized. Because of its high stability, FNfn10 could not be fully denatured in urea at 30° C. Thus GuHCl-induced chemical denaturation (FIG. 18) was used. The denaturation reaction was fully reversible under all conditions tested. In order to minimize errors caused by extrapolation, the free energy of unfolding at 4 M GuHCl was used for comparison (FIG. 18). The stability increased as the pH was lowered, with apparent plateaus at both ends of the pH range. The pH dependence curve has an apparent transition midpoint near pH 4. In addition, a gradual increase in the m value, the dependence of the unfolding free energy on denaturant concentration was noted. Pace et al. reported a similar pH dependence of the m value for barnase (Pace, C. N., Laurents, D. V. & Erickson, R. E. (1992) *Biochemistry* 31, 2728-2734). These results indicate that FNfn10 contains interactions that stabilize the protein at low pH, or those that destabilize it at neutral pH. The results also suggest that by identifying and altering the interactions that give rise to the pH dependence, one may be able to improve the stability of FNfn10 at neutral pH to a degree similar to that found at low pH.

Determination of $pK_a$'s of the Side Chain Carboxyl Groups in Wild-type FNfn10

The pH dependence of FNfn10 stability suggests that amino acids with $pK_a$ near 4 are involved in the observed transition. The carboxyl groups of Asp and Glu generally have $pK_a$ in this range (Creighton, T. E. (1993) *Proteins: structures and molecular properties*, Freeman, New York). It is well known that if a carboxyl group has unfavorable (i.e. destabilizing) interactions in the folded state, its $pK_a$ is shifted to a higher value from its unperturbed value (Yang, A.-S. &

Honig, B. (1992) *Curr. Opin. Struct. Biol.* 2, 40-45). If a carboxyl group has favorable interactions in the folded state, it has a lower $pK_a$. Thus, the $pK_a$ values of all carboxylates in FNfn10 using heteronuclear NMR spectroscopy were determined in order to identify stabilizing and destabilizing interactions involving carboxyl groups.

First, the $^{13}C$ resonance for the carboxyl carbon of each Asp and Glu residue in FN3 was assigned (FIG. 19). Next, pH titration of the $^{13}C$ resonances for these groups was performed (FIG. 20). Titration curves for Asp 3, 67 and 80, and Glu 38 and 47 could be fit well with the Henderson-Hasselbalch equation with a single $pK_a$. The $pK_a$ values for these residues (Table 9) are either close to or slightly lower than their respective unperturbed values (3.8-4.1 for Asp, and 4.1-4.6 for Glu (Kuhlman, B., Luisi, D. L., Young, P. & Raleigh, D. P. (1999) *Biochemistry* 38, 4896-4903)), indicating that these carboxyl groups are involved in neutral or slightly favorable electrostatic interactions in the folded state.

TABLE 9

$pK_a$ values for Asp and Glu residues in FN3[1].

| Residue | Protein | | |
|---|---|---|---|
| | Wild-Type | D7N | D7K | E9 |
| | 3.84, 5.40[2] | 4.98 | 4.53 | |
| E38 | 3.79 | 3.87 | 3.86 | |
| E47 | 3.94 | 3.99 | 3.99 | |
| D3 | 3.66 | 3.72 | 3.74 | |
| D7 | 3.54, 5.54[2] | — | — | |
| D23 | 3.54, 5.25[2] | 3.68 | 3.82 | |
| D67 | 4.18 | 4.17 | 4.14 | |
| D80 | 3.40 | 3.49 | 3.48 | |

[1]The standard deviations in the $pK_a$ values are less than 0.05 pH units for those fit with a single $pK_a$ and less than 0.15 pH unit for those with two $pK_a$'s.
[2]Data for E9, D7 and D23 were fit with a transition curve with two $pK_a$ values.

The titration curves for Asp 7 and 23, and Glu 9 were fit better with the Henderson-Hasselbalch equation with two $pK_a$ values, and one of the two $pK_a$ values for each were shifted higher than the respective unperturbed values (FIG. 19B). The titration curves with two apparent $pK_a$ values of these carboxyl groups may be due to influence of an ionizable group in the vicinity. In the three-dimensional structure of FNfn10 (Main, A. L., Harvey, T. S., Baron, M., Boyd, J. & Campbell, I. D. (1992) *Cell* 71, 671-678), Asp 7 and 23, and Glu 9 form a patch on the surface (FIG. 21), with Asp 7 centrally located in the patch. Thus, it is reasonable to expect that these residues influence each other's ionization profile. In order to identify which of the three residues have a highly upshifted $pK_a$, the H(C)CO spectrum of the protein in 99% $D_2O$ buffer at pH* 5.0 (direct pH meter reading) was then collected. Asp 23 and Glu 9 showed larger deuterium isotope shifts (0.33 and 0.32 ppm, respectively) than Asp 7 (0.18 ppm). These results show that Asp 23 and Glu 9 are protonated to a greater degree than Asp 7. Thus, we concluded that Asp 23 and Glu 9 have highly upshifted $pK_a$'s, due to strong influence of Asp 7.

Mutational Analysis

The spatial proximity of Asp 7 and 23, and Glu 9 explains the unfavorable electrostatic interactions in FNfn10 identified in this study. At low pH where these residues are protonated and neutral the repulsive interactions are expected to be mostly relieved. Thus, it should be possible to improve the stability of FNfn10 at neutral pH, by removing the electrostatic repulsion between these residues. Because Asp 7 is centrally located among the three residues, it was decided to mutate Asp 7. Two mutants, D7N and D7K were prepared. The former neutralizes the negative charge with a residue of virtually identical size. The latter places a positive charge at residue 7 and increases the size of the side chain.

The $^1H$, $^{15}N$-HSQC spectra of the two mutant proteins were nearly identical to that of the wild-type protein, indicating that these mutations did not cause large structural perturbations (data not shown). The degrees of stability of the mutant proteins were then characterized using thermal and chemical denaturation measurements. Thermal denaturation measurements were performed initially with 100 mM sodium chloride, and 6.3 M urea was included to ensure reversible denaturation and to decrease the temperature of the thermal transition All the proteins were predominantly folded in 6.3 M urea at room temperature. All the proteins underwent a cooperative transition, and the two mutants were found to be significantly more stable than the wild type at neutral pH (FIG. 22 and Table 10). Furthermore, these mutations almost eliminated the pH dependence of the conformational stability of FNfn10. These results confirmed that destabilizing interactions involving Asp 7 in wild-type FNfn10 at neutral pH are the primary cause of the pH dependence.

TABLE 10

The midpoint of thermal denaturation (in ° C.) of wild-type and mutant FN3 in the presence of 6.3 M urea.

| | pH 2.4 | | pH 7.0 | |
|---|---|---|---|---|
| Protein | 0.1 M NaCl | 1M NaCl | 0.1 M NaCl | 1 M NaCl |
| wild type | 72 | 82 | 62 | 70 |
| D7N | 68 | 82 | 69 | 80 |
| D7K | 69 | 77 | 70 | 78 |

The error in the midpoints for the 0.1 M NaCl data is ±0.5° C.. Because most of the 1M NaCl data did not have a sufficient baseline for the denatured state, the error in the midpoints for these data was estimated to be ±2° C.

The effect of increased sodium chloride concentration on the conformational stability of the wild type and the two mutant proteins was next investigated. All proteins were more stable in 1 M sodium chloride than in 0.1 M sodium chloride (FIG. 22). The increase of the sodium chloride concentration elevated the $T_m$ of the mutant proteins by approximately 10° C. at both acidic and neutral pH (Table 10). Remarkably the wild-type protein was also equally stabilized at both pH, although it contains unfavorable interactions among the carboxyl groups at neutral pH but not at acidic pH.

Chemical denaturation of FNfn10 proteins was monitored using fluorescence emission from the single Trp residue of FNfn10 (FIG. 23). The free energies of unfolding at pH 6.0 and 4 M GuHCl were determined to be 1.1 (±0.3), 1.7 (±0.2) and 1.4 (±0.1) kcal/mol for the wild type, D7N and D7K, respectively, indicating that the two mutations also increased the conformational stability against chemical denaturation.

Determination of the $pK_a$'s of the Side Chain Carboxyl Groups in the Mutant Proteins The ionization properties of carboxyl groups in the two mutant proteins was investigated. The 2D H(C)CO spectra of the mutant proteins at the high and low ends of the pH titration (pH ~7 and ~1.5, respectively) were nearly identical to the respective spectra of the wild type, except for the loss of the cross peaks for Asp 7 (data not shown). This similarity allowed for an unambiguous assignment of resonances of the mutants, based on the assignments for wild-type FNfn10. The pH titration experiments revealed that, except for Glu 9 and Asp 23, the behaviors of Asp and Glu carboxyl groups are very close to their counterparts in the wild-type protein (FIG. 24 Panels A, C, D, F and G, and Table 9), indicating that the two mutations have marginal effects on the electrostatic environments for these carboxylates. In contrast, the titration curves for E9 and D23 show significant changes upon mutation (FIG. 24 Panels B and E). The $pK_a$ of D23 was lowered by more than 1.6 and 1.4 pH units in the D7N and D7K mutants, respectively. These results clearly show that the repulsive interaction between D7 and D23 contributes to the increase in $pK_a$ of Asp 23 in the wild-type protein, and that it was eliminated by the neutralization of the negative charge at residue 7. The $pK_a$ of Glu 9 was reduced by 0.4 pH unit by the D7N mutation, while it was decreased by 0.8 pH units in the D7K mutant. The greater reduction of Glu 9 $pK_a$ by the D7K mutation suggests that there is a favorable interaction between Lys 7 and Glu 9 in this mutant protein.

Discussion

The present inventor has identified unfavorable electrostatic interactions in FNfn10, and improved its conformational stability by mutations on the protein surface. The results demonstrate that repulsive interactions between like charges on protein surface significantly destabilize a protein. The results are also consistent with recent-reports by other groups (Loladze, V. V., Ibarra-Molero, B., Sanchez-Ruiz, J. M. & Makhatadze, G. I. (1999) *Biochemistry* 38, 16419-16423; Perl D., Mueller, U., Heinemann, U. & Schmid, F. X. (2000) *Nat Struct Biol* 7, 380-383; Spector, S., Wang, M., Carp, S. A, Robblee, J., Hendsch, Z. S., Fairman, R., Tidor, B. & Raleigh, D. P. (2000) *Biochemistry* 39, 872-879; Grimsley, G. R., Shaw, K. L., Fee, L. R., Alston, R. W., Huyghues-Despointes, B. M., Thurlkill, R. L., Scholtz, J. M. & Pace, C. N. (1999) *Protein Sci* 8, 1843-1849), in which protein stability was improved by eliminating unfavorable electrostatic interactions on the surface. In these studies, candidates for mutations were identified by electrostatic calculations (Loladze, V. V., Ibarra-Molero, B., Sanchez-Ruiz, J. M. & Makhatadze, G. I. (1999) *Biochemistry* 38, 16419-16423; Spector, S., Wang, M., Carp, S. A., Robblee, J., Hendsch, Z. S., Fairman, R., Tidor, B. & Raleigh, D. P. (2000) *Biochemistry* 39, 872-879; Grimsley, G. R., Shaw, K. L., Fee, L. R., Alston, R. W., Huyghues-Despointes, B. M., Thurlkill, R. L., Scholtz, J. M. & Pace, C. N. (1999) *Protein Sci* 8, 1843-1849) or by sequence comparison of homologous proteins with different stability (Perl, D., Mueller, U., Heinemann, U. & Schmid, F. X. (2000) *Nat Struct Biol* 7, 380-383). The present strategy using $pK_a$ determination using NMR has both advantages and disadvantages over the other strategies. The present method directly identifies residues that destabilize a protein. Also it does not depend on the availability of the high-resolution structure of the protein of interest. Electrostatic calculations may have large errors due to the flexibility of amino acid side chains on the surface, and the uncertainty in the dielectric constant on the protein surface and in the protein interior. For example, in the NMR structure of FNfn10 (Main, A. L., Harvey, T. S., Baron, M., Boyd, J. & Campbell, I. D. (1992) *Cell* 71, 671-678), the root mean squared deviations among 16 model structures for the $O^\epsilon$ atom of Glu residues are 1.2-2.4 Å, and those for Lys $N^\zeta$ atoms are 1.5-3.1 Å. Such uncertainties in atom position can potentially cause large differences in calculation results. On the other hand, the present strategy requires the NMR assignments for carboxyl residues, and NMR measurements over a wide pH range. Although recent advances in NMR spectroscopy have made it straightforward to obtain resonance assignments for a small protein, some proteins may not be sufficiently soluble over the desired pH range. In addition, knowledge of the $pK_a$ values of ionizable groups in the denatured state is necessary for accurately evaluating contributions of individual residues to stability (Yang, A.-S. & Honig, B. (1992) *Curr. Opin. Struct. Biol.* 2, 40-45). Kuhlman et al. (Kuhlman, B., Luisi, D. L., Young, P. & Raleigh, D. P. (1999) *Biochemistry* 38, 4896-4903) showed that $pK_a$'s of carboxylates in the denatured state has a considerably large range than those obtained from small model compounds. Despite these limitations, the present method is applicable to many proteins.

The inventor showed that the unfavorable interactions involving the carboxyl groups of Asp 7, Glu 9 and Asp23 were no longer present if these groups are protonated at low pH or if Asp 7 was replaced with Asn or Lys. The similarity in the measured stability of the mutants and the wild type at low pH (Table 10) suggests that no other factors significantly contribute to the pH dependence of FNfn10 stability and that the mutations caused minimal structural perturbations. The little structural perturbation was expected, since the carboxyl groups of these three residues are at least 50% exposed to the solvent, based on the solvent accessible surface area calculation on the NMR structure (Main, A. L., Harvey, T. S., Baron, M., Boyd, J. & Campbell, I. D. (1992) *Cell* 71, 671-678).

The difference in thermal stability of the wild-type protein between acidic and neutral pH persisted in 1 M sodium chloride (Table 10). Likewise, the wild-type protein exhibited a large pH-dependence in stability in 4 M GuHCl (FIG. 18). Furthermore, upon the increase in the sodium chloride concentration from 0.1 to 1.0 M, the $T_m$ of the wild-type and mutant proteins all increased by ~10° C., which is in the same magnitude as the change in $T_m$ of the wild type by the pH shift. These data indicate that the unfavorable interactions identified in this study were not effectively shielded in 1 M NaCl or in 4 M GuHCl. Because the effect of increased sodium chloride was uniform, this stabilization effect of sodium chloride is likely due to the nonspecific salting-out effect (Timasheff, S. N. (1992) *Curr. Op. Struct. Biol.* 2, 35-39). Other groups also reported little shielding effect of salts on electrostatic interactions (Perutz, M. F., Gronenborn, A. M., Clore, G. M., Fogg, J. H. & Shih, D. T. (1985) *J Mol Biol* 183, 491-498; Hendsch, Z. S., Jonsson, T., Sauer, R. T. & Tidor, B. (1996) *Biochemistry* 35, 7621-7625). Electrostatic interactions are often thought to diminish with increasing ionic strength, particularly if the site of interaction is highly exposed. Accordingly, the present data at neutral pH (Table 10) showing no difference in the salt sensitivity between the wild type and the mutants could be interpreted as Asp 7 not being responsible for destabilizing electrostatic interactions. Although the reason for this salt insensitivity is not yet clear, the present results provide a cautionary note on concluding the presence and absence of electrostatic interactions solely based on salt concentration dependence.

The carboxyl triad (Asp 7 and 23, and Glu 9) is highly conserved in FNfn10 from nine different organisms that were available in the protein sequence databank at National Center for Biotechnology Information (see the World-Wide-Web at ncbi.nlm.nih.gov). In these FNfn10 sequences, Asp 9 is conserved except one case where it is replaced with Asn, and Glu 9 is completely conserved. The position 23 is either Asp or Glu, preserving the negative charge. As was discovered in this study, the interactions among these residues are destabilizing. Thus, their high conservation, despite their negative effects on stability, suggests that these residues have functional importance in the biology of fibronectin. In the structure of a four-FN3 segment of human fibronectin (Leahy, D. J., Aukhil, I. & Erickson, H. P. (1996) *Cell* 84, 155-164), these residues are not directly involved in interactions with adjacent domains. Also these residues are located on the opposite face of FNfn10 from the integrin-binding RGD sequence in the FG loop (FIG. 21). Therefore, it is not clear why these destabilizing residues are almost completely conserved in FNfn10. In contrast, no other FN3 domains in human fibronectin contain this carboxyl triad (for a sequence alignment, see ref Main, A. L., Harvey, T. S., Baron, M., Boyd, J. & Campbell, I. D. (1992) Cell 71, 671-678). The carboxyl triad of FNfn10 may be involved in important interactions that have not been identified to date.

Clarke et al. (Clarke, J., Hamill, S. J. & Johnson, C. M. (1997) J Mol Biol 270, 771-778) reported that the stability of the third FN3 of human tenascin (TNfn3) increases as pH was decreased from 7 to 5. Although they could not perform stability measurements below pH 5 due to protein aggregation, the pH dependence of TNfn3 resembles that of FNfn10 shown in FIG. 18. TNfn3 does not contain the carboxylate triad at positions 7, 9 and 23 (Leahy, D. J., Hendrickson, W. A., Aukhil, I. & Erickson, H. P. (1992) Science 258, 987-991), indicating that the destabilization of TNfn3 at neutral pH is caused by a different mechanism from that for FNfn10. A visual inspection of the TNfn3 structure revealed that it has a large number of carboxyl groups, and that Glu 834 and Asp 850 (numbering according to ref Leahy, D. J., Hendrickson, W. A., Aukhil, I. & Erickson, H. P. (1992) Science 258, 987-991) forms a cross-strand pair. It will be interesting to examine whether altering this pair can increase the stability of TNfn3.

In conclusion, a strategy has been described to experimentally identify unfavorable electrostatic interactions on the protein surface and improve the protein stability by relieving such interactions. The present results have demonstrated that forming a repulsive interaction between carboxyl groups significantly destabilize a protein. This is in contrast to the small contributions of forming a solvent-exposed ion pair. Unfavorable electrostatic interactions on the surface seem quite common in natural proteins. Therefore, optimization of the surface electrostatic properties provides a generally applicable strategy for increasing protein stability (Loladze, V. V., Ibarra-Molero, B., Sanchez-Ruiz, J. M. & Makhatadze, G. I. (1999) Biochemistry 38, 16419-16423; Perl, D., Mueller, U., Heinemann, U. & Schmid, F. X. (2000) Nat Struct Biol 7, 380-383; Spector, S., Wang, M., Carp, S. A., Robblee, J., Hendsch, Z. S., Fairman, R., Tidor, B. & Raleigh, D. P. (2000) Biochemistry 39, 872-879; Grimsley, G. R., Shaw, K. L., Fee, L. R., Alston, R. W., Huyghues-Despointes, B. M., Thurlkill, R. L., Scholtz, J. M. & Pace, C. N. (1999) Protein Sci 8, 1843-1849). In addition, repulsive interactions between carboxylates can be exploited for destabilizing undesirable, alternate conformations in protein design ("negative design").

EXAMPLE XX

An Extension of the Carboxyl-terminus of the Monobody Scaffold

The wild-type protein used for stability measurements is described under Example 19. The carboxyl-terminus of the monobody scaffold was extended by four amino acid residues, namely, amino acid residues (Glu-Ile-Asp-Lys) (SEQ ID NO:119), which are the ones that immediately follow FNfn10 of human fibronectin. The extension was introduced into the FNfn10 gene using standard PCR methods. Stability measurements were performed as described under Example 19. The free energy of unfolding of the extended protein was 7.4 kcal mol$^{-1}$ at pH 6.0 and 30° C., very close to that of the wild-type protein (7.7 kcal mol$^{-1}$). These results demonstrate that the C-terminus of the monobody scaffold can be extended without decreasing its stability.

EXAMPLE XXI

Reconstitution of Proteins

Design and Production of Fragments by Cyanogen Bromide Cleavage of a Mutant FNfn10
Choice of Cyanogen Bromide for the Cleavage To produce fragments of the FNfn10 protein, a cleavage site was engineered into loop regions. The insertion of a methionine residue flanked by two glycine residues on each side presented a cyanogen bromide cleavage site in a flexible region. This method had the benefit that the protein could be expressed and purified with already existing protocols, and both fragments were produced at the same time. Since no methionine residue is present in the wild type sequence of FNfn10, this method allowed specific cleavage at the introduced site.

Location of the Introduced Cleavage Site within FNfn10

A suitable site for the separation of two fragments of FNfn10 had to be determined. Both practical aspects of the cleavage and its intended application in selection experiments constrained the position of the cleavage site. A cleavage site within a more flexible loop region is more likely to result in protein reconstitution. With library construction in mind, an ideal split of the protein would result in fragments that each contained a portion of the molecule amendable for the introduction of a library. In the original design, the BC and FG loop have been utilized to host restrained peptide libraries, therefore these loops should ideally remain uncut (see FIG. 1B, 1D). The DE loop is also a potential cleavage site, though its proximity to the FG and the BC loop may interfere target binding of BC and/or FG loops. To separate BC and FG loops into two different fragments, the CD loop or the EF loop region remained as possible cleavage sites.

The elongation of loop regions introduces a destabilizing effect on the protein conformation. In FNfn10, the destabilization effect of modifications in the CD loop tended to be much less pronounced than the effect of modifications in the EF loop. The cleavage of a peptide bond in a loop region introduces an increased degree of freedom to nearby residues compared to loop elongation. For reconstitution, a more stable protein should give an advantage. Consequently, it was tested whether a stabilizing mutation far away from the cleavage site, such as a surface charge alteration that has been demonstrated (Koide et al. 2001), increase the affinity of a reconstitution reaction. To that end, a total of four mutations for cleavage were constructed (Table 11).

TABLE 11

| | Constructed proteins for fragmentation experiments and their free energy of unfolding $\Delta G$. | | | | |
|---|---|---|---|---|---|
| Name | Basis protein | Insertion | $\Delta G_0$ (kcal/ mol) | $\Delta G_{3MGuHCl}$ (kcal/ mol) | m (kcal mol$^{-1}$ M$^{-1}$) |
| CD 45 | Wild type | GGMGA (SEQ ID NO: 142) in CD-loop | 6.4 | 1.4 | 1.69 |
| CD92 | D7KE9Q | GGMGG (SEQ ID NO: 122) in CD-loop | 7.9 | 1.6 | 2.10 |

TABLE 11-continued

Constructed proteins for fragmentation experiments and their free energy of unfolding ΔG.

| Name | Basis protein | Insertion | ΔG$_0$ (kcal/mol) | ΔG$_{3MGuHCl}$ (kcal/mol) | m (kcal mol$^{-1}$ M$^{-1}$) |
|---|---|---|---|---|---|
| EF 45 | Wild type | GGMGG (SEQ ID NO: 122) in EF-loop | 6.3 | -1.0 | 2.43 |
| EF92 | D7KE9Q | GGMGG (SEQ ID NO: 122) in EF-loop | 6.9 | -1.2 | 2.69 |

Either the wild type or the D7KE9Q mutant were used as the template. The cleavage site, GGMGG (SEQ ID NO:122), was inserted either in the CD or EF loop regions (see FIG. 25).

Constructs to Obtain Mutant Protein

Site directed mutagenesis was performed on the FNfn10 gene to obtain expression vectors for mutant proteins that contained a GGMGG (SEQ ID NO:122) insertion in either the CD loop or the EF loop. The insertion was encoded in oligonucleotides (Operon Technologies Inc.), which was used to produce the N-terminal part of the FNfn10 gene by standard PCR. The purified DNA fragment was cut at an existing NdeI site and either at an EcoRI or a SalI restriction site to process the gene for the CD or the EF loop insertion respectively. Following the digest, the fragments were ligated into a suitably cut parental vector. All constructs were confirmed by gene sequencing. Unfortunately, one of the CD loop insertion mutants contained a glycine to alanine mutation within the inserted glycines. Since the purpose of the glycine was solely to provide a flexible environment around the methionine residue for more effective cleavage, no significant alteration was expected due to this mutation Nevertheless, only the N-terminal fragment of this protein was used in experiments. For the reconstitution of this protein, the C-terminal fragment of CD 92 was utilized, as it was designed to be exactly the same as for the wild type CD loop insertion (CD45), including the artificial GG sequence at the beginning instead of GA. All the mutant proteins were expressed as soluble protein and subsequently purified using metal affinity chromatography, as previously described for the wild type protein (Koide et al. 1998).

Residues 1-42 of FN3 were also expressed as a fusion protein, His 6-ubiquitin-FN3(residue 1-42) (6×His disclosed as SEQ ID NO:136) by cloning the gene corresponding to the FN3 fragment in a vector for ubiquitin (Kohno, 1998). This fusion protein was expressed and purified as described before (Koide et al. 1998) except that protein purification was performed in 4M urea.

Protein Cleavage and Fragment Purification

Figure 29:
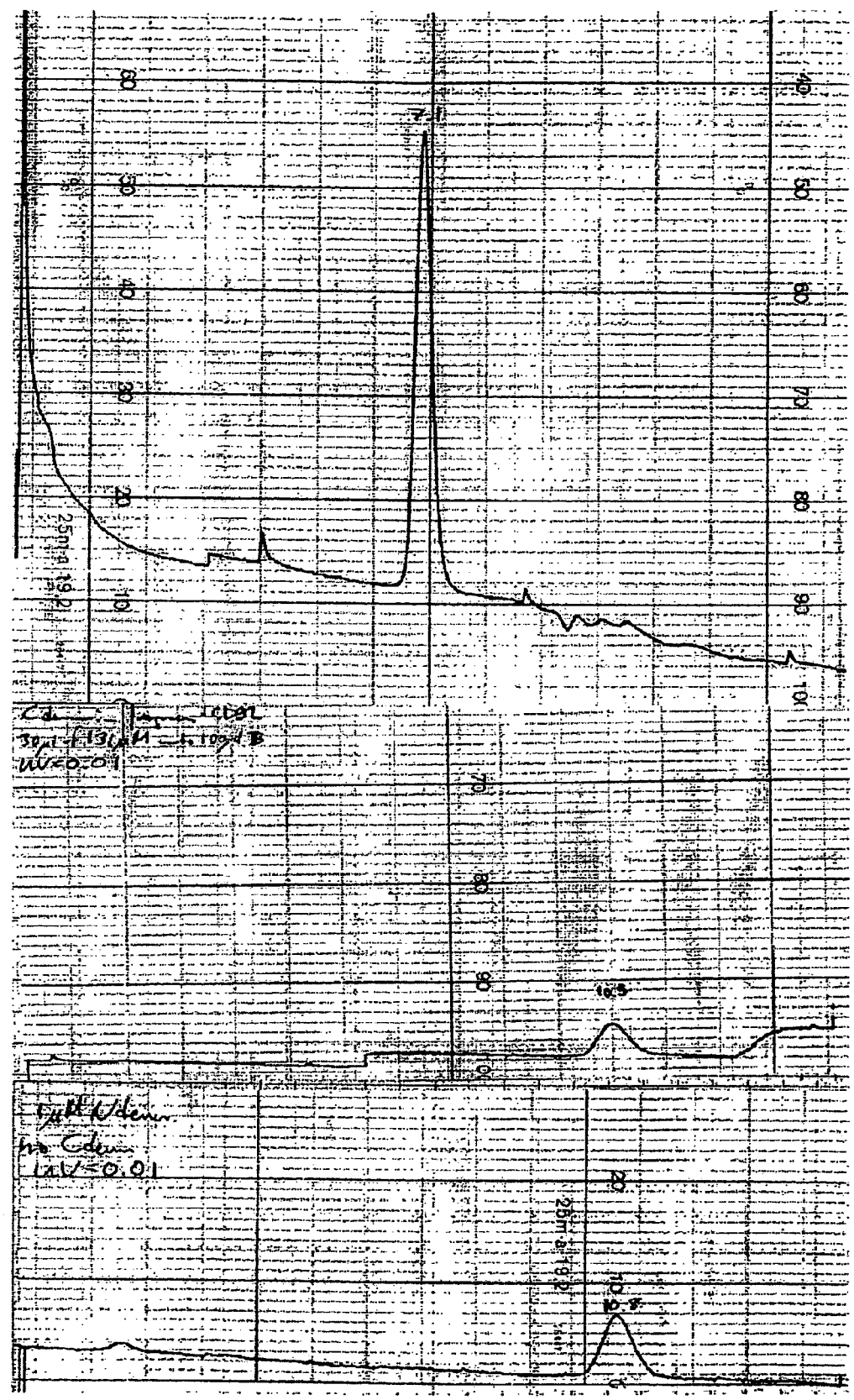

Protein was diluted into 0.1M HCl at protein concentrations of approx. 2 mg/ml and degassed. Approximately 2-5 mg of cyanogen bromide (CNBr) was dissolved and the reaction container was sealed under Argon to minimize tryptophan oxidation, and incubated for 2 h at room temperature. The well-established reaction of CNBr cleaving the peptide bond following a methionine is shown in FIG. 29. The reaction mixture was then passed through a single-use reverse phase cartridge (Waters) to remove any remaining CNBr and bound proteins were recovered by eluting with 0.1M HCl containing 60% Acetonitrile (CH$_3$CN) and kept on ice. Elution fractions that exhibited significant UV absorption were combined and diluted to approx. 25% CH$_3$CN. The samples were immediately loaded onto a reverse phase column (Resource™ RPC, Pharmacia Amersham) and fragments were separated by a CH$_3$CN gradient from 20% to 45% (see FIG. 30). Eluted fractions containing pure fragment were immediately frozen to −80° C. and lyophilized to minimize acid degradation.

NMR Spectroscopy

NMR experiments were performed at 30° C. on an INOVA 600 spectrometer (Varian Instruments). $^{15}$N-labeled sample of the CD92 protein (see Table 11) was expressed and purified. A $^1$H, $^{15}$N-HSQC spectrum of the uncleaved protein was recorded in 20 mM sodium phosphate buffer at pH 6.0 containing 100 mM sodium chloride and 5% (v/v) deuterium oxide at a sample concentration of 0.95 mM. as described previously (Kay et al. 1992). The labeled protein sample was then recovered, cleaved with approximately 10× molar excess of cyanogen bromide and the resulting fragments purified. Experiments on the fragments were also performed in 20 mM sodium phosphate buffer at pH 6.0 containing 100 mM sodium chloride and 5% (v/v) deuterium oxide on samples at a concentration of 0.5 mM for the C-terminal fragment and 0.25 mM for the N-terminal fragment sample. 10% glycerol was added to the N-terminal fragment sample to prevent aggregation. The two samples for the reconstituted complex were prepared by dissolving both C and N terminal fragments in a pH 6.0 buffer containing 4 M GuHCl, where one of the fragments in the sample was $^{15}$N-labeled while the complementary part was not. GuHCl was then gradually diluted out by a series of dialyses. Additionally, the samples were concentrated and buffer exchanged using a Centricon® spin filter (Amicon® Inc.) with a molecular weight cutoff at 3 kDa. Sample concentration for the complex was measured to 0.2 mM of $^{15}$N-labeled fragment respectively. For both samples, the starting unlabeled fragments was added in 3 fold excess. NMR data were processed using the NMRPipe package (Delaglio et al. 1995), and analyzed using the NMRView software (Johnson and Blevins 1994).

Protein dynamics were probed using a heteronuclear $^1$H$^{15}$N steady state Nuclear Overhauser Effect (NOE) experiment (Farrow et al. 1994). An NOE is observed due to cross relaxation of two spins that are in close proximity (Cavanagh et al. 1996). The NOE enhancement of a coupled proton-nitrogen pair was measured as a ratio of peak volume while NOE transfer was allowed to the peak volume of a control experiment without the saturation of $^1$H resonances (Kay et al. 1989).

Monitoring Reconstitution of the Fragments by Fluorescence Spectroscopy

To measure the affinity of the interaction, a technique is preferable that requires lower sample concentration than NMR. Therefore, the reaction was investigated using the inherent fluorescence of the tryptophan residue present in the N-terminal domain.

Proteins were dissolved to a final concentration of 500 nM in 20 mM sodium phosphate buffer at pH 6.0 containing 100 mM sodium chloride, 750 mM glycerol unless otherwise noted and various urea concentration between 1 M and 2.5 M. Urea concentration was deter using an Abbe refractometer (Spectronic Instruments) as described (Pace and Sholtz 1997). To obtain data on the reconstitution at conditions without the addition of urea and glycerol, a series of C-terminal fragment-titration experiments with varying urea or glycerol concentrations, respectively, were performed. The dissociation constants in the absence of urea or glycerol were estimated by extrapolation based on experimental data.

The reconstitution reaction follows the scheme

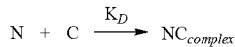

where: (1)

$$K_D = \frac{[N]*[C]}{[NC_{complex}]}$$

With: (2, 3)

$[N] + [NC_{complex}] = [N]_0$ $[C] + [NC_{complex}] = [C]_0$ the equation results in; (4)

$$[N] = \frac{([N]_0 - [C]_0 - K_D)}{2} + \frac{1}{2}\sqrt{([N]_0 - [C]_0 - K_D)^2 + 4*K_D*[N]_0}$$

where [N] is the concentration of free N-terminal fragment, [NC$_{complex}$] the concentration of complex in solution, [N]$_0$ the total concentration of N-terminal fragment, which is the fluorophore. The concentration of the C-terminal fragment [C] and [C]$_0$ is treated similarly. This relationship allows the fitting of titration experiments where the fluorescence F is fitted by: (5)

$$F = \frac{[N]}{[N]_0}*F_{isolated} + \left(1 - \frac{[N]}{[N]_0}\right)*F_{complex}$$

F$_{isolated}$ and F$_{complex}$ represent two more fitting parameters given by the starting and the asymptotic endpoint of a titration. The resulting fluorescence decay at a particular wavelength was fitted for each titration experiment, which required the use of four fitting parameters: [N-terminal], F$_{isolated}$ and F$_{complex}$, and the dissociation constant of the reconstitution. Even though approximate values of the first three parameters were known, all parameters were allowed to vary in order to obtain a best fit. The fitting resulted in parameters close to the expected, approximate values and restricting parameters to the expectation values lead only to minor changes in the observed dissociation constant.

The linear dependency of the free energy of unfolding of many proteins on urea concentration has been well established. As reconstitution results in a folding of the peptides comparable to the folding of the intact protein, the free energy of the reconstitution was assumed to depend linearly on urea concentration as well. As the free energy of the reconstitution depends exponentially on the dissociation constant, the dependence of the K$_D$ on the urea concentration required a linear fit of the logarithm of the K$_D$ (see FIG. 39). Glycerol concentration was kept constant at 750 mM in this set of experiments. For the glycerol concentration dependence, no precedent has been established in the literature. The dissociation constant was therefore assumed to depend linearly on glycerol concentration (see FIG. 40). A logarithmic fit similar to the urea concentration dependence did not represent the data well. However, the dependence of the dissociation constant on glycerol was not very strong, and thus similar values were obtained even if other dependencies were assumed.

Circular Dichroism

The far UV-circular dichroism spectrum of C-terminal fragment was recorded at concentrations of 5 µM to 100 µM in 20 mM sodium phosphate buffer (pH 6.0) containing 100 mM sodium chloride. A sample at 1.5 µM fragment concentration was investigated to test for the presence of secondary structure in buffer conditions of the fluorescence experiments (sodium phosphate buffer with 1M urea and 750 mM glycerol). The N-terminal fragment was measured at a fragment concentration of 5 µM in 20 mM sodium phosphate buffer (pH 6.0) containing 100 mM sodium chloride and 750 mM glycerol. Circular dichroism measurements were performed using a Model 202 spectrometer equipped with a Peltier temperature controller (Aviv Instruments) using a 1 cm pathlength.

The temperature dependence of the secondary structure in the C-terminal fragment was investigated as well. The maximum of the inflection in the spectrum at low temperature at 232 nm (see FIG. 41) was recorded as the sample temperature was raised at a rate of approximately 1° C. per minute. The thermal denaturation data were fitted with the standard two-state model (Pace and Sholtz 1997):

$$\Delta G(T) = \Delta H_m(1-T/T_m) - \Delta C_P[(T_m-T)+T\ln(T/T_m)]$$

where $\Delta G(T)$ is the Gibbs free energy of unfolding at temperature T, $\Delta H_m$ is the enthalpy change upon unfolding at the midpoint of the transition, $T_m$, and $\Delta C_P$ is the heat capacity change upon unfolding. A $\Delta C_P$ was approximated to 1.04 kcal mol$^{-1}$ K$^{-1}$, based on Myers et al. (Myers et al. 1995) and kept constant for all measurements.

Results

Denaturant Induced Unfolding of Proteins with Inserted Cleavage Site

The stability of the mutant proteins was investigated before cleavage using guanidine hydrochloride induced unfolding and refolding reactions monitored by tryptophan fluorescence. The fluorescence was quenched in the folded protein and allowed a convenient way to measure the unfolding transition. The unfolding curves of all four proteins are shown in FIGS. 26A and 26B. The standard two state transition was assumed in the analysis and resulting parameters of the fitting are given in Table 11. The difference in stability between CD loop and EF loop elongation mutant was observed for these mutants featuring a five-residue insertion. The effect of the altered surface charge D7KE9Q at the N-terminal end was difficult to judge from this measurement, since the unfolding reaction in GuHCl was shown least sensitive to the mutation with only a marginal increase in stability (see FIG. 26B). For the unfolding of the proteins with a cleavage site, no stabilizing effect of the D7KE9Q mutations within error was seen. The additional methionine had no unexpected effect in addition to what was seen in the four glycine insertion.

Separation of N- and C-terminal Fragments

The peptide bond following a methionine residue was cleaved under acidic conditions using cyanogen bromide. Initial tests exhibited successful, albeit incomplete cleavage of all the proteins at mildly acidic conditions. Further optimization for the preparation was found at more acidic reaction and purification conditions and a strict limitation of cleavage time to minimize deamidation under the acidic conditions. A typical reverse phase chromatogram for the CD loop cleavage is shown in FIG. 28. The N- and C-terminal fragments identity was confirmed by mass spectroscopic analysis. Although there is no methionine in the wild type FNfn10 sequence, there is a secondary cleavage site at the start of the protein separating a multiple histidine (HisTag) leader sequence from the N-terminal fragment. The N-terminal fragment that has the HisTag still attached was shown to run as the contaminant peak number 2. Contaminant peak number 3 was shown to be of slightly smaller mass than the N-terminal fragment. Its volume increased with prolonged exposure to an acidic environment regardless of CNBr presence, and likely resulted from a deamidation event. Contaminant peak number 1 appeared to include uncleaved FNfn10 as well as both fragments. Its volume was sensitive to the exact loading conditions, where moderate amount of acetonitrile present in the loading buffer decreased the peak volume. Most likely, reconstitution of the fragments was taking place even at acidic conditions and complexed fragments resulted in peak number 1.

Initial Tests Revealed Different Fragment Characteristics Between Cut Sites

Trials to observe reconstitution using fluorescence were obstructed by the presence of nonspecific adhesion, however, qualitative data could be obtained. The Trp fluorescence of FNfn10 was highly quenched in the folded state. If the reconstituted complex formed the same three-dimensional structure, quenching of the fluorescence signal was expected upon a reconstitution reaction. Both N-terminal fragments produced by a cleavage in the CD loop, with or without the surface charge mutations, revealed such quenching upon the addition of the C-terminal fragment, indicating that reconstitution had occurred. The fragments produced by a cleavage in the EF loop, however, showed no indication of reconstitution. The wild-type N-terminal fragment from CD45 (see Table 11) exhibited a poorer solubility compared to the D7KE9Q counterpart, CD92. The mutant CD-loop fragments were chosen for a detailed study of the reconstitution reaction.

Size Exclusion Chromatography Confirmed Reconstitution of CD Cut Fragments

Size exclusion chromatography was performed on the fragments of CD92 using a Sephadex75 gel filtration column. When a mixture of N- and C-terminal fragment at 5 µM concentration were loaded onto the gel filtration column (see FIG. 29) the elution showed only a single peak at the retention time of uncut protein, compared to a significantly slower elution of C-terminal fragment alone. The qualitative pattern is consistent with the formation of a complex with a dissociation constant well below 1 µM. However, both fragments in isolation appeared to bind to the column, hampering a quantitative analysis.

Fragments Reconstitute the Native Fold of the Uncut Protein

Further experiments were performed to distinguish any specific binding from nonspecific binding. To investigate if the apparent complex formation was observed by gel filtration chromatography stemmed from a specific binding event, nuclear magnetic resonance (NMR) spectroscopy was applied. NMR offers atom-specific information because nuclear spins of an atom within a protein represent extremely sensitive probes for their local electromagnetic environment. The exact conformation of a protein determines the chemical shift of a nuclear spin.

Multidimensional heteronuclear NMR spectroscopy allows the correlation of chemical shift of nearby atoms, giving rise to a distinct pattern that is specific for a conformation of a protein. It is apparent whether the protein is unfolded or folded since the electromagnetic environment changes drastically during folding for most atoms in a protein. Similarly, if two proteins form a complex due to specific interactions, the resulting pattern of chemical shifts of each nuclei will reflect changes compared to that in isolation for residues involved in those specific interactions. If a fragments is disordered in isolation, chemical shifts of all atoms are clustered in a narrow regime characteristic for random coil, and most atoms will experience significant change in their local environment and thus in chemical shift upon folding into a structure. To test the conformation of the fragments in isolation and when combined, $^{15}$N labeled protein was purified and NMR analysis was performed.

The $^1$H-$^{15}$N HSQC spectrum of the uncut protein exhibited a peak distribution matching that of wild type FNfn10 for most amides (see FIG. 30). As expected, there were additional peaks that likely originated from the inserted residues, and there were changes in the peak position for residues in the immediate vicinity of the surface charge mutations D7KE9Q. Nevertheless, the changes in chemical shift were limited to structurally adjacent residues, e.g., D23, which were likely to be affected. Thus, the β-sandwich fold of FNfn10 was maintained in the protein featuring both the D7KE9Q and the cleavage site insertion mutation.

The spectrum of each fragment by itself showed limited peak dispersion indicative of an unstructured peptide (see FIG. 31). For the C-terminal fragment, additional peaks appeared that stem from a reversible transition to an oligomeric state. When reducing the temperature to 5° C., the population of this alternative conformation was reduced, resulting in a spectrum indicative of an unfolded peptide.

The N-terminal fragment in isolation was not soluble at high protein concentrations and required the presence of 10% glycerol to record a spectrum (see FIG. 31). Though peak broadening indicates formation of larger aggregates, the spectrum did not exhibit a significant spread of chemical shifts, suggesting that the aggregate conformers were unstructured.

Once N- and C-terminal fragments were combined, the tendency of the N-terminal fragment to aggregate decreased significantly, allowing higher concentrations of fragment. This indicated that a more folded complex was formed. An HSQC-spectrum on a complex formed of labeled N-terminal fragment and unlabeled C-terminal fragment exhibited a drastic change to a well-dispersed distribution of peaks (see FIG. 35A, B).

Similarly, addition of unlabeled N-terminal to labeled C-terminal sample revealed a conformational change to a well-dispersed spread of chemical shifts. The overlap of these two spectra, equivalent to the spectrum of a fully labeled complex, was virtually identical to the previously recorded spectrum of the uncut protein (see FIG. 36A, B). Therefore, the reconstitution of the two fragments resulted in the formation of a complex that had the same fold as the original protein.

Reconstituted Protein Appears as Rigid as the Uncut Protein

The next question investigated was whether the formation of a complex with similar fold as the original protein would result in a more dynamic assembly. The association could lead to a more loose assembly, where regions could exhibit motion on much larger scale than possible in the uncleaved protein. Steady-state{$^1$H}-{$^{15}$N}-NOE measurements yield information on fast, picosecond to nanosecond time scale dynamics of a molecule. For a qualitative judgement of the overall changes in dynamics, a full assignment of the resonances is not necessary, as it is not important to identify particular residues at this point. Thus, the NOE experiment was analyzed for each peak found in the investigated spectra (see FIGS. 35 and 36). A tentative assignment based on the similarity of the complex spectrum to the known assignment of wild type FNfn10 was shown as well.

For both N-terminal and C-terminal fragment in the complex the $^{15}$N-NOE signal was predominantly above 0.75, indicating a rigid assembly comparable to the uncut protein in this motion regime. In contrast, the isolated C-terminal fragment showed significantly lower values for the majority of resonances, characteristic of a flexible peptide in a random coil conformation. The lack of fast dynamic motion further showed that the reconstitution resulted in a fragment complex that had very similar characteristics comparable to the uncleaved protein.

Determination of the Dissociation Constant of the Reconstitution Reaction Glycerol and Urea Limit Non-specific Binding Initial tests had already confirmed that the reconstituted complex exhibited similar quenching of the signal as the uncut protein, which was to be expected after NMR experiments had confirmed that the same three-dimensional structure was formed. When the N-terminal fragment containing the fluorophore was studied in isolation, the observed fluorescence appeared inconsistent. Further investigation revealed that the fluorescence of the N-terminal fragment decreased over time when the sample was kept in the quartz cuvette for the measurement (see FIG. 37). This was due to adherence of the fragment to the cuvette walls. The effect was also observed on plastic surfaces of storage tubes. It was most prevalent at the low concentration used in the fluorescence experiments. The adherence was found to be on a slower time scale, not coming to an equilibrium within minutes and also was found to be reversible on a slow time scale. The exponential decay of fluorescence signal interfered with the detection of reconstitution as quenching of the reconstitution and signal loss were indistinguishable. A series of different sample buffer conditions were tested. It was found that the addition of glycerol and denaturing co-solutes such as urea or guanidine hydrochloride decreased the magnitude of adherence. At concentration of 750 mM glycerol and 1M urea or higher, the fluorescence signal was found to be nearly constant over time.

Unusually High Affinity of the Reconstitution

A dissociation constant can be determined from a titration experiment where the concentration of the fluorophore is held constant and its corresponding binding partner is added. At a glycerol concentration of 750 mM, 1M urea and the N-terminal fragment of approximately 500 nM, the titration of the C-terminal fragment was fitted to approximately 10 nM (see FIG. 38). However a $K_D$ of 0.1 nM resulted in a nearly identical fit, indicating that the dissociation constant lies outside the accurately assessable range. When measuring the dissociation constant, the concentration of the fluorophore has to be lower than or near the dissociation constant. To obtain a more accurate value, a series of titration experiments were performed at higher urea concentration, followed by subsequent extrapolation to compensate for the addition of urea. The resulting dissociation constants over the concentration of Urea present are shown in FIG. 39. The line in FIG. 39 indicates that the detection limit of this method was set at 10 nM, which is 50× lower than the concentration of fluorophore. Accurate determination of the dissociation constant was no longer possible at or below this limit. As indicated by the linear fit, an extrapolation to the absence of urea was made with reasonable accuracy. The dissociation constant in the absence of urea, but in the presence of 750 mM glycerol, was estimated to be 1.5 nM.

Interestingly, the reconstitution reaction equilibrated in 20-30 seconds, much slower than expected for the measured high affinity. Partially, a delay was necessary for the diffusion of a small titrated aliquot throughout the sample containing glycerol and urea. In addition, a competing reaction could be responsible, for example the dissociation of an oligomeric state.

An additional series of experiments was performed to extrapolate over glycerol concentration as well. Here, no relationship had previously been established. Thus, simple models were applied to obtain a fit that yielded best match with the experimental data. The data indicate that the results were best represented by a direct linear correlation to glycerol concentration, as displayed in FIG. 40.

To gain an extrapolation that excluded both glycerol and urea, a stepwise approach was taken that assumed that the two co-solutes had independent effects on the dissociation constant. Here a first extrapolation resulted in an adjusted value in the absence of urea. A second extrapolation was then adjusted to exclude the presence of glycerol, resulting in a dissociation constant of 3.6 nM in plain buffer. An alternative path by reversing order of the extrapolation yielded a value of 3.9 nM, which was in reasonable agreement with the previous one.

The dissociation constant for the C-terminal fragment and the His6-ubiquitin-N-terminal fragment (fusion protein) was also determined using the fluorescence method described above. Unlike the free N-terminal fragment, the ubiquitin fusion protein remained soluble at 0.5 nM in the absence of urea or glycerol at pH 2.4 (20 mM glycine HCL buffer containing 100 mM sodium chloride). In these conditions, the dissociation constants was determined to be 14.4±0.2 nM. This is close to the value determined for the fragments generated from the chemical cleavage of FN3 described above. These results indicate that connecting a foreign protein at the N-terminus of FN3 does not inhibit the fragment reconstitution reaction.

Indication of an Oligomeric Structure in the C-terminal Fragment

In addition to the observation of secondary signals at higher temperature in the NMR experiments, the circular dichroism spectrum of the C-terminal fragment showed evidence of secondary structure. The spectrum showed an inflection in the far UV regime at 230-235 nm (see FIG. 41), which has been associated with β-hairpin structures.

As shown in FIG. 42, B-turn structures exhibited a cooperative temperature dependence, with a melting curve of around 37° C. for a protein concentration of 50 µM. The phenomenon was concentration dependent, which was a clear indication that it involved an oligomerization process, not an intramolecular folding reaction. Both the midpoint of the melting curve as well as the cooperativity of the reaction changed when the concentration was varied. At a concentration 1.5 µM C-terminal fragment in the presence of 1M urea and 750 mM glycerol the temperature increase resulted in a dependency that could only be fitted if the same baseline slope seen at higher concentration was assumed (see FIG. 42). The higher baseline matched that of the higher concentration measurements, while the lower one was outside the temperature range, given the low cooperativity of the transition. Nevertheless, it was possible to distinguish a transition even at this low concentration.

Discussion

The reconstitution of the FNfn10 fragments generated from a cleavage in the CD loop could be observed and the formation of the original structure was demonstrated utilizing fluorescence, gel filtration and NMR experiments. The NMR spectra indicated that the structure of the FNfn10 domain was reestablished. The NMR data also demonstrate that the whole complex was as rigid as the uncut protein.

The dissociation constant of the reconstitution was determined to be 3.6 nM using fluorescence spectroscopy. Fragments of a number of proteins have been reported to reconstitute structure and function. However, only a few reports the dissociation constants of the reconstitution reaction. The $K_d$ of the reconstitution of the CD92 protein is one of the lowest reported values to date (Table 12).

TABLE 12

Comparison of $K_D$ values for reconstitution reaction reported in the literature.

| Protein | $K_D$ (nM) | Number of Residues | Comment | Reference |
|---|---|---|---|---|
| FNfn10 | 3.6 | 42 + 47 | | (our data) |
| Chymotrypsin Inhibitor-2 (wild type) | 40 | 40 + 24 | | (Ladurner et al. 1997) |
| Ubiquitin | 38 000 | 35 + 40 | | (Jourdan and Searle 2000) |
| Protein G B1 domain | 10 000 | 40 + 15 | | (Honda et al. 1999) |
| Barnase | 600 | 36 + 73 | | (Sancho and Fersht 1992) |
| S-protein/S-peptide | 599 (wild type) | 20 + 104 | Large unit folds independent | (Dwyer et al. 2001) |
| S-protein/LB2 variant S-peptide | 5.4 (best selected) | 20 + 104 | Improvement by phase display | (Dwyer et al. 2001) |
| Calbindin D9K EF-hands | 0.003 | 43 + 31 | $Ca^{2+}$ dependent, Fragments fold independently | (Berggard et al. 2001) |

Only one case (Berggard et al. 2001) reported a lower value, though in that particular case, both fragments folded independently and the $Ca^{2+}$ binding was essential for the reconstitution. Metal binding has been known to stabilize the three dimensional structure of proteins [Savchenko, 2002 #1248] (Lee et al. 1989) [Pabo, 2001 #1186][Li, 2001 #1251], which likely applies to a reconstitution as well. This might impede direct comparison to this reconstitution reaction with the others. The high affinity of the FNfn10 fragments compared to other reconstitution reactions is consistent with a correlation to a high stab of the parental protein.

Fragment reconstitution has been reported for a number of proteins indicating that the phenomenon is not an extraordinary characteristic (de Prat Gay and Fersht 1994; Kippen et al. 1994; Tasayco and Chao 1995; Ladurner et al. 1997; Pelletier et al. 1998; Tasayco et al. 2000; Berggard et al. 2001). A similar reaction could potentially be found for any protein because the driving force to form the particular three-dimensional structure is generally independent of the maintenance of a single peptide bond. Cyclic permutations of proteins confirm that if two amino acids are in proximity to each other within a fold, the addition of a bond is generally possible as well (Zhang, 1993) (Hennecke, 1999), as long as important folding elements stay intact. However, not every peptide bond is expendable, and removing more than one at a time may not be possible. Each peptide bond must carry some information on the three-dimensional. Obviously, the importance of the information contained in any one peptide bond varies within a protein, which gives rise to differences seen in the capability of fragments to reconstitute a protein between two cleavage sites.

Folding of a protein, and therefore reconstitution of a protein from fragments, is primarily driven by the burial of hydrophobic surface away from water. If the total surface burial upon folding from disordered peptides were responsible, two cleavage sites would not result in different affinities as the same protein is folded. If the interaction between fragments were needed to maintain a complex, then the burial in the interface between the fragments is more relevant. As an approximation, the amount of newly exposed surface in the interface upon separation of the fragments was calculated using the Connolly algorithm (Connolly, 1983) in the program GRASP (Nicholls et al. 1991). 1930 $Å^2$ were exposed upon cleavage in the CD loop, while 1181 $Å^2$ were exposed upon cleavage in the EF loop based on the crystal structure of FNfn10 (Dickenson et al. 1994). The surface area found for both cleavage sites were comparable to binding interfaces with reasonable affinity. If the buried interface was the only determining factor, both cut sites would produce fragments that reconstitute readily, and less of a difference in affinity would be expected between the differently cut fragments.

Most cleavage sites reported were in a flexible region of the reconstituted protein. A peptide bond necessitated the proximity of two residues, which thereby applied a conformational constant on the polypeptide that was absent in a complex of fragments missing this peptide bond. The region surrounding the cleavage site of a reconstituted complex therefore exhibits an increased flexibility compared to the uncut protein. An entropic penalty applies to a protein if a region is mutated to be more flexible. A region that is already flexible suffers a smaller penalty upon cleavage. The highest possible stability for a complex is achieved if a protein is cleaved in a flexible region.

The significant decrease in stability in the EF loop elongation mutant indicated the importance of interactions in the EF loop for the protein fold. The inability of the EF loop fragments to reconstitute compared to the CD loop fragments was correlated with the significantly lower stability of the EF loop elongation mutant. This indicated that for a moderate to high affinity, the determining factor was the stability of the parental protein. As the cleaved proteins had a significant elongation inserted at the cleavage site, the stability for these proteins had already suffered an entropic penalty. The EF loop had suffered an aggravated penalty due to the disruption of important interactions in the FNfn10 fold. The data suggest that the stability of an insertion mutant can be utilized to predict if reconstitution is possible.

The presence of distinct resonances in the HSQC, whose chemical shifts were far from random coil values, was evidence for an oligomerization of the C-terminal fragment. Additionally, the oligomers cause a concentration dependent inflection in the CD spectra indicative of secondary structure, which was not completely vanished at 1.5 µM C-terminal fragment concentration. The oligomeric structure monitored by CD exhibits a clear cooperative temperature melting (see FIG. 42). The presence of this inflection at the low concentration indicated the presence of oligomers at the concentration used in the fluorescence experiments. However, the detected presence of distinct peaks in the HSQC and the solubility to more than 1 mM concentration suggested the absence of large insoluble aggregates. More likely much smaller oligomers containing a limited number of molecules existed under these conditions. Formation of larger oligomers resulted in increased linewidth in the NMR, similar to what was seen for the N-terminal fragment. Oligomerization of the N-terminal domain caused significant line broadening compared to the similarly sized C-terminal domain, indicating much larger oligomers. However, the N-terminal fragment did not exhibit a more dispersed spectrum at the same time. Thus, the comparably large oligomers were not in a distinct structure. The C-terminal fragment exhibited characteristics in the CD and the NMR data, indicating formation of small oligomers with a distinct structure, most likely a β-sheet conformation, that were present even at low micromolar concentrations.

A consequence of an oligomer formation was its competition with the reconstitution reaction. One possibility to influence the reconstitution arises if the dissociation of an oligomer is rate-limiting for the formation of the reconstituted complex of – and C-terminal fragments. The reconstitution complex forms rapidly, judging from the exceptionally high affinity measured. The reaction is slowed by a possible dissociation of oligomer that has occur prior to reconstitution. Consistent with such a competing oligomerization reaction are observations made in the fluorescence experiments, that equilibration of the complex formation is slower than expected for the measured high affinity. Additional indication was obtained while mixing highly concentrated samples for the NMR experiments. Even longer equilibration times and consequently careful sample preparation were necessary to attain reconstituted complex at high fragment concentration, possibly reflecting an increased population of C-terminal fragment in the oligomeric state unavailable for the reconstitution reaction. The dissociation of the oligomeric structure of the C-terminal domain is therefore likely to be rate limiting for the formation of the reconstituted complex.

The Reconstitution Reaction can be Observed in vivo

Evidence on the possibilities to apply the observed reconstitution of FNfn10 to a yeast two hybrid selection suggested that the reaction occurs in yeast. A yeast two-hybrid selection was previously applied to isolate FNfn10 based proteins that bind to human estrogen receptor ligand binding domain [Koide, 2002 #1160]. Selected proteins, termed 'monobodies' were isolated in a ligand specific manner. Utilizing binding proteins from this selection, yeast two-hybrid assays were constructed to test if monobody fragments reconstitute into a FNfn10 fold in vivo. Fragments that featured either a wild type or a mutated FG loop were assayed for the occurrence of the reconstitution of FNfn10 proteins (see FIG. 44). All FNfn10 reconstituted specifically in vivo. The results confirmed that all fragments with a mutant FG loop reconstituted nearly as well as the wild type fragments, indicating that the FG loop does not contribute significantly to FNfn10 stability.

EXAMPLE XXII

Reconstitution of Monobodies in Yeast Cells

This example demonstrates that the fragment reconstitution reaction of FN3 has sufficiently high affinity and specificity as means to heterodimerize proteins of interest. The results in this example also strongly suggest that yeast two-hybrid libraries based on FN3 fragment reconstitution can be constructed for large scale screening.

Strains and Media

Yeast strains EGY48, MATα his3 trp1 ura3 leu2::6Lex-Aop-LEU2, and RFY206, MATα his3Δ200 leu2-3 lys2Δ201 trp1Δ::hisG ura3-52, have been described (Gyuris et al. 1993; Finley and Brent 1994) and were purchased from Origene. Yeast was grown in YPD media or YC dropout media following instructions from Origene and Invitrogen. Manipulation of Escherichia coli was according to Sambrook et al (Sambrook et al. 1989).

Constructions of Plasmids for the Yeast Two-hybrid Screening and Monobody Libraries The plasmids for monobody-reconstitution were constructed as follows. The plasmid pFNB42, that encodes FLAG tag-FNfn10-NLS (nuclear localization signal)-B42 fusion protein, was constructed by PCR. The oligonucleotides used for the construction of the plasmids for monobody-reconstitution are found in Table 13.

TABLE 13

The oligonucleotides used for the construction of the plasmids for monobody reconstitution

| Name | DNA sequence |
|---|---|
| FNABCGGKpnR | ACCACCGGTACCACCACCGTTACCACCGGTTT CACC (SEQ ID NO: 125) |
| FNDGGBamF | CGGGGATCCAAGGTGGTGGCTCCCCGTTCAGG AATTC (SEQ ID NO: 126) |
| NcoFLAGFNF | CATGCCATGGACTACAAGGACGACGATGACAA GGGTATGCAGGTTTCTGATGTTC (SEQ ID NO: 127) |
| KpnGGTGGSNLSF | GTGGTACCGGTGGTTCCCCTCCAAAAAAGAAG AGAAG (SEQ ID NO: 128) |
| FNKpnGGTGGSR | GGAACCACCGGTACCACCGGTACGGTAGTTAA TCGAG (SEQ ID NO: 129) |
| B42TAAXhoR | CCGACTCGAGTTAATCTCCACTCAGCAAGAG (SEQ ID NO: 131) |
| T7F | TAATACGACTCACTATAGGG (SEQ ID NO: 130) |
| FN5R | CGGGATCCTCGAGTTACTAGGTACGGTAGTTA ATCGA (SEQ ID NO: 132) |

The oligonucleotides NcoFLAGFNF and KpnGGTGGSR were used to amplify FNfn10 gene from pAS45 (Koide et al. 1998), and the oligonucleotides KpnGGTGGSNLSF and B42TAAXhoR were used to amplify NLS-B42 gene from pYesTrp2 (Invitrogen™). The two PCR fragments were annealed and extended using PCR, then digested with NcoI and XhoI. The fragment was ligated in pYesTrp2 that was digested with the same restriction enzymes. The FNfn10 gene of pFNB42 was replaced with the gene of the N-terminal fragment of FNfn10 (the ABC-strands of FNfn10) to construct the plasmid pFNABCB42, that encodes FLAG tag-N terminal fragment of FNfn10 (ABC strands)-NLS (nuclear localization signal) -B42 fusion protein, using the restriction enzyme NcoI and KpnI. The gene of FNfn10 ABC strands was amplified from pFNB42 or vectors of ERαEF-binding monobodies whose AB-loop had been mutated, using oligonucleotides T7P and FNABCGGKpnR. For the construction of pEGFNDEFG, that encodes LexA-C terminal fragment of FNfn10 (DEFG strands) fusion protein, was constructed by cloning a gene of FNfn10 DEFG strands in pEG202 (Origene) using restriction enzymes BamHI and XhoI. The gene of FNfn10 DEFG strands was amplified from pAS45 or the vector that encodes yeast ORF-binding monobody whose FG-loop has been mutated, using oligonucleotides FNDGG-BamF and FN5R.

β-Galactosidase Assay for Monobody-reconstitution

The yeast strain EGY48 was transformed with a derivative of the pFNABCB42 plasmid encoding a fusion of N terminal fragment of particular monobody-NLS-B42. The yeast strain RFY206 that has the plasmid pSH18-34 was transformed with a derivative of the pEGFNDEFG plasmid encoding a fusion of LexA-C terminal fragment of particular monobody. The EGY48 strains and the RFY206 strains were mated, replicated onto YC Gal Raf-his -ura -trp plate, then the β-galactosidase activity of the mated strains was measured by agarose overlay method (Duttweiler 1996).

Results

EGY48 strains harboring a derivative of pFNABCB42, that encodes the N terminal fragment of FNfn10-NLS-B42 fusion protein, were mated with RFY206 strains harboring β-galactosidase reporter plasmid and a derivative of pEGFN-DEFG, that encodes LexA-C terminal fragment of monobody fusion protein. The mated strains were tested for β-galactosidase activity, and the results are shown in FIG. 27. The amino acid sequence of the FG loop region of the C terminal half of monobodies are listed on Table 14. The results show that not only FNfn10, but also monobodies can be reconstituted in vivo.

TABLE 14

The sequence of the FG-loop regions of the C-terminal half of monobodies

| clone name | amino acid sequence of the FG loop | |
|---|---|---|
| pEGFNDEFG | VTGRGDSPASSKP | (SEQ ID NO: 133) |
| pEGFNDEFG0319 | VTGQWALYLSSKP | (SEQ ID NO: 134) |
| pEGFNDEFG4699 | VTGGEVRCVRDAASWSSWLKP | (SEQ ID NO: 135) |

EXAMPLE XXIII

Examples of Mutations to be Introduced to Alter the Association Specificity of N-FN3 and C-FN3

The inventor previously demonstrated that charged residues on the surface of FN3 have large effects on the stability of FN3 (Koide et al., 2001). Mutations of residues on the protein surface cause small perturbations on the overall structure of a protein. Also interactions between residues at "cross strand" positions (i.e., residues on neighboring beta-strands that are directly adjacent to each other) are known to influence the beta-sheet stability (Smith & Regan, 1995). Control of peptide association using charged surface residues has been well documented, particularly for coiled coil peptides (see Oakley and Kim, and references therein). Therefore, such mutations are used to modulate the affinity between N-FN3 and C-FN3. Below is a general strategy for using N-FN3 and C-FN3 that are separated in the CD loop. Note, however, this strategy is applicable to FN3 fragments that are separated at other points beside in the CD loop.

Strands B and E are aligned in the anti-parallel manner in one sheet of FN3 (see FIG. 45). These two strands belong to different fragments. Mutations such as D21 (or E21) and D56 (or E56) cause electrostatic repulsion between negative charges on strand B and strand E, thus destabilizing the complex of N-FN3 and C-FN3. Similarly, R21 (or K21) and R56 (or K56) cause repulsion between positive charges on strands B and E, thus destabilizing the complex. In contrast, when N-FN3 with D21 (or E21) and C-FN3 with R56 (or K56) are combined, the electrostatic repulsion is eliminated, and the two fragments form a stable complex. Likewise, a combination of R21 (or K21) and E56 (or E56) also facilitate the association. These "cross strand" positions that introduce such mutations include residues 19 and 58, 17 and 60, and 23 and 54 on strands B and E; residues 37 and 45, 35 and 47, 33 and 49 and 31 and 51 on strands C and D; residues 37 and 69, 35 and 71, 33 and 73, and 31 and 75 on strands C and F. Mutations at these positions are combined to adjust the affinity and specificity of association.

For a combination of N-FN3 and C-FN3 with a different separation point, cross strand pairs are identified using the same principle.

The second class of mutations that can be used to alter the specificity of FN3 fragment reconstitution is those in the core of FN3. The core of a protein is generally tightly packed and mutations in the core are often highly destabilizing (Matthews 1993). Thus, multiple mutations can be introduced in the core (for example, positions 10, 20, 36, 70 and 90 can be simultaneously mutated). Because a large number of residues are in close contact in the core, one should need to introduce multiple mutations to achieve tight interaction of fragments. Core mutations and surface mutations can be used in combination, which should provide a high degree of interaction specificity.

EXAMPLE XXIV

Procedures for Library Construction and Screening Using "Split FN3"

Nomenclature

N-FN3 and C-FN3 denote N-terminal and C-terminal fragments of FN3 that are produced by separating FN3 at a position within a loop. For example, if the separation is within the CD loop, N-FN3 contains the A, B and C strands, the AB and BC loops and a section of the CD loop. C-FN3 then contains the remaining section of the CD loop, the DE, EF, and FG loops and the D, E, F, and G strands.

A binding pair denotes a pair of molecules that associate with each other, having a dissociation constant of less than $10^{-5}$ $M^{-1}$. Binding pairs can be used to augment the association (reconstitution) of N-FN3 and C-FN3. One example of a binding pair is coiled coils.

1. Phage Display a. Two Vector System

N-FN3 is fused to a phage coat protein in such a way that it is displayed on the surface of bacteriophage (Kay et al., 1996; Koide et al., 1998). Alternatively, C-FN3 may be fused to a phage coat protein such as pIII and pVIII. An N-terminal secretion sequence is added to the complementary fragment (the fragment that is not fused to a phage coat protein) in such a way that the fragment is secreted into the periplasmic space of *Escherichia coli*. Genes of these fusion proteins are encoded on a phagemid vector, such as pBlueScript (Stratagene) under the control of a regulatable promoter. Alternatively, the phage genome can be used. The phagemid encoding N-FN3 contains a drug resistance marker (such as ampicillin resistance), and the phagemid encoding C-FN3 contains a different marker (such as kanamycin resistance), so that they are easily separated.

A binding pair can be added to N-FN3 and C-FN3 in such a way that the binding pair enhances the association of N-FN3 and C-FN3. This is done by fusing the gene for one component of the binding partner to the N-FN3 gene and the other to the C-FN3 gene using a flexible linker sequence (e.g., poly-Gly) between fused peptides.

Combinatorial libraries of N-FN3 and C-FN3 in appropriate phagemids as described above, in which residues in a loop region are diversified (including insertions and deletions), are made using standard methods (Koide et al., 1998). Phagemid particles for N-FN3 and C-FN3 are separately generated using a helper phage as described (Koide et al., 1998). Subsequently, *E. coli* cells (such as XL1-blue, Stratagene) harboring an N-FN3 library are further infected with the phagemids encoding a C-FN3 library so that in a single *E. coli* cell both one (or more) clone of the N-FN3 library and one (or more) clone of the C-FN3 library coexists. Phagemid particles are then produced from these cells under conditions where N-FN3 and C-FN3 are expressed. N-FN3 and C-FN3 associate in the periplasm of *E. coli* and thus phagemid particles display the reconstituted FN3 representing one clone from the N-FN3 library and one from the C-FN3 library. The phagemid transfection process is very efficient, so that one can construct a large library.

Screening of displayed FN3 is performed using standard methods (Kay et al., 1996; Koide et al., 1998). Note that a phagemid particle contains the gene for either N-FN3 or C-FN3, and thus it is necessary to recover at least two phagemid particles to identify the correct combination of N-FN3 and C-FN3 variants with desired binding function.

Recovered phages are amplified and again used to infect *E. coli* so that a single *E. coli* cell harbors both N-FN3 clone and C-FN3 clone. Phagemid particles are then produced as described above. After a few cycles of these selection and amplification processes, genes encoding the contiguous, full-length monobodies are constructed from the genes for N-FN3 and C-FN3 variants in the selected pool using PCR techniques and cloned into a phagemid vector. Standard phagemid selection experiments are then performed to identity full-length monobodies with desired binding properties.

b. One Vector System

A phagemid vector expressing N-FN3 fused to a phage coat protein and a secretion signal and C-FN3 fused to a secretion signal (or vise versa) under a single promoter is constructed. A recombinase recognition site such as wild-type lox is introduced in the intergenic region between the N-FN3 and C-FN3 genes. Another recombination site, which is orthogonal to the first one, such as loxP511 is introduced after the two FN3 fragment genes. Examples of such phagemid vectors have been described in the literature (Sblattero and Bradbury 2000; Sblattero et al. 2001). Mutations are introduced in a loop region within the N-FN3 gene using standard methods to generate a library of N-FN3. To this ensemble of phagemid vectors encoding the library, further mutations in a loop region of the C-FN3 gene are introduced. Phagemid particles are prepared from this ensemble of vectors encoding both N-FN3 and C-FN3 libraries using helper phages. *E. coli* cells that constitutively expresses an appropriate recombinase, such as Cre recombinase, are infected with the phagemid particles with a high multiplicity of infection so that a single cell is infected with multiple phagemids. The recombinase in the *E. coli* cells recombine the phagemids at the recombination sites, thus creating further diversity. Phagemid particles are then produced from these cells and then used to infect another *E. coli* cell line that does not express the recombinase at a low multiplicity of infection. Phagemid particles are produced from these *E. coli* cells for library selection. Library selection and amplification of selected phagemids are performed using standard methods, except that the recombination step can be introduced to further increase the library diversity.

2. Yeast Two-hybrid

A binding target ("bait") is fused to a DNA binding domain, and N-FN3 (optionally with a component of a binding pair) is fused to an activation domain using standard methods (Golemis & Serebriiskii, 1997; Koide et al., 2002). C-FN3 (optionally with the other component of a binding pair) is expressed without fusing it to an activation domain under a strong promoter such as Gal so that it associates with the N-FN3-activation domain fusion. A library of N-FN3 is constructed in yeast cells of one mating type (e.g., the strain EGY48) and a library of C-FN3 is constructed in yeast cells of the other mating type (e.g., the strain RFY206). The bait plasmid is introduced in one of the yeast cells before constructing a library. The two yeast strains are mated and yeast two-hybrid screening is performed using standard methods as described previously (Golemis & Serebriiskii, 1997; Koide et al., 2002). Alternatively, C-FN3 can be fused to an activation domain and N-Fn3 can be expressed without fusing it to an activation domain.

3. Yeast Surface Display.

N-FN3 (optionally with a component of a binding pair) is fused to the Aga2 protein in such a way that it allows the surface display of N-FN3 (Boder & Wittrup, 1997; Boder & Wittrup, 2000). A vector such as pYD1 (Invitrogen) is used for this purpose. C-FN3 (optionally with the other component of a binding pair) is fused to an N-terminal secretion sequence and the gene coding for this fusion protein is placed under an appropriate promoter such as GAL on a vector. Alternatively C-FN3 can be displayed on the yeast surface and N-FN3 can be expressed without fusing it to Aga2. A library of N-FN3 is constructed using standard methods (Koide et al., 2002) in the yeast strain EBY100 (Invitrogen™), and a library of C-FN3 is constructed in the yeast strain BJ5464 (ATCC). A collection of EBY100 cells containing a N-FN3 library and a collection of BJ5464 containing a C-FN3 library are mated to produce diploid cells each containing one member of the N-FN3 library and one of the C-FN3 library. N-FN3 and C-FN3 variants are then displayed on the yeast surface, and selection of clones are performed as described (Boder & Wittrup, 1997; Boder & Wittrup, 2000).

The following section describes a specific example of yeast surface display. The plasmid pYDFN1 was constructed by inserting the FN3 gene into pYD1 vector (Invitrogen™), and the gene is expressed under the Gal promoter. The FN3 gene was prepared by PCR, and the termination codon of the FN3 gene was removed in such a way that the FN3 gene and the V5 tag sequence is in frame. N-FN3 (residues 1-42) was fused to the secretion signal of the Aga2 protein and the FLAG tag in such a way that it allows the secretion of N-FN3 followed by the FLAG tag. The secretion signal-N-FN3-FLAG gene was constructed using PCR, and pYDFN1 was used as a template. The secretion signal-N-FN3-FLAG gene was cloned in the plasmid pRS425 (Sikorski 1989). The resulting plasmid is named pGalsecFN(N)FLAG. A yeast surface display vector for C-FN3 (residues 43-94) was constructed from the plasmid pYDFN1. The DNA segment encoding the Express tag and residues 1-42 of FN3 was deleted by PCR so that it encodes the Aga2-C-FN3-V5-His fusion protein. The resulting plasmid is pGalAgaFN(C)V5. Schemes of these vectors are shown in FIG. 46. In addition, a pGalAgaFN(C)V5 containing a FG-loop from a monobody "STAV11" that binds to streptavidin was constructed (pGalAgaFN(C)V5-STAV11). The STAVII clone contains an PG loop sequence of HPM-NEKN (SEQ ID NO:138) in place of the wild-type sequence, RGDSPAS (SEQ ID NO:48).

Yeast EBY100 was transformed with the plasmid pGalsecFN(N)FLAG, and BJ5464 was transformed with the plasmid pGalAgaFN(C)V5 or pGalAgaFN(C)V5-STAV11. These two strains were mated, and the diploid cells were analyzed using fluorescence activated cell sorter (FACS).

Mated cells were grown in YC Glc ura- trp- leu-media, followed by YC Gal Raf ura- trp- leu-media in order to induce the expression of the fusion proteins. These media are according to Boder and Wittrup (Boder and Wittrup 1997). Cells were spun down, washed with BSS (Tris-Cl pH7.4, NaCl, 1 mg/ml BSA). The cells were mixed with rabbit anti-FLAG antibody (Sigma) and monoclonal anti-V5 antibody (Sigma)

in BSS and incubated on ice for 40 minutes. The cells were spun down, washed with BSS, and mixed with anti-rabbit antibody-PE (Sigma) and anti-mouse antibody-FITC (Sigma) in BSS and incubated on ice for 40 minutes. The cells were spun down, washed with BSS, and subjected to a cell sorter (FACScanII™, Beckton Dickinson). In this staining scheme, FITC fluorescence intensity indicates the amount of C-FN3 on the yeast surface and PE intensity indicates the amount of N-FN3 on the surface.

As shown in FIG. 47, the FITC fluorescence monitoring the V5 epitope tag attached to C-FN3 was correlated to the expression of C-FN3 and C-FN3-STAV11. The PE fluorescence monitoring the FLAG tag attached to N-FN3 was correlated to the expression of N-FN3 when C-FN3 was co-expressed. The surface display of N-FN3 was dependent on C-FN3 expression, indicating that N-FN3 and C-FN3 reconstituted on the yeast surface. These results show that combinatorial libraries can be constructed from fragment libraries using yeast mating as described above.

Once specific pairs of N-FN3 and C-FN3 with desired binding properties are identified, genes encoding contiguous, full-length monobodies containing the identified loops sequences are constructed from the genes for the fragments. The genes for such full-length monobodies are cloned into vectors for library screening and/or into expression vectors, and these new vectors are used for further library screening and protein production.

The complete disclosure of all patents, patent documents and publications cited herein are incorporated by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

References

Alzari, P. N., Lascombe, M.-B. & Poljak, R. J. (1988) Three-dimensional structure of antibodies. *Annu. Rev. Immunol.* 6, 555-580.

Archer, S. J., Ikura, M., Torchia, D. A. & Bax, A. (1991) An alternative 3D NMR technique for correlating backbone 15N with side chain Hb resonances in large proteins *J. Magn. Reson.* 95, 636-641.

Aukhil, I., Joshi P., Yan, Y. & Erickson, H. P. (1993) Cell- and heparin-binding domains of the hexabrachion arm identified by tenascin expression protein *J. Biol. Chem.* 268, 2542-2553.

Barbas, C. F., III, Kang, A. S., Lerner, R. A., and Benkovic, S. J. 1991. Assembly of combinatorial antibody libraries on phage surfaces: the gene III site. *Proc. Natl. Acad. Sci. USA* 88: 7978-7982.

Barbas, C. F., III, Bain, J. D., Hoekstra, D. M. & Lerner, R. A. (1992) Semisynthetic combinatorial libraries: A chemical solution to the diversity problem *Proc. Natl. Acad. Sci. USA* 89, 4457-4461.

Baron, M., Main, A. L., Driscoll, P. C., Mardon, H. J., Boyd, J. & Campbell, I. D. (1992) $^1$H NMR assignment and secondary structure of the cell adhesion type II module of fibronectin *Biochemistry* 31, 2068-2073.

Baron, M., Norman, D. G. & Campbell, I. D. (1991) Protein modules *Trends Biochem. Sci.* 16, 13-17.

Bass, S., Greene, R. & Wells, J. A. (1990) Hormone phage: An enrichment method for variant proteins with altered binding properties *Proteins: Struct. Funct. Genet.* 8, 309-314.

Bax, A. & Grzesiek, S. (1993) Methodological advances in protein NMR. *Acc. Chem. Res.* 26, 131-138.

Becktel W. J. & Schellman, J. A. (1987) Protein stability curves. *Biopolymer* 26, 1859-1877.

Berggard, T., Julenius, K., Ogard, A., Drakenberg, T., and Linse, S. 2001. Fragment complementation studies of protein stabilization by hydrophobic core residues. *Biochemistry* 40: 1257-1264.

Bhat, T. N., Bentley, G. A., Boulot, G., Greene, M. I., Tello, D., Dall'acqua, W., Souchon, H., Schwarz, F. P., Mariuzza, R. A. & Poljak, R. J. (1994) Bound water molecules and conformational stabilization help mediate an antigen-antibody association. *Proc. Natl. Acad. Sci. USA* 91, 1089-1093.

Bianchi, E., Venturini, S., Pessi, A., Tramontano, A. & Sollazzo, M. (1994) High level expression and rational mutagenesis of a designed protein, the minibody. From an insoluble to a soluble molecule. *J. Mol. Biol.* 236, 649.659.

Billeter, M., Neri, D., Otting, G., Qian, Y. Q. & Wüthrich, K. (1992) Precise vicinal coupling constants 3JHNa in proteins from nonlinear fits of J-modulated [$^{15}$N, $^1$H]-COSY experiments. *J. Biomol. NMR* 2, 257-274.

Bodenhausen, G. & Ruben, D. J. (1980) Natural abundance nitrogen-15 NMR by enhanced heteronuclear spectroscopy. *Chem. Phys. Lett.* 69, 185-189.

Boder, E. T., and Wittrup, K. D. 1997. Yeast surface display for screening combinatorial polypeptide libraries. *Nat Biotechnol* 15: 553-557.

Boder, E. T., and Wittrup, K. D. 2000. Yeast surface display for directed evolution of protein expression, affinity, and stability. *Methods Enzymol* 328: 430-444.

Bork, P. & Doolittle, R. F., *PNAS* 89:8990-8994 (1992).

Bork, P. & Doolittle, R. F. (1992) Proposed acquisition of an animal protein domain by bacteria. *Proc. Natl. Acad. Sci. USA* 89, 8990-8994.

Bork, P., Hom, L. & Sander, C. (1994) The immunoglobulin fold. Structural classification, sequence patterns and common core. *J. Mol. Biol.* 242, 309-320.

Brünger, A. T. (1992) X-PLOR (Version 3.1): *A system for X-ray crystallography and NMR*., Yale Univ. Press, New Haven.

Burke, T., Bolger, R., Checovich, W. & Lowery, R. (1996) in *Phage display of peptides and proteins* (Kay, B. K., Winter, J. and McCafferty, J., Ed.) Vol. pp305-326, Academic Press, San Diego.

Campbell, I. D. & Spitzfaden, C. (1994) Building proteins with fibronectin type III modules *Structure* 2, 233-337.

Cavanagh, J., Fairbrother, W. J., Palmer, A. G. I., and Skelton, N. J. 1996. *Protein NMR spectroscopy: principles and practice*. Academic Press, San Diego.

Chen, Y., Reizer, J., Saier, M. H., Fairbrother, W. J. & Wright, P. E. (1993) Mapping the binding interfaces of the proteins of the bacterial phaphotransferase system, HPr and IIAglc. *Biochemistry* 32, 32-37.

Clarke, J., Hamill S. J. & Johnson, C. M. (1997) *J Mol Biol* 270, 771-778.

Clackson & Wells, (1994) *Trends Biotechnology* 12, 173-184.

Clore, G. M. & Gronenborn, A. M. (1991) Structure of larger proteins in solution: Three- and four-dimensional heteronuclear NMR spectroscopy. *Science* 252, 1390-1399.

Connolly, M. L. 1983. Solvent-accessible surfaces of proteins and nucleic acids. *Science* 221: 709-713.

Cordingley, M. G., Callahan, P. L., Sardana, V. V., Garsky, V. M., and Colonno, R. J. 1990. Substrate requirements of human rhinovirus 3C protease for peptide cleavage in vitro. *J Biol Chem* 265: 9062-9065.

Corey, D. R., Shiau, A. K., Q., Y., Janowski, B. A. & Craik, C. S. (1993) Trypsin display on the surface of bacteriophage. *Gene* 128, 129-134.

Cota, E. & Clarke, J. (2000) *Protein Sci* 9, 112-120.

Creighton, T. E. (1993) *Proteins: structures and molecular properties*, Freeman, New York, pp. 38-40.

Dao-pin, S., Sauer, U., Nicholson, H. & Matthews, B. W. (1991) *Biochemistry* 30, 7142-7153.

Davies, J. & Riechmann, L. (1996). Single antibody domains as small recognition units: design and in vitro antigen selection of camelized, human VH domains with improved protein stability. *Protein Eng.*, 9(6), 531-537.

Davies, J. & Riechmann, L. (1995) Antibody VH domains as small recognition units. *Bio/Technol.* 13, 475-479.

Delaglio, F., Grzesiek, S., Vuister, G. W., Zhu, G., Pfeifer, J. & Bax, A. (1995) NMRPipe: a multidimensional spectral processing system based on UNIX pipes. *J. Biomol. NMR* 6, 277-293.

Deng, W. P. & Nickoloff, J. A. (1992) Site-directed mutagenesis of virtually any plasmid by eliminating a unique site. *Anal. Biochem.* 200, 81-88.

de Prat Gay, G., and Fersht, A. R. 1994. Generation of a family of protein fragments for structure-folding studies. 1. Folding complementation of two fragments of chymotrypsin inhibitor-2 formed by cleavage at its unique methionine residue. *Biochemistry* 33: 7957-7963.

deVos, A. M., Ultsch, M. & Kossiakoff, A. A. (1992) Human Growth hormone and extracellular domain of its receptor: crystal structure of the complex. *Science* 255, 306-312.

Dickinson, C. D., Veerapandian, B., Dai X. P., Hal R. C., Xuong, N.-H., Ruoslahti E. & Ely, K. R. (1994) Crystal structure of the tenth type III cell adhesion module of human fibronectin *J. Mol. Biol.* 236, 1079-1092.

Dill, K. A. (1990) *Biochemistry* 29, 7133-7155.

Djavadi-Ohaniance, L., Goldberg, M. E. & Friguet, B. (1996) in *Antibody Engineering. A Practical Approach* (McCafferty, J., Hoogenboom, H. R. and Chiswell, D. J., Ed.) Vol. pp. 77-97, Oxford Univ. Press, Oxford.

Dougall, W. C., Peterson, N. C. & Greene, M. I. (1994) Antibody-structure-based design of pharmacological agents. *Trends Biotechnol.* 12, 372-379.

Duttweiler, H. M. 1996. *Trends in Genetics* 12: 340-341.

Dwyer, J. J., Dwyer, M. A., and Kossiakoff, A. A. 2001. High Affinity RNase S-Peptide Variants Obtained by Phage Display Have a Novel "Hot-Spot" of Binding Energy. *Biochemistry* 40: 13491-13500.

Farrow, N. A., Muhandiram, R., Singer, A. U., Pascal, S. M., Kay, C. M., Gish, G., Shoelson, S. E., Pawson, T., Forman-Kay, J. D., and Kay, L. E. 1994. Backbone dynamics of a free and phosphopeptide-complexed Src homology 2 domain studied by $^{15}$N NMR relaxation. *Biochemistry* 33: 5984-6003.

Fields, S., and Song, O. 1989. A novel genetic system to detect protein-protein interactions. *Nature* 340: 245-246.

Finley, R. L., Jr., and Brent, R. 1994. Interaction mating reveals binary and ternary connections between *Drosophila* cell cycle regulators. *Proc Natl Acad Sci USA* 91: 12980-12984.

Fujiwara, K., Poikonen, K., Aleman, L., Valtavaara, M., Saksela, K., and Mayer, B. J. 2002. A single-chain antibody/epitope system for functional analysis of protein-protein interactions. *Biochemistry* 41: 12729-12738.

Garrett, D. S., Powers, R., Gronenborn, A. M. & Clore, G. M. (1991) A common sense approach to peak picking in two-, three- and four-dimensional spectra using automatic computer analysis of contour diagrams. *J. Magn. Reson* 95, 214-220.

Geyer, C. R., and Brent, R. 2000. Selection of genetic agents from random peptide aptamer expression libraries. *Methods Enzymol* 328: 171-208.

Ghosh, G., Van Duyne, G., Ghosh, S. & Sigler, P. B. (1995) Structure of NF-kB p50 homodimer bound to a kB site. *Nature* 373, 303-310.

Golemis, E. & Serebriiskii I. (1997) Two-hybrid system/interaction trap in *Cells: A laboratory manual* Ed.) pp69.1-40, CSH Laboratory Press, Cold Spring Harbor, N.Y.

Gribskov, M., Devereux, J. & Burgess, R. R. (1984) The codon preference plot: graphic analysis of protein coding sequences and prediction of gene expression. *Nuc. Acids. Res.* 12, 539-549.

Grimsley, G. R, Shaw, K. L., Fee, L. R., Alston, R. W., Huyghues-Despointes, B. M., Thurlkill, R. L., Scholtz, J. M. & Pace, C. N. (1999) *Protein Sci* 8, 1843-1849.

Groneborn, A. M., Filpula, D. R., Essig, N. Z., Achari, A., Whitlow, M., Wingfield, P. T. & Clore, G. M. (1991) A novel, highly stable fold of the immunoglobulin binding domain of Streptococcal protein G. *Science* 253, 657-661.

Gronenborn, A. M. & Clore, G. M. (1993) Identification of the contact surface of a Streptococcal protein G domain complexed with a human Fc fragment. *J. Mol. Biol.* 233, 331-335.

Grzesiek, S., Anglister, J. & Bax, A. (1993) Correlation of backbone amide and aliphatic side-chain resonances in 13C/15N-enriched proteins by isotropic mixing of 13C magnetization *J. Magn. Reson. B* 101, 114-119.

Grzesiek, S. & Bax, A. (1992) Correlating backbone amide and side chain resonances in larger proteins by multiple relayed triple resonance NMR. *J. Am. Chem. Soc.* 114, 6291-6293.

Grzesiek, S. & Bax, A. (1993) Amino acid type determination in the sequential assignment procedure of uniformly 13C/15N-enriched proteins. *J. Biomol. NMR* 3, 185-204.

Gyuris, J., Golemis, E., Chertkov, H., and Brent, R. 1993. Cdil, a human G1 and S phase protein phosphatase that associates with Cdk2. *Cell* 75: 791-803.

Harlow, E. & Lane, D. (1988) *Antibodies. A laboratory manual*, Cold Spring Harbor Laboratory, Cold Spring Harbor.

Harpez, Y. & Chothia, C. (1994) Many of the immunoglobulin superfamily domains in cell adhesion molecules and surface receptors belong to a new structural set which is close to that containing variable domains *J. Mol. Biol.* 238, 528-539.

Hawkins, R. E., Russell, S. J., Bay, M. & Winter, G. (1193) The contribution of contact and non-contact residues of antibody in the affinity of binding to antigen. The interaction of mutant D1.3 antibodies with lysozyme. *J. Mol. Biol.* 234, 958-964.

Hawkins, R. E., Russel S. J., and Winter, G. 1992. Selection of phage antibodies by binding affinity. Mimicking affinity maturation *J. Mol. Biol.* 226: 889-896.

Hendsch, Z. S., Jonsson, T., Sauer, R. T. & Tidor, B. (1996) *Biochemistry* 35, 7621-7625.

Hendsch, Z. S. & Tidor, B. (1994) *Protein Sci.* 3, 211-226.

Hennecke, J., Sebbel, P., and Glockshuber, R. 1999. Random circular permutation of DsbA reveals segments that are essential for protein folding and stability. *J Mol Biol* 286: 1197-1215.

Hoess, R. H. 2001. Protein design and phage display. *Chem Rev* 101: 3205-3218.

Holliger, P. et al., (1993) *Proc. Natl. Acad. Sci.* 90, 6444-6448.

Honda, S., Kobayashi N., Munekata, E., and Uedaira, H. 1999. Fragment reconstitution of a small protein: folding energetics of the reconstituted immunoglobulin binding domain B1 of streptococcal protein G. *Biochemistry* 38: 1203-1213.

Hu, S-z, et al., *Cancer Res.* 56:3055-3061 (1996).

Ikura, M. & Bax, A. (1992) Isotope-filtered 2D NMR of a protein-peptide complex: study of a skeletal muscle myosin light chain kinase fragment bound to calmodulin. *J. Am. Chem. Soc.* 114, 2433-2440.

Ikura, M., Kay, L. E. & Bax, A. (1991) Improved three-dimensional 1H-13C-1H correlation spectroscopy of a 13C-labeled protein using constant-time evolution. *J. Biomol. NMR* 1, 299-304.

Jacobs, J. & Schultz, P. G. (1987) Catalytic antibodies. *J. Am. Chem. Soc.* 109, 2174-2176.

Janda, K. D., et al., *Science* 275:945-948 (1997).

Johnson, B. A. & Blevins, R. A. (1994) *J. Biomol. NMR* 4, 603-614.

Johnsson, N., and Varshavsky, A. 1994. Split ubiquitin as a sensor of protein interactions in vivo. *Proc Natl Acad Sci USA* 91: 10340-10344.

Jones, E. Y. (1993) The immunoglobulin superfamily *Curr. Opinion struct. Biol.* 3, 846-852.

Jones, P. T., Dear, P. H., Foote, J., Neuberger, M. S. & Winter, G. (1986) Replacing the complementarity-determining regions in a human antibody with those from a mouse *Nature* 321, 522-525.

Jourdan, M., and Searle, M. S. 2000. Cooperative assembly of a nativelike ubiquitin structure through peptide fragment complexation: energetics of peptide association and folding. *Biochemistry* 39: 12355-12364.

Kabsch, W. & Sander, C. (1983) Dictionary of protein secondary structure: pattern recognition of hydrogen-bonded and geometrical features. *Biopolymers* 22, 2577-2637.

Kamtekar, S. Schiffer J M, Xiong H, Babik J M, Hecht M H. (1993) Protein design by binary patterning of polar and nonpolar amino acids. *Science* 262(5140):1680-1685.

Kapust, R. B., Tozser, J., Fox, J. D., Anderson, D. E., Cherry, S., Copeland, T. D., and Waugh, D. S. 2001. Tobacco etch virus protease: mechanism of autolysis and rational design of stable mutants with wild-type catalytic proficiency. Protein Eng 14: 993-1000.

Kauzmann, W. (1959) *Adv. Prot. Chem.* 14, 1-63.

Kay, B. K., Winter, J. & McCafferty, J. (1996) Phage display of peptides and proteins: a laboratory manual, Academic Press, San Diego.

Kay, L. E. (1995) Field gradient techniques in NMR spectroscopy. *Curr. Opinion Struct. Biol.* 5, 674-681.

Kay, L. E., Keifer, P. & Saarinen, T. (1992) Pure absorption gradient enhanced heteronuclear single quantum correlation spectroscopy with improved sensitivity *J. Am. Chem. Soc.* 114, 10663-10665.

Kay, L. E., Torchia, D. A, and Bax, A. 1989. Backbone dynamics of proteins as studied by $^{15}$N inverse detected heteronuclear NMR spectroscopy: application to staphylococcal nuclease. *Biochemistry* 28: 8972-8979.

Kay, L. E., Keifer, P., and Saarinen, T. 1992. Pure absorption gradient enhanced heteronuclear single quantum correlation spectroscopy with improved sensitivity. *J. Am. Chem. Soc.* 114: 10663-10665.

Kay, L. E. (1993) *J. Am. Chem. Soc.* 115, 2055-2057.

Kay, L. E., Xu, G.-Y. & Singer, A. U. (1993) A Gradient-Enhanced HCCH-TOCSY Experiment for Recording Side-Chain 1H and 13C Correlations in H2O Samples of Proteins. *J. Magn. Reson. B* 101, 333-337.

Kippen, A. D., Sancho, J., and Fersht, A. R. 1994. Folding of barnase in parts. *Biochemistry* 33: 3778-3786.

Kohno, T., Kusunoki, H., Sato, K., and Wakamatsu, K. 1998. A new general method for the biosynthesis of stable isotope-enriched peptides using a decahistidine-tagged ubiquitin fusion system: an application to the production of mastoparan-X uniformly enriched with 15N and 15N/13C. *J. Biomol. NMR* 12:109-121.

Koide, S., Dyson, H. J. & Wright, P. E. (1993) Characterization of a folding intermediate of apoplastcyanin trapped by proline isomerization. *Biochemistry* 32, 12299-12310.

Koide, A., Bailey, C. W., Huang, X. & Koide, S. (1998) *J. Mol. Biol.* 284, 1141-1151.

Koide, S., Bu, Z., Risal, D., Pham, T.-N., Nakagawa, T., Tamura, A. & Engelman, D. M. (1999) *Biochemistry* 38, 4757-4767.

Koide, A. et al., *PNAS* 99:1253-1258 (2002)

Koide, A., Jordan, M. R., Horner, S. R., Batori V. & Koide, S. (2001) Stabilization of a fibronectin type III domain by the removal of unfavorable electrostatic interactions on the protein surface. *Biochemistry* 40, 10326-33.

Koide, A, Abbatiello, S., Rothgery, L., and Koide, S. 2002. Probing protein conformational changes in living cells by using designer binding proteins: Application to the estrogen receptor. *PNAS* 99: 1253-1258.

Kornblihtt, A. R., Umezawa, K., Vibe-Pederson, K. & Baralle, F. E. (1985) Primary structure of human fibronectin: differential splicing may generate at least 10 polypeptides from a single gene *EMBO J.* 4, 1755-1759.

Kraulis, P. (1991) MOLSCRIPT: a program to produce both detailed and schematic plots of protein structures. *J. Appl. Cryst.* 24, 946-950.

Kuhlman, B., Luisi D. L., Young, P. & Raleigh, D. P. (1999) *Biochemistry* 38, 4896-4903.

Kunkel, T. A. (1985) Rapid and efficient site-specific mutagenesis without phenotypic selection *Proc. Natl. Acad. Sci. USA* 82, 488-492.

Ladurner, A. G., Itzhaki, L. S., de Prat Gay, G., and Fersht, A. R. 1997. Complementation of peptide fragments of the single domain protein chymotrypsin inhibitor 2. *J Mol Biol* 273: 317-329.

Leahy, D. J., Aukhil, I. & Erickson, H. P. (1996) *Cell* 84, 155-164.

Leahy, D. J., Hendrickson, W. A., Aukhil, I. & Erickson, H. P. (1992) Structure of a fibronectin type III domain from tenascin phased by MAD analysis of the selenomethionlyl protein *Science* 258, 987-991.

Lee, M. S., Gippert, G. P., Soman, K. V., Case, D. A., and Wright, P. E. 1989. Three-dimensional solution structure of a single zinc finger DNA-binding domain. *Science* 245: 635-637.

Lee, W., Revington, M. J., Arrowsmith, C. & Kay, L. E. (1994) A pulsed field gradient isotope-filtered 3D 13C HMQC-NOESY experiment for extracting intermolecular NOE contacts in molecular complexes. *FEBS lett.* 350, 87-90.

Lerner, R. A. & Barbas III, C. F., *Acta Chemica Scandinavica*, 50 672-678 (1996).

Lesk, A. M. & Tramontano, A. (1992) Antibody structure and structural predictions useful in guiding antibody engineering. In *Antibody engineering. A practical guide.* (Borrebaeck, C. A. K., Ed.) Vol. W. H. Freeman & Co., New York.

Li, B., Tom, J. Y., Oare, D., Yen, R., Fairbrother, W. J., Wells, J. A. & Cunningham, B. C. (1995) Minimization of a polypeptide hormone *Science* 270, 1657-1660.

Li, Z., Stafford, W. F., and Bouvier, M. 2001. The metal ion binding properties of calreticulin modulate its conformational flexibility and thermal stability. *Biochemistry* 40: 11193-11201.

Litvinovich, S. V., Novokhatny, V. V., Brew, S. A. & Inhgam, K. C. (1992) Reversible unfolding of an isolated heparin and DNA binding fragment, the first type III module from fibronectin. *Biochim. Biophys. Acta* 1119, 57-62.

Logan, T. M., Olejniczak, E. T., Xu, R. X. & Fesik, S. W. (1992) Side chain and backbone assignments in isotopically labeled proteins from two heteronuclear triple resonance experiments. *FEBS lett.* 314, 413-418.

Loladze, V. V., Ibarra-Molero, B., Sanchez-Ruiz, J. M. & Makhatadze, G. I. (1999) *Biochemistry* 38, 16419-16423.

Main, A. L., Harvey, T. S., Baron, M., Boyd, J. & Campbell, I. D. (1992) The three-dimensional structure of the tenth type III module of fibronectin: an insight into RGD-mediated interactions. *Cell* 71, 671-678.

Malakauskas, S. M. & Mayo, S. L. (1998) *Nat Struct Biol* 5, 470-475.

Masat, L., et al., (1994) *PNAS* 91:893-896.

Martin, F., Toniatti C., Ciliberto, G., Cortese, R. & Sollazzo, M. (1994) The affinity-selection of a minibody polypeptide inhibitor of human interleukin-6. *EMBO J.* 13, 5303-5309.

Martin, M. T., *Drug Discov. Today,* 1:239-247 (1996)

Matthews, B. W. 1993. Structural and genetic analysis of protein stability. *Ann. Rev. Biochem.* 62: 139-160.

McCafferty, J., Griffiths, A. D., Winter, G. & Chiswell, D. J. (1990) Phage antibodies: filamentous phage displaying antibody variable domains. *Nature* 348, 552-554.

McClain, D. L et al., *J. Am. Chem. Soc.* 123:3151-3152 (2001).

McConnell, S. J., & Hoess, R. H., *J. Mol. Biol.* 250:460-470 (1995).

McIntosh, L. P., Hand, G., Johnson, P. E., Joshi M. D., Koerner, M., Plesniak, L. A., Ziser, L., Wakarchuk, W. W. & Withers, S. G. (1996) *Biochemistry* 35, 9958-9966.

Merkel, J. S., and Regan, L. 2000. Modulating protein folding rates in vivo and in vitro by side-chain interactions between the parallel beta strands of green fluorescent protein. *J Biol Chem* 275: 29200-29206.

Metzler, W. J., Leiting, B., Pryor, K., Mueller, L. & Farmer, B. T. I. (1996) The three-dimensional solution structure of the SH2 domain from p55blk kinase. *Biochemistry* 35, 6201-6211.

Michnick, S. W., Remy, I., Campbell-Valois, F. X., Vallee-Belisle, A., and Pelletier, J. N. 2000. Detection of protein-protein interactions by protein fragment complementation strategies. *Methods Enzymol* 328: 208-230.

Minor, D. L. J. & Kim, P. S. (1994) Measurement of the β-sheet-forming propensities of amino acids. *Nature* 367, 660-663.

Muhandiram, D. R., Xu, G. Y. & Kay, L. E. (1993) An enhanced-sensitivity pure absorption gradient 4D 15N, 13C-edited NOESY experiment. *J. Biomol. NMR* 3, 463-470.

Müller, C. W., Rey, F. A., Sodeoka, M., Verdine, G. L. & Harrison, S. C. (1995) Structure of the NH-kB p50 homodimer bound to DNA. *Nature* 373, 311-117.

Myers, J. K., Pace, C. N. & Scholtz, J. M. (1995) *Protein Sci.* 4, 2138-2148.

Nicholls, A., Sharp, K. A., and Honig, B. 1991. Protein folding and association: insights from the interfacial and thermodynamic properties of hydrocarbons. *Proteins* 11: 281-296.

Nilges, M., Clore, G. M. & Gronenborn, A. M. (1988) Determination of three-dimensional structures of proteins from interproton distance data by hybrid distance geometry-dynamical simulated annealing calculations. *FEBS lett.* 229, 317-324.

Nilges, M., Kuszewski, J. & Brünger, A. T. (1991) in *Computational aspects of the study of biological macromolecules by nuclear magnetic resonance spectroscopy.* (Hoch, J. C., Poulsen, F. M. and Redfield, C., Ed.) Vol. pp. 451-455, Plenum Press, New York.

Ojennus D D et al., *Protein Science* 10:2162-2175 (2001).

Oakley M G et al., *Biochemistry* 37:12603-12610 (1998).

O'Neil et al., (1994) in *Techniques in Protein Chemistry V* (Crabb, L., ed.) pp. 517-524, Academic Press, San Diego.

O'Neil, K. T. & Hoess, R. H. (1995) Phage display: protein engineering by directed evolution. *Curr. Opinion Struct. Biol.* 5, 443-449.

Pabo, C. O., Peisach, E., and Grant, R. A. 2001. Design and selection of novel Cys2His2 zinc finger proteins. *Annu Rev Biochem* 70: 313-340.

Pace, C. N. & Scholtz, J. M. (1997) Measuring the conformational stability of a protein. In *Protein structure. A practical approach* (Creighton, T. E., Ed.) Vol. pp. 299-321, IRL Press, Oxford.

Pace, C. N., Shirley, B. A., McNutt, M. & Gajiwala, K. (1996) *Faseb J* 10, 75-83.

Pace, C. N., Laurents, D. V. & Erickson, R. E. (1992) *Biochemistry* 31, 2728-2734.

Parmley, S. F. & Smith, G. P. (1988) Antibody-selectable filamentous fd phage vectors: affinity purification of target genes *Gene* 73, 305-318.

Pascal S. M., Muhandiram, D. R., Yamazaki T., Forman-Kay, J. D. & Kay, L. E. (1994a) Simultaneous acquisition of 15N- and 13C-edited NOE spectra of proteins dissolved in H2O. *J. Magn. Reson. B* 103, 197-201.

Pascal, S. M., Singer, A. U., Gish, G., Yamazaki T., Shoelson, S. E., Pawson, T., Kay, L. E. & Forman-Kay, J. D. (1994b) Nuclear magnetic resonance structure of an SH2 domain of phospholipase C-g1 complexed with a high affinity binding peptide. *Cell* 77, 461-472.

Patten, P. A., Howard, R. J., and Stemmer, W. P. C. 1996. Applications of DNA shuffling to pharmaceuticals and vaccines. *Curr. Opin. Biotechnol.* 8: 724-733.

Pelletier, J. N., Campbell-Valois, F. X., and Michnick, S. W. 1998. Oligomerization domain-directed reassembly of active dihydrofolate reductase from rationally designed fragments. *Proc. Natl. Acad. Sci. USA* 95: 12141-12146.

Perl, D., Mueller, U., Heinemann, U. & Schmid, F. X. (2000) *Nat Struct Biol* 7, 380-383.

Perutz, M. F., Gronenborn, A. M., Clore, G. M., Fogg, J. H. & Shih, D. T. (1985) *J Mol Biol* 183, 491-498.

Pessi A., Bianchi, E., Crameri, A., Venturini, S., Tramontano, A. & Sollazzo, M. (1993) A designed metal-binding protein with a novel fold. *Nature* 362, 3678-369.

Pierschbacher, M. D. & Ruoslahti E. (1984) *Nature* 309, 30-33.

Plaxco, K. W., Spitzfaden, C., Campbell, I. D. & Dobson, C. M. (1996) *Proc. Natl. Acad. Sci. USA* 93, 10703-10706.

Plaxco, K. W., Spitzfaden, C., Campbell, I. D. & Dobson, C. M. (1997) *J. Mol. Biol.* 270, 763-770.

Rader, C., and Barbas, C. F., 3rd. 1997. Phage display of combinatorial antibody libraries. *Curr Opin Biotechnol* 8: 503-508.

Raquet, X., Eckert, J. H., Muller, S., and Johnsson, N. 2001. Detection of altered protein conformations in living cells. *J Mol Biol* 305: 927-938.

Rees, A. R., Staunton, D., Webster, D. M., Searle, S. J., Henry, A. H. & Pedersen, J. T. (1994) Antibody design: beyond the natural limits. *Trends Biotechnol.* 12, 199-206.

Roberts et al., (1992) *Proc. Natl. Acad. Sci. USA* 89, 2429-2433.

Roberts, B. L., Markland, W., and Ladner, R. C. 1996. Affinity maturation of proteins displayed on surface of M13 bacteriophage as major coat protein fusions. *Methods Enzymol* 267: 68-82.

Rosenblum, J. S. & Barbas, C. F. I. (1995) in *Antibody Engineering* (Borrenbaeck, C. A. K, Ed.) Vol. pp89-116, Oxford University Press, Oxford.

Sali, D., Bycroft, M. & Fersht, A. R. (1991) *J. Mol. Biol.* 220, 779-788.

Sambrook, J., Fritsch, E. F. & Maniatis, T. (1989) *Molecular Cloning: A laboratory manual*, 2nd Ed., Cold Spring Harbor Laboratory, Cold Spring Harbor.

Sancho, J., and Fersht, A. R. 1992. Dissection of an enzyme by protein engineering. The N and C-terminal fragments of barnase form a native-like complex with restored enzymic activity. *J Mol Biol* 224: 741-747.

Sandhu, G. S., Aleff, R. A. & Kline, B. C. (1992) Dual asymmetric PCR: one-step construction of synthetic genes. *BioTech.* 12, 14-16.

Santoro, M. M. & Bolen, D. W. (1988) Unfolding free energy changes determined by the linear extrapolation method. 1. Unfolding of phenyl ethanesulfonyl α-chymotrypsin using different denaturants *Biochemistry* 27, 8063-8068.

Savchenko, A., Vieille, C., Kang, S., and Zeikus, J. G. 2002. *Pyrococcus furiosus* alpha-Amylase Is Stabilized by Calcium and Zinc. *Biochemistry* 41: 6193-6201.

Sblattero, D., and Bradbury, A. 2000. Exploiting recombination in single bacteria to make large phage antibody libraries. *Nat Biotechnol* 18: 75-80.

Sblattero, D., Lou, J., Marzari, R., and Bradbury, A. 2001. In vivo recombination as a tool to generate molecular diversity in phage antibody libraries. *J Biotechnol* 74: 303-315.

Skerra, A. 2000. Engineered protein scaffolds for molecular recognition. *J Mol Recognit* 13: 167-187.

Smith, G. P. & Scott, J. K. (1993) Libraries of peptides and proteins displayed on filamentous phage. *Methods Enzymol.* 217, 228-257.

Smith, G. P. (1985) Filamentous fusion phage: novel expression vectors that display cloned antigens on the virion surface. *Science* 228, 1315-1317.

Smith, C. K. & Regan, L. (1995) Guidelines for protein design: The energetics of β sheet side chain interactions. *Science* 270, 980-982.

Smith, C. K., Munson, M. & Regan, L. (1995). Studying α-helix and β-sheet formation in small proteins. *Techniques Prot. Chem.*, 6, 323-332.

Smith, C. K., Withka, J. M. & Regan, L. (1994) A thermodynamic scale for the b-sheet forming tendencies of the amino acids. *Biochemistry* 33, 5510-5517.

Smyth, M. L. & von Itzstein, M. (1994) Design and synthesis of a biologically active antibody mimic based on an antibody-antigen crystal structure. *J. Am. Chem. Soc.* 116, 2725-2733.

Spector, S., Wang, M., Carp, S. A., Robblee, J., Hendsch, Z. S., Fairman, R., Tidor, B. & Raleigh, D. P. (2000) *Biochemistry* 39, 872-879.

Studier, F. W., Rosenberg, A. H., Dunn, J. J. & Dubendorff, J. W. (1990) Use of T7 RNA polymerase to direct expression of cloned genes *Methods Enzymol.* 185, 60-89.

Suzuki, H. (1994) Recent advances in abzyme studies. *J. Biochem.* 115, 623-628.

Tasayco, M. L., and Chao, K. 1995. NMR study of the reconstitution of the beta-sheet of thioredoxin by fragment complementation. *Proteins* 22: 41-44.

Tasayco, M. L., Fuchs, J., Yang, X. M., Dyalram, D., and Georgescu, R. E. 2000. Interaction between two discontiguous chain segments from the beta-sheet of *Escherichia coli* thioredoxin suggests an initiation site for folding. *Biochemistry* 39: 10613-10618.

Tello, D., Goldbaum, F. A., Mariuzza, R. A., Ysern, X., Schwarz, F. P. & Poljak, R. J. (1993) Immunoglobulin superfamily interactions. *Biochem. Soc. Trans.* 21, 943-946.

Thomas, N. R. (1994) Hapten design for the generation of catalytic antibodies. *Appl. Biochem. Biotech.* 47, 345-372.

Timasheff, S. N. (1992) *Curr. Op. Struct. Biol.* 2, 35-39.

Verhoeyen, M., Milstein, C. & Winter, G. (1988) Reshaping human antibodies: Grafting an antilysozyme activity. *Science* 239, 1534-1536.

Venturini et al., (1994) *Protein Peptide Letters* 1, 70-75.

Vuister, G. W. & Bax, A. (1992) Resolution enhancement and spectral editing of uniformly 13C-enriched proteins by homonuclear broadband 13C decoupling. *J. Magn. Reson.* 98, 428-435.

Vuister, G. W., Clore, G. M., Gronenborn, A. M., Powers, R., Garrett, D. S., Tschudin, R. & Bax, A. (1993) Increased resolution and improved spectral quality in four-dimensional 13C/13C-separated HMQC-NOESY-HMQC spectra using pulsed filed gradients. *J. Magn. Reson. B* 101, 210-213.

Ward, E. S., Güssow, D., Griffiths, A. D., Jones, P. T. & Winter, G. (1989) Binding activities of a repertoire of single immunoglobulin variable domains secreted from *Escherichia coli Nature* 341, 554-546.

Webster, D. M., Henry, A. H. & Rees, A. R. (1994) Antibody-antigen interactions *Curr. Opinion Struct. Biol.* 4, 123-129.

Williams, A. F. & Barclay, A. N., *Ann. Rev. Immunol.* 6:381-405 (1988).

Wilson, I. A. & Stanfield, R. L. (1993) Antibody-antigen interactions. *Curr. Opinion Struct. Biol.* 3, 113-118.

Wilson, I. A. & Stanfield, R. L. (1994) Antibody-antigen interactions: new structures and new conformational changes *Curr. Opinion Struct Biol.* 4, 857-867.

Winter, G., Griffiths, A. D., Hawkins, R. E. & Hoogenboom, H. R. (1994) Making antibodies by phage display technology *Annu. Rev. Immunol.* 12, 433-455.

Wiseman, T., Williston, S., Brandts, J. F. & Lin, L.-N. (1989) Rapid measurement of binding constants and heats of binding using a new titration calorimeter. *Anal Biolchem.* 179, 131-137.

Wittenkind, M. & Mueller, L. (1993) HNCACB, a high-sensitivity 3D NMR experiment to correlate amide-proton and nitrogen resonances with the alpha- and beta-carbon resonances in proteins *J. Magn. Reson. B* 101, 201-205.

Wittke, S., Lewke, N., Muller, S., and Johnsson, N. 1999. Probing the molecular environment of membrane proteins in vivo. *Mol Biol Cell* 10: 2519-2530.

Wu, T. T., Johnson, G. & Kabat, E. A. (1993) Length distribution of CDRH3 in antibodies *Proteins: Struct. Funct. Genet.* 16, 1-7.

Wüthrich, K. (1986) NMR of proteins and nucleic acids, John Wiley & Sons, New York.

Yamazaki, T. et al., *J. Am. Chem. Soc.* 120, 5591-5592 (1998).

Yamazaki, T., Forman-Kay, J. D. & Kay, L. E. (1993) Two-Dimensional NMR Experiments for Correlating 13C-beta and 1H-delta/epsilon Chemical Shifts of Aromatic Residues in 13C-Labeled Proteins via Scalar Couplings. *J. Am. Chem. Soc.* 115, 11054.

Yang, A.-S. & Honig, B. (1992) *Curr. Opin. Struct. Biol.* 2, 40-45.

Zhang, T., Bertelsen, E., Benvegnu, D., and Alber, T. 1993. Circular permutation of T4 lysozyme. *Biochemistry* 32: 12311-12318.

Zhang, O., Kay, L. E., Olivier, J. P. & Forman-Kay, J. D. (1994) Backbone 1H and 15N resonance assignments of the N-terminal SH3 domain of drk in folded and unfolded states using enhanced-sensitivity pulsed field gradient NMR techniques. *J. Biomol. NMR* 4, 845-858.

What is claimed is:

1. A fibronectin monobody polypeptide comprising a first fibronectin type III (Fn3) monobody fragment having at least two to five Fn3 beta-strand domains in the Fn3 wild-type arrangement with a loop region linked between each beta-strand domain, and at least one additional complementary fibronectin monobody fragment comprising at least two to five Fn3 beta strand domains in the Fn3 wild-type arrangement with a loop region linked between each beta-strand domain, wherein the loop regions correspond to wild-type Fn3 loop regions, or comprise an AB, BC, CD, DE, or FG loop region sequence that is randomized or varies from a corresponding wild-type Fn3 loop region by deletion of one to all except one amino acid in the loop region, insertion of one to 25 amino acids, and/or replacement of at least one amino acid in the loop region.

2. The monobody of claim 1, wherein the first fibronectin type III (Fn3) monobody fragment is a tenth fibronectin type III fragment (Fn3$^{10}$) and the at least one additional fibronectin monobody fragment is a fibronectin type III (Fn3) fragment.

3. The monobody of claim 1, wherein at least one loop region of the first or the at least one additional monobody fragment is capable of binding to a specific binding partner (SBP) to form a monobody:SBP complex.

4. The monobody of claim 1, wherein at least one loop region of the first fibronectin type III (Fn3) monobody fragment or of at least one additional complementary fibronectin monobody fragment comprises amino acid residues: i) from 15 to 16 inclusive in an AB loop; ii) from 22 to 30 inclusive in a BC loop; iii) from 39 to 45 inclusive in a CD loop; iv) from 51 to 55 inclusive in a DE loop; v) from 60 to 66 inclusive in an EF loop; or vi) from 76 to 87 inclusive in an FG loop.

5. The monobody of claim 1, wherein at least one loop region of the first fibronectin type III (Fn3) monobody fragment or of at least one additional complementary fibronectin monobody fragment comprises an AB, BC, CD, DE, or FG loop region sequence that varies from a corresponding wild-type Fn3 loop region by deletion of one to all except one amino acid in the loop region, insertion of one to 25 amino acids, and/or replacement of at least one amino acid in the loop region.

6. The monobody of claim 1, wherein at least one loop region of the first fibronectin type III (Fn3) monobody fragment or of at least one additional complementary fibronectin monobody fragment comprises an AB, BC, CD, DE, or FG loop region sequence that varies from a corresponding wild-type Fn3 loop region by deletion of one to all except one amino acid and/or replacement of at least one amino acid.

7. The monobody of claim 1, wherein at least one loop region of the first fibronectin type III (Fn3) monobody fragment or of at least one additional complementary fibronectin monobody fragment comprises an AB, BC, CD, DE, or FG loop region sequence that varies from a corresponding wild-type Fn3 loop region by insertion of one to 25 amino acids.

8. The monobody of claim 1, wherein the first fragment comprises a first cysteine and the at least one additional fragment comprises a second cysteine, and wherein the first cysteine and the second cysteine form a disulfide bond.

9. The monobody of claim 8, wherein the first cysteine is located in a loop region.

10. The monobody of claim 8, wherein the second cysteine is located in a loop region.

11. The monobody of claim 8, wherein the first cysteine is located in a beta-strand region.

12. The monobody of claim 8, wherein the second cysteine is located in a beta-strand region.

13. The monobody of claim 2, wherein the first fibronectin type III (Fn3) monobody fragment is a tenth fibronectin type III fragment)(Fn3$^{10}$) and the at least one additional fibronectin monobody fragment is a Fn3$^{10}$ fragment.

* * * * *

SEQUENCE LISTING

<160> NUMBER OF SEQ ID NOS: 142

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Arg Glu Arg Asp Tyr Arg Leu Asp Tyr Trp Gly Gln Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Arg Gly Ala Val Val Ser Tyr Tyr Ala Met Asp Tyr Trp Gly Gln
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ala Val Thr Gly Arg Gly Asp Ser Pro Ala Ser Ser Lys Pro Ile
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ala Glu Arg Asp Tyr Arg Leu Asp Tyr Pro Ile
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ala Val Arg Asp Tyr Arg Leu Asp Tyr Pro Ile
1               5                   10

<210> SEQ ID NO 6
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 6

Tyr Ala Val Arg Asp Tyr Arg Leu Asp Tyr Ala Ser Ser Lys Pro Ile
 1               5                  10                  15

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ala Val Arg Asp Tyr Arg Leu Asp Tyr Lys Pro Ile
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ala Val Arg Asp Tyr Arg Ser Lys Pro Ile
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Ala Val Thr Arg Asp Tyr Arg Leu Ser Ser Lys Pro Ile
 1               5                  10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ala Val Thr Glu Arg Asp Tyr Arg Leu Ser Ser Lys Pro Ile
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ala Val Ala Val Val Ser Tyr Tyr Ala Met Asp Tyr Pro Ile
 1               5                  10                  15
```

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Ala Val Thr Ala Val Val Ser Tyr Tyr Ala Ser Ser Lys Pro Ile
 1               5                  10                  15

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgggatccca tatgcaggtt tctgatgttc cgcgtgacct ggaagttgtt gctgcgacc        59

<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taactgcagg agcatcccag ctgatcagca ggctagtcgg ggtcgcagca acaac            55

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctcctgcagt taccgtgcgt tattaccgta tcacgtacgg tgaaaccggt g                51

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgaattcct gaaccgggga gttaccaccg gtttcaccg                              39

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aggaattcac tgtacctggt tccaagtcta ctgctaccat cagcgg                      46
```

```
<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtatagtcga cacccggttt caggccgctg atggtagc                              38

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgggtgtcga ctataccatc actgtatacg ct                                    32

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgggatccga gctcgctggg ctgtcaccac ggccagtaac agcgtataca gtgat           55

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagcgagctc caagccaatc tcgattaact accgt                                 35

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgggatcctc gagttactag gtacggtagt taatcga                               37

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgggatccac gcgtgccacc ggtacggtag ttaatcga                              38

<210> SEQ ID NO 24
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgggatccac gcgtccattc gtttgtgaat atcaaggcca atcg                    44

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccggaagctt taagactcct tattacgcag tatgttagc                          39

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctgttactgg ccgtgagatc taaccagcga gctcca                             36

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g, t, unknown or other
<220> FEATURE:
<221> NAME/KEY: modified_base
<222> LOCATION: (23)..(24)
<223> OTHER INFORMATION: a, c, g, t, unknown or other
<220> FEATURE:
<221> NAME/KEY: modified_base
<222> LOCATION: (26)..(27)
<223> OTHER INFORMATION: a, c, g, t, unknown or other
<220> FEATURE:
<221> NAME/KEY: modified_base
<222> LOCATION: (29)..(30)
<223> OTHER INFORMATION: a, c, g, t, unknown or other
<220> FEATURE:
<221> NAME/KEY: modified_base
<222> LOCATION: (32)..(33)
<223> OTHER INFORMATION: a, c, g, t, unknown or other

<400> SEQUENCE: 27
gatcagctgg gatgctcctn nknnknnknn knnktattac cgtatcacgt a            51

<210> SEQ ID NO 28
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
```

```
<223> OTHER INFORMATION: a, c, g, t, unknown or other
<220> FEATURE:
<221> NAME/KEY: modified_base
<222> LOCATION: (23)..(24)
<223> OTHER INFORMATION: a, c, g, t, unknown or other
<220> FEATURE:
<221> NAME/KEY: modified_base
<222> LOCATION: (26)..(27)
<223> OTHER INFORMATION: a, c, g, t, unknown or other
<220> FEATURE:
<221> NAME/KEY: modified_base
<222> LOCATION: (29)..(30)
<223> OTHER INFORMATION: a, c, g, t, unknown or other
<220> FEATURE:
<221> NAME/KEY: modified_base
<222> LOCATION: (32)..(33)
<223> OTHER INFORMATION: a, c, g, t, unknown or other
<220> FEATURE:
<221> NAME/KEY: modified_base
<222> LOCATION: (35)..(36)
<223> OTHER INFORMATION: a, c, g, t, unknown or other
<220> FEATURE:
<221> NAME/KEY: modified_base
<222> LOCATION: (38)..(39)
<223> OTHER INFORMATION: a, c, g, t, unknown or other

<400> SEQUENCE: 28
tgtatacgct gttactggcn nknnknnknn knnknnknnk tccaagccaa tctcgat      57

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: a, c, g, t, unknown or other
<220> FEATURE:
<221> NAME/KEY: modified_base
<222> LOCATION: (24)..(25)
<223> OTHER INFORMATION: a, c, g, t, unknown or other
<220> FEATURE:
<221> NAME/KEY: modified_base
<222> LOCATION: (27)..(28)
<223> OTHER INFORMATION: a, c, g, t, unknown or other
<220> FEATURE:
<221> NAME/KEY: modified_base
<222> LOCATION: (30)..(31)
<223> OTHER INFORMATION: a, c, g, t, unknown or other

<400> SEQUENCE: 29
ctgtatacgc tgttactggc nnknnknnkn nkccagcgag ctccaag      47

<210> SEQ ID NO 30
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(24)
<223> OTHER INFORMATION: a, c, g, t, unknown or other
<220> FEATURE:
<221> NAME/KEY: modified_base
<222> LOCATION: (26)..(27)
<223> OTHER INFORMATION: a, c, g, t, unknown or other
<220> FEATURE:
<221> NAME/KEY: modified_base
<222> LOCATION: (29)..(30)
<223> OTHER INFORMATION: a, c, g, t, unknown or other
<220> FEATURE:
```

```
<221> NAME/KEY: modified_base
<222> LOCATION: (32)..(33)
<223> OTHER INFORMATION: a, c, g, t, unknown or other
<220> FEATURE:
<221> NAME/KEY: modified_base
<222> LOCATION: (35)..(36)
<223> OTHER INFORMATION: a, c, g, t, unknown or other

<400> SEQUENCE: 30
catcactgta tacgctgtta ctnnknnknn knnknnktcc aagccaatct c          51

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 31

Cys Ala Arg Arg Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 32

Arg Trp Ile Pro Leu Ala Lys
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 33

Cys Trp Arg Arg Ala
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 34

Arg Trp Val Gly Leu Ala Trp
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 35

Cys Lys His Arg Arg
```

```
<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 36

Phe Ala Asp Leu Trp Trp Arg
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 37

Cys Arg Arg Gly Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 38

Arg Gly Phe Met Trp Leu Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 39

Cys Asn Trp Arg Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 40

Arg Ala Tyr Arg Tyr Arg Trp
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody
```

```
<400> SEQUENCE: 41

Ser Arg Leu Arg Arg
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 42

Pro Pro Trp Arg Val
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 43

Ala Arg Trp Thr Leu
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 44

Arg Arg Trp Trp Trp
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 45

Gly Gln Arg Thr Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence of a ubiquitin-binding monobody

<400> SEQUENCE: 46

Arg Arg Trp Trp Ala
1               5

<210> SEQ ID NO 47
<211> LENGTH: 5
<212> TYPE: PRT
```

-continued

```
<213> ORGANISM: Artificial Sequence
<220> FEATURE:
<223> OTHER INFORMATION: Description of Artificial Sequence: Synthetic
      clone from Library #2

<400> SEQUENCE: 47

Ala Val Thr Val Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 48

Arg Gly Asp Ser Pro Ala Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 49

Cys Asn Trp Arg Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 50

Arg Ala Tyr Arg Tyr Arg Trp
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 51

Cys Met Trp Arg Ala
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 52

Arg Trp Gly Met Leu Arg Arg
1               5
```

```
<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 53

Ala Arg Met Arg Glu
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 54

Arg Trp Leu Arg Gly Arg Tyr
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 55

Cys Ala Arg Arg Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 56

Arg Arg Ala Gly Trp Gly Trp
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 57

Cys Asn Trp Arg Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 58
```

```
Arg Ala Tyr Arg Tyr Arg Trp
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 59

Arg Trp Arg Glu Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 60

Arg His Pro Trp Thr Glu Arg
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 61

Cys Asn Trp Arg Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 62

Arg Ala Tyr Arg Tyr Arg Trp
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 63

Glu Arg Arg Val Pro
1               5

<210> SEQ ID NO 64
<211> LENGTH: 7
<212> TYPE: PRT
<213> ORGANISM: Artificial Sequence
<220> FEATURE:
```

<223> OTHER INFORMATION: Description of Artificial Sequence: Synthetic
      clone from Library #2

<400> SEQUENCE: 64

Arg Leu Leu Leu Trp Gln Arg
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 65

Gly Arg Gly Ala Gly
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 66

Phe Gly Ser Phe Glu Arg Arg
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 67

Cys Arg Trp Thr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 68

Arg Arg Trp Phe Asp Gly Ala
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 69

Cys Asn Trp Arg Arg
1               5

<210> SEQ ID NO 70

```
<211> LENGTH: 7
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 70

Arg Ala Tyr Arg Tyr Arg Trp
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 71

Ala Val Thr Val Arg
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 72

Gly Arg Gly Asp Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 73

Gly Gln Arg Thr Phe
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 74

Arg Arg Trp Trp Ala
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 75

Gly Gln Arg Thr Phe
```

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 76

Arg Arg Trp Trp Ala
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 77

Gly Gln Arg Thr Phe
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 78

Arg Arg Trp Trp Ala
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 79

Leu Arg Tyr Arg Ser
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 80

Gly Trp Arg Trp Arg
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

```
<400> SEQUENCE: 81

Gly Gln Arg Thr Phe
 1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 82

Arg Arg Trp Trp Ala
 1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 83

Gly Gln Arg Thr Phe
 1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 84

Arg Arg Trp Trp Ala
 1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 85

Leu Arg Tyr Arg Ser
 1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 86

Gly Trp Arg Trp Arg
 1               5

<210> SEQ ID NO 87
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      clone from Library #2

<400> SEQUENCE: 87

Leu Arg Tyr Arg Ser
 1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 88

Gly Trp Arg Trp Arg
 1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 89

Gly Gln Arg Thr Phe
 1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 90

Arg Arg Trp Trp Ala
 1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 91

Leu Arg Tyr Arg Ser
 1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      clone from Library #2

<400> SEQUENCE: 92

Gly Trp Arg Trp Arg
 1               5
```

```
<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 93
gcagttaccg tgcgt                                                    15

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 94

Ala Val Thr Val Arg
1               5

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 95
ggccgtggtg acagcccagc gagc                                          24

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 96

Gly Arg Gly Asp Ser Pro Ala Ser
1               5

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 97
tcgaggttgc ggcgg                                                    15

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 98

Ser Arg Leu Arg Arg
1               5
```

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 99
ccgccgtgga gggtg                                                15

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 100

Pro Pro Trp Arg Val
 1               5

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 101
ggtcagcgaa ctttt                                                15

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 102

Gly Gln Arg Thr Phe
 1               5

<210> SEQ ID NO 103
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 103
aggcggtggt gggct                                                15

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 104

Arg Arg Trp Trp Ala

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 105
gcgaggtgga cgctt                                                    15

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 106

Ala Arg Trp Thr Leu
1               5

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 107
aggcggtggt ggtgg                                                    15

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      sequence in the variegated loops of enriched clones

<400> SEQUENCE: 108

Arg Arg Trp Trp Trp
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      solubility tail

<400> SEQUENCE: 109

Gly Lys Lys Gly Lys
1               5

<210> SEQ ID NO 110
<211> LENGTH: 94
<212> TYPE: PRT
<213> ORGANISM: Artificial Sequence
<220> FEATURE:
<223> OTHER INFORMATION: Description of Artificial Sequence: Synthetic
      Fn3 gene

<400> SEQUENCE: 110

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                85                  90
```

<210> SEQ ID NO 111
<211> LENGTH: 300
<212> TYPE: DNA
<213> ORGANISM: Artificial Sequence
<220> FEATURE:
<223> OTHER INFORMATION: Description of Artificial Sequence: Synthetic designed Fn3 gene

<400> SEQUENCE: 111

```
catatgcagg tttctgatgt tccgcgtgac ctggaagttg ttgctgcgac cccgactagc     60
ctgctgatca gctgggatgc tcctgcagtt accgtgcgtt attaccgtat cacgtacggt    120
gaaaccggtg gtaactcccc ggttcaggaa ttcactgtac ctggttccaa gtctactgct    180
accatcagcg gcctgaaacc gggtgtcgac tataccatca ctgtatacgc tgttactggc    240
cgtggtgaca gcccagcgag ctccaagcca atctcgatta actaccgtac ctagtaactc    300
```

<210> SEQ ID NO 112
<211> LENGTH: 98
<212> TYPE: PRT
<213> ORGANISM: Artificial Sequence
<220> FEATURE:
<223> OTHER INFORMATION: Description of Artificial Sequence: Synthetic designed Fn3 gene

<400> SEQUENCE: 112

```
Met Gln Val Ser Asp Val Pro Arg Asp Leu Glu Val Val Ala Ala
 1               5                  10                  15

Thr Pro Thr Ser Leu Leu Ile Ser Trp Asp Ala Pro Ala Val Thr Val
            20                  25                  30

Arg Tyr Tyr Arg Ile Thr Tyr Gly Glu Thr Gly Gly Asn Ser Pro Val
            35                  40                  45

Gln Glu Phe Thr Val Pro Gly Ser Lys Ser Thr Ala Leu Thr Ile Ser
 50                  55                  60

Gly Leu Lys Pro Gly Val Asp Tyr Thr Ile Thr Val Tyr Ala Val Thr
 65                  70                  75                  80

Gly Arg Gly Asp Ser Pro Ala Ser Ser Lys Pro Ile Ser Ile Asn Tyr
                85                  90                  95

Arg Thr
```

<210> SEQ ID NO 113

<400> SEQUENCE: 113

000

<210> SEQ ID NO 114

```
<211> LENGTH: 20
<212> TYPE: PRT
<213> ORGANISM: Artificial Sequence
<220> FEATURE:
<223> OTHER INFORMATION: Description of Artificial Sequence: Synthetic
      N-terminal histag

<400> SEQUENCE: 114

Met Gly Ser Ser His His His His His His Ser Ser Gly Leu Val Pro
1               5                   10                  15

Arg Gly Ser His
            20

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gln Arg Thr Phe Arg Arg Trp Trp Ala
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Leu Arg Tyr Arg Ser Gly Trp Arg Trp Arg
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Asn Trp Arg Arg Arg Ala Tyr Arg Tyr Trp Arg
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Arg Met Arg Glu Arg Trp Leu Arg Gly Arg Tyr
1               5                   10

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 119

Glu Ile Asp Lys
1

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Asp Tyr Arg
1

<210> SEQ ID NO 121
<211> LENGTH: 96
<212> TYPE: PRT
<213> ORGANISM: Artificial Sequence
<220> FEATURE:
<223> OTHER INFORMATION: Description of Artificial Sequence: Synthetic
      amino acid sequence of FNfn10

<400> SEQUENCE: 121

Met Gln Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Gly Arg
65                  70                  75                  80

Gly Asp Ser Pro Ala Ser Ser Lys Pro Ile Ser Ile Asn Tyr Arg Thr
                85                  90                  95

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      cleavage site

<400> SEQUENCE: 122

Gly Gly Met Gly Gly
1               5

<210> SEQ ID NO 123
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Met Gln Val Ser Asp Val Pro Thr Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
```

```
                35                  40                  45
Glu Phe Thr Val Pro Gly Ser Lys Ser Thr Ala Thr Ile Ser Gly Leu
    50                  55                  60
Lys Pro Gly Val Asp Tyr Thr Ile Thr Val Tyr Ala Val Thr Gly Arg
65                  70                  75                  80
Gly Asp Ser Pro Ala Ser Ser Lys Pro Ile Ser Ile Asn Tyr Arg Thr
                85                  90                  95
```

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: homoserine lactone

<400> SEQUENCE: 124

```
Gly Gly Asn Gly Gly Xaa
 1               5
```

<210> SEQ ID NO 125
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 125
accaccggta ccaccaccgt taccaccggt ttcacc                         36

<210> SEQ ID NO 126
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 126
cggggatcca aggtggtggc tccccgttca ggaattc                        37

<210> SEQ ID NO 127
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 127
catgccatgg actacaagga cgacgatgac aagggtatgc aggtttctga tgttc    55

<210> SEQ ID NO 128
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

```
<400> SEQUENCE: 128
gtggtaccgg tggttcccct ccaaaaaaga agagaag                              37

<210> SEQ ID NO 129
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 129
ggaaccaccg gtaccaccgg tacggtagtt aatcgag                              37

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 130
taatacgact cactataggg                                                 20

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 131
ccgactcgag ttaatctcca ctcagcaaga g                                    31

<210> SEQ ID NO 132
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide for the construction of plasmids
      for monobody reconstitution

<400> SEQUENCE: 132
cgggatcctc gagttactag gtacggtagt taatcga                              37

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence: Synthetic
      sequence of an FG-loop region of the C-terminal half of monobodies

<400> SEQUENCE: 133

Val Thr Gly Arg Gly Asp Ser Pro Ala Ser Ser Lys Pro
 1               5                   10

<210> SEQ ID NO 134
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      sequence of an FG-loop region of the C-terminal half of monobodies

<400> SEQUENCE: 134

Val Thr Gly Gln Trp Ala Leu Tyr Leu Ser Ser Lys Pro
  1               5                  10

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
      sequence of an FG-loop region of the C-terminal half of monobodies

<400> SEQUENCE: 135

Val Thr Gly Gly Glu Val Arg Cys Val Arg Asp Ala Ala Ser Trp Ser
  1               5                  10                  15

Ser Trp Leu Lys Pro
            20

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 136

His His His His His His
  1               5

<210> SEQ ID NO 137
<211> LENGTH: 95
<212> TYPE: PRT
<213> ORGANISM: Artificial Sequence
<220> FEATURE:
<223> OTHER INFORMATION: Description of Artificial Sequence: Synthetic
      Fn3 gene

<400> SEQUENCE: 137

Met Gln Ser Asp Val Pro Arg Asp Leu Glu Val Val Ala Ala Thr Pro
  1               5                  10                  15

Thr Ser Leu Leu Ile Ser Trp Asp Ala Pro Ala Val Thr Val Arg Tyr
                 20                  25                  30

Tyr Arg Ile Thr Tyr Gly Glu Thr Gly Gly Asn Ser Pro Val Gln Glu
             35                  40                  45

Phe Thr Val Pro Gly Ser Lys Ser Thr Ala Thr Ile Ser Gly Leu Lys
     50                  55                  60

Pro Gly Val Asp Tyr Thr Ile Thr Val Tyr Ala Val Thr Gly Arg Gly
 65                  70                  75                  80

Asp Ser Pro Ala Ser Ser Lys Pro Ile Ser Ile Asn Tyr Arg Thr
                 85                  90                  95

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138
```

```
His Pro Met Asn Glu Lys Asn
  1               5
```

<210> SEQ ID NO 139
<211> LENGTH: 96
<212> TYPE: PRT
<213> ORGANISM: Artificial Sequence
<220> FEATURE:
<223> OTHER INFORMATION: Description of Artificial Sequence: Synthetic
      Fn3 gene
<220> FEATURE:
<221> NAME/KEY: MOD_RES
<222> LOCATION: (8)
<223> OTHER INFORMATION: Thr or Arg

<400> SEQUENCE: 139

```
Met Gln Val Ser Asp Val Pro Xaa Asp Leu Glu Val Val Ala Ala Thr
  1               5                  10                  15

Pro Thr Ser Leu Leu Ile Ser Trp Asp Ala Pro Ala Val Thr Val Arg
                 20                  25                  30

Tyr Tyr Arg Ile Thr Tyr Gly Glu Thr Gly Gly Asn Ser Pro Val Gln
             35                  40                  45

Glu Phe Thr Val Pro Gly Ser Lys Ser Thr Ala Thr Ile Ser Gly Leu
 50                  55                  60

Lys Pro Gly Val Asp Tyr Thr Ile Thr Val Tyr Ala Val Thr Gly Arg
 65                  70                  75                  80

Gly Asp Ser Pro Ala Ser Ser Lys Pro Ile Ser Ile Asn Tyr Arg Thr
                 85                  90                  95
```

<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Ala Val Thr Val
  1
```

<210> SEQ ID NO 141
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Thr Gln Arg Gln
  1
```

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      cleavage site

<400> SEQUENCE: 142

```
Gly Gly Met Gly Ala
  1               5
```